(12) United States Patent
Wang et al.

(10) Patent No.: US 9,078,789 B2
(45) Date of Patent: Jul. 14, 2015

(54) OUTER COVERS AND DISPOSABLE ABSORBENT INSERTS FOR PANTS

(71) Applicant: The Procter & Gamble Company, Cincinnati, OH (US)

(72) Inventors: Samantha Chen-Yee Wang, Cincinnati, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 103 days.

(21) Appl. No.: 13/789,735

(22) Filed: Mar. 8, 2013

(65) Prior Publication Data

US 2014/0257229 A1 Sep. 11, 2014

(51) Int. Cl.
| | |
|---|---|
| *A61F 13/15* | (2006.01) |
| *A61F 13/49* | (2006.01) |
| *A61F 13/496* | (2006.01) |
| *A61F 13/505* | (2006.01) |

(52) U.S. Cl.
CPC ......... *A61F 13/4906* (2013.01); *A61F 13/4902* (2013.01); *A61F 13/49003* (2013.01); *A61F 13/496* (2013.01); *A61F 13/49006* (2013.01); *A61F 13/49011* (2013.01); *A61F 13/505* (2013.01)

(58) Field of Classification Search
CPC .................. A61F 3/496; A61F 3/4906; A61F 2013/49068; A61F 2013/49063
USPC ............. 604/385.22, 385.24, 385.14, 385.25, 604/385.26, 385.28, 385.29, 385.3
See application file for complete search history.

(56) References Cited

U.S. PATENT DOCUMENTS

| | | | |
|---|---|---|---|
| 2,119,610 | A | 6/1938 | Robert |
| 2,530,647 | A | 11/1950 | Buchler |
| 2,688,328 | A | 9/1954 | Marcus |
| 2,793,642 | A | 5/1957 | Andruhovici |
| 3,077,193 | A | 2/1963 | Mann |
| 3,496,259 | A | 2/1970 | Guenther |
| 3,560,292 | A | 2/1971 | Butter |
| 3,719,736 | A | 3/1973 | Woodruff |
| 3,735,424 | A | 5/1973 | Maggio et al. |
| 3,860,003 | A | 1/1975 | Buell |
| 3,911,173 | A | 10/1975 | Sprague, Jr. |
| 3,926,189 | A | 12/1975 | Taylor |
| 3,929,135 | A | 12/1975 | Thompson |
| 3,955,575 | A | 5/1976 | Okuda |
| 4,022,210 | A | 5/1977 | Glassman |
| 4,072,150 | A | 2/1978 | Glassman |
| 4,081,301 | A | 3/1978 | Buell |

(Continued)

FOREIGN PATENT DOCUMENTS

| | | |
|---|---|---|
| AU | 642 386 | 10/1993 |
| CA | 2 103 537 | 2/1995 |

(Continued)

OTHER PUBLICATIONS www.gdiapers.com—Web pages dated Nov. 23, 2009.

(Continued)

*Primary Examiner* — Jacqueline Stephens
(74) *Attorney, Agent, or Firm* — Christian M. Best

(57) ABSTRACT

The present disclosure is generally directed to pants that include reusable outer covers and disposable absorbent inserts.

20 Claims, 49 Drawing Sheets

(56) References Cited

U.S. PATENT DOCUMENTS

| | | |
|---|---|---|
| 4,116,892 A | 9/1978 | Schwarz |
| 4,195,634 A | 4/1980 | DiSalvo et al. |
| 4,223,059 A | 9/1980 | Schwarz |
| 4,265,245 A | 5/1981 | Glassman |
| 4,284,424 A | 8/1981 | Martin |
| 4,284,454 A | 8/1981 | Joa |
| 4,324,246 A | 4/1982 | Mullane et al. |
| 4,326,302 A | 4/1982 | Lowe et al. |
| 4,338,939 A | 7/1982 | Daville |
| 4,342,314 A | 8/1982 | Radel et al. |
| 4,352,356 A | 10/1982 | Tong |
| 4,438,167 A | 3/1984 | Schwarz |
| 4,463,045 A | 7/1984 | Ahr et al. |
| 4,475,912 A | 10/1984 | Coates |
| 4,496,360 A | 1/1985 | Joffe et al. |
| 4,573,986 A | 3/1986 | Minetola et al. |
| 4,578,073 A | 3/1986 | Dysart et al. |
| 4,579,556 A | 4/1986 | McFarland |
| 4,582,550 A | 4/1986 | Sigl |
| 4,597,760 A | 7/1986 | Buell |
| 4,597,761 A | 7/1986 | Buell |
| 4,609,518 A | 9/1986 | Curro et al. |
| 4,610,678 A | 9/1986 | Weisman et al. |
| 4,615,695 A | 10/1986 | Cooper |
| 4,625,245 A | 11/1986 | White |
| 4,629,643 A | 12/1986 | Curro et al. |
| 4,643,726 A | 2/1987 | Gegelys |
| 4,650,483 A | 3/1987 | Joffe |
| 4,657,539 A | 4/1987 | Hasse |
| 4,661,102 A | 4/1987 | Shikata et al. |
| 4,673,402 A | 6/1987 | Weisman et al. |
| 4,695,278 A | 9/1987 | Lawson |
| 4,701,170 A | 10/1987 | Wilson et al. |
| 4,704,114 A | 11/1987 | Wilson et al. |
| 4,704,116 A | 11/1987 | Enloe |
| 4,710,187 A | 12/1987 | Boland et al. |
| 4,747,846 A | 5/1988 | Boland et al. |
| 4,756,709 A | 7/1988 | Stevens |
| 4,770,656 A | 9/1988 | Proxmire et al. |
| 4,785,996 A | 11/1988 | Ziecker et al. |
| 4,795,452 A | 1/1989 | Blaney et al. |
| 4,795,454 A | 1/1989 | Dragoo |
| 4,808,176 A | 2/1989 | Kielpikowski |
| 4,808,177 A | 2/1989 | Desmarais et al. |
| 4,808,178 A | 2/1989 | Aziz et al. |
| 4,816,026 A | 3/1989 | Richardson |
| 4,834,735 A | 5/1989 | Alemany et al. |
| 4,834,736 A | 5/1989 | Boland et al. |
| 4,834,737 A | 5/1989 | Khan |
| 4,834,738 A | 5/1989 | Kielpikowski et al. |
| 4,842,666 A | 6/1989 | Werenicz |
| 4,872,871 A | 10/1989 | Proxmire et al. |
| 4,888,231 A | 12/1989 | Angstadt |
| 4,892,536 A | 1/1990 | Desmarais et al. |
| 4,892,598 A | 1/1990 | Stevens et al. |
| 4,906,243 A | 3/1990 | Dravland |
| 4,908,247 A | 3/1990 | Baird et al. |
| 4,909,803 A | 3/1990 | Aziz et al. |
| 4,955,880 A | 9/1990 | Rodriquez |
| 4,961,736 A | 10/1990 | McCloud |
| 4,964,857 A | 10/1990 | Osborn |
| 4,968,311 A | 11/1990 | Chickering et al. |
| 4,968,312 A | 11/1990 | Khan |
| 4,978,046 A | 12/1990 | Hagmann et al. |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,019,068 A | 5/1991 | Perez et al. |
| 5,021,051 A | 6/1991 | Hiuke |
| 5,032,120 A | 7/1991 | Freeland et al. |
| 5,037,416 A | 8/1991 | Allen et al. |
| 5,069,672 A | 12/1991 | Wippler et al. |
| 5,087,253 A | 2/1992 | Cooper |
| 5,108,385 A | 4/1992 | Snyder |
| 5,127,108 A | 7/1992 | Weiss |
| 5,137,537 A | 8/1992 | Herron et al. |
| 5,141,870 A | 8/1992 | Bedbrook et al. |
| 5,147,345 A | 9/1992 | Young et al. |
| 5,156,793 A | 10/1992 | Buell et al. |
| 5,167,897 A | 12/1992 | Weber et al. |
| 5,185,011 A | 2/1993 | Strasser |
| 5,202,173 A | 4/1993 | Wu et al. |
| 5,207,663 A | 5/1993 | McQueen |
| 5,210,882 A | 5/1993 | Moretz et al. |
| 5,217,447 A | 6/1993 | Gagnon |
| 5,234,423 A | 8/1993 | Alemany et al. |
| 5,254,111 A | 10/1993 | Cancio et al. |
| 5,260,345 A | 11/1993 | Desmarais et al. |
| 5,261,901 A | 11/1993 | Guay |
| 5,269,775 A | 12/1993 | Freeland et al. |
| 5,283,910 A | 2/1994 | Flint |
| 5,290,270 A | 3/1994 | Fisher |
| 5,296,184 A | 3/1994 | Wu et al. |
| 5,306,267 A | 4/1994 | Hahn et al. |
| 5,342,338 A | 8/1994 | Roe |
| 5,354,597 A | 10/1994 | Capik et al. |
| 5,360,422 A | 11/1994 | Brownlee et al. |
| 5,368,584 A | 11/1994 | Clear et al. |
| 5,368,585 A | 11/1994 | Dokken |
| 5,387,207 A | 2/1995 | Dyer et al. |
| 5,401,266 A | 3/1995 | Runeman et al. |
| 5,405,342 A | 4/1995 | Roessler et al. |
| 5,415,650 A | 5/1995 | Sigl |
| 5,435,014 A | 7/1995 | Moretz et al. |
| 5,458,591 A | 10/1995 | Roessler et al. |
| 5,476,457 A | 12/1995 | Roessler et al. |
| 5,509,915 A | 4/1996 | Hanson et al. |
| 5,514,121 A | 5/1996 | Roe et al. |
| 5,518,801 A | 5/1996 | Chappell et al. |
| 5,554,142 A | 9/1996 | Dreier et al. |
| 5,562,648 A | 10/1996 | Peterson |
| 5,571,096 A | 11/1996 | Dobrin et al. |
| 5,607,760 A | 3/1997 | Roe |
| 5,609,587 A | 3/1997 | Roe |
| 5,613,959 A * | 3/1997 | Roessler et al. ............. 604/364 |
| 5,624,425 A | 4/1997 | Gray et al. |
| 5,624,429 A | 4/1997 | Long et al. |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,667,503 A | 9/1997 | Roe et al. |
| 5,671,615 A | 9/1997 | Kjærgaard et al. |
| 5,716,349 A | 2/1998 | Taylor et al. |
| H1732 H | 6/1998 | Johnson |
| 5,769,838 A | 6/1998 | Buell et al. |
| 5,772,649 A | 6/1998 | Siudzinski |
| 5,776,121 A | 7/1998 | Roe et al. |
| 5,795,347 A | 8/1998 | Roe et al. |
| 5,795,348 A | 8/1998 | Roe et al. |
| 5,814,037 A | 9/1998 | Coates |
| 5,827,261 A | 10/1998 | Osborn et al. |
| 5,843,065 A | 12/1998 | Wyant |
| 5,843,267 A | 12/1998 | Cashaw et al. |
| 5,846,232 A | 12/1998 | Serbiak et al. |
| H1788 H | 2/1999 | Christon et al. |
| 5,865,823 A | 2/1999 | Curro |
| 5,906,603 A | 5/1999 | Roe et al. |
| 5,911,713 A | 6/1999 | Yamada et al. |
| 5,938,648 A | 8/1999 | Lavon et al. |
| 5,941,864 A | 8/1999 | Roe |
| 5,947,946 A | 9/1999 | Fisher et al. |
| 5,968,025 A | 10/1999 | Roe et al. |
| 5,984,911 A | 11/1999 | Siebers et al. |
| 6,007,528 A | 12/1999 | Osborn |
| 6,010,491 A | 1/2000 | Roe et al. |
| 6,120,487 A | 9/2000 | Ashton |
| 6,142,983 A | 11/2000 | Suprise et al. |
| 6,207,738 B1 | 3/2001 | Zuckerman et al. |
| 6,213,991 B1 | 4/2001 | Kling et al. |
| 6,229,061 B1 | 5/2001 | Dragoo et al. |
| 6,240,569 B1 | 6/2001 | Van Gompel et al. |
| 6,251,097 B1 | 6/2001 | Kline et al. |

(56) References Cited

U.S. PATENT DOCUMENTS

| | | |
|---|---|---|
| 6,254,583 B1 | 7/2001 | Coates |
| 6,258,308 B1 | 7/2001 | Brady et al. |
| 6,278,037 B1 | 8/2001 | Schmidt et al. |
| 6,287,169 B1 | 9/2001 | Willms et al. |
| 6,291,039 B1 | 9/2001 | Combe et al. |
| 6,307,119 B1 | 10/2001 | Cammarota et al. |
| 6,368,444 B1 | 4/2002 | Jameson et al. |
| 6,414,215 B1 | 7/2002 | Roe |
| 6,420,627 B1 | 7/2002 | Ohnishi et al. |
| 6,423,042 B1 | 7/2002 | Sasaki |
| 6,423,043 B1 | 7/2002 | Gustafsson |
| 6,432,098 B1 | 8/2002 | Kline et al. |
| 6,468,257 B1 | 10/2002 | Ono et al. |
| 6,482,191 B1 | 11/2002 | Roe et al. |
| 6,514,362 B1 | 2/2003 | Zuckerman et al. |
| 6,526,631 B1 | 3/2003 | Alberg et al. |
| 6,547,773 B2 | 4/2003 | Kleinschmidt et al. |
| 6,547,774 B2 | 4/2003 | Ono et al. |
| 6,562,016 B2 | 5/2003 | Shinkai |
| 6,575,951 B1 | 6/2003 | Ono et al. |
| 6,579,273 B2 | 6/2003 | Dupuy |
| 6,623,466 B1 | 9/2003 | Richardson |
| 6,669,618 B2 | 12/2003 | Reising et al. |
| 6,680,422 B2 | 1/2004 | Roe |
| 6,709,423 B1 | 3/2004 | Herrlein et al. |
| 6,716,441 B1 | 4/2004 | Osborne et al. |
| 6,764,477 B1 | 7/2004 | Chen et al. |
| 6,764,478 B2 | 7/2004 | Ashton et al. |
| 6,786,895 B1 | 9/2004 | Schmitz |
| 6,794,023 B1 | 9/2004 | Melik et al. |
| 6,807,685 B1 | 10/2004 | Hasegawa et al. |
| 6,811,643 B2 | 11/2004 | McAmish et al. |
| 6,817,992 B1 | 11/2004 | Sassak et al. |
| 6,821,612 B1 | 11/2004 | Melik et al. |
| 6,843,949 B2 | 1/2005 | Brady et al. |
| 6,878,647 B1 | 4/2005 | Rezai et al. |
| 6,884,494 B1 | 4/2005 | Curro et al. |
| 6,890,872 B2 | 5/2005 | Bond et al. |
| 6,893,388 B2 | 5/2005 | Reising et al. |
| 6,905,987 B2 | 6/2005 | Noda et al. |
| 6,921,393 B2 | 7/2005 | Tears et al. |
| 6,936,039 B2 | 8/2005 | Kline et al. |
| 6,964,720 B2 | 11/2005 | Schneider et al. |
| 6,966,720 B2 | 11/2005 | Moss |
| 6,980,872 B2 | 12/2005 | Kano et al. |
| 7,037,569 B2 | 5/2006 | Curro et al. |
| 7,060,149 B2 | 6/2006 | Ortega et al. |
| 7,101,359 B2 | 9/2006 | Kline et al. |
| 7,166,095 B1 | 1/2007 | Coates |
| 7,175,613 B2 | 2/2007 | Sugiyama et al. |
| 7,211,531 B2 | 5/2007 | Schneider et al. |
| 7,223,818 B2 | 5/2007 | Autran et al. |
| 7,250,549 B2 | 7/2007 | Richlen et al. |
| 7,264,615 B2 | 9/2007 | Sherrod et al. |
| 7,344,526 B2 | 3/2008 | Yang et al. |
| 7,387,620 B2 | 6/2008 | Watanabe et al. |
| 7,407,468 B2 | 8/2008 | Reising et al. |
| 7,458,961 B2 | 12/2008 | Carstens |
| 7,462,173 B2 | 12/2008 | Carstens |
| 7,481,801 B2 | 1/2009 | Carstens |
| 7,491,196 B2 | 2/2009 | Franke et al. |
| 7,537,587 B2 | 5/2009 | Carstens |
| 7,576,019 B2 | 8/2009 | Bond et al. |
| 7,591,811 B2 | 9/2009 | Wilkinson |
| 7,629,501 B2 | 12/2009 | Labit et al. |
| 7,666,175 B2 | 2/2010 | Trennepohl |
| 7,695,463 B2 | 4/2010 | Lavon et al. |
| 7,771,406 B2 | 8/2010 | Mueller et al. |
| 7,771,408 B2 | 8/2010 | Mueller et al. |
| 7,776,770 B2 | 8/2010 | Wang et al. |
| 7,776,771 B2 | 8/2010 | Autran et al. |
| 7,820,875 B2 | 10/2010 | Roe et al. |
| 7,824,387 B2 | 11/2010 | LaVon |
| 7,833,211 B2 | 11/2010 | Mansfield |
| 7,842,627 B2 | 11/2010 | Gao et al. |
| 7,872,169 B2 | 1/2011 | Ruiz et al. |
| 7,875,014 B2 | 1/2011 | Hendren et al. |
| 7,887,527 B2 | 2/2011 | Hayashi et al. |
| 7,914,507 B1 | 3/2011 | Magee |
| 7,985,210 B2 | 7/2011 | Ashton et al. |
| 7,993,322 B2 | 8/2011 | Brud et al. |
| 8,062,276 B2 | 11/2011 | Labit et al. |
| 8,066,685 B2 | 11/2011 | Olson et al. |
| 8,118,801 B2 | 2/2012 | Macura et al. |
| 8,158,043 B2 | 4/2012 | Gibson et al. |
| 8,206,366 B2 | 6/2012 | Datta et al. |
| 8,262,635 B2 | 9/2012 | Labit et al. |
| 8,377,023 B2 | 2/2013 | Sawyer et al. |
| 8,585,667 B2 | 11/2013 | Roe et al. |
| 2002/0010452 A1 | 1/2002 | Dupuy |
| 2002/0035747 A1 | 3/2002 | Kusibojoska et al. |
| 2002/0045874 A1 | 4/2002 | Kumasaka et al. |
| 2002/0076520 A1 | 6/2002 | Neeb et al. |
| 2002/0128619 A1 | 9/2002 | Carlbark et al. |
| 2003/0055394 A1 | 3/2003 | Gibbs |
| 2003/0088220 A1 | 5/2003 | Molander et al. |
| 2003/0091807 A1 | 5/2003 | Desai et al. |
| 2003/0114805 A1 | 6/2003 | Rainville et al. |
| 2003/0125701 A1 | 7/2003 | Widlund |
| 2003/0163104 A1 | 8/2003 | Tears et al. |
| 2003/0233082 A1 | 12/2003 | Kline et al. |
| 2004/0023771 A1 | 2/2004 | Reising et al. |
| 2004/0030311 A1 | 2/2004 | Suzuki et al. |
| 2004/0127867 A1 | 7/2004 | Odorzynski et al. |
| 2005/0033258 A1 | 2/2005 | Suzuki et al. |
| 2005/0096624 A1 | 5/2005 | Hoshino et al. |
| 2005/0148974 A1 | 7/2005 | Datta et al. |
| 2005/0164587 A1 | 7/2005 | Melik et al. |
| 2005/0175269 A1 | 8/2005 | Ashton et al. |
| 2005/0177123 A1 | 8/2005 | Catalan |
| 2005/0215965 A1 | 9/2005 | Schmidt et al. |
| 2005/0215968 A1 | 9/2005 | Henderson |
| 2005/0215970 A1 | 9/2005 | Kline et al. |
| 2005/0215971 A1 | 9/2005 | Roe et al. |
| 2005/0234411 A1 | 10/2005 | Ashton et al. |
| 2006/0035055 A1 | 2/2006 | Schneider et al. |
| 2006/0047260 A1 | 3/2006 | Ashton et al. |
| 2006/0058766 A1 | 3/2006 | Mueller et al. |
| 2006/0069372 A1 | 3/2006 | Chakavarty et al. |
| 2006/0087053 A1 | 4/2006 | O'Donnell et al. |
| 2006/0095012 A1 | 5/2006 | Cohen |
| 2006/0107505 A1 | 5/2006 | Desai et al. |
| 2006/0129114 A1 | 6/2006 | Mason et al. |
| 2006/0129116 A1 | 6/2006 | Hughes et al. |
| 2006/0178652 A1 | 8/2006 | Miller |
| 2006/0189956 A1 | 8/2006 | Catalan |
| 2006/0229582 A1 | 10/2006 | LaVon |
| 2006/0247599 A1 | 11/2006 | Mullen et al. |
| 2006/0264865 A1 | 11/2006 | Carstens |
| 2006/0264867 A1 | 11/2006 | Carstens |
| 2006/0264868 A1 | 11/2006 | Carstens |
| 2006/0264869 A1 | 11/2006 | Carstens |
| 2006/0264870 A1 | 11/2006 | Carstens |
| 2006/0264871 A1 | 11/2006 | Carstens |
| 2006/0264872 A1 | 11/2006 | Carstens |
| 2006/0264873 A1 | 11/2006 | Carstens |
| 2006/0264874 A1 | 11/2006 | Carstens |
| 2006/0264877 A1 | 11/2006 | Carstens |
| 2006/0264878 A1 | 11/2006 | Carstens |
| 2006/0264879 A1 | 11/2006 | Carstens |
| 2006/0264880 A1 | 11/2006 | Carstens |
| 2006/0264881 A1 | 11/2006 | Carstens |
| 2006/0264882 A1 | 11/2006 | Carstens |
| 2006/0264883 A1 | 11/2006 | Carstens |
| 2006/0264884 A1 | 11/2006 | Carstens |
| 2006/0264885 A1 | 11/2006 | Carstens |
| 2006/0282056 A1 | 12/2006 | McDonald |
| 2006/0293637 A1 | 12/2006 | La Von et al. |
| 2007/0005038 A1 | 1/2007 | Mansfield et al. |
| 2007/0032772 A1 | 2/2007 | Ehrnsperger et al. |
| 2007/0123834 A1 | 5/2007 | McDowall et al. |
| 2007/0142798 A1 | 6/2007 | Goodlander et al. |
| 2007/0142816 A1 | 6/2007 | Carstens |
| 2007/0191806 A1 | 8/2007 | Mueller et al. |

(56) References Cited

U.S. PATENT DOCUMENTS

| | | |
|---|---|---|
| 2007/0203301 A1 | 8/2007 | Autran et al. |
| 2007/0239130 A1 | 10/2007 | Trennepohl |
| 2007/0249254 A1 | 10/2007 | Mansfield |
| 2007/0287348 A1 | 12/2007 | Autran et al. |
| 2007/0287982 A1 | 12/2007 | Lodge et al. |
| 2007/0287983 A1 | 12/2007 | Lodge et al. |
| 2007/0293111 A1 | 12/2007 | Mansfield |
| 2008/0004582 A1 | 1/2008 | Lodge et al. |
| 2008/0004583 A1 | 1/2008 | Desai et al. |
| 2008/0004584 A1 | 1/2008 | Langdonl et al. |
| 2008/0004586 A1 | 1/2008 | Lodge et al. |
| 2008/0004587 A1 | 1/2008 | Lodge et al. |
| 2008/0004589 A1 | 1/2008 | Roe et al. |
| 2008/0004590 A1 | 1/2008 | Lodge et al. |
| 2008/0004591 A1 | 1/2008 | Desai et al. |
| 2008/0004592 A1 | 1/2008 | Lodge et al. |
| 2008/0004593 A1 | 1/2008 | Lodge et al. |
| 2008/0009817 A1 | 1/2008 | Norrby |
| 2008/0015537 A1 | 1/2008 | Lodge et al. |
| 2008/0033388 A1 | 2/2008 | Muellerg et al. |
| 2008/0045917 A1 | 2/2008 | Autran et al. |
| 2008/0081854 A1 | 4/2008 | Wang et al. |
| 2008/0108963 A1 | 5/2008 | Ashton et al. |
| 2008/0114327 A1 | 5/2008 | Barge |
| 2008/0119813 A1 | 5/2008 | Carstens |
| 2008/0119814 A1 | 5/2008 | Carstens |
| 2008/0119815 A1 | 5/2008 | Carstens |
| 2008/0119816 A1 | 5/2008 | Carstens |
| 2008/0125739 A1 | 5/2008 | Lodge et al. |
| 2008/0188822 A1 | 8/2008 | Lodge et al. |
| 2008/0215027 A1 | 9/2008 | Labit et al. |
| 2008/0215028 A1 | 9/2008 | Brown et al. |
| 2008/0224351 A1 | 9/2008 | Curro et al. |
| 2008/0287983 A1 | 11/2008 | Smith et al. |
| 2008/0312617 A1 | 12/2008 | Hundorf et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312628 A1 | 12/2008 | Hundorf et al. |
| 2008/0319407 A1 | 12/2008 | Erdem et al. |
| 2009/0069722 A1 | 3/2009 | Flaction et al. |
| 2009/0069772 A1 | 3/2009 | Sauer et al. |
| 2009/0069773 A1 | 3/2009 | Sauer et al. |
| 2009/0069774 A1 | 3/2009 | Sauer et al. |
| 2009/0069775 A1 | 3/2009 | Sauer et al. |
| 2009/0069777 A1 | 3/2009 | Sauer et al. |
| 2009/0069778 A1 | 3/2009 | Sauer et al. |
| 2009/0069779 A1 | 3/2009 | Sauer et al. |
| 2009/0069781 A1 | 3/2009 | Sauer et al. |
| 2009/0069782 A1 | 3/2009 | Sauer et al. |
| 2009/0127742 A1 | 5/2009 | Qureshi et al. |
| 2009/0216209 A1 | 8/2009 | Ekstrom |
| 2010/0004616 A1 | 1/2010 | Nakamura |
| 2010/0005570 A1 | 1/2010 | Rachman |
| 2010/0179495 A1 | 7/2010 | Roe |
| 2010/0179496 A1 | 7/2010 | Roe et al. |
| 2010/0179498 A1 | 7/2010 | Roe |
| 2010/0179499 A1 | 7/2010 | Roe |
| 2010/0179500 A1 | 7/2010 | Roe et al. |
| 2010/0179501 A1 | 7/2010 | Roe et al. |
| 2010/0179502 A1 | 7/2010 | Roe |
| 2010/0179503 A1 | 7/2010 | Roe |
| 2010/0201024 A1 | 8/2010 | Gibson et al. |
| 2010/0331803 A1 | 12/2010 | Saito |
| 2011/0137277 A1 | 6/2011 | Hough et al. |
| 2011/0172622 A1 | 7/2011 | Roe et al. |
| 2011/0288518 A1 | 11/2011 | Roe et al. |
| 2012/0022485 A1 | 1/2012 | Roe et al. |
| 2012/0022491 A1 | 1/2012 | Roe |
| 2012/0049404 A1 | 3/2012 | Gibson et al. |
| 2013/0006207 A1 | 1/2013 | Roe et al. |
| 2013/0102986 A1 | 4/2013 | Ruiz et al. |
| 2013/0226122 A1 | 8/2013 | Roe et al. |
| 2014/0013490 A1 | 1/2014 | Evenson et al. |
| 2014/0018756 A1 | 1/2014 | De Bruin et al. |
| 2014/0018757 A1 | 1/2014 | De Bruin et al. |
| 2014/0018760 A1 | 1/2014 | Orchard, IV et al. |
| 2014/0018761 A1 | 1/2014 | Orchard, IV et al. |
| 2014/0018762 A1 | 1/2014 | Vignali et al. |
| 2014/0018763 A1 | 1/2014 | Evenson et al. |
| 2014/0018764 A1 | 1/2014 | Johnston et al. |

FOREIGN PATENT DOCUMENTS

| | | |
|---|---|---|
| CA | 2221209 | 11/1996 |
| CA | 2 365 577 | 6/2003 |
| DE | 103 03 903 | 11/2003 |
| EP | 0 023 804 | 2/1981 |
| EP | 0 187 726 | 7/1986 |
| EP | 319314 | 6/1989 |
| EP | 0667136 | 8/1995 |
| EP | 549988 | 6/1998 |
| EP | 796069 | 8/2000 |
| EP | 763353 | 6/2002 |
| FR | 2532337 | 3/1984 |
| GB | 112638 | 1/1918 |
| GB | 2 440 314 | 1/2008 |
| JP | 57-181003 | 11/1982 |
| JP | 57-184864 | 12/1982 |
| JP | 59-5656 | 1/1984 |
| JP | 59-5657 | 1/1984 |
| JP | 59-147214 | 9/1984 |
| JP | 59-147215 | 9/1984 |
| JP | 60-87139 | 6/1985 |
| JP | 60-91191 | 6/1985 |
| JP | 61-98628 | 6/1986 |
| JP | 62-110903 | 7/1987 |
| JP | 03-091325 | 1/1990 |
| JP | 4-7792 | 11/1990 |
| JP | 06-178795 | 1/1993 |
| JP | H11104180 | 4/1999 |
| JP | 2001-346826 | 12/2001 |
| JP | 2002-325786 | 11/2002 |
| JP | 2003-038564 | 2/2003 |
| JP | 2003-093438 | 4/2003 |
| JP | 2003-190213 | 7/2003 |
| JP | 2004-261332 | 9/2004 |
| JP | 2005-6827 | 1/2005 |
| JP | 2005-111119 | 4/2005 |
| JP | 2005-118533 | 5/2005 |
| JP | 3109189 | 5/2005 |
| JP | 2007-244506 | 3/2006 |
| JP | 2008-237231 | 10/2008 |
| JP | 2009-153736 | 7/2009 |
| JP | 47-40720 | 8/2011 |
| WO | WO-90/08524 | 8/1990 |
| WO | WO-91/16871 | 11/1991 |
| WO | WO-92/01431 | 2/1992 |
| WO | WO-92/15444 | 9/1992 |
| WO | WO-94/15563 | 7/1994 |
| WO | WO-94/15663 | 7/1994 |
| WO | WO-95/10992 | 4/1995 |
| WO | WO-95/16746 | 6/1995 |
| WO | WO-96/17572 | 6/1996 |
| WO | WO-96/24319 | 8/1996 |
| WO | WO-96/32912 | 10/1996 |
| WO | WO-00/65348 | 11/2000 |
| WO | WO-02/066086 | 8/2002 |
| WO | WO-2004/060229 | 7/2004 |
| WO | WO-2005/039469 | 5/2005 |
| WO | WO-2005/052052 | 6/2005 |
| WO | WO-2005/096855 | 10/2005 |
| WO | WO-2005/097031 | 10/2005 |
| WO | WO-2008/030984 | 3/2008 |
| WO | WO-2008/120959 | 10/2008 |
| WO | WO-2008/142634 | 11/2008 |
| WO | WO-2010/053006 | 5/2010 |

(56) References Cited

FOREIGN PATENT DOCUMENTS

| WO | WO-2010/078661 | 7/2010 |
|----|----|----|
| WO | WO-2012/167844 | 12/2012 |
| WO | WO-2013/059533 | 4/2013 |

OTHER PUBLICATIONS www.fuzzibunz.com—Web pages dated Nov. 23, 2009.
www.greenmountaindiapers.com—Web pages dated Nov. 23, 2009.
www.bumgenius.com—Web pages dated Nov. 23, 2009.
www.thirstiesbaby.com—Web pages dated Nov. 23, 2009.
www.crickettsdiaper.com—Web pages dated Nov. 23, 2009.
Archived web page from www.bummis.com, Aug. 8, 2005, obtained via www.waybackmachine.org.
"Green Life; Earth-Friendly Disposable Diaper Lets Parents Flush Away the Guilt", The Oregonian (Apr. 7, 2005).
"Crazy for Cloth: The Benefits of Cotton Diapers", Mothering Magazine (Jan. 1, 2003).
"Not Your Grandma's Diapers", E: The Environmental Magazine (Mar.-Apr. 2006).
"Y2K Babyware: Your Green Guide to Carefree Diapering for Your Millennium Bundle of Joy". The Gazette (Montreal, Quebec) (Oct. 5, 2000).
"The Evolution of Diapers: Cloth Meets Cute for Some Mothers (and Grandmothers), The Changes in Cloth Diapers Have Made Them all the Rage. Learning the Lingo Navigating Cloth" Omaha World Herald (Mar. 22, 2004).
37 photographs (obtained from Marketing Technology Service, Inc.) of a product believed to be a product of Kao Corp. and sold in Japan in 1986 (translations provided by Applicants.
All Office Actions, U.S. Appl. No. 13/789,707.
All Office Actions, U.S. Appl. No. 13/789,709.
All Office Actions, U.S. Appl. No. 13/789,711.
All Office Actions, U.S. Appl. No. 13/789,731.
All Office Actions, U.S. Appl. No. 13/789,738.
International Search Report and Written Opinion, PCT/US2014/020843, date of mailing Jun. 20, 2014.
All Office Actions, Responses, and Claims for U.S. Appl. No. 13/789,707.
All Office Actions, Responses, and Claims for U.S. Appl. No. 13/789,709.
All Office Actions, Responses, and Claims for U.S. Appl. No. 13/789,711.
All Office Actions, Responses, and Claims for U.S. Appl. No. 13/789,731.
All Office Actions, Responses, and Claims for U.S. Appl. No. 13/789,738.

\* cited by examiner

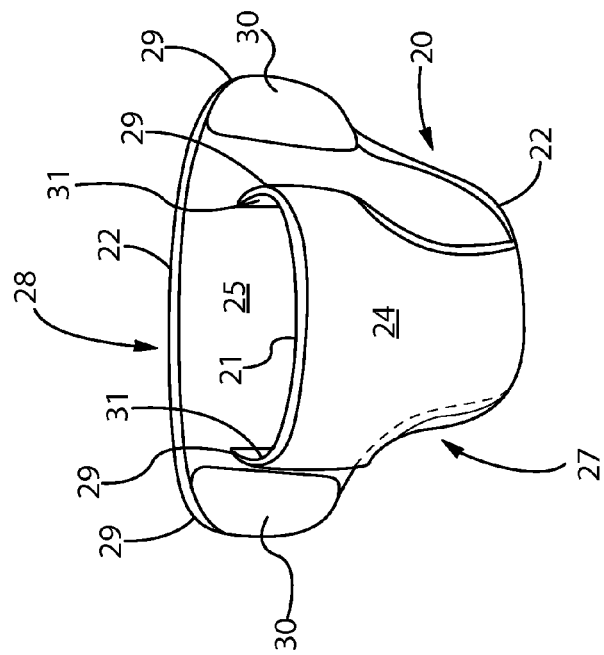
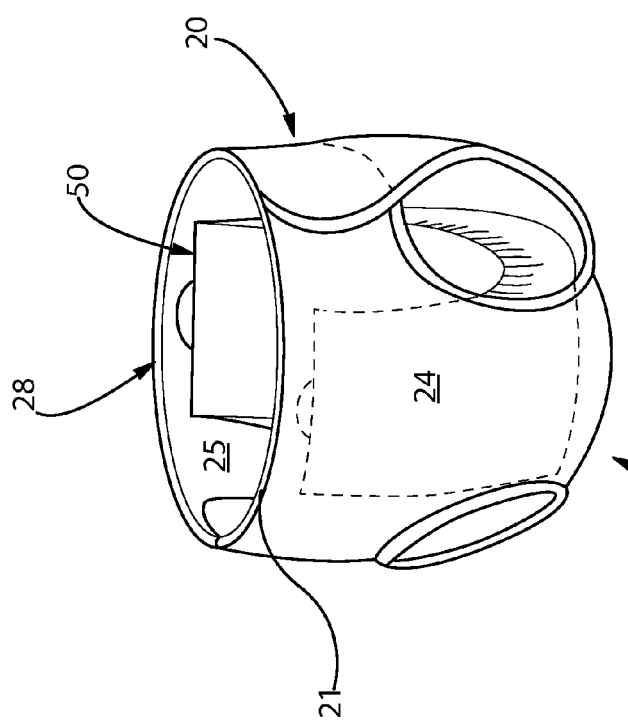
Fig. 1D
Fig. 1C

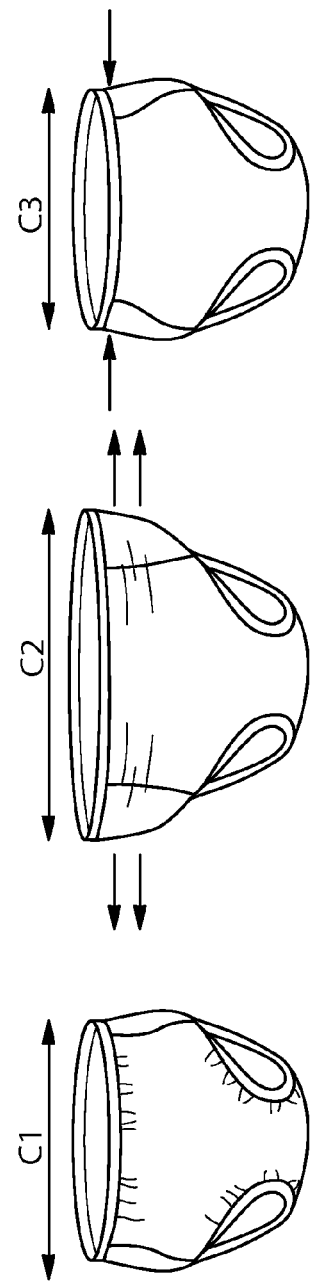

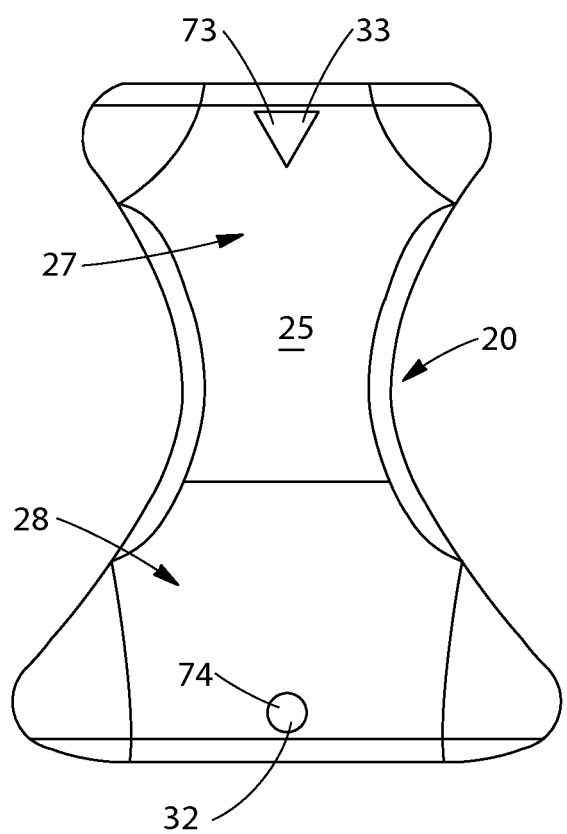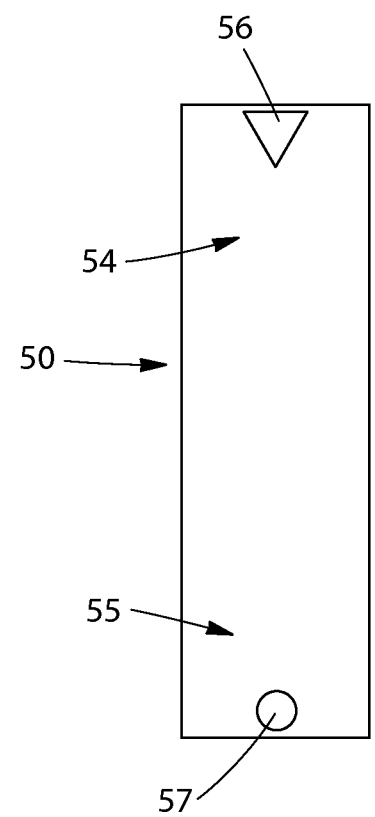
Fig. 2I                               Fig. 2J

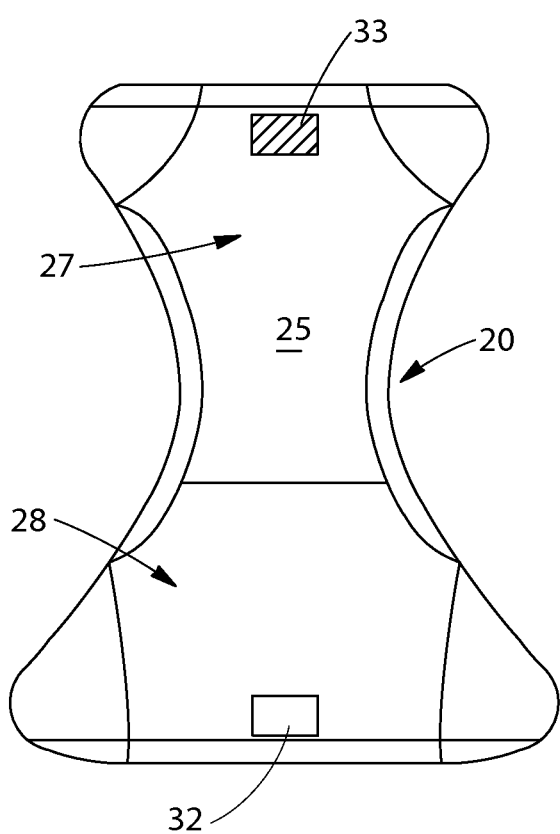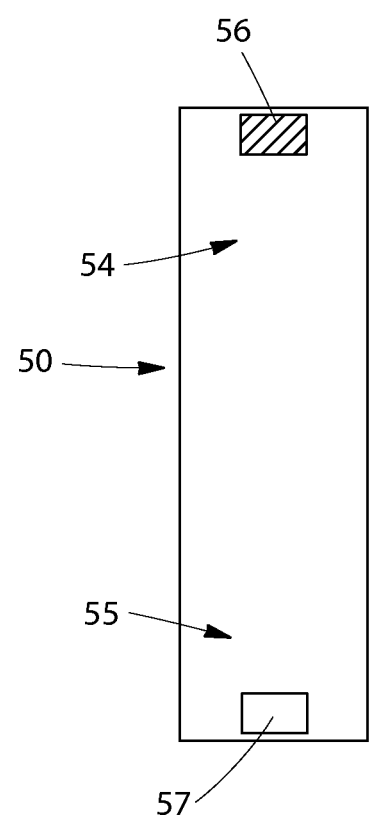
Fig. 2K
Fig. 2L

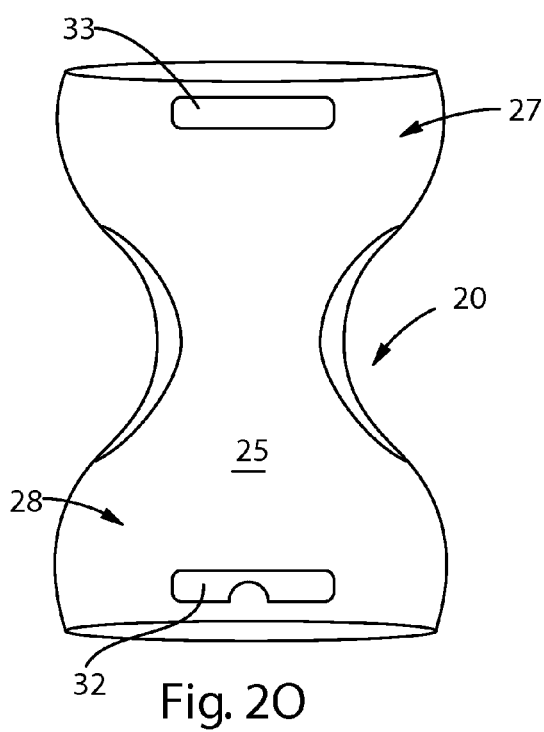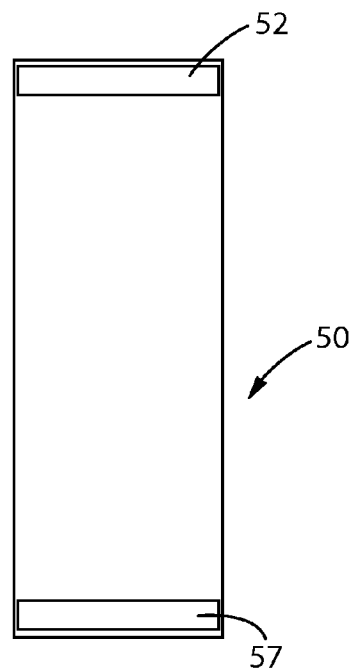
Fig. 2O    Fig. 2P
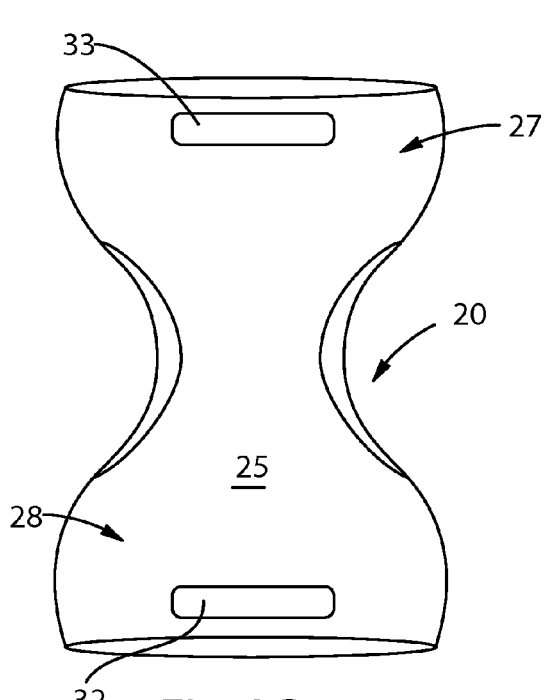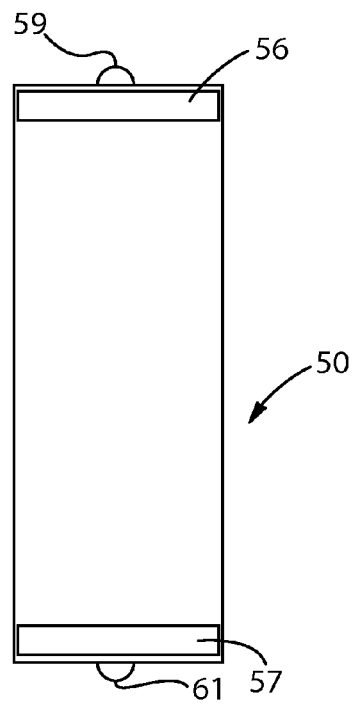
Fig. 2Q    Fig. 2R

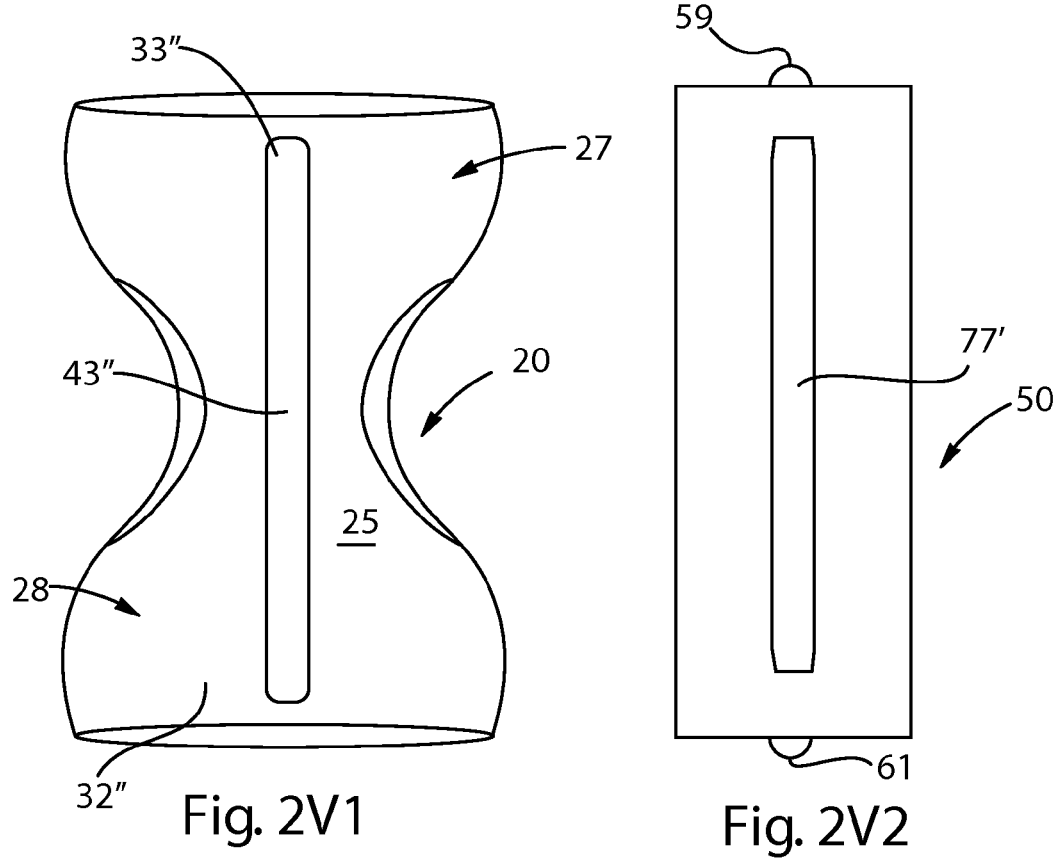

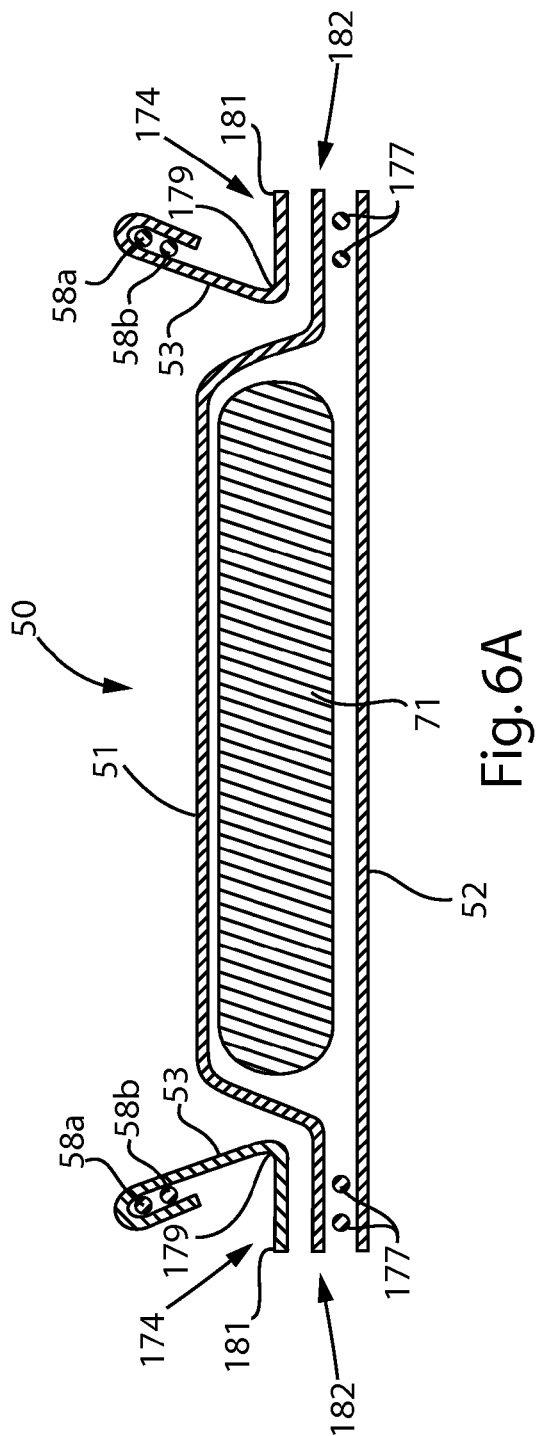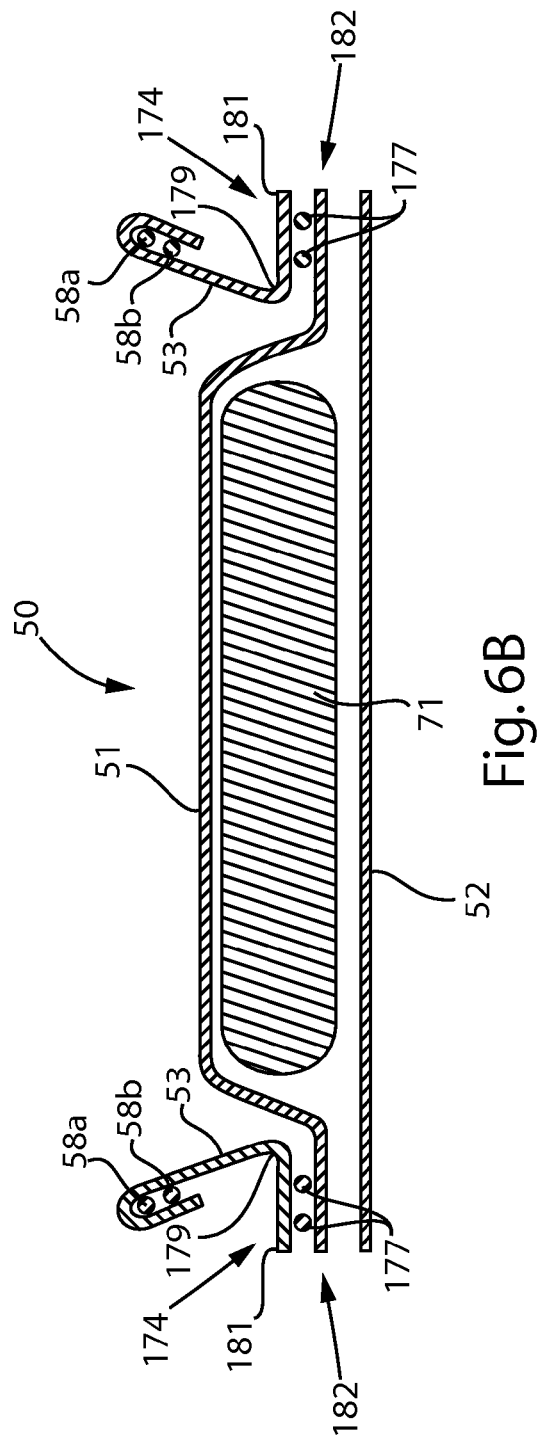

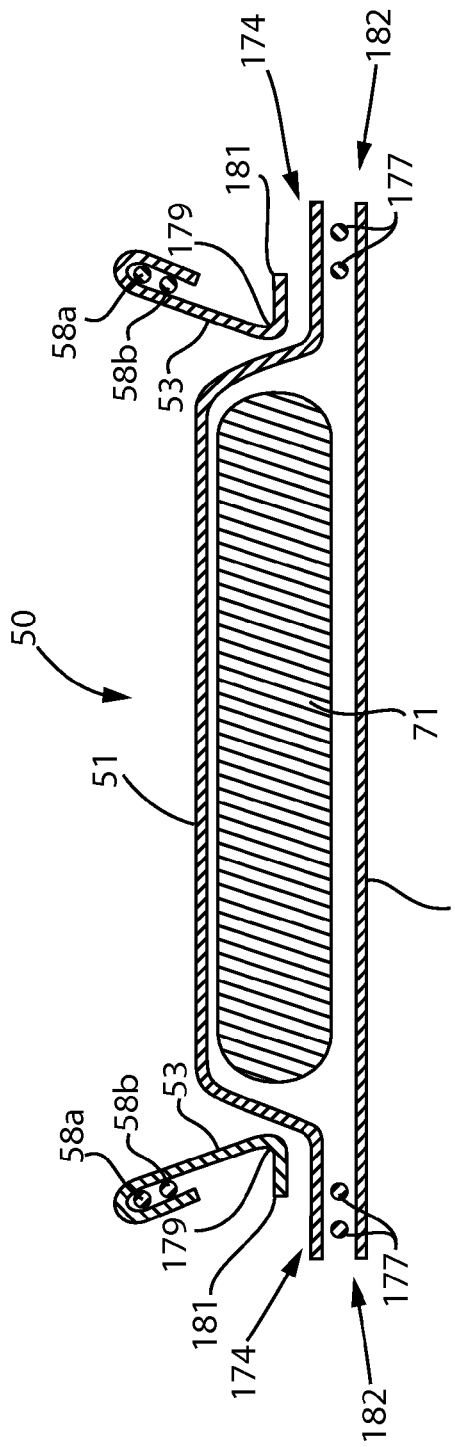
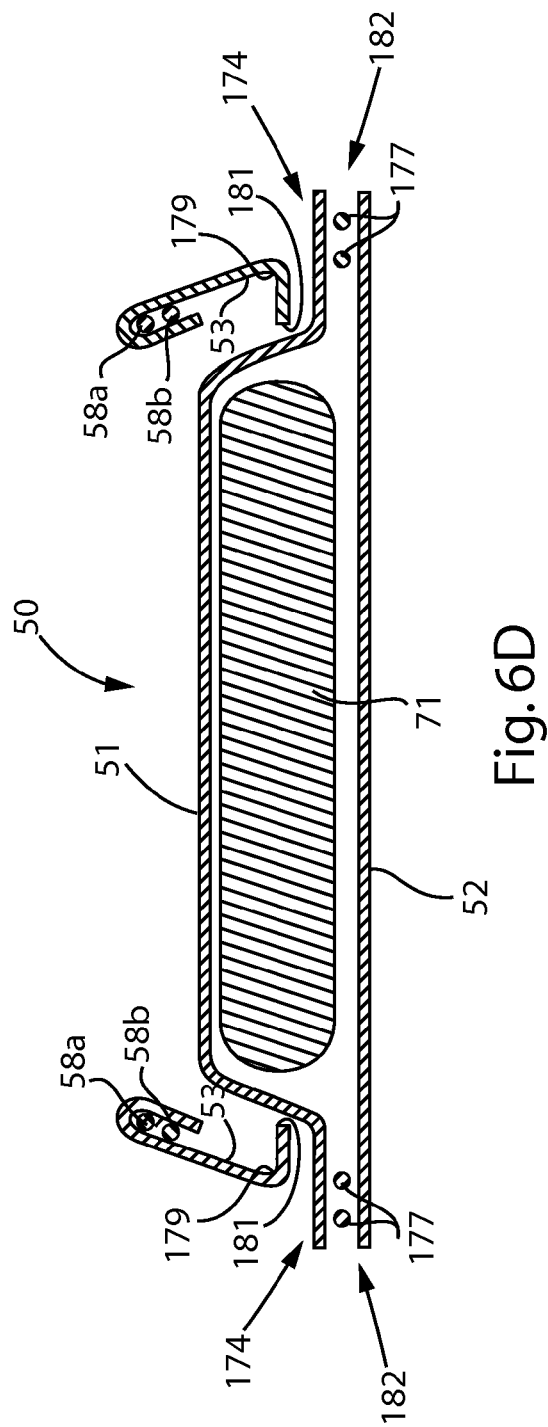

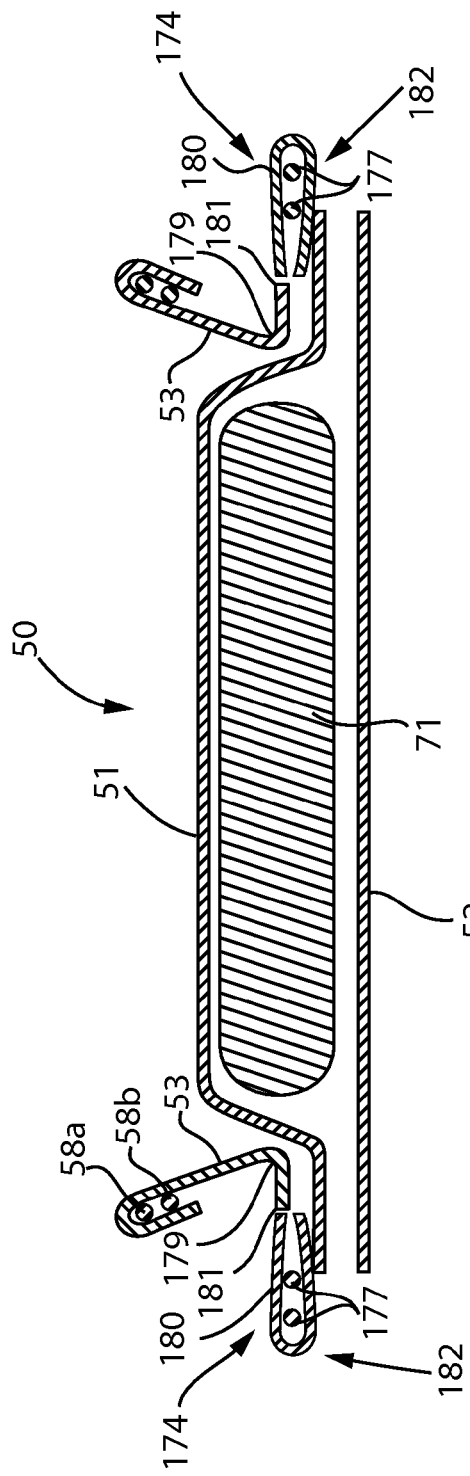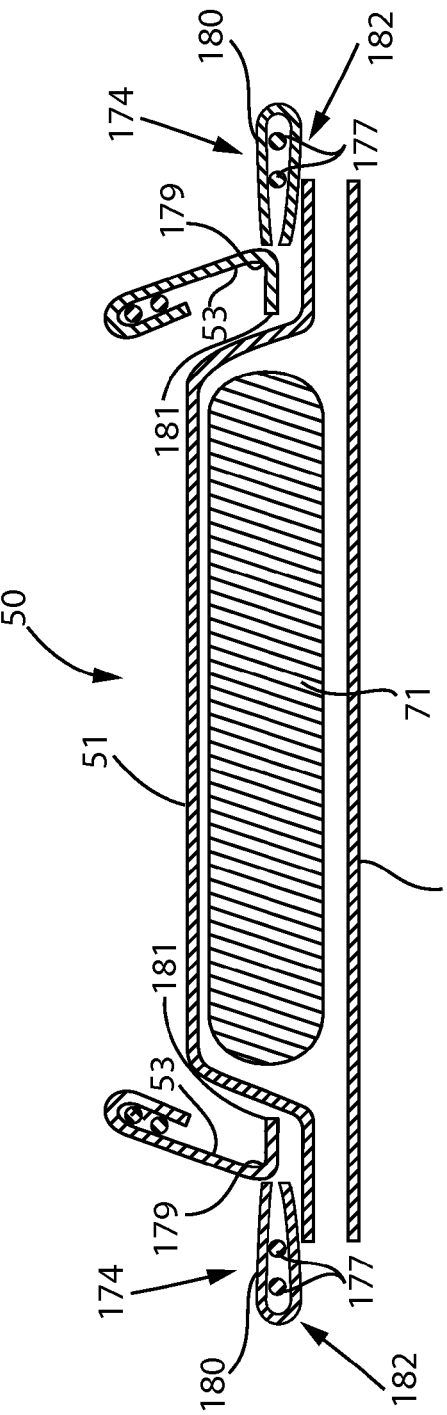
Fig.6E
Fig.6F

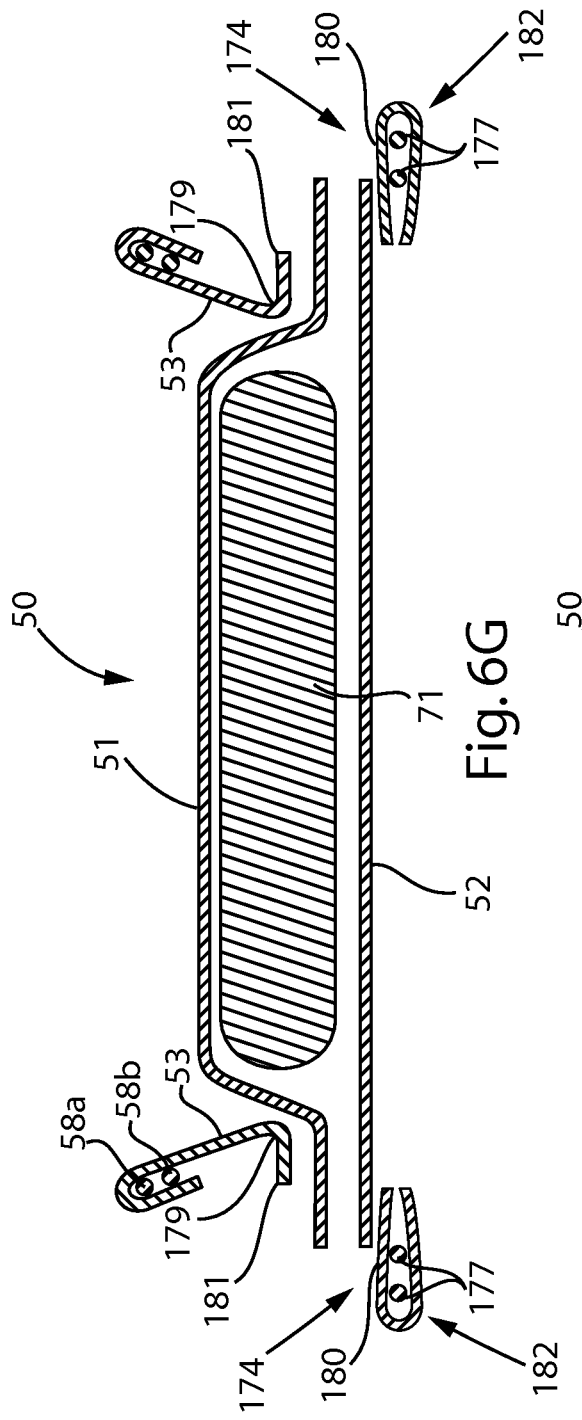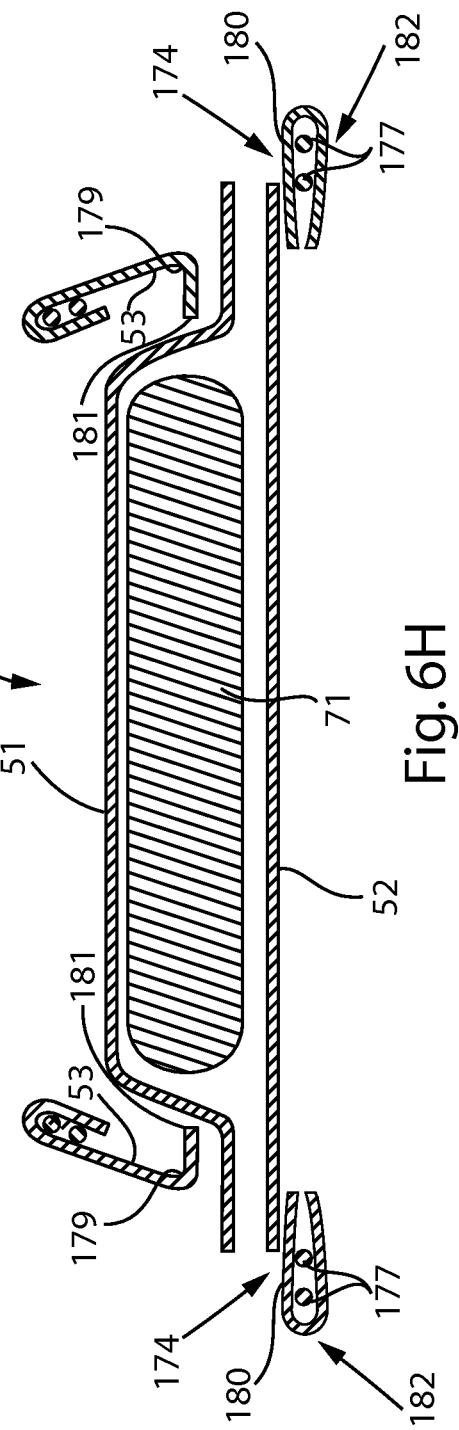

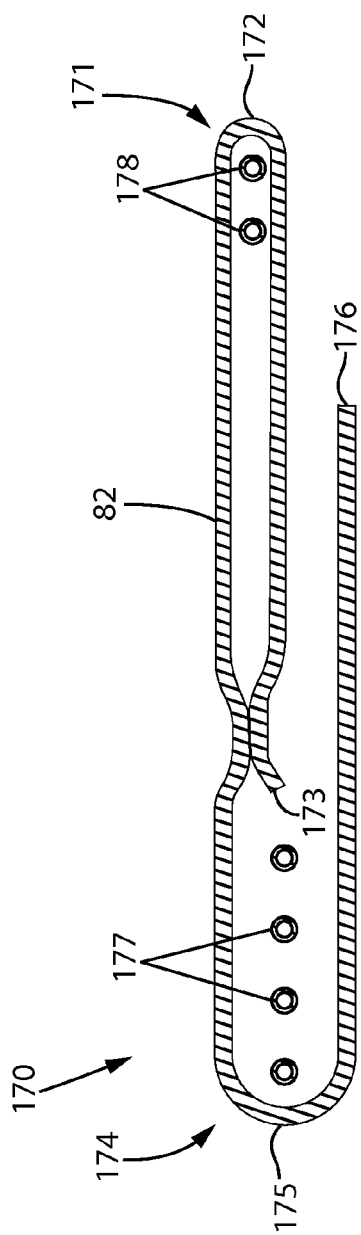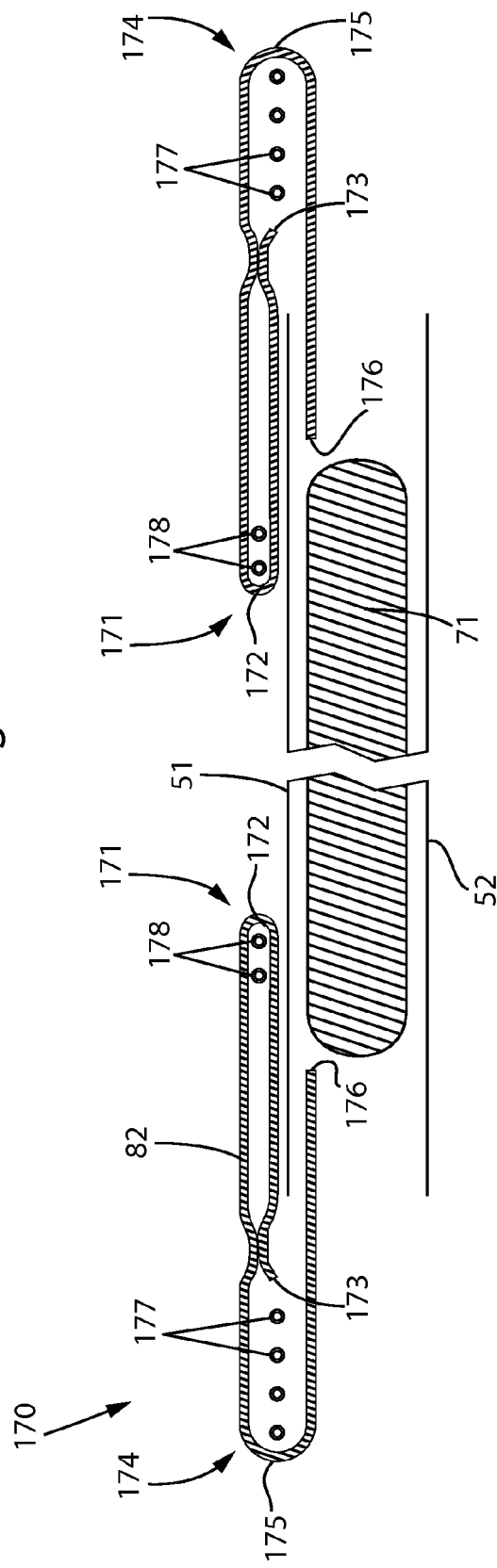

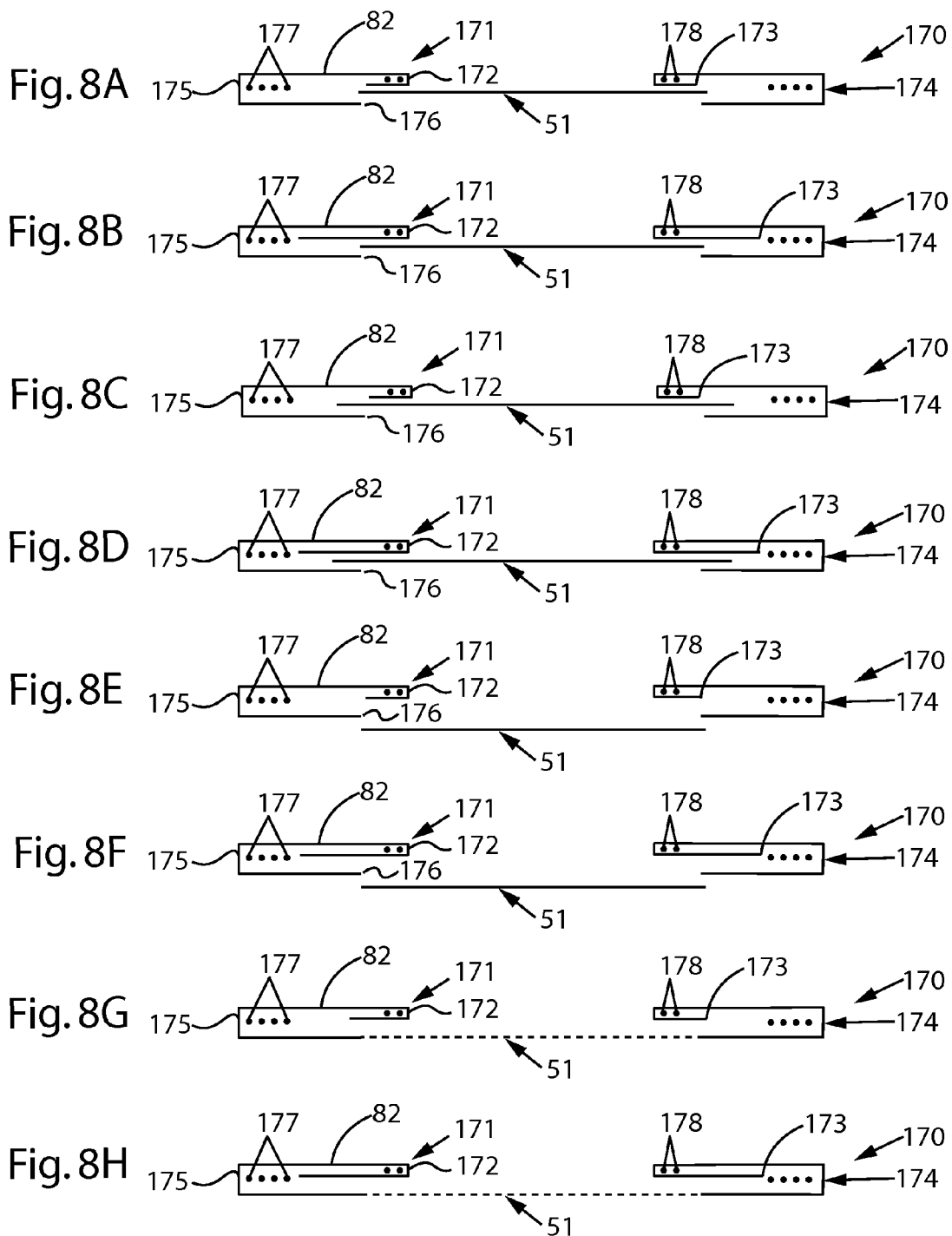

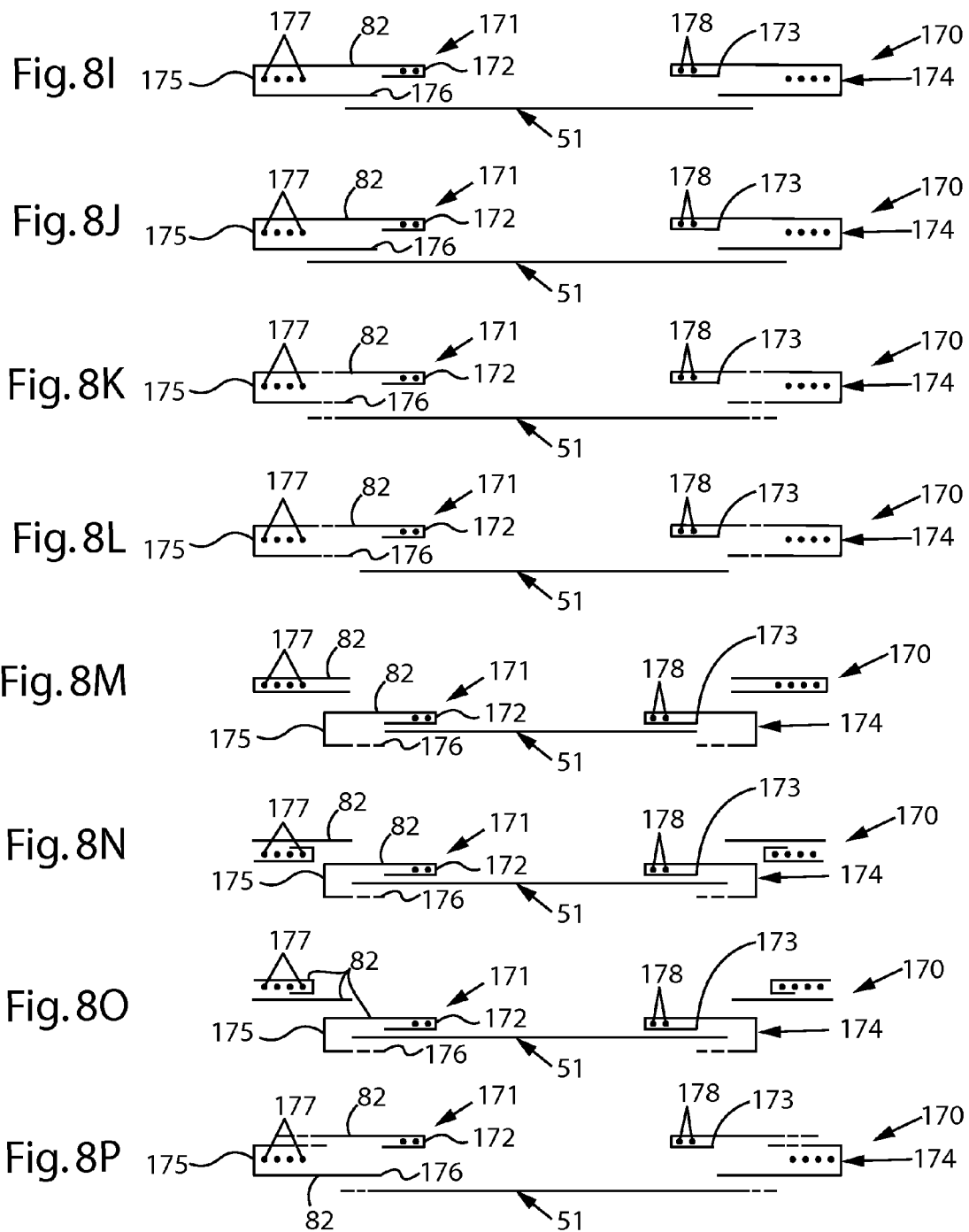

OUTER COVERS AND DISPOSABLE ABSORBENT INSERTS FOR PANTS

FIELD

The present disclosure relates generally to the field of diapers, adult incontinence products, and other wearable absorbent articles having features for the containment and absorption of bodily exudates, and more particularly, to such articles and products having disposable absorbent inserts and reusable outer covers that together form pants.

BACKGROUND

Reusable diapers made of cloth have been in use since the invention of cloth. Reusable cloth diapers, however, present difficulties relating to sanitation needs, in handling, laundering, and effectively sanitizing soiled diapers for re-use. Reusable cloth diapers also may be relatively unreliable with respect to containing bodily exudates (i.e., they may tend to leak). Because a wet cloth diaper may be in direct contact with the skin, unless wetness is quickly detected and the wet diaper removed, it may promote over-hydration of the wearer's skin, which may make the skin vulnerable to diaper rash.

The introduction of disposable diapers, including pant forms, in relatively recent times has mitigated these disadvantages for many. Generally, upon removal from a wearer, a soiled disposable diaper need not be emptied, laundered, or handled to any significant extent, but rather, may be discarded as is. Any soiled areas of the wearer's body may then be cleaned, and a clean new disposable diaper may be placed on the wearer as necessary. Many current disposable diapers have structures that make them relatively more effective at containing exudates than traditional cloth diapers. Many have structures and materials that make them relatively more effective at conveying and storing liquid exudates away from the wearer's skin. Some have features that enable them to "breathe", thereby reducing humidity inside the diaper, and some even include skin care compositions that are transferred to the skin when the diaper is worn. Such features may reduce the likelihood and/or extent of skin over-hydration and otherwise promote or help maintain skin health.

For economic reasons, currently most disposable diapers are made of substantial proportions of materials derived from petroleum, such as polypropylene and/or polyethylene. These materials often appear in the form of spun fibers forming cloth-like nonwoven web materials, or alternatively or in addition, films.

In recent years concerns have arisen concerning the "environmental footprint" of human activities of all kinds. The manufacture and use of diapers is no exception, particularly in view of the growing human population (i.e., the growing number of babies). One view seems to be that use of disposable diapers is detrimental to the environment because the materials of which they are typically made may be derived from non-renewable resources and require substantial amounts of energy in their manufacture. Additionally, because disposable diapers typically are not re-used or recycled, their use may be deemed by some to be unsatisfactorily taxing upon disposal facilities such as landfills. If the alternative is reusable cloth diapers, however, another view seems to be that the increased use of energy (e.g., for operating equipment, heating laundry water, and treating wastewater) and chemicals (e.g., detergents and water treatment agents), necessary for laundering soiled diapers at the rate they are typically used, and treating the associated wastewater, present their own set of stresses on the environment. As may be appreciated, analysis concerning which alternative is more "environmentally friendly" is complicated, and undisputed conclusions either way do not yet appear to exist.

Regardless of which alternative one may believe is more environmentally friendly, however, it appears that in developed nations, today's disposable diapers are generally favored over reusable cloth diapers among caregivers of babies and young children. This is probably attributable to the advantages of reducing or eliminating the unpleasantness, sanitary concerns, extra work, expense associated with handling and laundering soiled reusable cloth diapers, better containment of exudates, and/or effectiveness at promoting and/or helping maintain skin health.

Manufacture of wholly disposable diapers is generally considered a capital-intensive business. This is a consequence of the complex machinery required to produce product from incoming material streams at economically-feasible production rates, which often exceed 500 or more articles per manufacturing line, per minute. Any innovation that has the potential to simplify the process or the equipment required, or to reduce material costs, has the corresponding potential to reduce per-article costs for the manufacturer and the consumer.

Several designs of diapers that include a reusable cloth outer cover and either a reusable or a disposable absorbent insert have been manufactured and marketed. However, for the user, these designs have still presented at least some of the disadvantages of traditional cloth diapers, while not providing some of the advantages available from current disposable diaper designs.

In view of the concerns set forth above, it would be advantageous if wearable absorbent articles, in the form of pants, were available that provide the advantages afforded by both disposable and reusable diapers, while reducing the respective disadvantages of these alternatives.

SUMMARY

In one form, the present disclosure is directed, in part, to an outer cover forming a portion of a pant and having a longitudinal axis and a lateral axis. The outer cover comprises a front waist region positioned on a first side of the lateral axis, a rear waist region positioned on a second side of the lateral axis, and a crotch region positioned intermediate the front waist region and the rear waist region. The outer cover may further comprise a fastening zone positioned on a side of the longitudinal axis. The fastening zone may comprise a first portion in the front waist region and a second portion in the rear waist region. The outer cover is configured to at least partially receive a disposable absorbent insert to form the pant. The outer cover may have an average modulus between 170 mm extension and 110 mm extension in the range of 20 N/m to 250 N/m measured according to the Whole Outer Cover Waist Opening Circumference Extension Force Test.

BRIEF DESCRIPTION OF THE DRAWINGS

FIG. 1C is a perspective view of a wearable absorbent article with the fastening zones in a closed configuration and with a disposable absorbent insert positioned therein in accordance with a non-limiting embodiment of the present disclosure;

FIG. 1D is a perspective view of the wearable absorbent article of FIG. 1C with the fastening zones in an open configuration in accordance with a non-limiting embodiment of the present disclosure;

FIG. 1E is a perspective view of a pant in an unstretched configuration in accordance with a non-limiting embodiment of the present disclosure;

FIG. 1F is a perspective view of the pant of FIG. 1E in a stretched configuration simulating pulling the pant over the hips and buttocks of a wearer in accordance with a non-limiting embodiment of the present disclosure;

FIG. 1G is a perspective view of the pant of FIG. 1F in a partially stretched configuration simulating positioning on a lower torso of a wearer in accordance with a non-limiting embodiment of the present disclosure;

FIGS. 2E, 2G, 2I, 2K, 2M, 2O, 2Q, 2S, 2V1, and 2U are plan views of outer covers opened and laid flat, inner surfaces facing the viewer in accordance with various non-limiting embodiments of the present disclosure;

FIGS. 2F, 2H, 2J, 2L, 2N, 2P, 2R, 2T, 2V, and 2V2 are plan views of inserts opened and laid flat, outer surfaces facing the viewer in accordance with various non-limiting embodiment of the present disclosure;

FIGS. 6A-6H are schematic lateral cross sectional views of examples of inserts having a dual leg gasketing system, taken through a lateral axis of an insert, such as the insert of FIG. 4, in accordance with various non-limiting embodiments of the present disclosure;

FIG. 6I is a schematic lateral cross sectional view of an example of one side of a unitized dual leg gasketing system of an insert in accordance with a non-limiting embodiment of the present disclosure;

FIG. 7A is a schematic lateral cross sectional view of longitudinal side portions of an example of an insert having the unitized dual leg gasketing system depicted in FIGS. 6A-6H, taken through a lateral axis of an insert in accordance with a non-limiting embodiment of the present disclosure;

FIGS. 8A-8P are schematic lateral cross sectional views of various alternative examples of unitized dual leg gasketing system configurations, taken through lateral axes of an insert in accordance with various non-limiting embodiments of the present disclosure;

DETAILED DESCRIPTION

Definitions

Figure 1A:
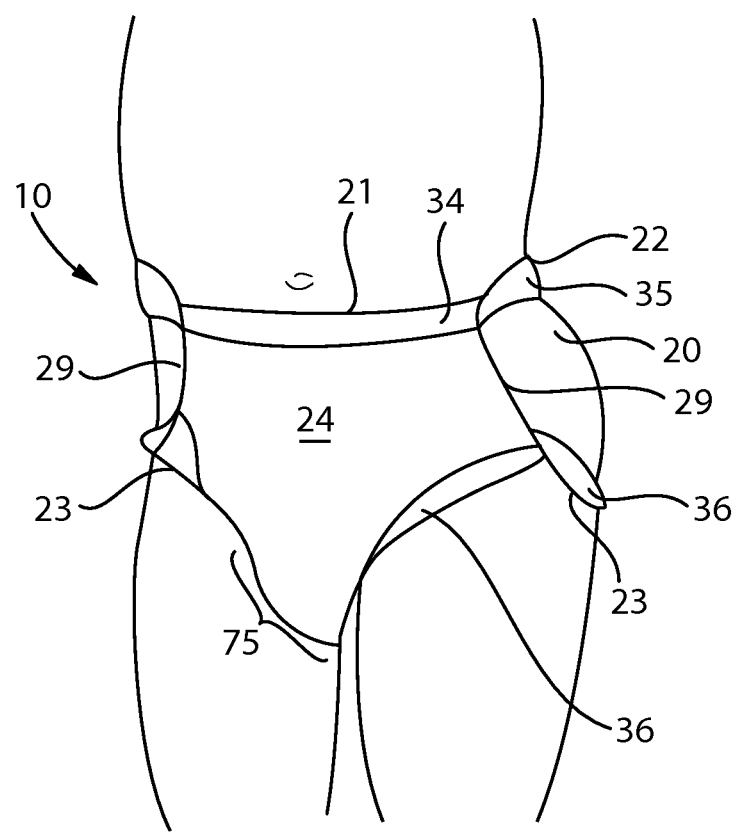
FIG. 1A is a perspective view of a wearable absorbent article as it might appear being worn by a wearer about the lower torso in accordance with a non-limiting embodiment of the present disclosure.

For purposes of this description, the following terms have the meanings set forth:

"Absorbent insert" and "insert" mean a component of a wearable absorbent article that is configured to contain and/or absorb urine, feces, menses, or any combination thereof, and is configured to be installed and removed as a modular unit, from a reusable outer cover. The insert may or may not comprise an absorbent core.

"Attachment zone" means one or more fastener components positioned on or formed on the inner surface of the outer cover which are used to removably attach or join an insert to an outer cover. The fastener components of the attachment zone may be hooks, loops, adhesives, cohesive, snaps, buttons, pockets, and/or any other suitable fastener components known to one of skill in the art.

"Chassis" means a component of a wearable absorbent article that is adapted to be worn about the lower torso of a wearer, and is adapted to support an absorbent insert and hold the insert next to the wearer's body. Herein, a chassis may also be referred to as an "outer cover". The terms "outer cover" and "chassis" are interchangeable for purposes herein.

"Disposable", when referring to an absorbent insert, means that the absorbent insert is not adapted or intended to be effectively sanitarily laundered in an ordinary household laundering process and ordinary household equipment, and thereby is ordinarily unsuitable for sanitary and effective reuse so as to provide as-new intended functions and performance, following soiling by exudates and removal from an outer cover. By way of non-limiting examples, effective laundering may be frustrated or prevented, causing the insert to be disposable, by inclusion of materials and/or construction: that do not retain their substantial as-new physical shape or structure through ordinary household laundering and drying so as to be effective as-new in reuse; that absorb aqueous liquids and cannot be sufficiently dried/dehydrated in ordinary household drying equipment and ordinary drying cycles so as to be effective as-new in reuse; that dissolve or substantially degrade in ordinary household laundering or drying, causing the insert to be substantially damaged or rendered useless; and/or that cannot be effectively cleaned of exudate material through ordinary laundering, so as to be sanitary and otherwise acceptable for re-use.

"Fastening zone" means an area of fastening, attachment, or joining of a portion of an outer cover (e.g., a portion in a front waist region) to another portion of the outer cover (e.g., a portion in a rear waist region) to form a seam. The fastening, attachment, or joining, may be permanent, releasable, or refastenable. The fastening zones may each form a seam, such as an overlap seam or a butt seam, configured to join a portion of a front waist region with a portion of a rear waist region. Fastener components of the fastening zones may comprise a single fastener, for example, an adhesive patch on a portion configured to adhere to one or more types of surfaces on another portion, or a hook, or patch of hooks on the portion, configured to catch on one or more types of surfaces on the other portion. By way of further example, any structure or component such as a pocket, strap, hook, buckle, etc. on the portion configured to capture and retain, in whole or in part, the other portion, may be a fastener component of a "fastening zone" as used herein. The fastening zones may also each comprise two or more fastener components, for example, respective components of a hook-and-loop fastening system (such as VELCRO), a loop-and-loop fastening system, respective surfaces having a cohesive material applied thereto; male and female snap fastener components, a button and button hole, slot or loop, other fastenably cooperating elements, etc. Other examples of fastening components include zipper components, "zip lock" engaging components, loops, posts, pockets, bands or straps, microfasteners, macrofasteners, and fastener components such as described in U.S. Pat. Nos. 6,936,039; 6,893,388; 6,669,618; 6,432,098; and 6,251,097, and U.S. Patent Application Publication Nos. 2005/0234419; 2005/0215971; 2005/0215970; 2005/0130821; 2004/0023771; 2003/0233082; 2003/0119641; 2003/0088220; and 2002/0169431. An outer cover may comprise one or more fastening zones. In an example embodiment where an outer cover comprises two fastening zones, one fastening zone may be positioned on a first side of a longitudinal axis of the outer cover and a second fastening zone may be positioned on a second side of the longitudinal axis. The first fastening zone may comprise a first portion on a first side of a lateral axis of the outer cover and a second portion on a second side of the lateral axis. Likewise, the second fastening zone may comprise a first portion on a first side of the lateral axis and a second portion on a second side of the lateral axis. The first portion of the first fastening zone may be joined to the second portion of the first fastening zone and, likewise, the first portion of the second fastening zone may be joined to the second portion of the second fastening zone to form seams of a pant. In other embodiments, an outer cover may only comprise one releasable fastening zone on a first side or a second side of the longitudinal axis with a permanent fastening zone on the other side of the longitudinal axis. The single fastening zone may comprise a first portion in a front waist region and a second portion in a rear waist region. The first portion may be joined to the second portion to create the fastening zone. Each portion of each fastening zones described herein may extend, at least in part, in the longitudinal direction (i.e., parallel to the longitudinal axis of the outer cover) or in generally the longitudinal direction (e.g., +/−20 degrees from the longitudinal axis). Each portion of each fastening zone may also extend in the lateral direction or in generally the lateral direction.

"Lateral" (and forms thereof), with respect to a wearer, means along a direction generally transverse or across the direction extending from the front to the rear of the wearer, or vice versa. With respect to a component of a wearable absorbent article, "lateral" (and forms thereof), means along a direction generally transverse, across, or perpendicular to the direction extending along the component as it would be properly situated on a wearer, from the front to the rear of the wearer, or vice versa.

"Longitudinal" (and forms thereof), with respect to a wearer, means along a direction generally extending from the front to the rear of the wearer, or vice versa. With respect to a component of a wearable absorbent article, "longitudinal" (and forms thereof), means along a direction generally extending along or parallel to the component as it would be properly situated on a wearer, from the front to the rear of the wearer, or vice versa.

"Outer cover" means a component of a wearable absorbent article that is configured to be worn about the lower torso of a wearer, and that is configured to support an insert and hold the insert next to the wearer's body. The outer cover may be attached to the insert through the use of attachment zones on the insert and attachment zones on the insert. The outer cover may form a pant or may be configured to form a pant by attaching or joining portions of the fastening zones together. Herein, an outer cover may also be referred to as a "chassis". The terms "outer cover" and "chassis" are interchangeable for purposes herein, and include, but are not limited to, garments having features as described herein and configured as diapers, diaper covers, underpants, briefs, training pants, boxer shorts, pants, and/shorts, for example.

"Pant" means a wearable absorbent article having a continuous perimeter waist opening and continuous perimeter leg openings in an outer cover thereof designed for infant, child, or adult wearers (e.g., adult incontinence). A pant may be configured with a continuous or closed waist opening and at least one continuous, closed, leg opening prior to the article being applied to the wearer. A pant may be preformed (e.g., by a manufacturer or a user) by various techniques including, but not limited to, joining together portions of fastening zones of an outer cover or using any refastenable and/or permanent closure member (e.g., seams, heat bonds, pressure welds, adhesives, cohesive bonds, mechanical fasteners, etc.). A pant may be preformed anywhere along the circumference of the wearable absorbent article in the waist region (e.g., side fastened or seamed, front waist fastened or seamed, rear waist fastened or seamed). A pant may be opened about one or both of the seams and then refastened. Pants having fastener components in fastening zones of the outer cover that form the circumference may be joined at the sides, in the front waist region, and/or in the rear waist region. A pant is formed by an outer cover and an absorbent insert, when the absorbent insert is joined with the outer cover. To be classified as a pant, the absorbent article should be designed such that in a closed configuration (e.g., the waist has a continuous circumference), the pant may be pulled up over the wearer's thighs and buttocks to the waist. Pants should have sufficient stretch and/or extension to enable such pulling up over the thighs and buttocks all while not having such a wide waist such that the pant falls down on smaller wearers once pulled up. These features, among others, differentiate pants from taped diapers that are wrapped around the wearer and not "pulled up".

"Reusable", when referring to an outer cover, means an outer cover that is configured to permit removal of at least a first insert, and replacement thereof with at least a second insert, without substantial destruction of any components of the outer cover that are necessary to provide the substantial as-new functionality of the outer cover, and without the necessity of any repair or reconstruction following such insert replacement.

"Stretchable region" means an area of the outer cover that is configured to stretch or elastically expand when placed under a tensile force and elastically contract when the force is released. A pant may have one or more than one stretchable region in the front and rear waist regions.

"Taped diaper" means a wearable absorbent article comprising an outer cover having an initial front waist region and an initial rear waist region that are not fastened, pre-fastened, or connected to each other, prior to being applied to the wearer. The taped diaper may also include an insert joined to the outer cover through the use of attachment zones on the outer cover and the insert. A taped diaper may be folded about its lateral central axis with the interior of one waist region in surface to surface contact with the interior of the opposing waist region without fastening or joining the waist regions together.

"Use," with respect to an outer cover, means one event of the wearing of the outer cover until the time an insert is replaced.

"User" means a caregiver or other person who may apply a wearable absorbent article to a wearer. Where the wearer is capable of donning the wearable absorbent article him/herself, the wearer is also a "user".

"Wearer" means a person who may wear the wearable absorbent article described herein.

"Wearable absorbent article" means any article designed to be worn about the lower torso and to contain and/or absorb urine, feces, menses, or any combination thereof "Wearable absorbent article" includes, but is not limited to, baby or children's diapers (of the "tape"-fastenable, otherwise fastenable, "pull-up" or any other variety), training pants and adult incontinence pants, briefs, and the like.

Two-Piece Wearable Absorbent Articles

In an embodiment, FIG. 1A depicts an example of a wearable absorbent article 10 that is a pant positioned about a lower torso of a wearer. The pant comprises an outer cover 20 having a front waist edge 21, a rear waist edge 22, leg opening edges 23, fastening ears 29, and leg bands. The outer cover comprises an inner, wearer-facing surface 25 (not illustrated in FIG. 1A) and outer, garment-facing surface 24. The outer cover 20 may be configured to receive an insert as discussed in further detail below. The fastening ears 29 may be used to permanently or refastenably join the rear waist region to the front waist region or vice versa to form the pant. In an embodiment, one of the fastening ears 29 may be permanently joined to the front waist region, while the other fastening ear 29 may be releasably joined to the front waist region. In an embodiment, the fastening ears 29 may be positioned on the front waist region and be permanently or refastenably joined to the rear waist region to form the pant. The pant may also comprise a pouch-like structure 75 in a crotch region thereof.

Figure 1B:
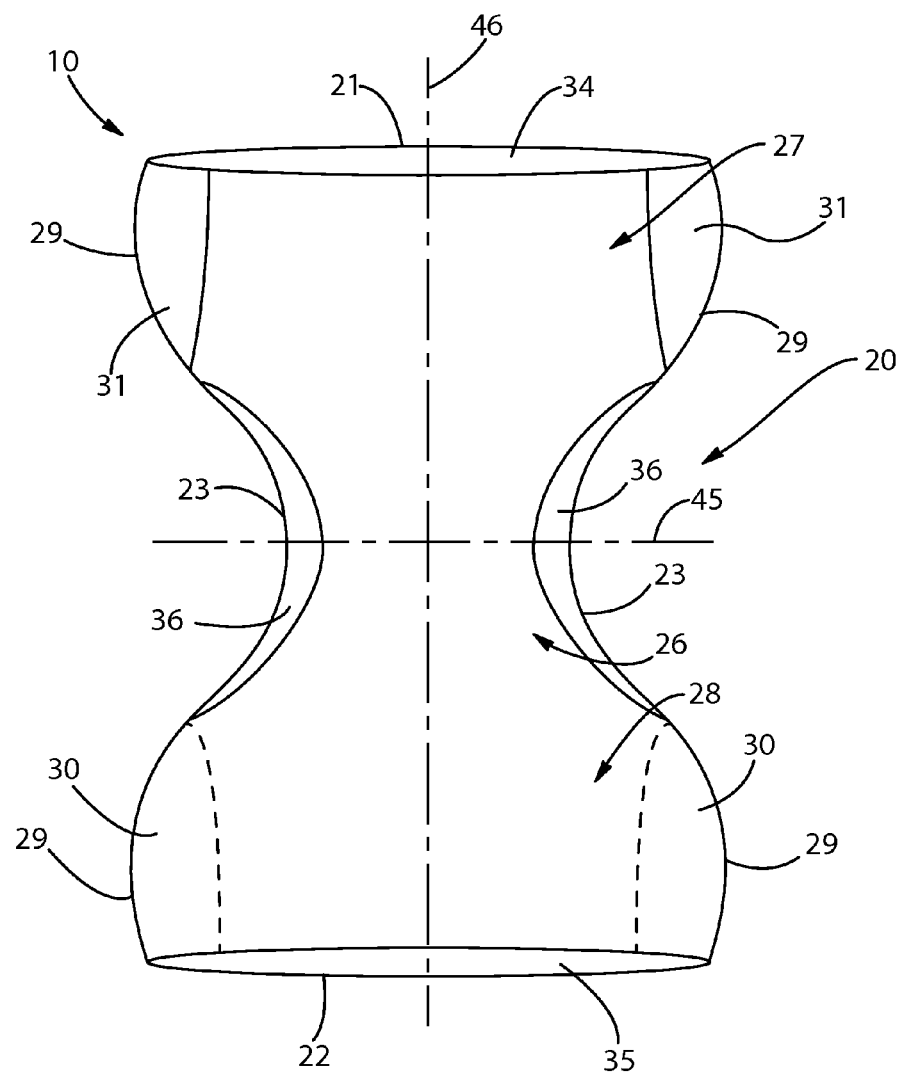
FIG. 1B is a plan view of an outer cover of FIG. 1A opened and laid flat, outer surface facing (i.e., garment-facing surface) the viewer in accordance with a non-limiting embodiment of the present disclosure.

FIG. 1B illustrates the outer cover 20 of the pant as it may appear open and laid flat. In FIG. 1B, the outer surface 24 faces the viewer. The outer cover 20 may comprise a front waist region 27, a crotch region 26, and a rear waist region 28. The front waist region 27 may be positioned on a first side of a lateral axis 45 and the rear waist region 28 may be positioned on a second side of the lateral axis 45. The crotch region 26 may extend across the lateral axis 45 such that a portion of the crotch region 26 is positioned on a first side of the lateral axis and a second portion of the crotch region 26 is positioned on a second side of the lateral axis. The outer cover 20 may comprise a front waist band 34, a rear waist band 35, and a longitudinal axis 46. The outer cover 20 may also comprise a first fastening zone formed of one of the fastening ears 29 in the front waist region 27 and one of the fastening ears 29 in the rear waist region 28. The first fastening zone may be positioned on a first side (e.g., right side) of the longitudinal axis 46. The first fastening zone may comprise a first portion positioned on a first side of the lateral axis 45 (i.e., in the front waist region 27) and a second portion positioned on a second side of the lateral axis 45 (i.e., in the rear waist region 28). The first portion of the first fastening zone may comprise ear panel 29 on the right side of the longitudinal axis 46 in the front waist region 27. The second portion of the first fastening zone may comprise ear panel 29 on the right side of the longitudinal axis 46 in the rear waist region 28. The outer cover 20 may also comprise a second fastening zone formed of one of the fastening ears 29 in the front waist region 27 and one of the fastening ears 29 in the rear waist region 28. The second fastening zone may be positioned on a second side (e.g., left side) of the longitudinal axis 46. The second fastening zone may comprise a first portion positioned on a first side of the lateral axis 45 (i.e., in the front waist region 27) and a second portion positioned on a second side of the lateral axis 45 (i.e., in the rear waist region 28). The first portion of the second fastening zone may comprise ear panel 29 on the left side of the longitudinal axis 46 in the front waist region 27. The second portion of the second fastening zone may comprise ear panel 29 on the left side of the longitudinal axis 46 in the rear waist region 28. The first portion of the first fastening zone may be releasably, removably, or permanently joined to the second portion of the first fastening zone and the first portion of the second fastening zone may be releasably, removably, or permanently joined to the second portion of the second fastening zone to form a closed outer cover 20.

FIG. 1C illustrates an outer cover 20 with an insert 50 positioned therein and attached thereto. In FIG. 1C the first and second fastening zones have been joined. FIG. 1D illustrates the outer cover 20 of FIG. 1C without the insert 50 and with the first and second fastening zones unjoined.

FIG. 1E illustrates a pant in an unstretched configuration (i.e., no force is being applied to the pant). FIG. 1F illustrates the pant of FIG. 1E in a stretched configuration. FIG. 1F simulates a pant being stretched to be pulled up over the thighs and buttocks of a wearer. The stretching force is applied in the direction of the arrows in FIG. 1F. FIG. 1G illustrates the pant of FIG. 1E in a partially stretched configuration. FIG. 1G simulates a pant fully pulled up and positioned about a lower torso of a wearer. FIG. 1E shows a length C1 of the waist region. FIG. 1F shows a length C2 of the waist region. FIG. 1G shows a length C3 of the waist region. Length C2 is greater than length C1 or C3 and length C3 is greater than length C1. Although the pant of FIGS. 1E-1G is illustrated with permanent seams joining the front and rear waist regions, it will be understood that the same logic will apply to pants having releasable seams.

Figure 1H:
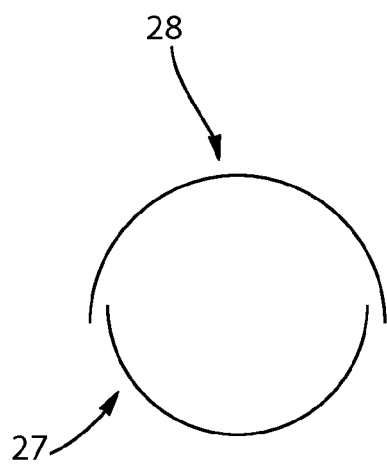
FIG. 1H is an illustration of a waist region of a pant having fastening zones on the sides in accordance with a non-limiting embodiment of the present disclosure.
Figure 1I:
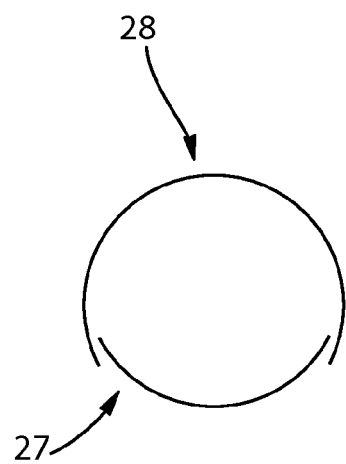
FIG. 1I is an illustration of a waist region of a pant having fastening zones in the front waist region in accordance with a non-limiting embodiment of the present disclosure.
Figure 1J:
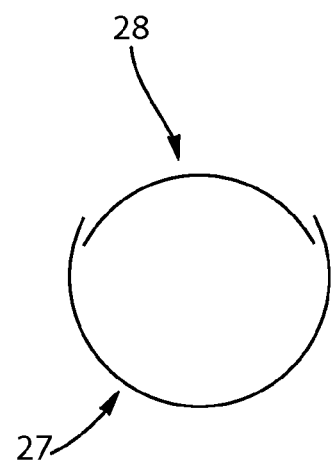
FIG. 1J is an illustration of a waist region of a pant having fastening zones in the rear waist region in accordance with a non-limiting embodiment of the present disclosure.

FIG. 1H is an illustration of a top view of a pant having fastening zones positioned on the side of the pant. FIG. 1I is an illustration of a top view of a pant having fastening zones positioned toward the front of the pant. FIG. 1J is an illustration of a top view of a pant having fastening zone positioned toward the rear of the pant. It will be understood that each embodiment disclosed herein may have fastening zones or seams at the side, in the front, or in the rear of the pant, although not specifically illustrated for each particular embodiment.

Figure 1K:
FIG. 1K is an illustration of an overlap seam in a fastening zone in accordance with a non-limiting embodiment of the present disclosure.
Figure 1L:
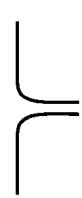
FIG. 1L is an illustration of a butt seam in a fastening zone in accordance with a non-limiting embodiment of the present disclosure.

Any of the fastening zones of the present disclosure may create overlap seams (FIG. 1K) or butt seams (FIG. 1L). Other seams known to those of skill in the art may also be provided.

Figure 1O:
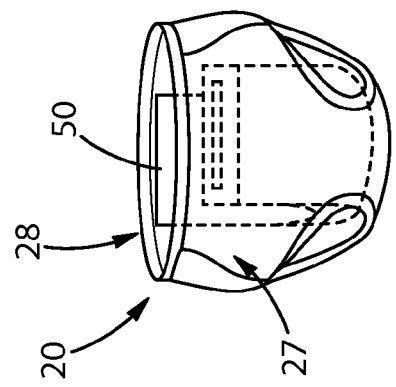
FIG. 1O is a perspective view of the outer cover of FIG. 1N with the insert fully positioned therein in accordance with a non-limiting embodiment of the present disclosure.
Figure 1N:
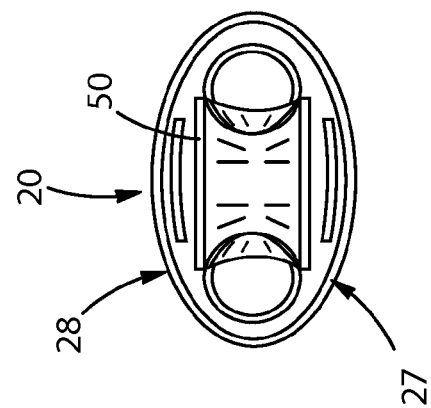
FIG. 1N is a top view of the insert being positioned into the closed outer cover of FIG. 1M in accordance with a non-limiting embodiment of the present disclosure.
Figure 1M:
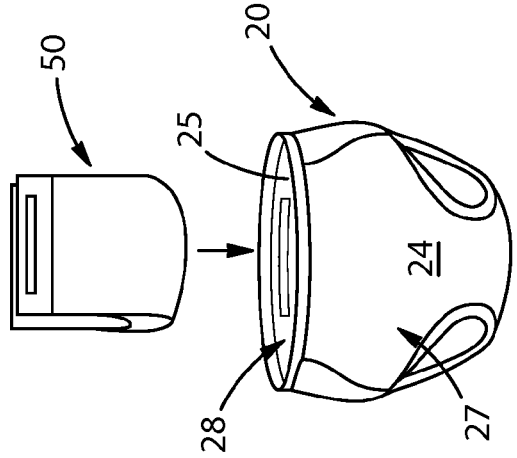
FIG. 1M is a front perspective view of an insert being positioned into a closed outer cover in accordance with a non-limiting embodiment of the present disclosure.

Referring to FIGS. 1M-1O, one method of joining an insert 50 with a closed outer cover 20 is disclosed. The insert 50 may be folded into a wearable shape and/or folded about its lateral axis and then inserted into the outer cover 20. Fastener components on the insert 50 may be engaged with attachment zones on the wearer-facing surface 25 of the outer cover 20 to join the insert 50 with the outer cover 20. In an embodiment, the insert 50 may have hooks and/or a lip extending outwardly therefrom in a waist region thereof that are configured to engage receiving slots or other members proximate to the waist band circumference of the outer cover 20. Such features may hold the insert 50 in position within the outer cover 20 when the pant 10 is being pulled up over the thighs and buttocks of a wearer.

In some embodiments, an adhesive, such as an undergarment or panty fastening adhesive, may be used to attach the insert 50 to the outer cover 20. This adhesive may be applied to the insert 50 and/or to the outer cover 20. One or more release papers may be attached over the adhesive in order to prevent, or at least inhibit, the adhesive from sticking to a surface until the appropriate time. The adhesive may be applied uniformly across the entire length and width of the insert, or it may be applied in a pattern, like multiple slots or spirals, for example, on all of or a portion of the insert.

The insert may be applied to the outer cover while the outer cover is pulled down around the knees or when the outer cover is not on the wearer. An incontinent wearer or other wearer may attach a new insert after removing and disposing of the old one. In this application, the user can stretch the outer cover with one hand, while using her other hand to place the insert into the right position on the outer cover. In most instances, the adhesive should be weak enough so that the user or caregiver can easily remove it from the outer cover, for readjustment during application and also during removal, yet be strong enough so that the insert does not shift relative to the outer cover during use. Impress Foodwrap technology, where the adhesive is inside tiny pockets in a film, can be used with the inserts and outer covers of the present disclosure. In such an embodiment, the insert may not stick to the outer cover until the insert is gently pressed into place on the outer cover. This feature provides the user with the option of positioning the insert correctly on the outer cover before locking it in place by gently pressing it against the outer cover. This adhesive approach would also be helpful when the insert is being attached to an outer cover that is not positioned on a wearer.

Figure 2A:
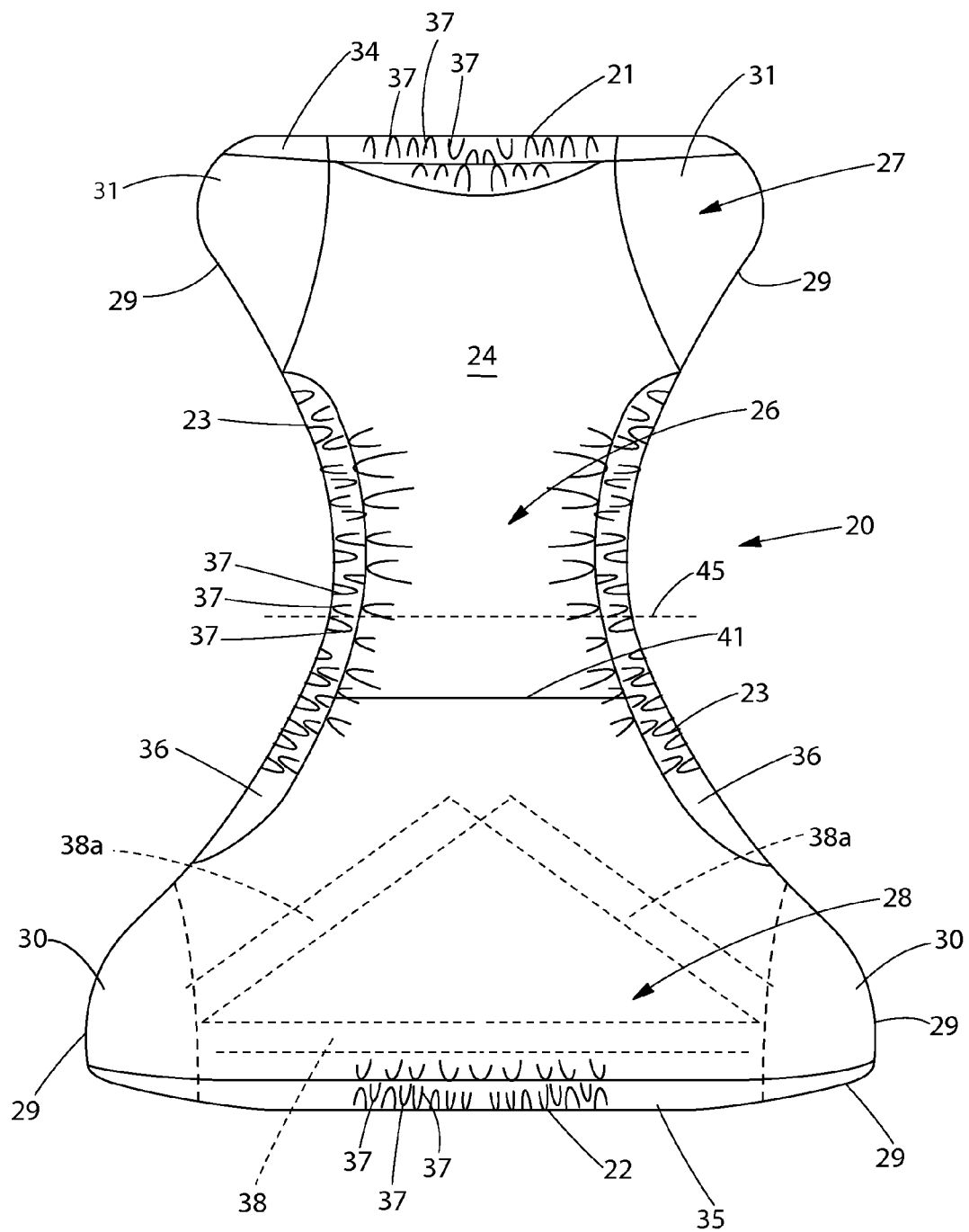
FIG. 2A is a plan view of an outer cover opened and laid flat, outer surface facing the viewer in accordance with a non-limiting embodiment of the present disclosure.
Figure 2B:
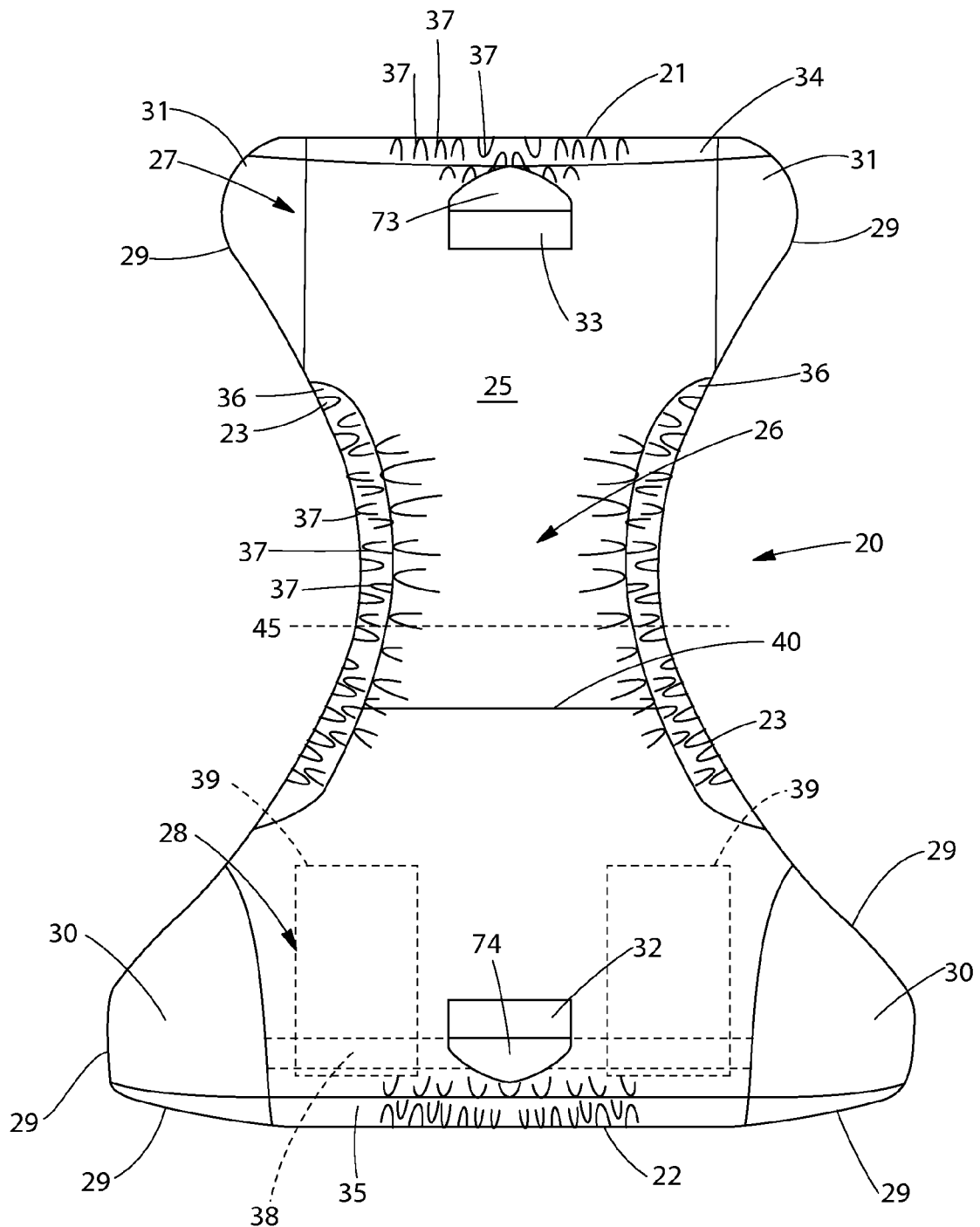
FIG. 2B is a plan view of an outer cover opened and laid flat, inner surface (i.e., wearer-facing surface) facing the viewer in accordance with a non-limiting embodiment of the present disclosure.
Figure 2C:
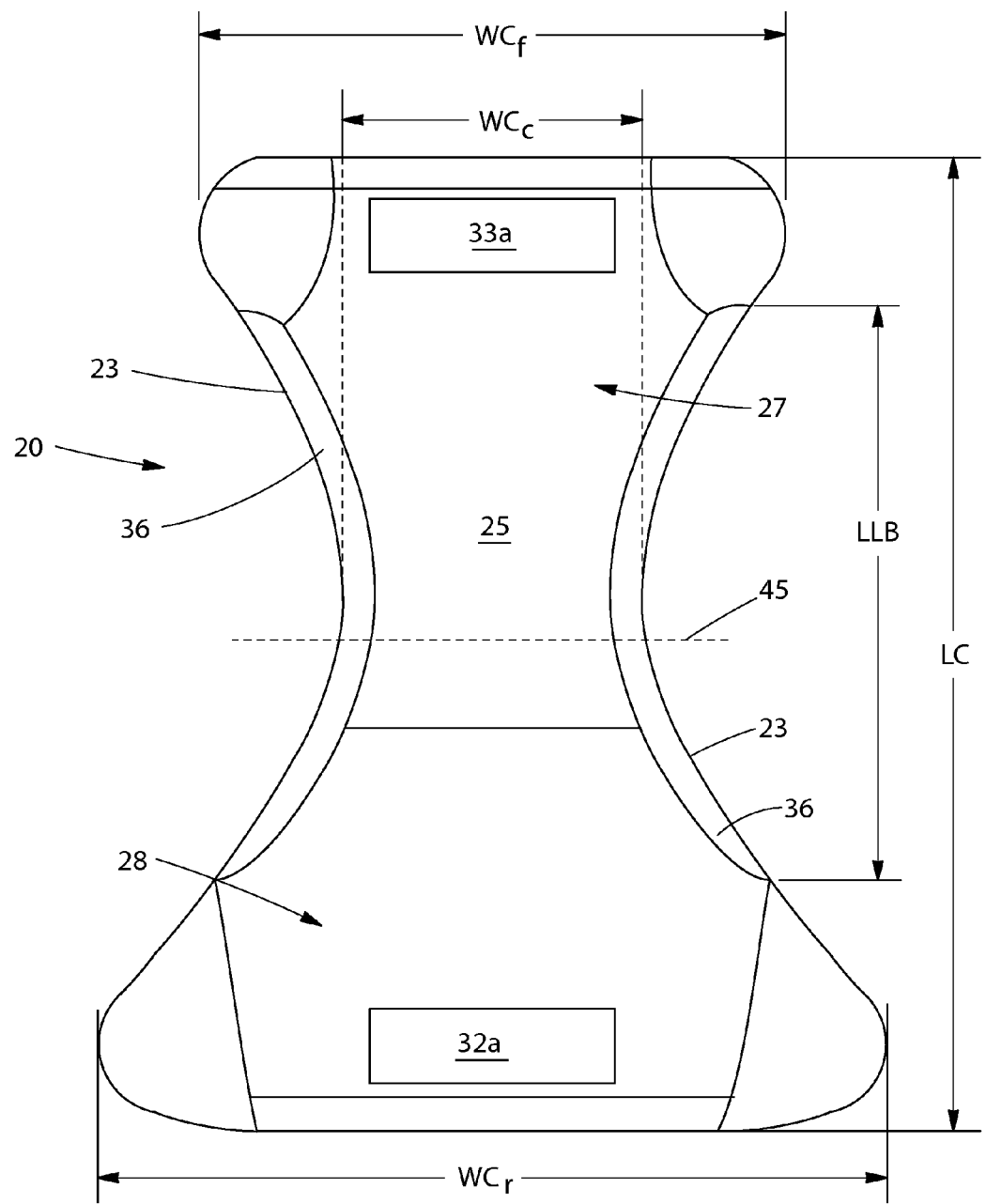
FIG. 2C is a plan view of an outer cover opened and laid flat, inner surface facing the viewer in accordance with a non-limiting embodiment of the present disclosure.

In some embodiments, FIGS. 2A, 2B and 2C depict an outer cover 20 of the present disclosure as it may appear opened and laid flat. In FIG. 2A, the outer, garment-facing surface of outer cover 20 face the viewer, while in FIGS. 2B and 2C, the inner, wearer-facing surfaces of outer cover 20 face the viewer. The front and rear waist edges 21, 22 are depicted at the top and bottom of the drawings, respectively. The outer covers 20 may have a crotch region 26, a front waist region 27, a rear waist region 28, and pairs of fastening ears 29 laterally extending from the rear waist region 28 and the front waist region 27. Each of the fastening ears 29 may comprise a fastening component 30 or a receiving fastening component 31. The fastening component 30 may engage the receiving fastening component 31 to form a seam in the pant. Although not illustrated, the fastening components 30 may be in the front waist region 28 and the receiving fastening components 31 may be in the rear waist region 27. The fastening components 30 and the receiving fastening components 31 may be any suitable fastening devices known to those of skill in the art, such as hook and loop, button and slot, snaps, adhesives, cohesives etc. The outer cover 20 may have a length LC from the forwardmost portion of the front waist edge 21 to the rearwardmost portion of the rear waist edge 22, and an outer cover lateral axis 45 equally dividing this length. Thus, the front waist region 27 may be positioned on a first side of the outer cover lateral axis 45 and the rear waist region 28 may be positioned on a second side of the outer cover lateral axis 45. The crotch region 26 may be positioned on the first side of the outer cover lateral axis 45 and on the second side of the outer cover lateral axis 45. The outer cover 20 may have disposed thereon one or more attachment zones such as front and rear attachment zones 33, 33a and 32, 32a for attachment of an insert to the outer cover 20.

Figure 3:
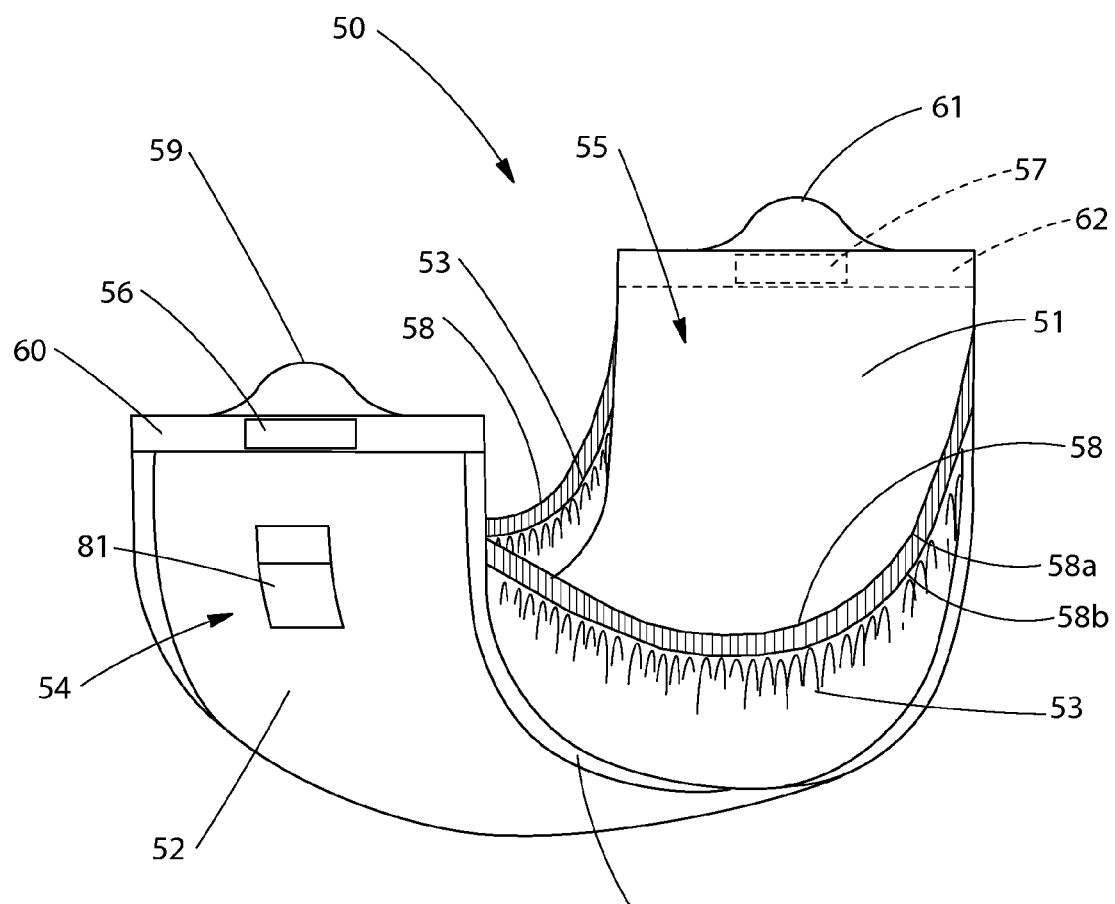
FIG. 3 is a perspective view of an insert shown apart from an outer cover, as it might appear in a free-standing, relaxed state in accordance with a non-limiting embodiment of the present disclosure.
Figure 4:
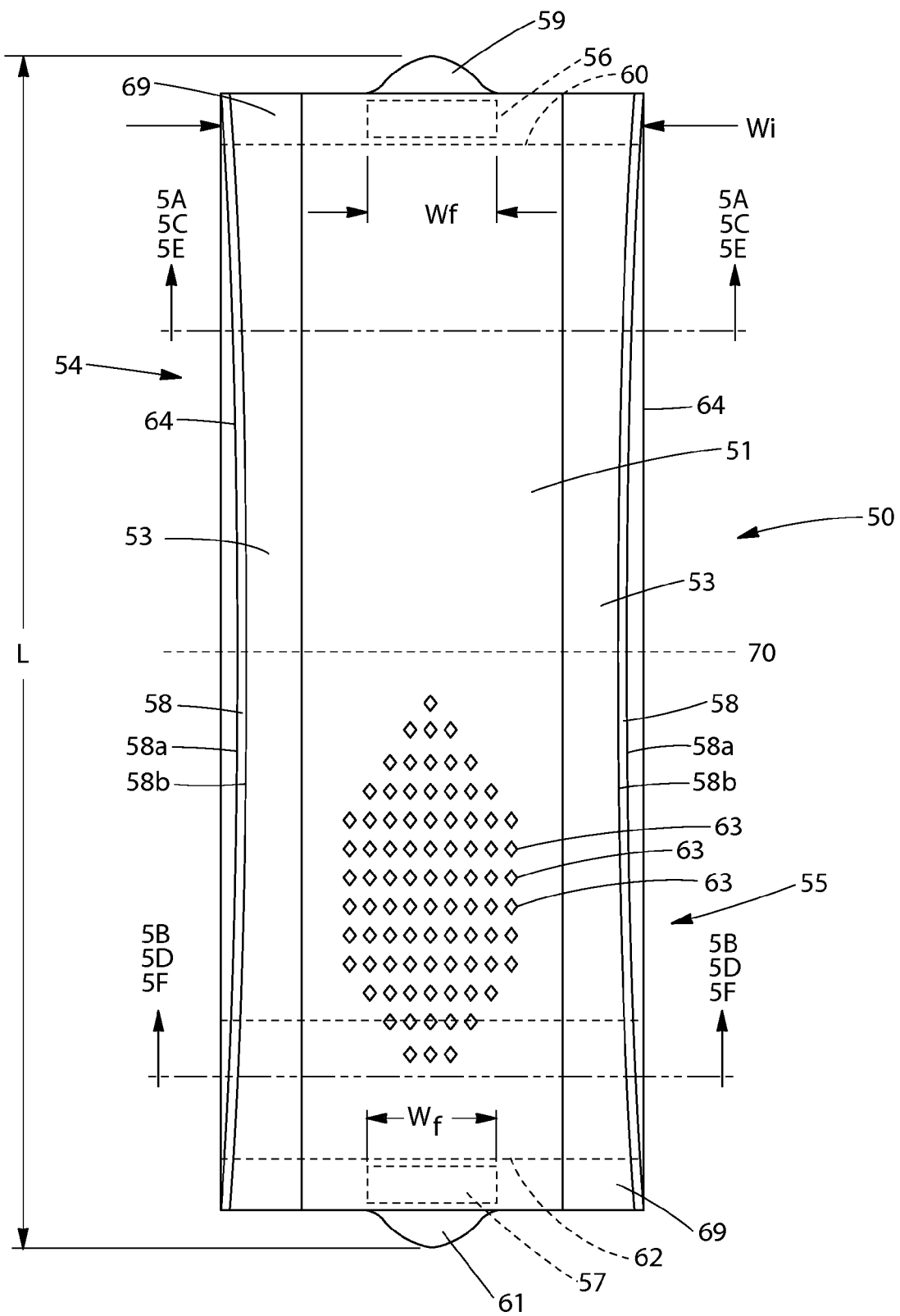
FIG. 4 is a plan view of an insert shown stretched out and laid flat, inner surface facing the viewer in accordance with a non-limiting embodiment of the present disclosure.

FIG. 3 depicts a disposable absorbent insert 50 that may form an inner component of the wearable absorbent article 10, shown in perspective view as it might appear in a free-standing, relaxed state, apart from the outer cover 20. The insert 50 may be designed to contain and/or absorb body exudates, and may be made of pliable materials as will be described further below. The insert 10 may have forward region 54 and rearward region 55, and may include one or more front fastener components 56 and one or more rear fastener components 57 configured to engage the front and rear attachment zones 33 and 32 on the outer cover 20. The insert 10 may include a body-facing liner or topsheet 51, an outer liner or backsheet 52, and a pair of standing cuffs 53. Referring to FIG. 4, the insert 50, when fully opened and laid flat, may have a length L from the forwardmost portion of the forward region 54 to the rearwardmost portion of the rearward region 55, and an insert lateral axis 70 equally dividing this length. Thus, the forward region 54 is positioned on a first side of the insert lateral axis 70 and rearward region 55 may be positioned on a second side of the insert lateral axis 70.

In an embodiment, referring to FIGS. 2B and 3, the insert 50 may have rear fastener component 57 disposed thereon. Alternatively, or in addition, the outer cover 20 may have rear insert fastener component 32 disposed thereon. Similarly, the insert 50 may have front fastener component 56 disposed thereon. Alternatively, or in addition, the outer cover 20 may have front insert fastener component 33 disposed thereon. If a two-component fastening system is used, fastener component pairs 57, 32 and 56, 33 may be cooperating components that affect fastening therebetween when these respective components are brought together. Thus, in the example depicted, in order to install the absorbent insert 50 into the outer cover 20, a user may lay the outer cover 20 flat, inner surface 25 facing up, stretch and orient the insert 50 such that the rear fastener component 57 faces the rear insert fastener component 32 and the front fastener component 56 faces the front insert fastener component 33, and bring these respective fastener component pairs 57, 32 and 56, 33 together to effect fastening therebetween.

If it is desired that the outer cover 20 be reusable, for the outer cover 20 to remain substantially sanitary and useful (without requiring laundering or disposal) after removal and replacement of an insert, it may be desired that all parts of the outer cover 20 remain substantially unsoiled after an exudation of waste (especially fecal matter) by the wearer. Thus, it may be desired that when the insert 50 is installed within an outer cover 20, there is no non-removable portion or component of the outer cover 20 that lies over or covers a substantial portion of wearer-facing surfaces of the insert 50. Stated another way, no non-removable portion or component of the outer cover 20 is situated between a substantial portion of the insert 50 and the wearer when the wearable absorbent article 10 is worn, at least in the areas proximate to wearer body features that discharge exudates. Thus, it may be desired that the outer cover 20 include no non-removable cover sheet or the like that covers or contains substantial portions of wearer-facing surfaces of the insert 50 within the outer cover 20, nor any overlying structures such as pockets, straps or flaps that substantially wrap or cover the insert proximate to exudate discharge points, or lie substantially between the insert 50 and the wearer's anus and/or genitals, when the wearable absorbent article 10 is worn. If the outer cover 20 lacks such overlying structures, this may increase the likelihood that the wearer's exudates will contact only the insert 50, and not portions of the outer cover 20.

Referring to FIGS. 1A, 2A and 2B, it can be seen that the wearable absorbent article 10 may be placed on a wearer by attaching the insert 50 to the outer cover 20, attaching the fastening components 30 to the receiving fastening components 31 to form a pant, and pulling The pant up the legs and over the thighs, hips, and buttock into the position illustrated in FIG. 1A. In an embodiment, the outer cover 20 may come from a manufacturer in a pre-formed state (i.e., continuous waist and leg perimeters) having permanent or refastenable seams, for example. In such an instance, the insert 50 may be inserted into the outer cover 20 and then pulled up the legs, over the thighs, hips, and buttocks into position on a wearer. When the insert 50 has been installed into the outer cover 20, the insert 50 may then be disposed within the outer cover 20, next to the wearer, with the standing cuffs 53 oriented and extending longitudinally adjacent the inner portions of leg edges 23 (i.e., longitudinally between the wearer's legs).

Examples of Possible Outer Cover Details
Fastening System

In some embodiments, referring to FIGS. 2A and 2B, to enable fastening of the fastening ears 29 to the front waist region 27, the fastening ears 29 may have outer cover fastener components 30 and fastener receiving components 31 disposed thereon. The fastener components 30 and receiving components 31 may be selected so as to be cooperative to effect fastening of the fastening ears 29.

In one example, the outer cover fastener components 30 may include a patch of hooks, and the receiving fastener component 31 may include a patch of loops. An example of a suitable hook-and-loop fastening system is a VELCRO system (a product of Velcro Industries B.V.) A hook-and-loop fastening system provides certain advantages. Because the respective hook and loop components are supplied in sheet form, they may be cut into suitably shaped patches that may be affixed to a cloth or nonwoven substrate by various mechanisms, including adhesive bonding, mechanical bonding, ultrasonic bonding, sewing, stitching, serging, and/or edging, for example. If patches of hooks or loops are affixed to the fastening ears 29 to form the outer cover fastener components 30, a laterally extended patch of cooperating hook or loop material may be affixed to the outer cover front region 27 to form one or more receiving fastener components 31. By providing for fastening of the ears 29 at laterally varying locations thereon, this arrangement provides for easy and simple adjustability of waist opening size of the wearable absorbent article 10. A plurality of snaps or magnets may be provided as the fastening components 30 and/or fastener receiving components 31 again to provide waist opening size adjustability. The fastening components 30 and the receiving fastening components may also provide longitudinal adjustability for the pant. In an example, the fastening components 30 and the receiving fastening components 31 may comprise a plurality of snaps or magnets positioned longitudinally on each or less than each fastening ear 29 such that the pants may be fastened closer to the front and rear waist edges 21 and 22 or further from the front and rear waist edges 21 and 22. As a result, the pant may be joined at the waist region using a suitable waist opening size and/or a "rise" (through-the-crotch region) size for a particular wearer.

Referring to FIG. 2B, the outer cover 20 also may have one or more respective fastener protectors 39 disposed thereon. This feature may prevent, or at least inhibit, fastener components 30 having features likely to randomly and unintentionally engage and catch on portions of the outer cover 20, or other articles, during storage, carrying, laundering and similar/related activities, from doing so, thereby avoiding potential bunching, entangling and/or damage to either the outer cover 20 or other articles during such activities. For example, if the fastener components 30 are patches of hooks, appropriately placed fastener protectors 39 may include patches of corresponding loops. This will enable the user to fold the ears 29 over to engage them with the fastener protectors 39, thereby holding them in the folded-over position such that hooks thereon will be concealed and prevented, or at least inhibited, from snagging other articles when the outer cover 20 is not being worn.

Materials

The outer cover 20 and/or layers or portions thereof may be made of any knitted, woven or nonwoven textile, film, or textile-like material that is appropriately compatible with skin of the intended wearer(s). The outer cover 20 may be constructed of durable and/or semi-durable materials. Generally, only for purposes of reference in this description, "durable" refers to a woven or knitted textile material of any kind that may be used as a component of a washable clothing article. As used herein, "durable" includes materials which are "launderable" as defined and described in U.S. Patent Application Publication Nos. 2010/0179495, 2010/0179503, and 2011/0172628, entitled, respectively, "REUSABLE OUTER COVER FOR AN ABSORBENT ARTICLE," "REUSABLE OUTER COVER FOR AN ABSORBENT ARTICLE HAVING ZONES OF VARYING PROPERTIES," and "LEG AND WAISTBAND STRUCTURES FOR AN ABSORBENT ARTICLE," by Donald C. Roe, filed on Jan. 14, 2010. Generally, only for purposes of this description, "semi-durable" refers to a nonwoven material or laminate thereof that when used as an outer cover material can withstand more than one use with an insert without losing its structural integrity to an extent that renders it unserviceable. As used herein, "semi-durable" includes materials which are "laundering resistant" as defined and described in the U.S. applications identified immediately above. Thus, the outer cover 20 may be constructed of materials and construction that make it reusable and/or washable.

The durable materials of which the outer cover 20 may be constructed may include any natural or synthetic textile materials known in the diaper, pant, underwear, performance clothing, sport clothing, or general clothing or textile arts. The durable materials may include woven or knitted textiles made of natural fibers such as cotton, linen, wool, bamboo, hemp, silk, and/or rayon, for example, as well as blends of any of these fibers with any other(s), or with synthetic fibers. Examples of synthetic fibers suitable for use as components of the durable materials include polyester, nylon, spandex and/or other elastomer fibers. The durable outer cover materials also may include breathable water repellent materials such as GORE-TEX (a product of W. L. Gore & Associates, Inc., Elkton, Md.), fabrics comprising microencapsulated phase-change polymer materials such as OUTLAST COMFORTEMP fabrics (products of Outlast Technologies, Boulder, Colo.—see U.S. Pat. No. 6,514,362 and U.S. Pat. No. 6,207,738, for example), and/or COOLMAX (a product of Invista, Wichita, Kans.), for example.

Suitable durable materials may be formed in any weave or knit fabric form, including birdseye fabric, terry, fleece, flannel, knits, stretch knits, sherpa, suedecloth, microfleece, satin, velour, Burley knits, etc. Suitable examples include POLARTECH POWER DRY, POWER STRETCH and WIND PRO (products of Polartec, LLC, Lawrence, Mass.). Knitted textiles, which may be more inherently stretchable and elastic than woven or nonwoven materials, may impart better fit, comfort and/or appearance to the outer cover 20. Incorporation of fibers of spandex or other elastomer also may also enhance stretchability and elasticity, and thereby impart better fit, comfort and/or appearance to the outer cover 20, than textiles not including such elastomeric fibers.

Specific suitable examples for the durable outer cover materials include jersey knits of blends of: rayon (93%) and spandex (7%) fibers; modal (94%) and spandex (6%) fibers; cotton and spandex fibers; and bamboo and spandex fibers. Materials that have stretch capability of equal to or greater than about 2× may be desired. Suitable examples of materials may have basis weights of about 0.09-0.15 gram/in.$^2$ per layer, or other basis weights.

Materials and stretch features as described in U.S. Patent Application Publication Nos. 2008/0119813, 2008/0119814, 2008/0119815 and 2008/0119816 may be used in the construction and configuration of the outer cover 20 or any portions thereof, such as the crotch region 26, for example.

The durable outer cover materials may be selected to impart desired comfort, appearance and performance to the outer cover 20. In some circumstances it may be desired to select durable outer cover materials which are sufficiently inexpensive to allow for disposal, if soiled extensively or damaged, with minimized issues of cost or conscience.

Semi-durable outer cover materials may include any natural or synthetic nonwoven web and/or film materials known in the diaper or pant arts. Semi-durable materials of which the outer cover 20 may be constructed may include nonwoven web materials of polypropylene and/or polyethylene fibers, polyester fibers, and any other synthetic fibers used to form nonwoven web materials used as components of disposable diapers, and blends thereof. Natural fibers such as cotton, linen, wool, bamboo, hemp, silk, rayon, and the like may be blended with synthetic fibers to form such a nonwoven web suitable as a component layer of the outer cover 20.

Non-limiting examples of fibers, nonwovens and laminates of nonwovens and films that might be considered for use as semi-durable outer cover materials may be found in U.S. Pat. Nos. 7,223,818; 7,211,531; 7,060,149; 6,964,720; 6,905,987; 6,890,872; 6,884,494; 6,878,647; and 5,518,801; and U.S. Patent Publication Nos. 2008/0319407; 2008/0045917; 2007/0293111; 2007/0287983; 2007/0287348; 2007/0249254; 2007/0203301; and 2005/0164587.

Semi-durable outer cover materials also may be selected to impart desired comfort, appearance and performance to the outer cover 20. In some circumstances it also may be desired to select semi-durable outer cover materials which are sufficiently inexpensive to allow for disposal, if soiled extensively or damaged, with minimized issues of cost or conscience.

The outer cover 20 also, or additionally, may include a laminated or substantially separate film layer, which may be elastic, to provide enhanced liquid penetration resistance and/or elastic properties. Elastic properties also can be added or enhanced via the addition of other materials to the outer cover 20 in layer, band or strip fashion, including elastic strands, bands, and/or scrims, for example. A film layer may be laminated with a durable material or semi-durable material.

Inclusion of an elastomeric material, either as a fibrous component of a cloth or non-woven layer, as a film layer, or as pre-stretched elastic strands sandwiched between two web layers provides for improved stretchability and elasticity where it may be deemed useful to accommodate the wearer's anatomy and movements, such as over the wearer's buttocks and/or around the waist areas, and improved fit and comfort. Additionally, where a film layer may be included, it may impart additional liquid containment capability to the outer cover. A film layer may include a film that is substantially liquid impermeable, but vapor permeable, so as to provide breathability and reduce humidity within the outer cover while it is being worn, reducing chances for over-hydration of the skin where liquid containment capability is desired. A breathable film also may be provided by mechanically perforating or aperturing a film by various processes. Examples of such processes are described in U.S. Pat. No. 8,158,043 and U.S. Patent Application Publication No. 2011/0024940.

Stretchability of the outer cover may be in one direction (e.g., lateral only) or in two directions (e.g., lateral and longitudinal). The direction or directions of stretch of the outer cover may be other than lateral and longitudinal.

In an embodiment comprising pre-stretched (contracted) elastic strands, the strands may be oriented laterally to provide stretch around a wearer's waist. A belt comprising a laminate of pre-stretched elastic strands may be provided in the front waist region 27, the back waist region 28, or in both of the waist regions. In the latter embodiment, the front and back waist belts may be connected by a web of material (e.g., nonwoven, film, or a laminate thereof). Insert attachment zones may be provided on the wearer-facing surface 25 of at least one of the belts or the connecting web or both. In another embodiment, the insert 50 may be attached directly to the belt regions without a connecting web providing support.

In an embodiment, referring to FIG. 2A, the outer surface 24 may be formed by a first layer of a durable or semi-durable material. The material selected may include fibers having hydrophobic properties, providing enhanced liquid containment attributes to such first layer. In another example, however, it may be desirable in some circumstances for the selected material to include hydrophilic fibers, or fibers treated to be hydrophilic, so as may cause the material to more readily absorb and/or transmit liquid therethrough. This may serve to provide supplemental absorbency within the outer cover 20 for the event in which liquid exudates escape the insert 50, or to provide one way of communicating to the user that liquid exudates have escaped the insert 50. Additionally, in some circumstances, it may be desirable that the material selected have soft tactile properties so as to have a pleasant feel that the user and/or wearer find attractive. The material also may be selected so as to have a desired appearance, including but not limited to coloration, sheen, and/or texture, for example.

The outer cover 20 may be formed of a single layer of a durable or semi-durable material, or may have two or more layers in the front waist region 27, the rear waist region 28, the crotch region 26, and the leg openings. Accordingly, referring to FIG. 2B, an example inner surface 25 may be formed by a second layer of a durable or semi-durable material. The material selected may include fibers having hydrophobic properties, providing enhanced liquid containment attributes to the second layer. In another example, however, it may be desirable in some circumstances for the selected material to include hydrophilic fibers, or fibers treated to be hydrophilic. This may be desired in some circumstances to cause the material forming the inner surface 25 to more readily absorb liquid, or transmit liquid therethrough. This may serve to provide supplemental absorbency within the outer cover for an event in which liquid exudates escape the insert 50, reducing the likelihood that the outer cover 20 will leak. Alternatively, it may provide one way of communicating to the user that liquid exudates have escaped the insert 50, by causing wetness to be transmitted through to the outer cover outer layer such that wetness is visible on outer surface 24. Alternatively, it may serve to provide a layer that tends to draw moisture away from the skin, for a drier, more comfortable feel.

Forming the outer cover 20 of more than one layer, for example, two or more layers, may provide various benefits. A second layer (and any additional layers) may provide supplemental tensile strength in both the lateral and longitudinal directions across the outer cover 20. Additionally, a first layer may be selected for a first set of properties, and a second layer may be selected for a second set of properties. For example, material forming a first layer may be selected for having comparatively greater elasticity and a particular texture, color and/or other appearance-related properties, and material forming a second layer may be selected for having comparatively greater hydrophobicity, hydrophilicity and/or softness to the skin for purposes of an inner layer, the two layers in combination imparting a combination of desirable attributes to the outer cover 20. For example, the inner layer may be formed of material(s) and/or treated to be more hydrophilic so as to provide for absorbency and reduced chances of fluid runoff (leakage), while the outer layer may be formed of material(s) that are more hydrophobic, so as to, e.g., resist environmental soiling, or resist liquid transmission from the inner layer to the outer layer. Additionally, a plurality of layers may better serve to conceal bumps, corners, seams or other features of an insert, as compared with a single layer, for a smoother, more attractive appearance.

Referring again to FIGS. 2A and 2B, in addition to forming differing layers of differing materials, it may be desirable to form a single layer of differing materials, for example, differing materials in the respective front, crotch, and/or rear regions 27, 26, and 28 of the outer cover 20. Such differing materials may be joined at a seam such as an inner seam 40 (FIG. 2B) and/or outer seam 41 (FIG. 2A). In other embodiments, the two different properties may be inherent to a single piece of fabric, for example. For example, the material predominately forming the inner surface of rear waist region 28 may be selected primarily for its elasticity features, which may better serve to provide snug fit about wearer body contours and accommodate wearer movement (i.e., about the buttocks and hips). By comparison, the material predominately forming the inner surface of front waist region 27 and/or crotch region 26 may be selected primarily for its hydrophobicity or hydrophilicity, which may better serve to contain liquid exudates.

Layers or other elements of the outer cover 20 may be joined to each other via any suitable mechanism, including, for example, adhesives, mechanical bonding, ultrasonic bonding, sewing, stitching, serging, edging, and the like.

Additionally or alternatively to the constructions and materials described above, the outer cover 20 may be constructed and may include materials and features as described in U.S. Patent Application Publication Nos. 2010/0179495, 2010/0179503, and 2011/0172628, entitled, respectively, "REUSABLE OUTER COVER FOR AN ABSORBENT ARTICLE," "REUSABLE OUTER COVER FOR AN ABSORBENT ARTICLE HAVING ZONES OF VARYING PROPERTIES," and "LEG AND WAISTBAND STRUCTURES FOR AN ABSORBENT ARTICLE," by Donald C. Roe, filed on Jan. 14, 2010. The outer cover 20 may also be constructed of materials used in the manufacture of disposable diapers, such as nonwoven materials or laminates thereof, films, and/or film/nonwoven laminates. Such an outer cover may be disposable or be reusable more than one time.

The outer cover 20 may also be formed of one or more materials having different properties. In one example, the outer cover 20 may be formed of a single material (not including fasteners or fastener receiving components or other "add on" components). That single material may have different properties through its area. For example, the single material may have greater elasticity or other property in one area when compared to another area. The material may also have more than two areas having different properties. These different properties may be created by the materials being thicker or thinner in different areas, for example. The material may be elastomeric so that no or few additional elastic strands, strips, or bands need to be added to the outer cover 20.

Elasticized Waistbands, Leg Bands

Referring again to FIGS. 1A, 2A and 2B, a front waist band portion 34, a rear waist band portion 35, and leg band portions 36 are depicted. One or more of these band portions 34, 35, 36 may be formed of one or more strands or strips including an elastomeric material, such as SPANDEX or a blend of SPANDEX and other fibers, enveloped by a nonwoven or textile material, which may include the edges of the material forming the inner and/or outer layers of outer cover 20, to form and elasticize the respective band portions. The elastic material may be affixed to or within an outer cover layer in a strained condition, or at zero applied strain. In other embodiments, the material of the outer cover may provide the waistband without separate elastomeric materials being present. Textile material(s) enveloping the elastic strand(s) or strip(s) may be sewn around elastic strand(s) or strip(s) to hold them in place within the respective band portions. If the elastic material is strained prior to, and while, being enveloped and affixed to form these band portions during the manufacturing process, upon relaxation the enveloping material and adjacent outer cover material may be caused to gather and form ruffles 37 therealong, which constitute gathered outer cover material. This can serve to promote snug fit, wearer comfort and appearance. The band portions may be disposed along the edge of the outer cover, and in some circumstances it may be desired to have the band portions situated along substantially the entire length of the leg and/or front or rear waist openings so as to form bands that substantially or completely encircle the wearer's legs and/or waist while outer cover 20 is worn. The gathered material within the ruffles 37 may serve to accommodate stretching of the waist band portions 34, 35 and the leg band portions 36. This arrangement including elasticized leg band portions 36 as described, not only may provide for better fit about the wearer's legs, but also may enable the outer cover 20, when formed of appropriately sized and shaped material, to form a pouch-like structure 75 in the crotch region 26 (see FIG. 1A) when worn, which may serve to provide space within the outer cover 10 to accommodate the insert 50 (FIG. 3) and help hold it in place within the outer cover 20, in a substantially laterally centered position within the crotch region 26. This may be deemed advantageous in examples in which an insert 50 is attached within the outer cover 20 by fastener components only located proximate to the respective ends of the insert 50, and not at any longitudinally intermediate locations, as described further below. Alternatively, or additionally, the elastic strands or strips in the waist band portions 34, 35 and the leg band portions 36 may be affixed within the outer cover 20 only at or near their respective ends, e.g., within a pouch, tube or envelope structure formed of outer cover material—referred to herein as a "drawstring elastic". This will allow the elastic material and associated outer cover material to stretch and move freely and independently of each other, which may promote fit and comfort. A snug fit about the wearer's legs provided by such elasticized leg band portions 36 may serve to enhance containment capability of the wearable absorbent article 10.

One or more of the waist band portions 34, 35 and the leg band portions 36 may be elasticized in the manner described above, or by other mechanisms. For example, elasticized band/strip material such as that used to form elastic waistbands and leg bands or other banding features of conventional cloth underwear, briefs, or other articles of clothing may be separately produced, and affixed to the materials forming the outer cover 20 in any suitable manner, during the manufacture thereof.

In another example, one or more of the waist band portions 34, 35 and the leg band portions 36 may be formed of elastic material simply affixed about the leg opening and/or waist opening edges by use of adhesive and/or compression bonding. In another example, an elastic strip material may be formed by affixing a plurality of strained elastomeric strands or strips to one or more strips of unstrained nonwoven web material, or film. When the resulting elastic strip material is allowed to relax, the unstrained material forms transverse rugosities that comprise gathered unstrained material, which may accommodate stretching of the elastic strip material. By affixing the elastic strip material at one or more of the waist band portions 34, 35 and/or the leg band portions 36, the elastic strip material may be used to form one or more of the elasticized waist band portions 34, 35 and/or the leg band portions 36.

Anchoring Bands

In an embodiment, the outer cover 20 also may include an anchoring supplement, such as anchoring band 38, disposed on or in the outer cover rear waist region 28 as indicated in FIGS. 2A, 2B. Anchoring bands may be especially important when the outer cover has bi-directional stretch or multi-directional stretch. In such embodiments, the anchoring bands may prevent, or at least inhibit, the absorbent articles (i.e., outer cover and insert) from drooping on a wearer when the insert is saturated or at least partially saturated with bodily exudates. Various anchoring bands may also extend into and/or through the crotch region 26 and/or the waist regions 27 and 28. In an embodiment, one anchoring band may cross over another anchoring band. For example, one anchoring band may extend from proximate a first corner of an insert to a diagonally opposite corner of the insert and another anchoring band may extend from proximate a second corner of an insert to a diagonally opposite corner of the insert thereby forming an X-like shape of the anchoring bands. As suggested in FIGS. 2A and 2B, the anchoring band 38 may be affixed along a layer, or disposed between layers, forming the inner surface 25 and the outer surface 24 of the outer cover 20. The anchoring band 38 may include an elastomeric or elasticized strip or band of material, affixed to the outer cover 20 at locations proximate to its rearward corners or proximate to fastening ears 29. Thus, the anchoring band 38 may be partially or substantially force-decoupled from the other layer(s) of the outer cover 20 along its lateral length from the layer(s) forming the inner and outer surfaces 25 and 24 of the outer cover 20, via attachment to the outer cover 20 only by the ends of the anchoring band 38, or only at a limited number of selected intermediate lateral locations along anchoring band 38. For example, the anchoring band 38 may be attached to the outer cover 20 only at the ends of the anchoring band 38. In another example, the anchoring band 38 may be attached to the outer cover 20 only at the ends and at the lateral center of the anchoring band 38. This substantially force-decoupled arrangement allows the anchoring band 38 and surrounding portions of the outer cover 20 to stretch and move substantially independently of one another, which may promote better fit and comfort. In another example, however, the anchoring band 38 may be an elastic band, strip or strap laminated with or otherwise affixed to a layer of stretchable material forming either of or both the inner and outer surfaces 25 and 24 of the outer cover 20, along substantially the entire length of the anchoring band 38.

When strained laterally by application to the wearer, the anchoring band 38 may serve to provide, or supplement, lateral tensile forces in the wearable absorbent article 10 about the wearer's waist, thereby tending to draw the waist opening snug, enhancing fit and enhancing securement of the wearable absorbent article 10 about the wearer's waist. The elastic property (e.g., elastic modulus and maximum elastic extension) of the anchoring band 38 may be higher than or different than the elastic property of the surrounding, adjacent, or coextensive outer cover materials.

In another example, instead of, or in addition to, being oriented substantially laterally as suggested by the depicted location of the anchoring band 38 in FIGS. 2A and 2B, one or more members forming anchoring bands may be oriented diagonally between the longitudinal and lateral directions. For example, as suggested in FIG. 2A, a pair of diagonal anchoring bands 38a may have respective waist ends thereof affixed at a location area proximate to corners of the outer cover 20 and/or the fastening ears 29, and respectively extend toward both the lateral and longitudinal center of the outer cover 20, as suggested in FIG. 2A. The respective center ends of anchoring bands 38a may be affixed to the outer cover 20 at locations proximate the lateral center of the outer cover 20 as suggested in FIG. 2A, and the anchoring bands 38a may be either force-decoupled or force-coupled to the outer cover 20 along the lengths of the anchoring bands 38a, as described above. In an example where an insert 50 is connected to an anchoring band for additional longitudinal support as described further below, diagonal anchoring bands such as the diagonal anchoring bands 38a may serve to provide supplementary longitudinal tension along the outer cover 20, providing supplemental longitudinal support therewithin.

In one embodiment, one or more anchoring bands may encircle the wearer, in a substantially lateral direction. These anchoring bands may be separate bands that are attached to or formed in the outer cover in additional to the anchoring bands discussed above. Alternatively, the high-modulus properties of the anchoring bands may also be built into the structure of the outer cover. For example, with an outer cover comprising elastic strands that run in the lateral direction, the strands that are in the anchoring band region(s) may have higher denier or lower strand spacing in order to deliver a higher modulus in that portion of the outer cover.

Outer Cover Asymmetry

In order to enhance and/or maximize fit, wearer comfort and appearance of the outer cover 20, it may be desirable to fashion the outer cover 20 so as to accommodate anatomical contours and body movements of the intended wearer. For example, as suggested by FIGS. 2A and 2B, the outer cover 20 may have differing shape and/or greater material surface area in the rear waist region 28 than in the front waist region 27. Human anatomy in the lower torso/hip/thigh region is asymmetric about the lateral plane of the body, i.e., the geometry of the front of the human body is different than that of the back. To provide for better fit and comfort, the outer cover geometry and functionality, including stretch properties, may be adapted accordingly. Differing shape and/or greater material surface area in the rear waist region 28 may serve to better cover the buttocks through movements of the wearer (including sitting and/or bending forward at the hips), while lesser material surface area in the front waist region 27 may serve to avoid material bunching and/or an ill-fitting appearance, particularly when the wearer is in positions including sitting and/or bending forward at the hips. As a result, the outer cover 20 may be asymmetric in shape or surface area across the outer cover lateral axis 45.

For purposes of this description, when used with respect to an outer cover 20, "asymmetric" and "asymmetry" mean that features, geometry (e.g., shape), materials and/or construction on one side of the outer cover lateral axis 45 differ substantially in some respect from those on the other side of the outer cover lateral axis 45. Such asymmetric construction results from having various features of the outer cover 20 designed to accommodate the body features and functions of the intended wearer as they differ front-to-rear, to enhance containment/absorbency performance, comfort, fit and/or appearance of the wearable absorbent article, and/or to economize on use of materials. "Asymmetric" and "asymmetry" do not refer to differences across the outer cover lateral axis 45 that are attributable to features that may be included on an outer cover 20 only for purposes of: purely cosmetic coloration or surface decoration; fastening an insert (such as fastening zones described herein); bundling, folding, storing or carrying the outer cover; indicia for orienting an insert within an outer cover 20 or vice versa (such as orientation indicia described herein), or for other purposes substantially unrelated to the body features and functions of the intended wearer as they differ front-to-rear, to affect performance, comfort, fit, and/or physical appearance of the wearable absorbent article 10, and/or to economize on use of materials.

In another example of asymmetry, materials of differing composition, construction and/or properties may predominately form the front waist region 27 as compared with the rear waist region 28. For example, the material(s) forming the rear region 28 may be selected for enhanced stretch/elastic properties, as compared with material(s) forming the front waist region 27. In this example, material(s) with enhanced stretch/elastic properties may serve to better accommodate, stretch and contract over contours of the buttocks, and accommodate body movements, such as sitting and bending forward at the hips, thereby providing better coverage and fit.

In still another example of asymmetry, the outer cover 20 may have structures such as elastic bands, anchoring bands and/or other members which differ between the front waist region 27 and the rear waist region 28.

In still other examples of asymmetry, the materials forming the outer cover 20 may have, or be imparted with, differing levels of hydrophilicity and/or hydrophobicity, differing levels of breathability, differing coefficients of friction, and/or other differing functional attributes in the front versus the rear regions.

It will be appreciated, therefore, that outer cover asymmetry across the outer cover lateral axis 45 is a result of design and construction of the outer cover 20 so as to have only one front region and only one rear region, i.e., the front and rear regions are not interchangeable, if the fit, comfort, performance and appearance of outer cover 20 are to be optimal.

Examples of Possible Absorbent Insert Details

Examples of features of an absorbent insert 50 will be described with reference to FIGS. 3, 4 and 5A-F.

As noted above, FIG. 3 depicts a disposable absorbent insert 50 that may form an inner component of a wearable absorbent article 10 as described herein, shown in perspective view as it might appear in a free-standing, relaxed state, apart from an outer cover 20. FIG. 4 depicts an example of an absorbent insert 50 shown stretched out and laid flat (against elastic-induced contraction to a position similar to that shown in FIG. 3), wearer-facing surfaces facing the viewer. FIGS. 5A-5F depict cross sectional views of an insert 50 as indicated in FIG. 4, in various possible examples.

The insert 50 may have a topsheet 51 and a backsheet 52 forming an envelope-like enclosure for absorbent core materials such as those described further below. The topsheet 51 and the backsheet 52 may be affixed together along longitudinal seams 64, and along lateral seams 69. The insert 50 also may have longitudinal standing cuffs 53 affixed therealong.

Topsheet

The topsheet 51 may be formed of a liquid-permeable nonwoven web material. It may be desired that the material forming the topsheet 51 is compliant, soft-feeling, and non-irritating to the wearer's skin. It may be desired that at least a portion of the topsheet 51 may be liquid pervious, permitting liquids to readily penetrate through its thickness. A suitable topsheet may be manufactured from a wide range of materials, such as porous foams, reticulated foams, apertured plastic films, apertured nonwoven materials, or woven or nonwoven materials of natural fibers (e.g., wood or cotton fibers), synthetic fibers (e.g., polyester or polypropylene fibers), or a combination of natural and synthetic fibers. If the topsheet 51 includes fibers, the fibers may be spunbond, carded, wet-laid, meltblown, hydroentangled, or otherwise processed as is known to those of skill in the art.

In some circumstances it may be desired that at least a portion of the topsheet 51 is made of a hydrophobic material or is treated to be hydrophobic in order to isolate the wearer's skin from liquids contained in an absorbent core 71. If the topsheet 51 is generally made of a hydrophobic material, it may be desired that at least a portion of the upper surface of the topsheet 51 is treated to be hydrophilic so that liquids will transfer through the topsheet 51 more rapidly. The topsheet 51 can be rendered hydrophilic by treating it with a surfactant or by incorporating a surfactant into the topsheet 51.

Backsheet

The backsheet 52 is generally that outer liner portion of the insert 50 forming the garment-facing surface thereof, and prevents, or at least inhibits, the exudates absorbed and contained within the insert 50 from wicking through and soiling the outer cover 20. In some circumstances it may be desired that the backsheet 52 is substantially impervious to liquids.

The backsheet 52 may be formed of a film, a nonwoven, or a laminate of a film and a nonwoven. The backsheet 52 may be formed of a substantially liquid-impermeable laminate or composite of film and non-woven web. The backsheet 52 may be formed of a substantially liquid impermeable nonwoven web, or laminate of nonwoven web and substantially liquid impermeable film, so as to contain and isolate liquid exudates from the outer cover 20, outer clothing and/or environment of the wearer. At the same time, the backsheet 52 may be vapor permeable to provide for breathability of the insert 50 and the wearable absorbent article 10, reducing humidity in the areas between the insert 50 and the wearer's body, and helping reduce the likelihood of skin irritation and/or rashes that may result from over-hydration of the skin. The backsheet 52 may be joined to the topsheet 51, the absorbent core 71 or any other element of the insert 50 by any suitable attachment mechanism known in the art.

It will be appreciated that the outer cover 20 described herein may be constructed of materials and construction so as to bear and sustain a majority of the structural loading generally imposed upon a disposable diaper, by stretching and accommodation of the wearer's anatomical features and body movements, and by absorption, swelling and added weight resulting from the wearer's exudations of waste. Thus, lesser requirements for structural strength of an insert might be present with use of such an outer cover 20, as compared with strength required of inside components of a disposable diaper. Therefore, a wearable absorbent article such as described herein may include a disposable absorbent insert manufactured from materials that are different from those ordinarily used in the manufacture of disposable diapers, such as petroleum-derived materials, e.g., polyethylene and polypropylene. For example, a disposable absorbent insert having one or more of a topsheet, backsheet, standing cuffs and/or other components formed of products of wood, cotton, flax (linen), hemp, bamboo, or other cellulose fibers (e.g., paper), in addition to the materials identified above, is contemplated. If resistance to aqueous liquid penetration or substantial liquid impermeability is desired, e.g., for a backsheet and/or standing cuffs, a material formed of ordinarily hydrophilic fibers, such as paper, may be coated or impregnated with a hydrophobic material, such as a skin-compatible oil or wax, to impart the desired resistance to aqueous liquid penetration. Each of the materials forming the insert may be selected so as to be dispersible in water or an aqueous solution, flushable, biodegradable and/or compostable (preferably to an agriculturally usable humus or soil amendment).

Absorbent Core

In an embodiment, referring to FIGS. 5A-F, the insert 50 may have an absorbent core 71 within the envelope-like structure formed by the topsheet 51 and the backsheet 52. The absorbent core 71 may comprise any absorbent material which is generally compressible, conformable, non-irritating to the wearer's skin, and capable of absorbing and retaining liquids, such as urine and other certain body exudates. The absorbent core 71 may comprise a wide variety of liquid-absorbent materials commonly used in disposable diapers and other absorbent articles such as comminuted wood pulp, which is generally referred to as airfelt.

The absorbent core 71 may include liquid acquisition/distribution material 65, and storage material 66. Generally, acquisition/distribution material 65 may have comparatively rapid absorption and wicking properties, but also may have limited absorption capacity. Conversely, generally, the storage material 66 may have comparatively slower absorption and wicking properties, but also may have greater absorption capacity. Thus, the acquisition/distribution material 65 may serve to rapidly absorb and distribute gushes of liquid such as urine, while the storage material 66, having greater absorption capacity, may serve to absorb such liquid from the acquisition/distribution material and store it for the time needed until the insert 50 may be replaced.

Standing Cuffs

The insert 50 also may have a pair of longitudinal standing cuffs 53 attached partially or entirely along the longitudinal length thereof. Suitable longitudinal standing cuffs (in various published examples identified as "leg cuffs", "barrier cuffs" "gasketing cuffs," etc., may be formed of materials and construction such as described in, but not limited to, U.S. Pat. Nos. 6,786,895; 6,420,627; 5,911,713; 5,906,603; 5,769,838; 5,624,425; 5,021,051 and 4,597,760; and U.S. Patent Application Publication No. 2007/0239130 and U.S. Pat. No. 8,002,760. As shown in FIG. 3, the standing cuffs 53 may have one or more strands or strips of cuff elastics 58*a*, 58*b* disposed longitudinally therealong. If such cuff elastics 58*a*, 58*b* are pre-strained prior to being affixed to the web material forming the standing cuffs 53, resulting longitudinal tensile forces therealong may cause the web material forming the standing cuffs 53 to gather as shown, and cause the cuffs 53 to extend from the body of the insert 50 (upwardly relative to FIG. 3), or causing them to "stand". This feature causes the standing cuffs 53 to form a gasketing structure along the wearer's body when the wearable absorbent article 10 including the insert 50 is worn, longitudinally on either side of the anatomical features where waste is exuded. Thus, the standing cuffs 53 may serve to enhance the exudate containment capability of the insert 50 and, and as a result, of the wearable absorbent article 10. As with the backsheet 52, the standing cuffs 53 may be formed of a substantially liquid impermeable web so as to contain and isolate liquid exudates from the outer cover 20, outer clothing and environment of the wearer. At the same time, the standing cuffs 53 may be vapor permeable to provide for breathability of the insert 50 and the wearable absorbent article 10, reducing humidity in the areas between the insert and the wearer's body, and helping reduce the likelihood of skin irritation and/or rashes that may result from over-hydration of the skin.

In one embodiment, the elastic cuffs may be made of slow recovery elastomers, as are known in the art. This would allow the insert to lay flat when stretched longitudinally for a short period of time (e.g., a few seconds), thus giving the user some time to position the insert correctly on the outer cover without having to deal with the cuff precontraction.

In another example, the material forming the standing cuffs 53 may be integral with the material forming the backsheet 52, such as described in, by way of non-limiting example, U.S. Patent Application Publication No. 2007/0239130. In this particular example, referring to and relative to the view in FIG. 3, a continuous piece of material may form one standing cuff 53, wrap beneath the insert to form the backsheet 52, and wrap up the other side to form the other standing cuff 53. This example of a wraparound construction may provide improved liquid containment capability to the insert 50, by eliminating seams along the outer liquid-containing surfaces that include the standing cuffs 53 and the backsheet 52. Another example of this construction is depicted and described in U.S. Pat. No. 4,808,178.

In some circumstances, however, manufacturing and/or economic constraints may discourage such construction, or else, it may be desirable for the materials forming the standing cuffs 53 and the backsheet 52 to have differing properties. For example, in some applications it may not be deemed necessary for the standing cuffs 53 to be substantially liquid impervious, if they are otherwise formed of a nonwoven web material comprising closely situated hydrophobic fibers, which may still tend to repel and contain fluid, but may be generally more breathable than substantially liquid impervious laminates including films. In this event, improved strength and liquid containment attributes may still be imparted by having the material forming the standing cuffs 53 wrap only partially beneath the lower longitudinal corners of the insert, and affixed at seams beneath the insert, rather than at its outermost lower corners as suggested by FIG. 3. One example of this construction is depicted and described in U.S. Pat. No. 7,695,463, and in particular, FIG. 13 therein and associated descriptive text.

Referring to FIGS. 6A-6H, for enhanced exudates containment functionality that may be particularly beneficial for an insert of the type described herein, the insert 50 may include a dual gasketing system. A dual gasketing system may include both the above-described elasticized standing cuffs 53, and outer cuffs 174 including outer cuff elastic members 177, and defining longitudinal side edges 182 of the insert 50. Outer cuff elastic members 177 may be sandwiched and/or enveloped between other layers of material, such as the portions of materials forming the bases or attached proximal portions of standing cuffs 53, and topsheet 51, or the materials forming topsheet 51, and backsheet 52, along their longitudinal side edges, or even separate outer cuff material 180.

The outer cuff elastic members 177 may be formed of the same, or differing, elastomeric material than barrier cuff elastic members 58*a*, 58*b*, and within each outer cuff 174 may be in the form of one or more longitudinally-oriented strands, bands, strips, etc. The outer cuff elastic members 177 may be incorporated into the structure, during manufacture, in a pre-strained condition, such that upon completion of manufacture and relaxation of the materials, the outer cuff elastic members 177 contract longitudinally and cause the materials within which they are contained, in areas proximate to the members 177, to gather longitudinally. The gathered materials and the contained elastic members 177 serve to provide elastic stretch and contraction, forming outer cuffs 174 that form a snug-fitting gasketing structure about the wearer's legs.

Outer cuff elastic members 177 may be disposed generally laterally outwardly of the longitudinal lines of attachment 179 along which the material forming the standing cuffs 53 is attached to the insert on one side and is free to extend away from the insert on the other. The materials sandwiching or enveloping outer cuff elastic members, e.g., materials forming topsheet 51 and backsheet 52, or materials forming standing cuffs 53 and topsheet 51, and/or materials 180 separately forming outer cuffs 174, may be bonded together along longitudinal paths about and proximate the elastic members 177 by any suitable means, including e.g., adhesive bonding, thermal bonding, compression bonding, or a combination thereof, to hold elastic members 177 in a relatively fixed lateral position within the materials containing them.

As will be evident from a comparison of FIGS. 6A-6H, the materials forming standing cuffs 53 may be disposed in various configurations, and may form portions of, overlap, or not overlap, outer cuffs 174. As reflected in, e.g., FIGS. 6A-6D, outer cuffs 174 may be effectively formed by the web materials forming the topsheet 51 and/or backsheet 52 along the longitudinal side edges of the insert 50 by the incorporation of outer cuff elastic members 177. This configuration may be desired for efficiency of manufacturing and control of material costs. Alternatively, as reflected in, e.g., FIGS. 6E-6H, outer cuffs 174 may be formed by separate web material(s) 180, sandwiching or enveloping outer cuff elastic members 177 and attached to the other materials of the insert to effectively form its longitudinal side edges 182. This configuration may be desired for greater flexibility in selection of outer cuff materials for purposes of e.g., comfort or appearance, or even material cost control, where selected material 180 used to form outer cuffs 174 may be less expensive than materials forming backsheet 52 and/or topsheet 51.

As noted, standing cuffs 53 may be formed of any suitable web materials but preferably are formed of web materials that are effectively liquid impermeable while being vapor permeable, so as to contain the wearer's liquid exudates within the insert while permitting the insert to "breathe" to avoid excess humidity within the insert (which may overhydrate the wearer's skin and promote conditions such as diaper rash). In order to reduce the chance of liquid exudate leakage at the longitudinal seams joining liquid permeable topsheet 51 and liquid impermeable standing cuffs 53, it may be desirable that a longitudinal, substantially continuous deposit of adhesive material be included between the material forming standing cuffs 53 and the material forming backsheet 52. When the standing cuff 53 is configured such that the proximal edge 181 of the web material forming it lies laterally outward of the line of attachment 179 (e.g., FIGS. 6A, 6B, 6C, 6E, 6G), the deposit of adhesive will be disposed at or laterally outward of the line of attachment 179. When the standing cuff 53 is configured such that the proximal edge 181 of the web material forming it lies laterally inward of the line of attachment 179 (e.g., FIGS. 6D, 6F, 6H), the deposit of adhesive will be disposed at or laterally inward of the line of attachment 179. Such a deposit of adhesive may serve both to adhere standing cuffs 53 to the insert structure including the topsheet 51 and backsheet 52, and to penetrate and fill the spaces between the fibers of nonwoven web material forming topsheet 51, providing a liquid barrier along lines of attachment 179.

Standing cuffs 53, and, if formed of separate material 180 (e.g., FIGS. 6E-6H), outer cuffs 174, may be formed of any of the materials described above (or in references descriptive of standing cuffs, incorporated herein by reference above), or may be formed of any of the materials described below that may be used to form inner barrier cuffs in unitized dual leg gasketing systems.

The gasketing structure of outer cuffs 174 may be desired to supplement and complement the gasketing structure of standing cuffs 53, to reduce the chance of leakage of the wearer's exudates from within the insert.

In further examples, the insert may include a unitized dual leg gasketing system 170. FIGS. 6I, 7A-7D and 8A-8P depict schematic cross section views of examples of unitized dual leg gasketing systems. The unitized dual leg gasketing system 170 may comprise an inner barrier cuff 171 comprising an inner barrier cuff folded edge 172 and an inner barrier cuff material edge 173. The unitized dual leg gasketing system 170 may further comprise an outer cuff 174 comprising an outer cuff folded edge 175 and an outer cuff material edge 176. The system effectively provides two gasketing structures about the wearer's body, rather than one, which may enhance exudate containment functionality and reduce chances that the outer cover will be soiled by the wearer's exudates. Additionally, the system may lend itself to relatively efficient manufacture and usage of materials.

In one example, the unitized dual leg gasketing system 170 may be formed of a single web of gasket material 82. (Herein, a structure formed of a "single" web of material means that the structure is formed of a web of material that is continuous through the structure, i.e., not formed of several cut and joined portions of web material.) A unitized dual leg gasketing system formed of a single web of material may provide a cost advantage over examples having more than one web of material. Further, an example formed of a single web of gasket material may be less likely to allow leaks, as it may be formed without creating holes resulting from mechanical bonding that may be used to join two or more portions of web material. Also, an example formed of a single web of material may be more aesthetically pleasing, as it can be manufactured such that fewer or no mechanical bonds are visible.

In one example, the unitized dual leg gasketing system 170 may have an inner barrier cuff 171 comprised of an inner barrier cuff folded edge 172 and an inner barrier cuff material edge 173. The unitized dual leg gasketing system 170 may further comprise an outer cuff 174 comprising an outer cuff folded edge 175 and an outer cuff material edge 176. In one example, the web of material may be folded over laterally inward to form the outer cuff folded edge 175 and folded over laterally outward to form the inner barrier cuff folded edge 172. In one example, the unitized dual leg gasketing system 170 may extend from the lateral seam 69 at the front of the insert to the lateral seam 69 at the rear of the insert (see FIG. 4) and may be joined to the topsheet 51 and/or backsheet 52 between the inner barrier cuff folded edge 172 and the outer cuff folded edge 175 in locations longitudinally between front and rear lateral seams 69. In one example, the outer cuff material edge 176 may be disposed laterally inboard the inner barrier cuff material edge 173.

In one example, the outer leg cuff 174 may include outer cuff elastic members 177 positioned in a lateral array between the outer cuff folded edge 175 and outer cuff material edge 176; the outer leg cuff 174 optionally may include at least two outer cuff elastic members 177, at least three elastic members 177, at least four outer cuff elastic members 177, at least five outer cuff elastic members 177, or at least six outer cuff elastic members 177. In one example, the outer cuff elastic members 177 may be disposed between the outer cuff folded edge 175 and the inner barrier cuff material edge 173.

In one example, the inner barrier cuff 171 may include an array of barrier cuff elastic members 178 in the area of the inner barrier cuff folded edge 172; the inner barrier cuff 171 optionally may include at least one elastic member 178, at least two barrier cuff elastic members 178, at least three barrier cuff elastic members 178, at least four barrier cuff elastic members 178, or at least five barrier cuff elastic members 178. In one example, the barrier cuff elastic members 178 may be disposed between the inner barrier cuff folded edge 172 and the outer cuff material edge 176.

In one example, the outer leg cuff 174 may include at least one more elastic member 177 than the inner barrier cuff 171 elastic member 178. In one example, the inner barrier cuff material edge 173 may be laterally outboard the outer cuff material edge 176.

In one example, the elastic members 177 and 178 may be laterally spaced at least 2 mm apart from one edge to the other edge, optionally at least 3 mm apart; optionally at least 3.5 mm apart; or optionally at least 4 mm apart. In one example, the outermost elastic members 177 and 178 may be less than about 2 mm from the outer cuff material edge 176 and inner barrier cuff material edge 173; optionally less than about 1.5 mm, or less than about 1 mm.

Figure 7B:
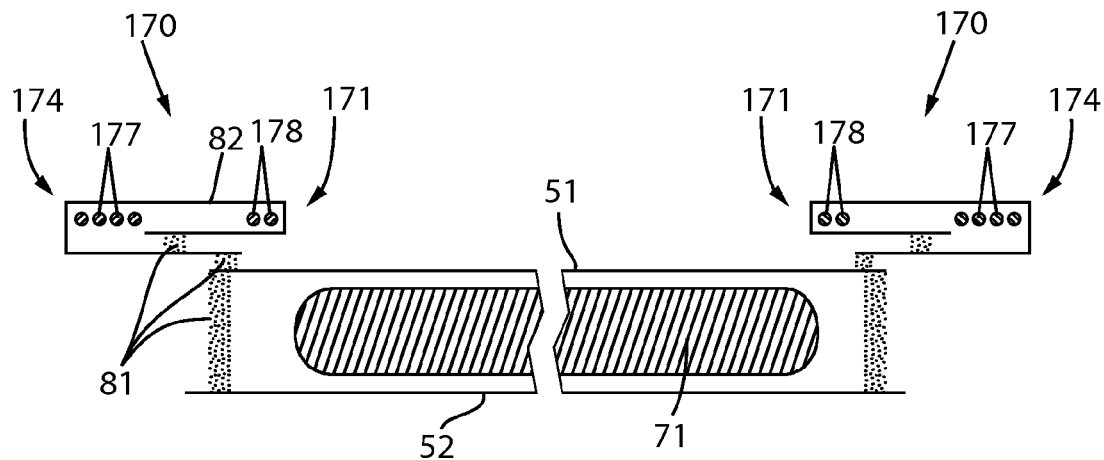
FIGS. 7B-7D are schematic lateral cross sectional views of longitudinal side portions of various alternative examples of an insert having the unitized dual leg gasketing system depicted in FIGS. 6A-6H, taken through lateral axes of an insert in accordance with various non-limiting embodiments of the present disclosure.
Figure 7C:
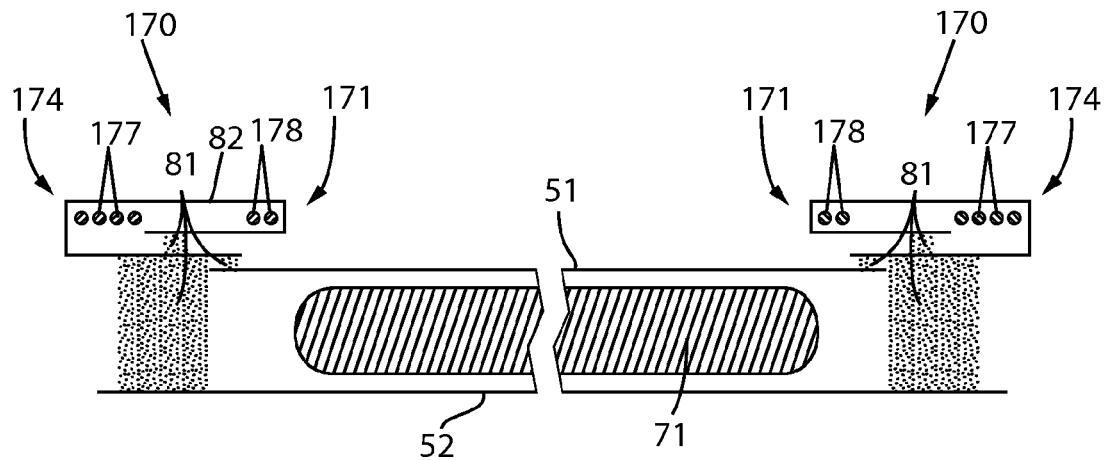
Figure 7D:
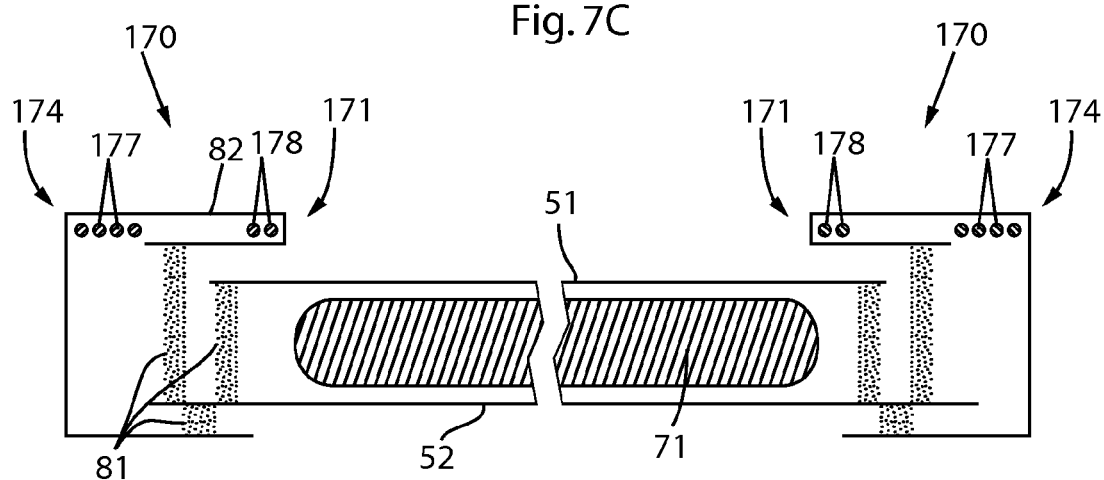

In one example, the outer cuff elastic members 177 may be located between the inner barrier cuff material edge 173 and the outer cuff folded edge 175. In one example, the barrier cuff elastic members 178 may be located between the outer cuff material edge 176 and the inner barrier cuff folded edge 172. In one example, an additional material may be located between the inner barrier cuff material edge 173 and the outer cuff material edge 176; such material may include a topsheet 51; backsheet 52; core 71; or any other material optimally positioned in the design of the system 170. One such example is shown in FIG. 7A wherein a topsheet 51 is positioned between the inner barrier cuff material edge 173 and the outer cuff material edge 176. FIGS. 7B-7D depict schematic cross sectional views of additional examples. In one example, the topsheet 51 is disposed between the inner 171 and outer cuff 174 edges laterally. FIGS. 7B-7D depict examples of locations in which bonds 81 may be disposed to affix backsheet 52, topsheet 51 and system 170 together to form the insert structure. Bonds 81 between components (schematically depicted) may be formed by mechanical bonding of the respective components, by deposits of adhesive, or a combination thereof. Deposits of adhesive also may serve as liquid barriers at locations where components are joined, for purposes of liquid containment. The example depicted in FIG. 7B wherein the entire unitized dual leg gasketing system is disposed above the topsheet 51 may be preferred in some circumstances because it may lend itself to relatively efficient manufacturing. The example depicted in FIG. 7C has a backsheet 52 that is laterally extended across substantial portions of the system 70 on each side, which may be desired in some circumstances for enhanced liquid containment (where backsheet 52 is liquid impermeable). In the example depicted in FIG. 7D, the gasket material 82 wraps beneath the backsheet 82, which is an alternative structure that may enhance liquid containment. FIGS. 8A-8P depict schematic cross sectional views of additional examples of configurations relative a topsheet 51 (the absorbent core and backsheet, which would be disposed beneath the topsheet 51, are not shown). In the examples shown in FIGS. 8G and 8H, the topsheet 51 may be formed of the same single web of material forming the system 170, and may be perforated or apertured as suggested to impart liquid permeability to allow liquids to pass through the topsheet to the absorbent core. Alternatively, the web may be inherently liquid permeable, and a liquid impermeable layer or treatment imparting liquid impermeability may be added to the portions of the web forming the gasketing system 170.

In one example, the unitized dual leg gasketing system 170 may have an inner barrier cuff 171 having an inner barrier cuff folded edge 172 and an inner barrier cuff material edge 173. The unitized dual leg gasketing system 170 may further have an outer cuff 174 having an outer cuff folded edge 175 and an outer cuff material edge 176. The unitized dual leg gasketing system may include a first material comprising the inner barrier cuff 171 and a second material comprising the outer cuff 174. The first and second materials may overlap and be joined together along a longitudinal edge of each material by any suitable bonding means. In one example, the web of material may be folded over laterally inward to form the outer cuff folded edge 175 and folded over laterally outward to form the inner barrier cuff folded edge 172. In one example, the proximal edges of the outer cuff 174 may be coterminous. In one example, the proximal edges of the outer cuff 174 may be spaced greater than about 2 mm apart; greater than about 4 mm; greater than about 6 mm; greater than about 10 mm apart. In one example, the proximal material edges of the cuff may both be bonded to the inner barrier cuff. In one example, only one of the proximal material edges of the outer cuff 174 is bonded to the inner barrier cuff. In one example, the proximal material edges of the outer cuff may be held together by any suitable bonding mechanism.

In one example, the unitized dual leg gasketing system may be spaced laterally inward of the longitudinal edge of the backsheet by about 10 mm, optionally about 20 mm, or optionally about 30 mm. In another example, the laterally outboard edge of the chassis may be defined by the lateral edge of the outer leg cuff. In another example, the backsheet and polymeric film may be spaced laterally inward of the outer cuff edge by about 10 mm; optionally about 20 mm; optionally about 30 mm; optionally about 40 mm.

In one example, the height of the inner barrier cuff 171 may be at least about 30 mm, at least about 32 mm, at least about 35 mm, or at least about 38 mm. In one example, the height of the outer leg cuff 174 may be at least about 23 mm, at least about 25 mm, at least about 27 mm, at least about 30 mm. The height of the inner barrier cuff is measured from inner barrier cuff folded edge 172 to the first point of connection to a material beyond the inner barrier cuff material edge. The outer cuff height is measured from the outer cuff folded edge 175 to the first point of connection the inner barrier cuff has to a material beyond the inner barrier cuff material edge. Thus, the inner and outer cuffs are measured from their respective folded edges to the point where the inner barrier cuff is connected to the first material beyond the inner barrier cuff material edge.

One advantage of the unitized dual leg gasketing system 170 is that when a substantially liquid-impervious material is used to form the cuff structure, a polymeric film component layer of the backsheet may be narrowed or in some circumstances dispensed with entirely, providing the possibility for less usage of film materials, and thereby more cost-effective designs. Utilizing adhesive technologies that are more reliably processed results in more reliable performance and creates substantially liquid impervious seals. This technology enables narrowing the film layer to be only slightly wider than the absorbent core by reducing the need for redundant seals.

The gasketing cuffs 171, 174 may be substantially inelastic or may be elastically extensible to dynamically fit at the wearer's leg. The gasketing cuff 170, 174 each may include one or more elastic members 177 and 178 (such as elastic strands) operably joined at their ends to the topsheet 51, backsheet 52, or any other suitable substrate used in the formation of the insert 50. Suitable gasketing cuff construction is further described in U.S. Pat. No. 3,860,003.

The inner barrier cuff 171 may span the entire longitudinal length of the insert 50 or all or substantially all of the length thereof between seams 69 (FIG. 4). The inner barrier cuff 171 may form a flap with one or more elastic members 178 (such as elastic strands). The inner barrier cuff 171 may be formed of a continuous extension of any of the existing materials or elements that form the insert 50.

The insert also may be provided with any of the cuff structures (and materials forming them) described in U.S. Patent Application Publication Nos. 2012/0277713 and 2012/0277702.

Insert Asymmetry

Referring to FIG. 4, the insert 50 may have an insert lateral axis 70 that equally divides its longitudinal length. The insert 50 may have a structure that is asymmetric across the insert lateral axis 70. For purposes of this description, with used with respect to an insert, "asymmetric" and "asymmetry"

mean that features, geometry (e.g., shape), materials and/or construction on one side of the insert lateral axis 70 differ substantially in some respect from those on the other side of the insert lateral axis 70. Such asymmetric construction results from having various features of the insert 50 designed to accommodate the body features and functions of the intended wearer (i.e., body contours, excretory and eliminatory functions) as they differ front-to-rear, to enhance containment/absorbency performance, comfort, fit and/or appearance of the wearable absorbent article 10, to economize on use of materials and/or to reduce volume of disposable waste. "Asymmetric" and "asymmetry" do not refer to differences across the insert lateral axis 70 that are attributable to features that may be included on an insert only for purposes of: purely cosmetic coloration or surface decoration; fastening to an outer cover (such as fastener components described herein); user grasping of the insert (such as a grasping structure described herein); as indicia for orienting an insert within an outer cover (such as orientation indicia described herein); or for other purposes substantially unrelated to the body features and functions of the intended wearer as they differ front-to-rear, to affect performance, comfort, fit and/or physical appearance of the wearable absorbent article 10, to economize on use of materials and/or to reduce volume of disposable waste.

As one example, the topsheet 51 may one or more have apertures 63 therethrough, predominately in the crotch and/or the rearward region 55 as suggested in FIG. 4. The apertures 63 may permit liquid or low viscosity fecal material to penetrate the topsheet 51 and reach absorbent materials in the absorbent core 71 more rapidly than would occur without such apertures, enhancing liquid feces absorption and containment capability of the insert 50.

In another example, a feces management feature may be disposed in the rear of the insert 50, including one or more pockets, spacers, low viscosity feces management elements, openings in suspended elasticized topsheets, and similar features, for example, as described in U.S. Pat. Nos. 8,016,803, 7,771,406 and 7,771,408. Thus, the topsheet 51 may comprise one or more larger apertures in the rear region to provide for unrestricted or comparatively less restricted movement of solid or higher viscosity waste therethrough. The size of an aperture may be important in achieving the desired fecal waste encapsulation performance. If the aperture is too small, the waste may not pass through the aperture, either due to poor alignment of the exudation point and the aperture location, or due to fecal masses having a size greater than the aperture. If the aperture is too large, however, the area of skin that may be exposed to "rewet" from the contained waste matter is increased. An aperture may have an area of between about 10 cm$^2$ and about 50 cm$^2$, specifically reciting all 0.1 cm$^2$ increments within the specified range and all ranges formed therein. In some circumstances it may be desired that an aperture has an area of between about 15 cm$^2$ and 35 cm$^2$, specifically reciting all 0.1 cm$^2$ increments within the specified range and all ranged formed therein.

An insert may have asymmetry in its absorbent core 71 (absorbent core asymmetry). Absorbent core asymmetry may result from arrangement of materials and features within the absorbent core 71 to locate particular materials and features of the absorbent core 71 where they are most needed and/or most effective, in accordance with features and functions of wearer anatomy as they differ front-to-rear.

For example, all or a portion of the rearward region 55 of insert 50 may include acquisition/distribution material 65 but less or no storage material 66 as compared with the forward region 54, as may be seen by comparison of FIGS. 5A and 5B, 5C and 5D, and 5E and 5F, respectively. By this particular absorbent core asymmetry, the storage material 66 may be located predominately in the front of the wearable absorbent article 10 when worn. This may provide a predominate proportion of the insert's urine storage capacity closer to the urine exudation point of the wearer to reduce the likelihood of leakage, and remove potentially uncomfortable and/or unsightly size and bulk from between the wearer's legs or the wearer's backside area, particularly relevant when the storage material 66 becomes swollen with absorbed liquid. Additionally, this particular asymmetry provides for economization of the amount of the storage material 66 used, by locating it in only a portion of the insert 50 rather than substantially along the entire insert 50. The liquid storage capacity of the forward region of the absorbent core 71 may be greater than that of the rearward region of the absorbent core 71 as measured by the Teabag Centrifuge Capacity test disclosed in U.S. Pat. No. 6,278,037. The liquid storage capacity of the forward region 54 of the absorbent core 71 may be at least about 10%, 20%, 50%, or even 100% or more greater than that of the rearward region 55. With such an arrangement, acquisition/distribution material 65 located in both forward and rearward regions 54, 55 may serve to acquire and move liquid (usually, urine) to the storage material 66 located predominately in the forward region 54. Alternatively, or additionally, the area and/or basis weight of the acquisition system or component materials in the forward region 54 of the insert 50 may be at least about 10%, 20%, 50%, or even 100% or more greater than that of the rearward region 55. Alternatively, or additionally, the surface area, cross-sectional area and/or lateral width of the absorbent core 71 may be greater in the forward region 54 as compared with the rearward region 55. For example, the surface area, cross-sectional area and/or lateral width of the absorbent core 71 may be greater in the forward region 54 as compared with the rearward region 55, to accommodate a greater proportion of the acquisition/distribution and/or storage material present in the forward region 54 of the absorbent core 71.

Figure 5A:
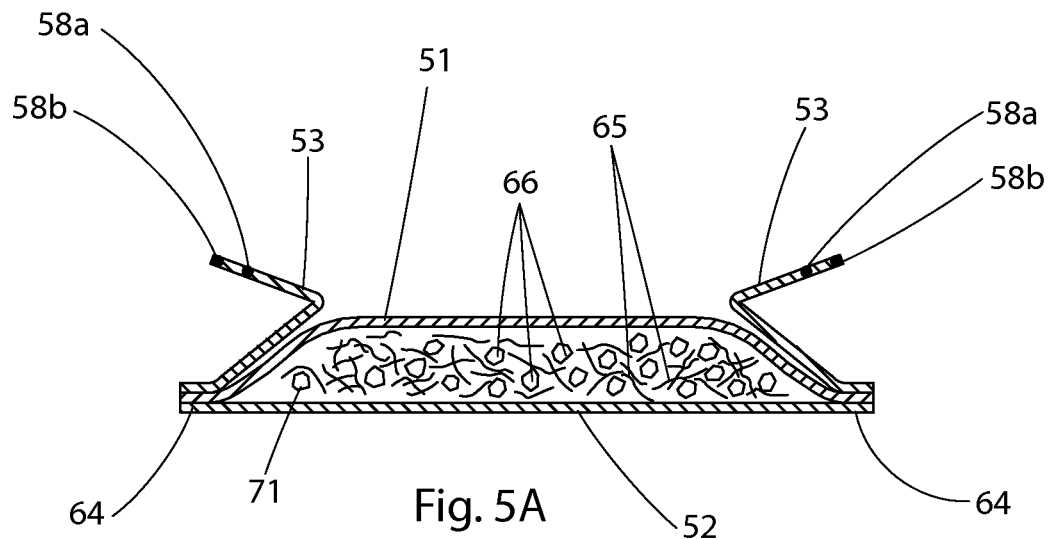
FIG. 5A is a cross-sectional view of an example of an insert such as shown in FIG. 4, taken at line 5A-5A in FIG. 4 of accordance with a non-limiting embodiment of the present disclosure.
Figure 5B:
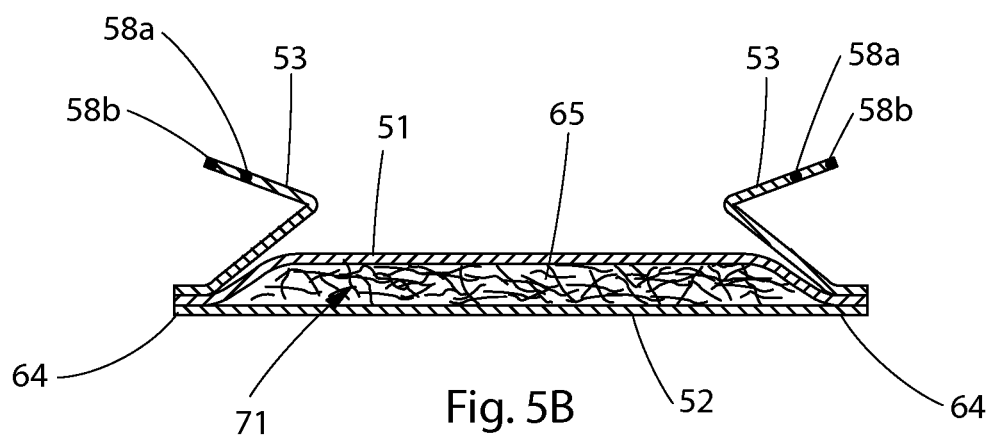
FIG. 5B is a cross-sectional view of an example of an insert such as shown in FIG. 4, taken along line 5B-5B of FIG. 4 in accordance with a non-limiting embodiment of the present disclosure.
Figure 5C:
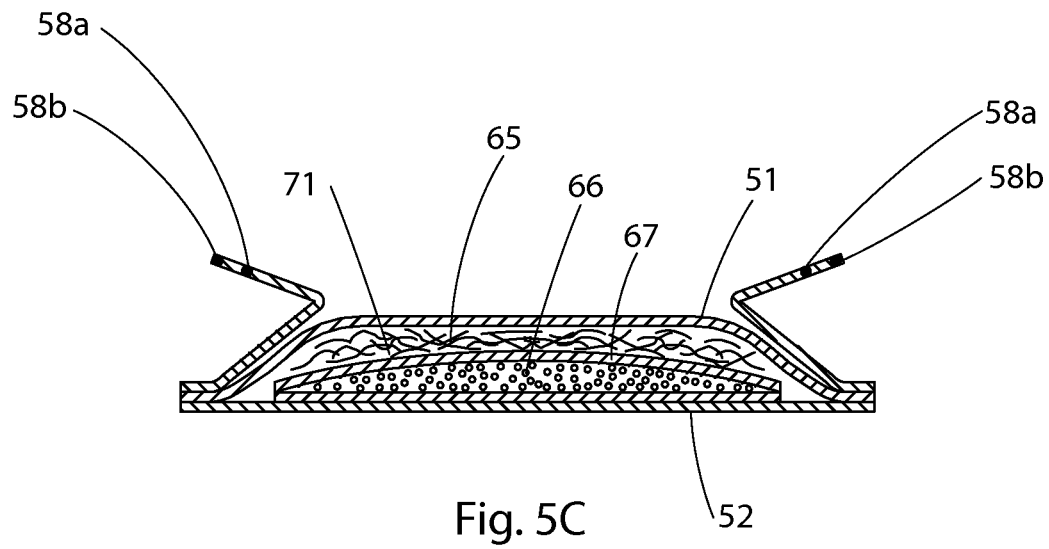
FIG. 5C is a cross-sectional view of another example of an insert such as shown in FIG. 4, taken along line 5C-5C of FIG. 4 in accordance with a non-limiting embodiment of the present disclosure.
Figure 5D:
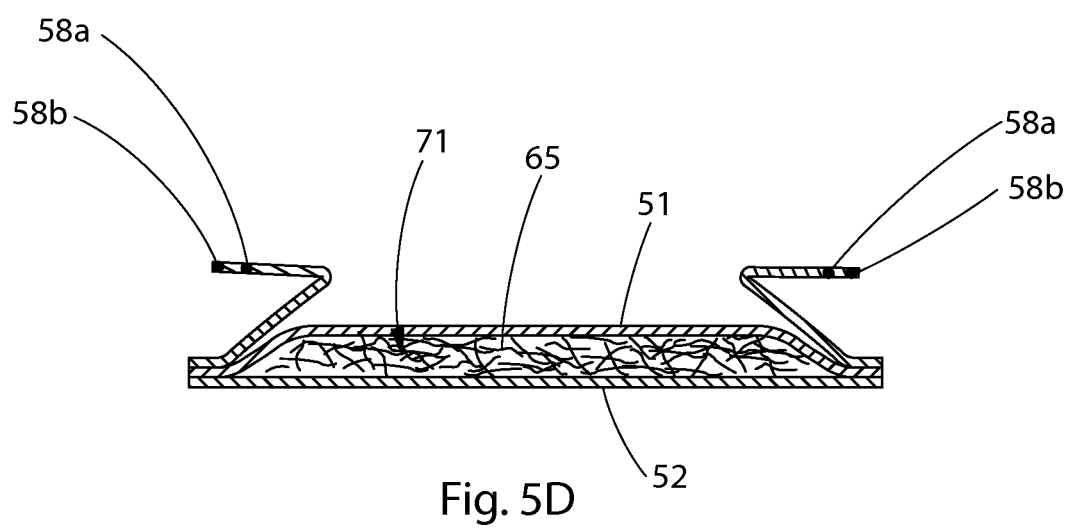
FIG. 5D is a cross-sectional view of another example of an insert such as shown in FIG. 4, taken along line 5D-5D of FIG. 4 in accordance with a non-limiting embodiment of the present disclosure.
Figure 5E:
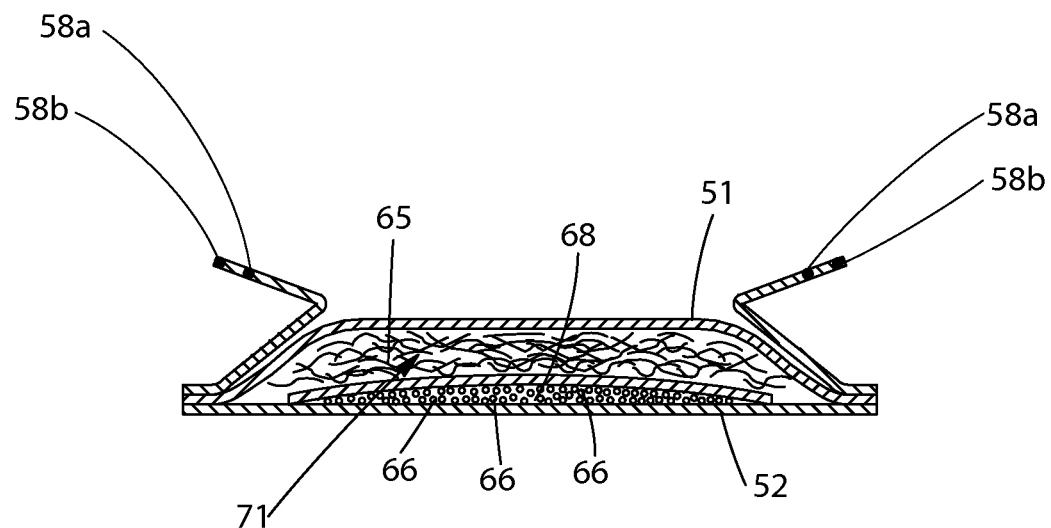
FIG. 5E is a cross-sectional view of another example of an insert such as shown in FIG. 4, taken along line 5E-5E of FIG. 4 in accordance with a non-limiting embodiment of the present disclosure.
Figure 5F:
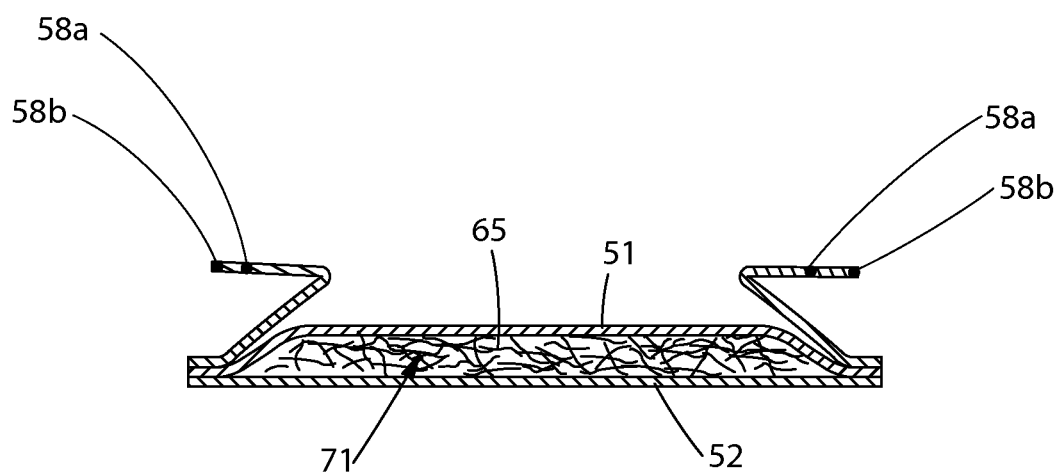
FIG. 5F is a cross-sectional view of another example of an insert such as shown in FIG. 4, taken along line 5F-5F of FIG. 4 in accordance with a non-limiting embodiment of the present disclosure.

Referring to FIGS. 5A, 5C and 5E, in other examples, the absorbent material 66 in the forward region 54 may be, respectively, dispersed within the acquisition/distribution material 65 (FIG. 5A), contained within a separate liquid permeable structure or envelope 67 in fluid communication with the acquisition/distribution material 65 (FIG. 5C); or dispersed on, or within an adherent matrix of, retaining material 68, and in fluid communication with the acquisition/distribution material 65 (FIG. 5E). Conversely, the rearward region 55 may predominately contain the acquisition/distribution material 65, but less storage material 66 as compared with the forward region 54, or none (FIGS. 5B, 5D, 5F). Materials in the forward region 54 also may be disposed according to construction described in one or more of U.S. Patent Application Publication Nos. 2008/0312617, 2008/0312618, 2008/0312628, 2008/0312619, 2008/0312620, 2008/0312621, 2008/0312622, 2008/0312625, 2008/0312624, and U.S. Pat. No. 8,017,827, with a differing construction in the rearward region 55.

In another example, the storage material 66 and the acquisition/distribution material 65 may occupying differing, distinct layers of the absorbent core 71, as suggested by FIG. 5C. It may be desirable in some circumstances to make the layer containing the acquisition/distribution material 65 larger in surface area (i.e., plan view surface area relative to the insert laid flat, as shown in FIG. 4) than the layer containing the storage material 66, or vice versa. For example, if the layer containing the acquisition/distribution material 65 is formed so as to have a larger surface area laterally across the insert in the forward region 54, this may serve to provide space for a greater quantity of the acquisition/distribution material 65 in the forward region 54. This may impart greater capacity in the forward region 54 to rapidly absorb and distribute relatively large gushes of urine discharged toward the forward region 54, as may be desired for wearable absorbent articles for, e.g., older male babies and toddlers—enhancing containment capability of the insert 50.

In another example, however, such as for newborns and young babies, large gushes of urine might not be expected, but comparatively substantial quantities of liquid or low-viscosity fecal material may be. Thus, a wearable absorbent article for this group of intended wearers may include an acquisition/distribution layer of larger size, occupying a greater surface area, in the rearward region 55 of the insert 50. This may impart greater capacity in the rearward region to rapidly absorb gushes of liquid or low viscosity fecal material discharged toward the rearward region 55, and thereby enhance containment capability of the insert 50.

Differences between the forward and the rearward regions 54, 55 also may be included for purposes of sleep-use inserts. While an insert designed for awake-use may have the predominate proportion of its liquid-storage capacity in the forward region 54 as described above, an insert designed for sleep-use with, e.g., young babies, may have the predominate proportion of its liquid-storage capacity in the rearward region 55, to accommodate babies who sleep lying on their backs, by locating the predominate proportion of storage capacity where fluid exudates will flow under influence of gravity.

The insert 50 also may have overall shape/backsheet asymmetry. For example, viewed in a laid-flat position as shown in FIG. 4, the insert 50 may occupy a larger surface area on one side of the insert lateral axis 70 than on the other. This may be useful for purposes of comfort, body coverage, appearance, performance and/or economization in use of backsheet material(s). For example, in conjunction with including a predominate proportion of the storage material 66, the forward region 54 of the insert 50 may occupy a larger surface area, associated with a larger space within the insert 50 to contain the storage material 66, e.g., so as to improve overnight absorption and containment capacity for wearers who sleep on their stomachs, and allow for the insert to remain flatter, particularly relevant when the absorbent material becomes swollen with absorbed liquid. Such larger surface area may be greater on one side of the insert lateral axis 70 than the surface area occupied by the rearward region 55 on the other side of the insert lateral axis 70.

The insert 50 also may have a narrowed region in the area which rests in the crotch region 26 of the outer cover 20. This narrowing in the crotch region 26 may serve to enhance wearer comfort by eliminating size and bulk between the legs and provide a more underwear-like fit. The outer cover 20 may also have a narrowed region in the crotch region to achieve the same or similar advantages. Referring to FIG. 2B, it may also serve to better enable the crotch region 26 of the outer cover 20 to contain and maintain a laterally centered position of the insert 50, by ensuring that the insert 50, by having limited quantities of absorbent materials therein and limited width, does not swell beyond the space capacity of the crotch region 26 of the outer cover 20. Such narrowing may continue, for example, into the rear portion 55 of the insert 50, thereby creating overall shape/backsheet asymmetry. In an embodiment, the insert may have an hourglass shape with all edges optionally being rounded. Such a shaped insert may improve the crotch fit of the insert.

The insert 50 may also be asymmetrical across the insert lateral axis 70 in other ways, to serve the same, related or other purposes as those described above.

It will be appreciated, therefore, that insert asymmetry across the insert lateral axis 70 is a result of design and construction of the insert 50 so as to have only one front region 54 and only one rear region 55, i.e., the front and rear regions 54 and 55 are not interchangeable, if the designed fit, comfort, performance and appearance of the insert 50 are to be fully realized.

In the event of a pant, the insert may be symmetric across the insert lateral axis 70.

Grasp Structures, Removal and Disposal Aids

Referring to FIGS. 2H, 2R, 2T, 2V, 2Y, 3, and 4, the insert 50 also may include respective user grasp structures 59, 61. The user grasp structures 59, 61 may be provided to enable the user to quickly and easily grasp the insert 50 proximate its respective ends.

Grasp structures as shown and/or suggested may enable the user to more quickly grasp and stretch the insert 50 from a contracted position similar to that depicted in FIG. 3, to an extended position similar to that depicted in FIG. 4, which may be desirable for installing the insert 50 into an outer cover 20. If the user grasp structures 59, 61 are centered proximate to the respective ends of the insert 50 as shown, this may also provide visual assistance to the user for co-locating respective centered fastener component pairs, described in more detail below.

Additionally, the user grasp structures 59, 61 may serve to enable the user to quickly and easily grasp the insert 50 proximate to its respective ends, which as a result of their distance from exudation points on a wearer's body, are less likely to be soiled at the time replacement of the insert 50 becomes necessary or desirable. Thus, the user may be better enabled to avoid contacting the wearer's exudates with the user's hands when removing a soiled insert 50 from an outer cover 20. A configuration having laterally extending grasp structures 59 near the insert corners as suggested in FIG. 2Y may better enable a user to avoid soiling his/her hands when removing a soiled insert 50 from an outer cover 20, and better enable the user to fold or roll up the soiled insert 50 for disposal.

Figure 2D:
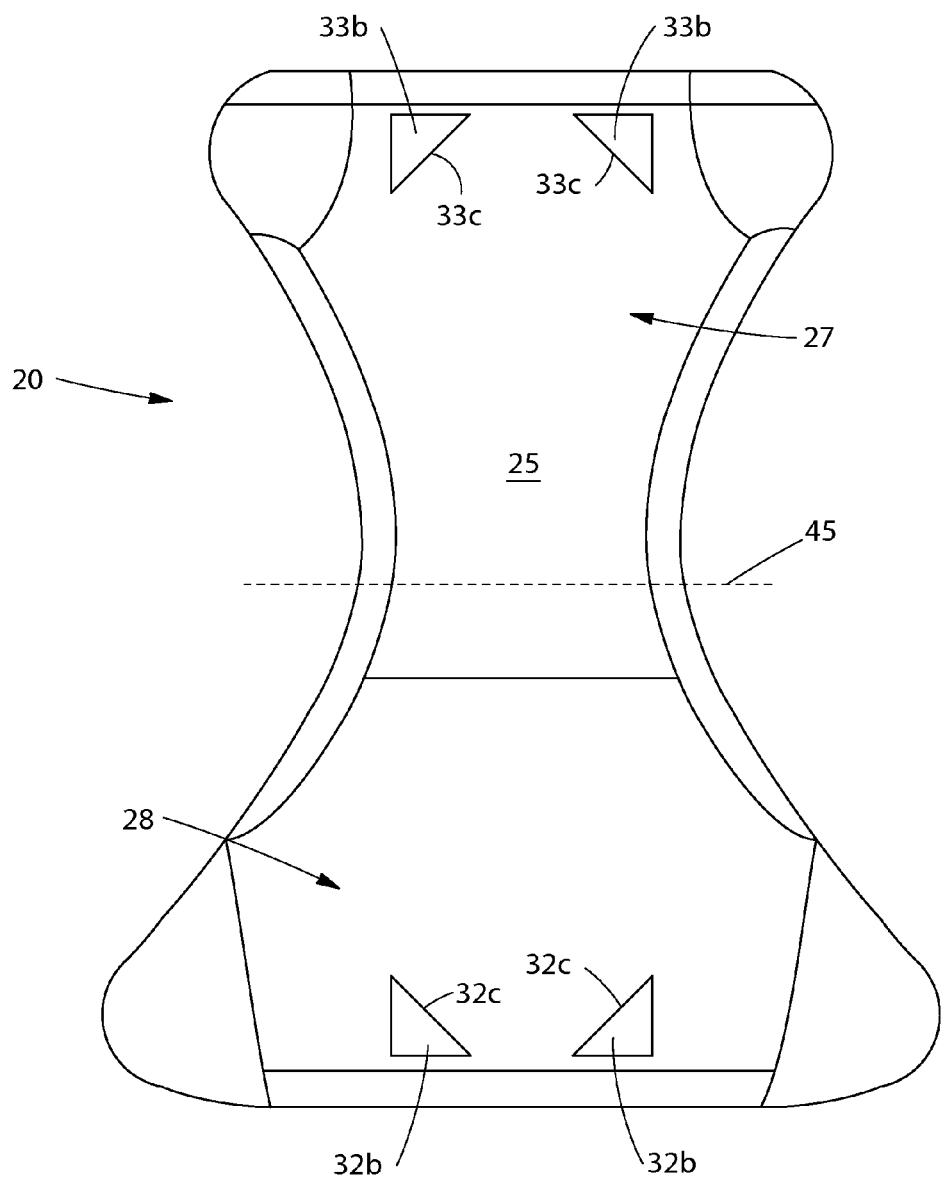
FIG. 2D is a plan view of an outer cover opened and laid flat, inner surface facing the viewer in accordance with a non-limiting embodiment of the present disclosure.
Figure 2E:
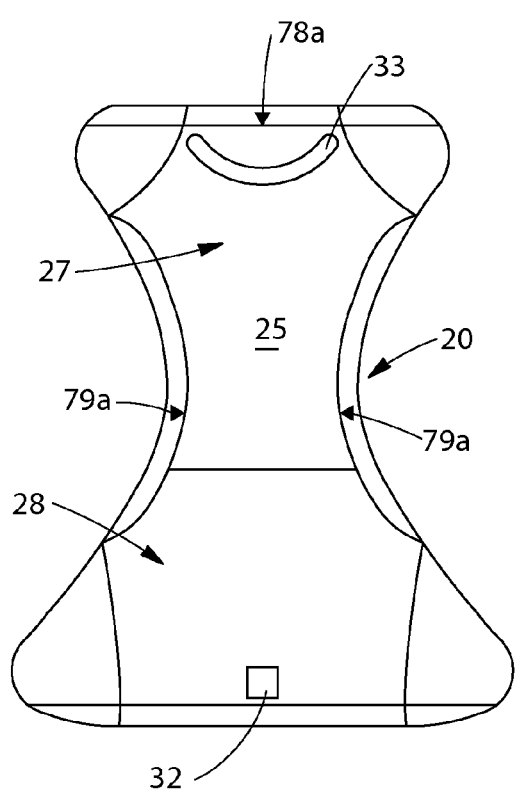
Figure 2F:
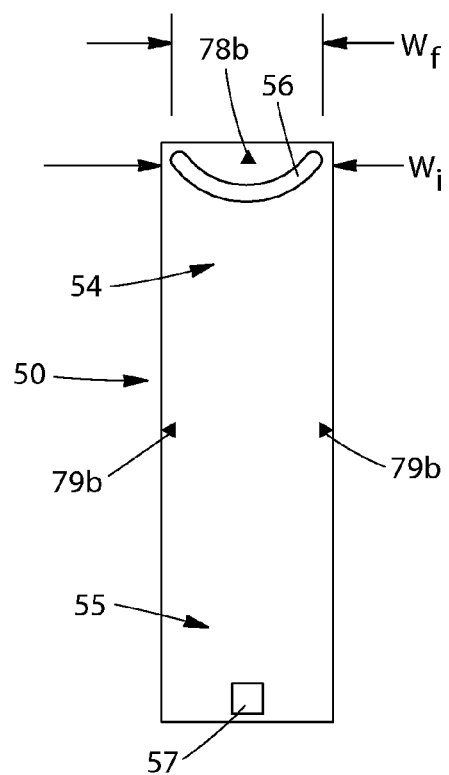
Figure 2G:
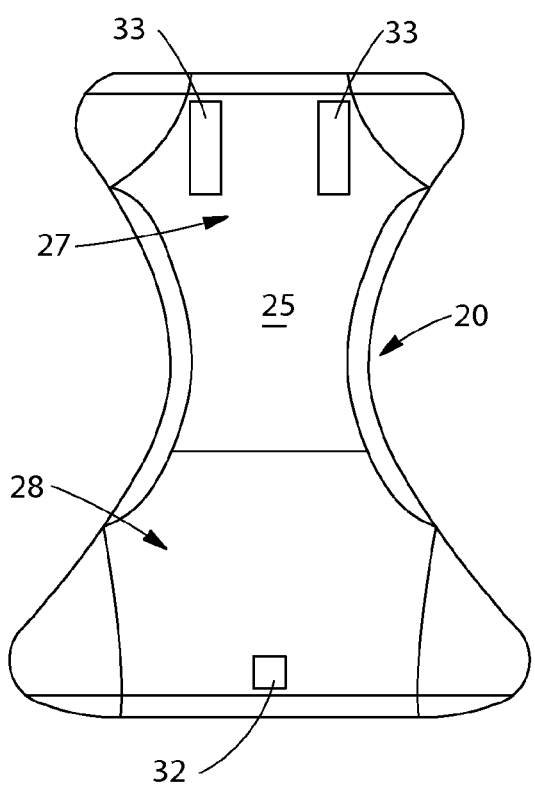
Figure 2H:
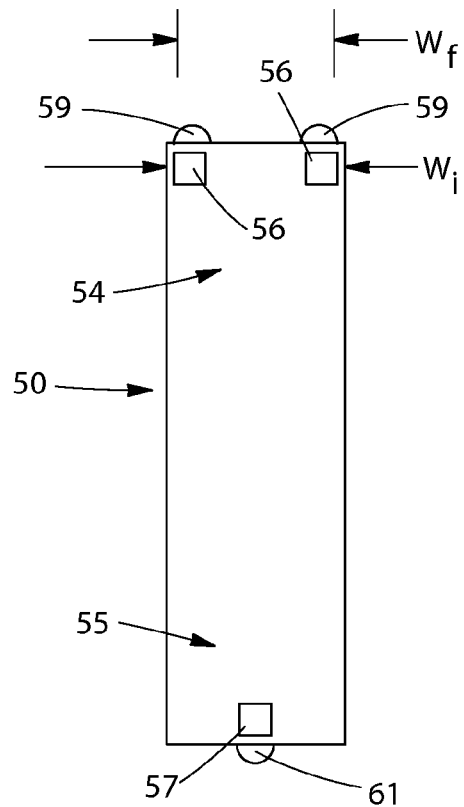
Figure 2M:
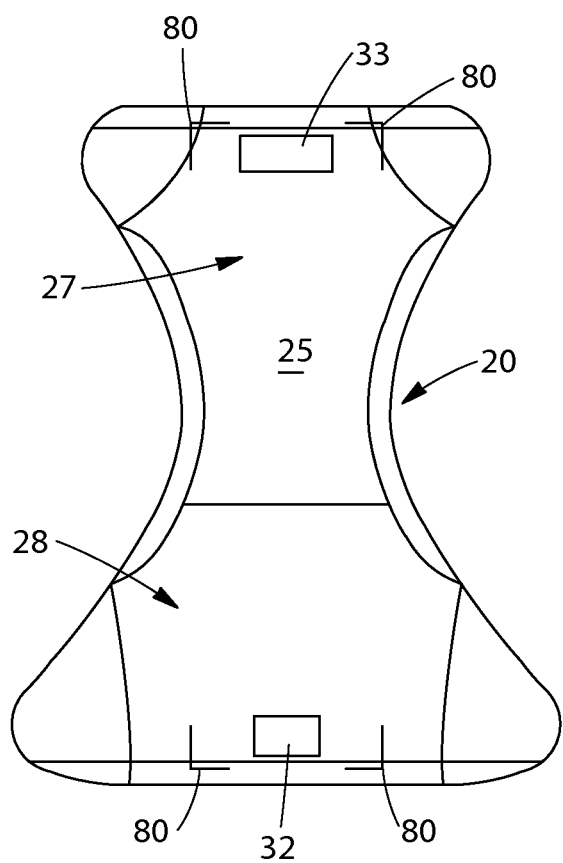
Figure 2N:
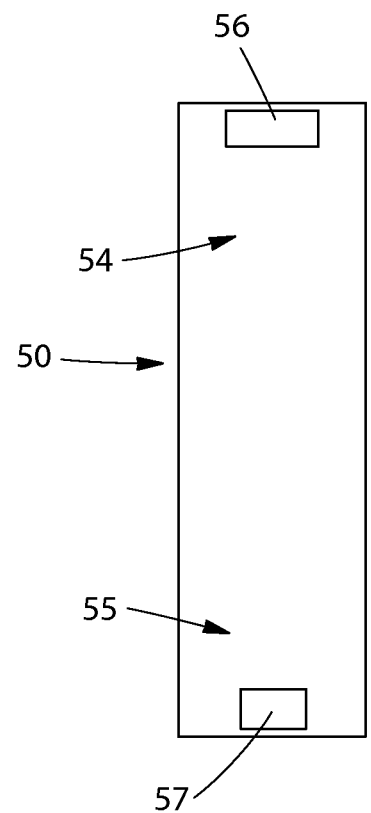
Figure 2S:
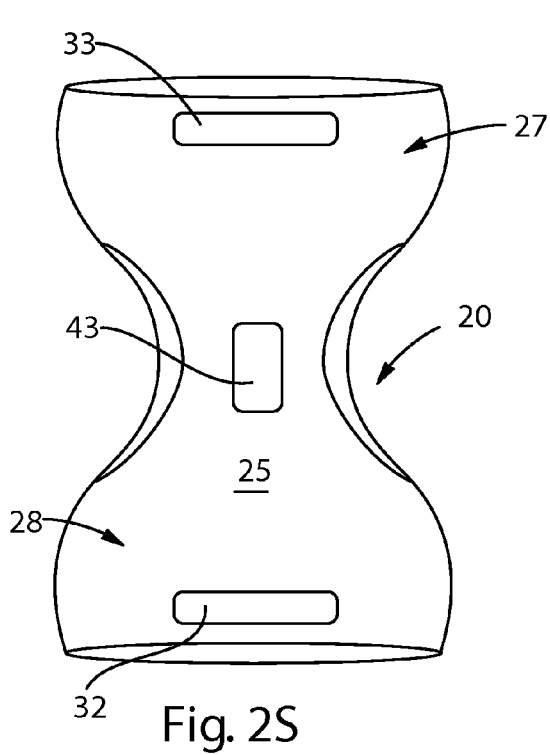
Figure 2T:
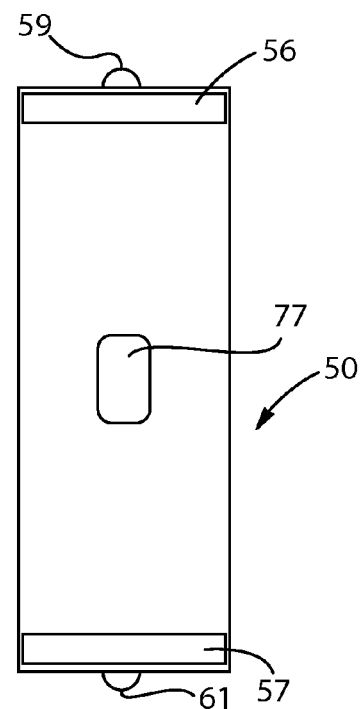
Figure 2U:
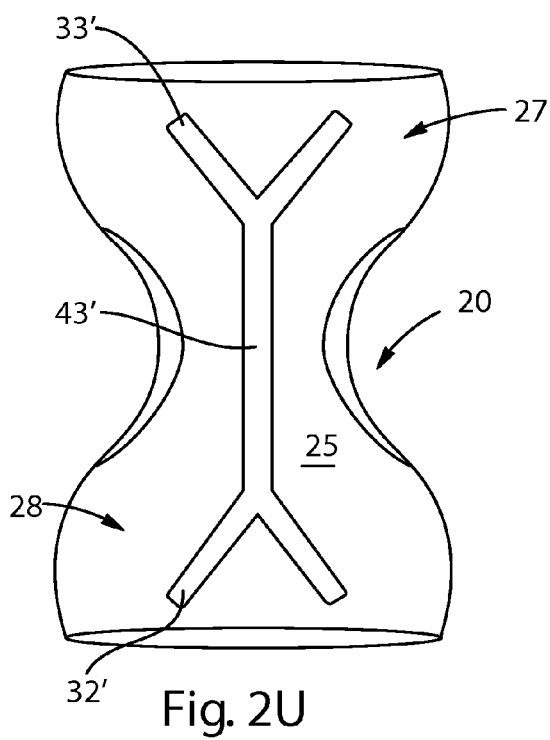
Figure 2V:
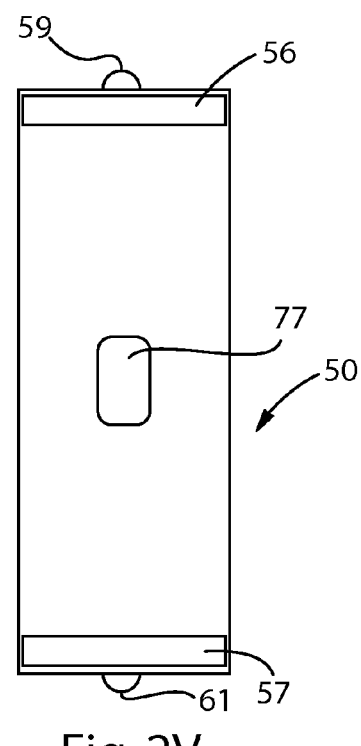
Figure 2W:
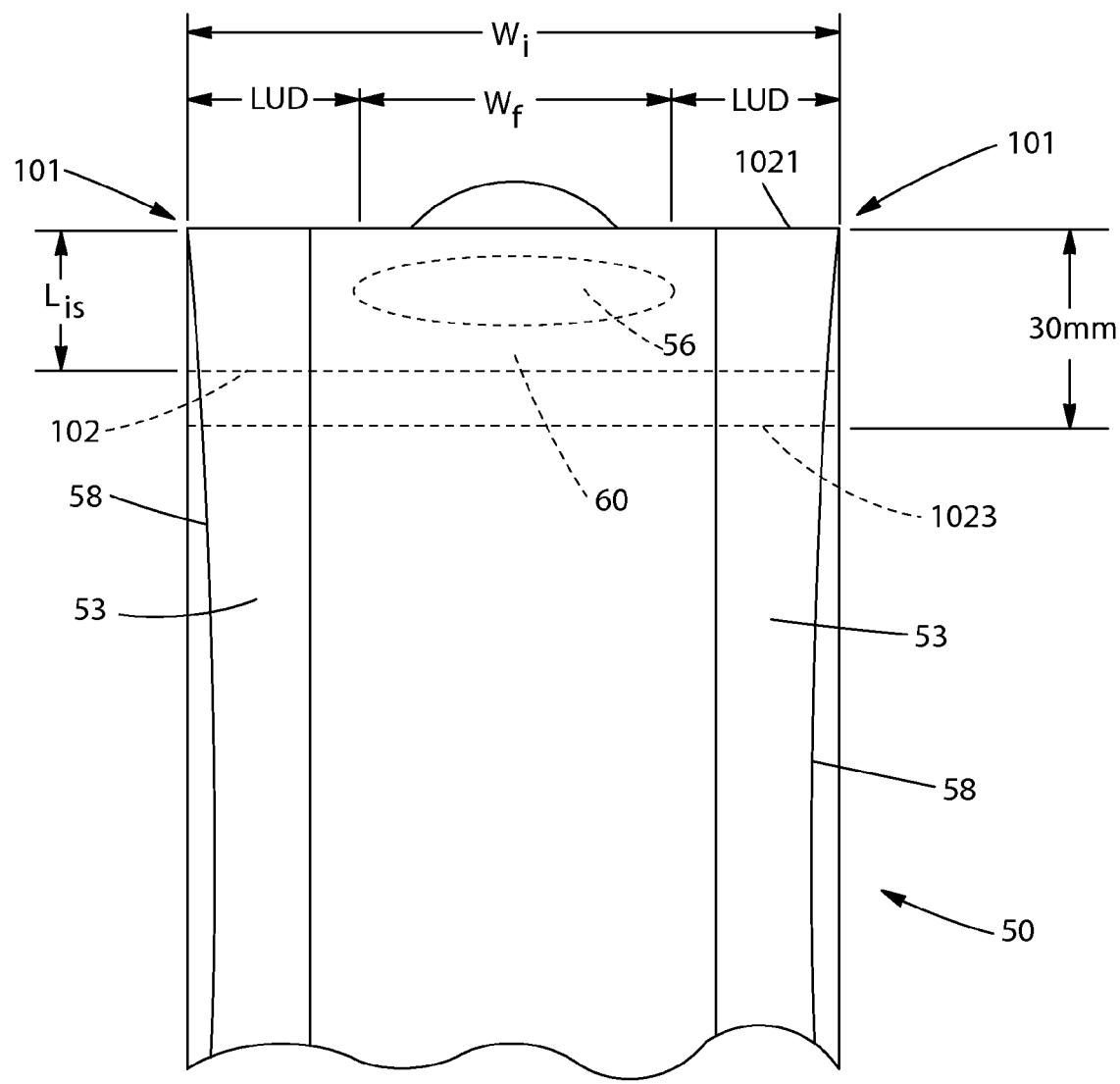
FIGS. 2W-2Y are plan views of ends of inserts opened and laid flat, inner surface facing the viewer in accordance with various non-limiting embodiments of the present disclosure.
Figure 2X:
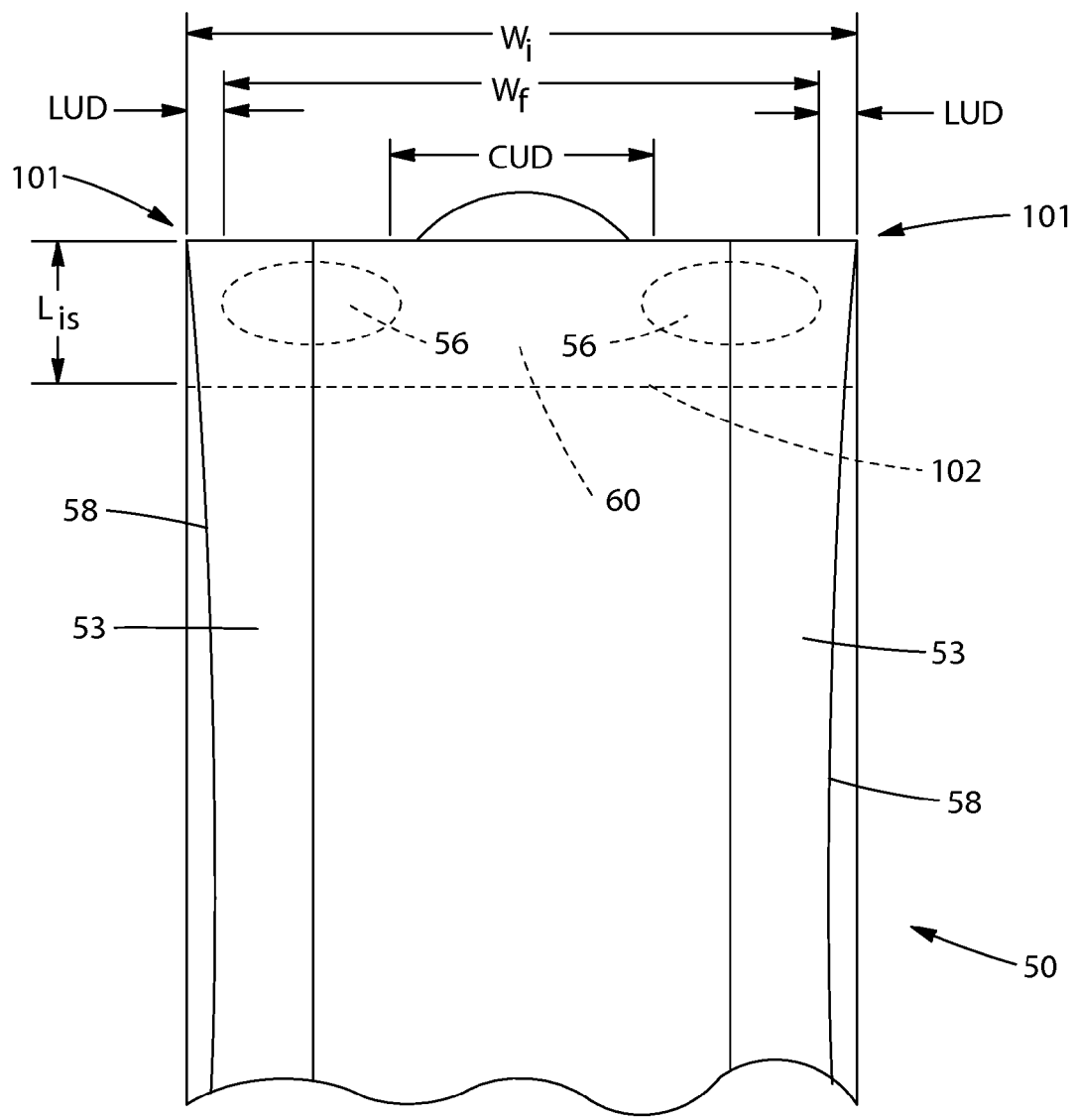
Figure 2Y:
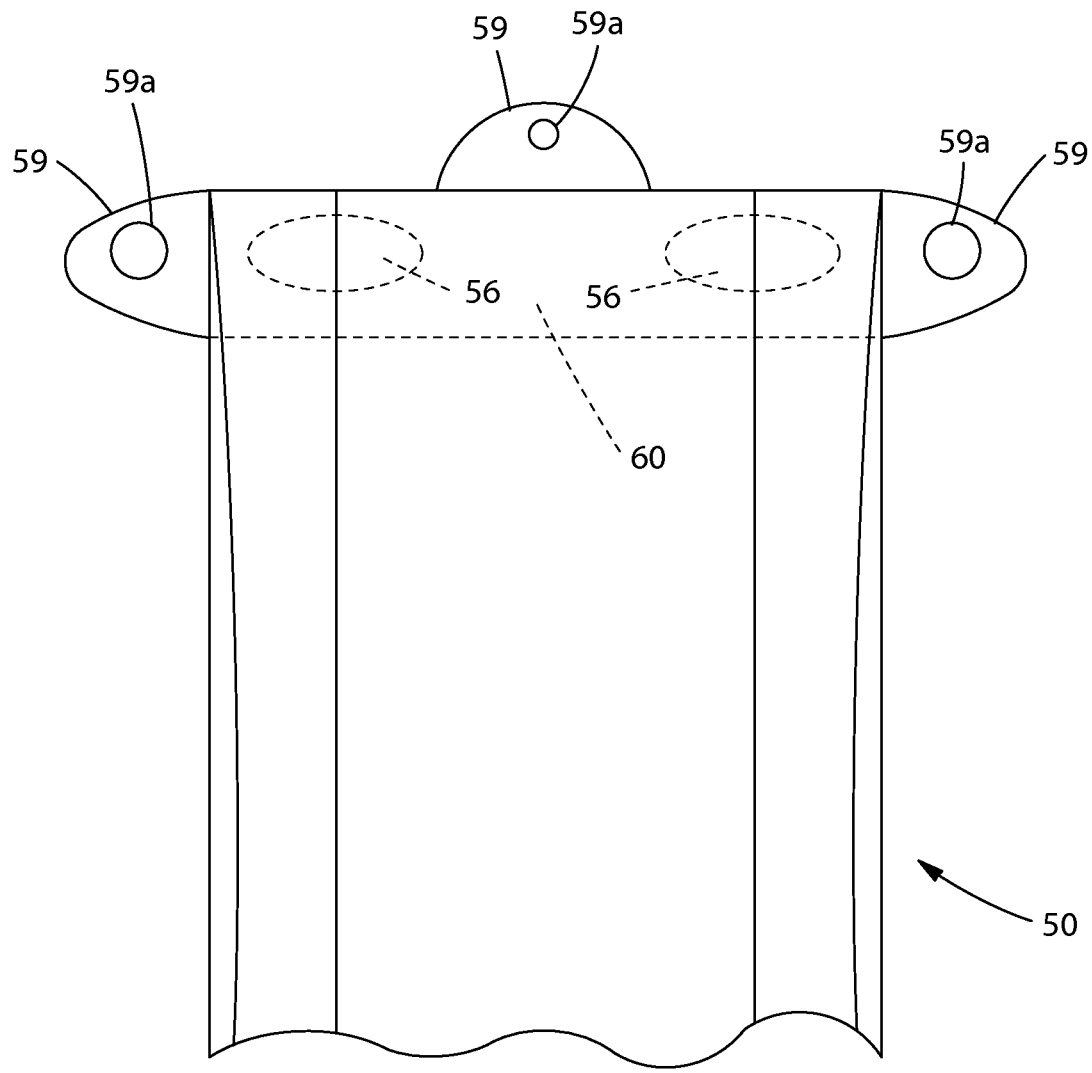
Figure 2Z:
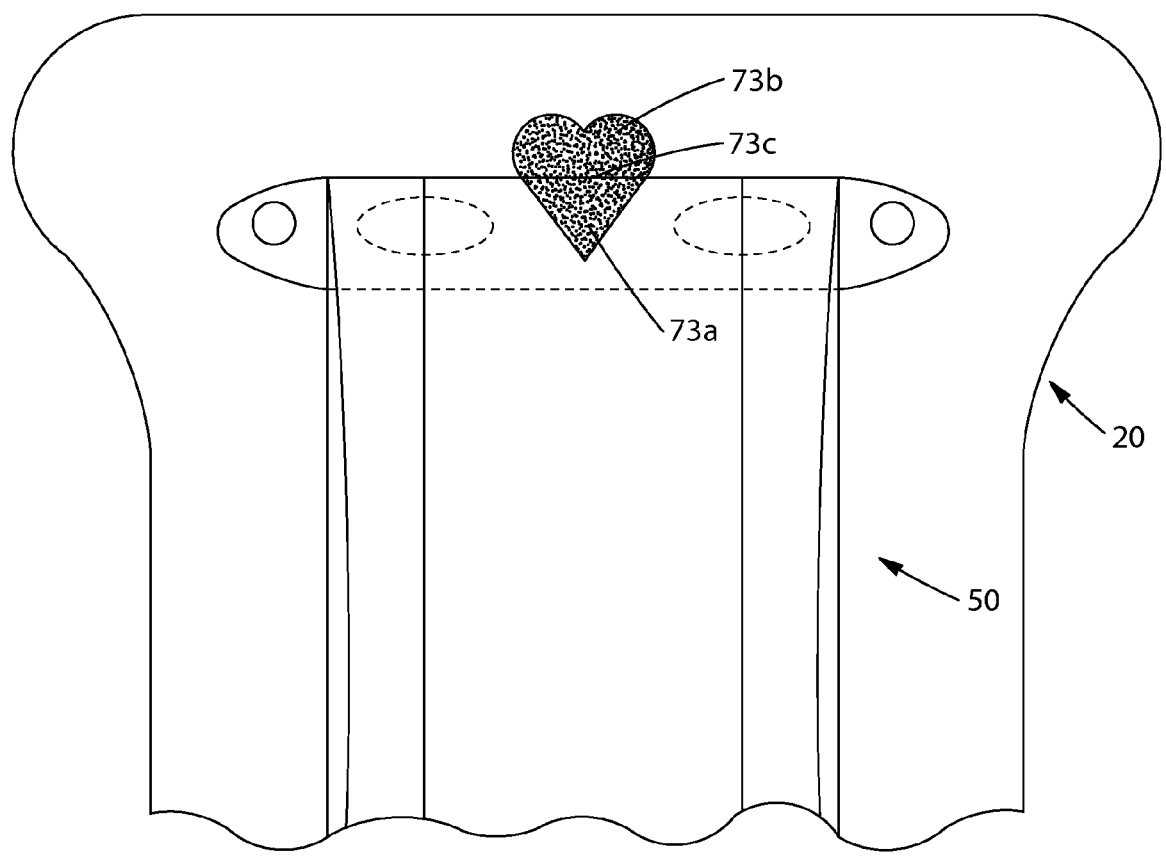
FIG. 2Z is a plan view of one end of an insert opened and laid flat, inner surface facing the view, shown overlaid on an outer cover in accordance with a non-limiting embodiment of the present disclosure.

In an embodiment, referring to the example depicted in FIGS. 2H and 2Y, it may be desirable in some circumstances to include more than one grasp structure 59 on the insert 50. This may be deemed useful in examples such as depicted in FIGS. 2H and 2Y, where more than one fastener component 56 is disposed on an end of an insert 50. In such circumstances, including a separate grasp structure 59 associated with and proximate to each fastener component 56 may enable a user to manipulate portions of an insert 50 to more easily accurately locate and install it within an outer cover 20 with the fastener components 59, 33 suitably co-located and/or aligned. It may also enable a user to more easily tug the fastener components 56 away from paired fastener components 33 to separate them, when it is necessary to remove the insert 50 from the outer cover 20, by localizing or focusing the user's tugging forces where they are needed to effect such separation.

The user grasp structures 59, 61 may include tab-like extensions as shown in FIGS. 2H, 2R, 2T, 2V, 2Y, 3 and 4, with free ends unattached to the outer cover 20 when the insert 50 is installed therein, which are easily graspable. The user grasp structures 59, 61 may have different forms as well. By way of non-limiting example, user grasp structures may take the form of loop-like extensions extending from the ends of the insert 50, finger holes through the insert 50 proximate the ends thereof, pockets with openings facing the lateral centerline 70 of the insert 50, and other structures that facilitate grasping and pulling of the insert 50 at locations proximate to its ends.

Additionally, the grasp structures 59, 61 may be formed of materials having a high coefficient of friction (e.g., at least about 0.5), resiliently compressible materials and/or surfaces having three-dimensional relief, to facilitate secure gripping and pulling the insert 50 by the user.

The grasp structures 59, 61 also may be configured or adapted so as can be folded over or under the respective ends of the insert 50 or the outer cover 20, toward the lateral centerline 70 of the insert 50. This may serve to conceal the grasp structures behind other materials and protect them from contamination by bodily exudates. Alternatively or in addition, it can serve to add convenience for the user and ease of pulling up a pant.

As suggested by FIGS. 2Y and 3, the grasp structures 59, 61 may be formed of, or be longitudinal, lateral or other extensions of, material(s) forming end support stiffeners 60, 62 (described further below).

Referring to FIGS. 2O and 2P, if the insert 50 does not comprise grasp structures, the attachment zones 32 and 33 may define recesses therein such that a user can grasp the ends of the insert 50 and remove it from the outer cover 20. Referring to FIGS. 2Q and 2R, if the insert 50 does comprise the graph structures 59, 61, the attachment zones 32 and 33 may not define such recesses.

Referring again to FIG. 3, an insert 50 may also include a disposal aid 81, configured to hold the insert 50 in a folded or rolled configuration for convenience of neat handling and disposal following removal of the soiled insert 50 from an outer cover 20. As suggested in FIG. 3, the disposal aid 81 may be in the form of a strip of removable/refastenable tape. Upon removing a soiled insert 50 from an outer cover 20, the user can fold or roll it up longitudinally, backsheet 52 facing out, and then lift and refasten a tape-form disposal aid 81 to the backsheet 52 to secure the insert 50 in the folded or rolled condition. Other forms of disposal aids, which serve to hold an insert 50 in a folded or rolled up condition with the topsheet 51 in and the backsheet 52 out, may be used.

Insert/Outer Cover Attachment Zone/Fastener Components; Orientation Indicia; Other Possible Features Referring to FIGS. 2B, 3 and 4, as previously noted, the outer cover 20 may have one or more insert attachment zones such as front and/or rear attachment zones 33, 32 disposed thereon. The insert 50 may have front and/or rear fastener components 56, 57 disposed thereon. Respective front and/or rear fastener components 56, 57 on the insert 50 may be selected and/or adapted to be cooperative to enable fastening with respective front and/or rear attachment zones 33, 32 disposed on the outer cover 20.

The insert may have one or more adhesives applied in some or all of the areas that are attached to the outer cover. For pants, the adhesive may be applied at the edges of the insert in order to ensure that the insert does not fold over at the edges during product use. Alternatively, or additionally, means may be provided that prevent fold over of the edges, such as stiffening of the insert edges.

Types, Locations and Localization of Fastening Locations

In one example, to enable fastening of respective front and rear fastener components 56, 57 of the insert 50 with respective front and rear attachment zones 33, 32 on the outer cover 20, respective fastening pairs 56, 33 and 57, 32 may include cooperating fastener components. An example of a suitable hook-and-loop fastening system is a VELCRO system, a product of Velcro Industries B.V., components of which are available from Velcro USA, Inc., Manchester, N.H. A hook-and-loop fastening system provides certain advantages. Because the respective hook and loop components are supplied in sheet or strip form, they may be cut into suitably shaped patches that can be affixed to a cloth substrate by various mechanisms, including adhesive bonding, mechanical bonding, ultrasonic bonding, sewing, stitching, serging, and/or edging, for example. If respective hook-and-loop patches are used as fastener components, relative ease of fastening, simplicity and convenience for the user (as compared with, for example, fastener components such as a button and button hole) are one among several advantages provided, because fastening is effected simply by placing the fastener components in face-to-face contact and applying gentle pressure.

Some types of hook components may, in some circumstances, tend to snag or catch undesirably on a variety of materials in addition to intended corresponding loop components, while most types of loop components currently available do not have this tendency. Thus, in some circumstances it may be desired that patches of hook components form one or both of attachment zones 33, 32, while patches of loop components form one or both of insert fastener components 56, 57. This arrangement places a non-snagging attachment zone component on the outer cover 20. This may be desirable in some circumstances, such as when the outer cover 20 is designed to be reusable—reducing the likelihood that attachment zones on an outer cover 20 will undesirably snag on other parts of the outer cover 20 or on other articles, such as clothing articles, being stored or laundered along with the outer cover 20.

However, fastening pairs 56, 33 and 57, 32 need not necessarily include respective components of a hook-and-loop fastening system, and need not necessarily include respective components of a two-component fastening system. Rather, a fastening system may require only one fastener component, or use other types of fastener components. The fastener components used may be adapted to engage, retain, and otherwise hold the insert 50 or a portion thereof. An attachment zone on the outer cover 20 may include a patch of adhesive; a structure having a region of relatively high coefficient of friction; a pocket; flap; strap; or other capturing, holding and/or retaining surface, device or structure. Thus, referring to FIG. 2C in one example, the inside of the outer cover 20 may include one or more pocket structures 32a, 33a situated on or along the inner surface 25 of the outer cover 20, in, e.g., the front waist region 27 or rear waist region 28. Such a pocket structure may have an opening facing downward or upward (relative to the wearer in a standing position, and relative to FIG. 2B). A pocket structure may be adapted to receive, fit and capture, for example, the forward edge and a portion of the forward region 54 of the insert 50. A pocket structure 32a, 33a may have an opening facing the lateral axis 45, such that an end of the insert 50 may be inserted therein and retained thereby. A pocket structure may alternatively have an opening facing away from the lateral axis 45, such that an end of the insert 50 may be inserted therein and retained thereby, and then the insert 50 may be folded back over such opening and toward the lateral axis 45. Referring to FIG. 2D, in another example, one or more pockets 32b, 33b may be provided in the front and/or back waist region 27, 28 on the inner surface 25 of the outer cover 20 positioned such that a corner of an insert 50 may be inserted into and retained by the pockets. Such pockets may have respective openings defined by edges of material 32c, 33c forming an angle with respect to both the lateral and longitudinal axes of between about 0 and 90 degrees, but more preferably, between about 30 degrees and 60 degrees, specifically reciting all 1 degree increments within the specified ranges and all ranges formed therein or thereby. One or more of such fastener components may be provided in lieu of, in addition to, or in combination with, other fastener components disposed at the front waist region 27 of the outer cover 20 and the forward region 54 of the insert 50. As one example, an outer cover 20 may have a pocket structure 33a in the front waist region 27 (see FIG. 2C) in combination with a patch of loops component forming the rear attachment zone 32 (see FIG. 2B). With such a structure and a suitably adapted insert 50 having a patch of hooks as fastener component 57, to install the insert 50 the user may insert the forward edge of the insert 50 into the pocket structure 33a, and then fasten the rearward portion of the insert 50 into the rear waist region 28 of the outer cover 20 by engaging the attachment zone 32 to the fastener component 57.

In another example, the attachment zones 32, 33 may be respective patches of hook components, while the fastener components 56, 57 may simply be surfaces formed of woven or nonwoven material adapted to be attachably engageable by such hook components. In yet another example, the fastener components 56, 57 may include respective patches of hook components, while the attachment zones 32, 33 may simply be surfaces formed of woven or nonwoven material suitable for, or adapted to be, attachably engageable by such hook components.

Also, a fastener component in any form, including a respective component of an attachment zone/fastening component pair 56, 33 and 57, 32 may be disposed on either of the insert 50 or the outer cover 20. For example, a hook patch may be disposed on either of the insert 50 or the outer cover 20, with a cooperating loop patch disposed on the other of the insert 50 or the outer cover 20.

An attachment zone such as the attachment zone 32 on the outer cover 20 may be attached or connected to at least a portion of an anchoring system, such as the anchoring band 38, or the diagonal anchoring band 38a. This may provide, as one advantage, the distribution of structural loading resulting from the weight of absorbed or contained exudates, as described in one or more of the patent applications cited above, in the description of anchoring bands.

In an embodiment, referring to FIGS. 2U and 2V, an attachment zone may take the form illustrated in FIG. 2U, for example. The attachment zone may have a front attachment zone 33', a rear attachment zone 32', and a central attachment zone 43'. The attachment zone may be continuous or discontinuous about its length. Providing an attachment zone as illustrated in FIG. 2U allows the insert 50 to be easily engaged with and adjusted relative to the outer cover 20 owing to the fastening components 56, 77, and 57 on the insert 50. In other embodiments, any suitable number of fastening components may be provided on an insert and any suitably shaped attachment zone may be provided on the outer cover 20. The example embodiment of FIGS. 2U and 2V, through the central attachment zone 43' and the fastening component 77, allows the insert 50 to be supported in its central region. Referring to FIG. 2S, another central attachment zone 43 on an outer cover 20 is illustrated. The outer cover 20 of FIG. 2S may be used with the insert 50 of FIG. 2T or the insert 50 of FIG. 2V, for example, and provide support to a central region of an insert. Referring to FIG. 2V1, another central attachment zone 43" on the outer cover 20 is illustrated. The attachment zone also comprises a front attachment zone 33" and a rear attachment zone 32". The insert 50 illustrated in FIG. 2V2 discloses a fastening component 77' for use with the outer cover 20 of FIG. 2V2 of FIG. 2S, for example. This outer cover 20 and insert 50 combination provides support for the insert 50 in the central region thereof. The attachment zone on the outer cover 20 and/or the fastener component on the insert 50 in FIGS. 2V1 and 2V2 may be continuous or discontinuous and still achieve the same benefit of supporting the central region of the insert 50 when the insert 50 is attached to the outer cover.

Fastening locations may be multiply disposed, for example, at each of the four corners of the insert 50 and corresponding locations on the outer cover 20, and even at other locations along the insert 50 and the outer cover 20, created by fastener components suitably selected and disposed. For example, the fastener components may be disposed along the longitudinal sides proximate the ends of the insert 50 in the forward and/or rearward region 54, 55 of the insert 50. The fastener components may be disposed adjacent an edge of the insert 50, or may be disposed laterally and longitudinally inboard of the edge. For example, a fastener component may be disposed at least 1, 2, or 3 cm from any or all edges of the insert 50. In certain embodiments, at least one fastener component is disposed at least a distance from the lateral or longitudinal edge, or both, of the insert 50 equivalent to one-fourth the width of the insert 50. In one embodiment, a fastener component may be disposed along at least about one-fifth of the length of the longitudinal axis of the insert 50.

A fastener component may have the form of a patch or strip, of material bearing adhesive, pressure-sensitive adhesive, or a cohesive material on a garment-facing surface, or otherwise be formed of adhesive, pressure-sensitive adhesive or cohesive material. The patch or strip may cover at least about 20%, 50%, 75%, or even substantially all of, the garment-facing surface of the insert 50. Such a patch or strip may be affixed to and cover at least a portion of the garment-facing surface of the insert 50 and may, optionally, be covered by release paper to preserve the adhesive/cohesive and prevent, or at least inhibit, contamination and unintended adhesion during storage and carrying, until the user is ready to install the insert 50. When the user is ready to install the insert 50 within an outer cover 20, the user may peel away the release paper, thereby exposing the adhesive/cohesive and making it available to function to adhere the insert 50 within the outer cover 20. A fastener component including an adhesive or cohesive may be combined in a fastening configuration with other types of fastener components described herein on an insert 50, at either or both ends; or one end of an insert 50 may have one or more adhesive or cohesive-type fastener components and the other end of the insert 50 may have one or more other type(s) of fastener components described herein.

A fastening system such as either of the attachment zone/ fastener component pairs 56, 33 and 57, 32 may form a singularized, laterally centered and localized fastening location proximate each of, or either, the forward/front and/or rearward/rear ends/regions as suggested in the Figures. Having a singularized, localized fastening location substantially laterally centered respectively on the insert 50 and the outer cover 20 at one or both of the insert ends, as suggested in FIGS. 2B and 3, for example, may provide certain advantages.

One advantage may be simplicity and ease of installation for the user, resulting from singularization and localization of a location at which the user must co-locate and fasten the insert 50 to the outer cover 20 at an end of the insert 50.

A second advantage may result from the partially force-decoupled attachment of the insert 50 within the outer cover 20 resulting from a singularized, localized fastening location. With this force-decoupled arrangement, the portions of the outer cover 20 surrounding the attachment zones 33, 32, such as the waistband portions 34, 35, and the front and, especially, rear waist regions 27, 28, may laterally stretch and contract substantially independently of and unimpeded by the structure of the insert 50 and portions thereof. This may avoid lateral buckling or bunching along the ends of the insert 50 with lateral contraction of the outer cover 20, which may cause discomfort and/or may create gaps between the wearer-facing surfaces at the end of the insert 50 and the wearer's skin, and a resulting vulnerability to leakage. It may also avoid having the structure of the insert 50 restrict the outer cover 20 from stretching or contracting laterally, which may otherwise occur as a result of a more force-coupled arrangement therebetween. Such lateral bunching, buckling or restricting of stretch and contraction of the outer cover 20 otherwise may be incidental to fastening the insert 50 within the outer cover 20 in a manner that force-couples a greater portion of the width of the insert 50 to outer cover 20, e.g., by use of more than one fastening location across the width of the insert 50 proximate a given longitudinal location, or by use of a laterally delocalized/extended continuous fastening location along a larger portion of the width of the insert 50. Force-decoupling, therefore, may provide for enhancement of fit, containment capability, appearance and wearer comfort, and improved capability for maintenance of intended insert shape and performance while worn.

Thus, in one example, referring to FIG. 2W, a patch of hook components forming a fastener component 56 and/or 57 attached to the insert 50 may be substantially laterally centered on the insert 50 as suggested in the figure, and may have an effective width $W_f$ attached along the insert 50 that extends no more than about 50% of the greatest lateral width $W_i$ of the insert 50 not including an end support stiffener (as described below). This provides that no more than about 50% of the width of the insert 50 will be force-coupled to the outer cover 20 by operation of the patch of hook components, and that, correspondingly, at least about 50% of such width (i.e., that portion of the width $W_i$ that is not attached to, or force-coupled to, the insert 50 along the width $W_f$) is force-decoupled from the outer cover 20 when the insert 50 is installed therein. In some circumstances, it may be desired that the portion of the lateral width of the forward region 54 and/or, especially, of the rearward region 55 of the insert 50 that is force-decoupled from the outer cover 20 is even greater than about 50%. Thus, it may be desired that the width $W_f$ of a fastener component 56 or 57, comprising, e.g., a continuously attached patch of hooks, is no more than about 40%, no more than about 30%, or even no more than about 20%, of the width $W_i$. In another example, it may be desired in some circumstances that at least about 50% of the width $W_i$ in the front and/or rear regions 54, 55, is force-decoupled from the outer cover 20. In some circumstances it may be desired that more than about 50%, more than about 60%, more than about 70%, or even more than about 80%, of width $W_i$, is force-decoupled from the outer cover 20 when installed therein. In an embodiment for pants, it may be desirable to force-couple 100% or less of the insert 50 to the outer cover 20.

In some circumstances, however, it might not be deemed important that more than 50% of the width $W_i$ is force-decoupled from the outer cover 20. In some circumstances a useful benefit may be derived from force-decoupling a lesser portion of the insert width, while satisfying another objective. For example, an insert 50 might include a fastener component 56 and/or 57 formed of a patch of hooks that is comparatively less aggressive than other hooks-type components available, and therefore requires relatively greater contact surface area to provide satisfactory fastening performance. In circumstances such as these, and others, it may be sufficient for achieving some force-decoupling benefits while still providing required fastening/holding performance, for less than about 90%, alternatively less than about 75%, or alternatively less than about 60%, of the lateral width of the insert 50 to be force-coupled to the outer cover 20.

Other fastener components that provide such singularized and relatively laterally localized fastening locations, providing limited force-coupling across the lateral width of at least one end of the insert 50, are possible. Other suitable fastener components may include tab and slot fasteners, macro hook and loop fasteners, button fasteners, magnet fasteners, interlocking fasteners, hook and slot fasteners, snap fasteners, adhesive fasteners, and other fastener types available.

While the singularized, localized fastening locations discussed above may provide the advantages described, in some circumstances they may also introduce disadvantages. In some insert embodiments, the outer corners of the insert 50, if not secured to the outer cover 20, may be prone to buckling, sagging or rotating toward the insert lateral axis 70, or out of the contour of the predominate portion of the insert 50 as worn, in response to forces resulting from wearer motion or position, or exudate loading, e.g., in the crotch region. Also, referring to FIG. 3, and from the description of the standing cuffs 53 with the cuff elastics 58a, 58b along the edges 58 as set forth above, it can be appreciated that, if longitudinal tensile forces are imparted by the pre-strained cuff elastics 58a, 58b, the standing cuffs 53 may tend to pull the respective outer corners of the insert 50 longitudinally toward each other. If there is not structure present to resist these forces, the outer corners of the insert 50 may sag or buckle, and the standing cuffs 53 may be loosened, sag, or even collapse. This may lead to gaps between the edges 58 of the standing cuffs 53 and the wearer's body. In turn, this may compromise the cuffs' gasketing function, and increase the risk of leakage.

The disadvantages identified above may in some circumstances be of greater concern in the front region 54 of the insert 50. While it may be important at both ends of the insert 50, control of the insert corners may be particularly important in the forward region 54, due to its closer proximity to the urethra. Insert designs in which exuded urine is predominately stored in the forward region 54 may concentrate the weight and expansion stress of exudate loading in the forward region 54, and thus, on the forward corners of the insert 50. Stresses in the front of the insert 50 acting at or near the forward corners also may be applied, or multiplied, by the wearer's forward articulation of the legs (together or alternately as when crawling or walking) or bending of the torso forward at the waist.

At the same time, in some circumstances force-decoupling may be more desirable in the rear region 55 of the insert 50 and the chassis 28, 55 because greater demands for waistband stretch in the rear may result from anatomical features and body movement modes. For example, because a wearer may ordinarily bend forward at the hips but not backward, such motion, combined with the contours of the buttocks and hips, may impose a greater demand for lateral stretch and contraction in the rear waistband area than in the front waistband area, for purposes of fit, comfort and appearance. In other instances, the force-decoupling may be more desirable in the rear region 55 than the front region 54 of the insert 50, especially in pant embodiments.

Thus, as depicted in FIGS. 2E-2F and 2G-2H, examples are contemplated wherein singularized/localized, laterally centered, force-decoupled attachment zone/fastener component pairs 32, 57 may be employed in only one of the front or rear waist regions of the wearable absorbent article 10, such as in the rear waist region 28 of the outer cover 20 and rearward region 55 of the insert 50, while attachment zone/fastener component pairs 33, 56 effectively controlling the forward corners of the insert 50 may be employed in the other region, such as the front waist region 27 of the outer cover 20 and the forward region 54 of the insert 50. This arrangement may serve to allow force decoupling in one region where force decoupling may be most desirable, and provide insert corner control in another region where corner control may be most desirable.

Control of the corners to reduce the likelihood of sagging and/or rotation of components or portions of an insert 50 may be improved, in one group of examples, by placement and/or shaping of fastener component pairs. Referring again to FIGS. 2E-2F and 2G-2H, it can be seen that the attachment zone/fastener component pairs 33, 56 in, e.g., the respective front/forward regions of the outer cover 20 and the insert 50 may be arranged, shaped, sized and/or placed such that the forward corners of the insert 50 are effectively captured and held to the outer cover 20 when the insert 50 is installed therein. The fastener component(s) 56 disposed on the insert 50 may, accordingly, have an effective width $W_f$ at least equal to about one-fourth, or one-half, of the width of the insert 50. In some examples, the width $W_f$ of the fastener component(s) may be between about 50% and 100%, or between about 75% and 95%, or even between about 85% and 95% of the width $W_i$. (See FIGS. 2W and 2X for reference with respect to $W_i$ and $W_f$.) If multiple fastener components 56 are included, e.g., in a line, array, or other pattern, the fastener component width $W_f$ is considered to be the lateral distance between the laterally outermost edges of the fastenably effective portions of the laterally outermost fastener components 56. (For purposes herein, "fastenably effective portion" means any portion of a fastener component that effectively force-couples a portion of the width of an insert to an outer cover.)

Referring to FIG. 2G-2H, in examples having more than one fastener component 56 at a given longitudinal end of the insert 50, an unattached portion of the insert lateral width along the end will be present between the laterally inside edges of the fastener components 56. This may create the possibility for sagging and/or buckling of the end of the insert 50 across the unattached portion, and in turn, the possibility for wearer discomfort or exudate leakage along the end.

Insert End Support Stiffeners

In order to further address issues which may be presented by force-decoupling or force-coupling and attachment zone/fastener component arrangements discussed above, it may be desirable to include one or more stiffening components proximate one or both ends of the insert 50 or through the length of an insert. For example, in some circumstances it may be desirable for an insert to be resistive to excessive bending, bunching or buckling about the insert lateral or longitudinal axis. In other circumstances it may be desirable for insert corners or insert ends to be resistive to sagging or buckling.

In an embodiment, referring to FIGS. 3 and 4, an end support stiffener 60 and/or 62 may be included at one or both ends of the insert 50. Such an end support stiffener may serve to aid the user in engaging the insert 50 with the outer cover 20, and to help the insert 50 maintain its intended shape and configuration while being worn beneath an outer cover, i.e., help maintain its intended shape, position and gasketing functions (e.g., of the standing cuffs 53). An end support stiffener 60, 62 also may help control the corners of the insert 50 regardless of the size, type or location of fastener components included on the insert 50. In addition to providing resistance to longitudinal pull of the cuff edges 58, the end support stiffeners 60, 62 may provide resistance to bending in any direction or plane.

An end support stiffener 60, 62 may be affixed to, or incorporated within, the insert 50 proximate one or both ends thereof as suggested by FIGS. 3 and 4. In addition to increasing the tendency of the insert 50 to maintain optimal shape while in use, such an end support stiffener may increase the tendency of the associated end of the insert 50 to stay open and flat before the insert 50 is installed in an outer cover 20. Because the ends of the insert 50 may otherwise be folded over or bunched while being stored and/or carried by the user before installation, an end support stiffener may enhance user convenience, by causing the associated end of the insert 50 to maintain or seek a shape/configuration that requires less manipulation by the user to install it into and/or remove it from an outer cover 20.

Referring to FIG. 4, one or more of the end support stiffeners 60, 62 may be disposed in a lateral orientation with respect to the insert 50 and formed of any flat, sheet-like or card-like material, or any flat, stiffened assembly that adds stiffness to the insert end that exceeds the stiffness of the adjacent portion lying nearer the insert lateral axis 70. In one example, an end support stiffener may be formed by folding over a portion of the insert end material(s) to create a stiffened region comprising folded layers of material. In another example, an end support stiffener 60, 62 may be formed by depositing onto the end of the insert 50 lateral bands, strips or other shapes or patterns of deposits of liquid or semi-liquid adhesive or other material that cures or cools to a stiffened state, and thereby imparts added stiffness to the substrate to which it is applied. In another example, an end support stiffener may be formed of cardboard in sheet form, or similar material. One example of suitable stiffener material is 0.031 in. thick VOLARA 6A foam supplied in sheet form (a product of Sekisui Voltek, LLC, Lawrence, Mass.); other thicknesses of this and like materials are available and may be used. Stiffener materials may be laminated with or adhesively applied to portions of the insert 50 to be stiffened, or applied, affixed or included by any other suitable method. Other examples of suitable stiffening materials may include added layers of nonwovens; tufted nonwovens; films; laminates of films, nonwovens and/or other materials; patches of fastener loops or hooks components; portions of a suitable grasp structure; portions of one or more of the other insert and/or core materials, etc. Persons of ordinary skill in the art will readily appreciate that stiffness as described and measured by tests herein may be increased by the selection and/or addition of materials to the construction of an insert end in a variety of ways.

The end support stiffeners 60, 62 may increase planar, lateral and/or longitudinal stiffness of the areas of the insert 50 in which they are located, as compared with portions of the insert 50 adjacent such stiffeners and closer to the lateral axis 70 with respect to a plan view (such as FIG. 4). These differing orientational aspects of stiffness may affect various attributes of the insert 50. For example, referring to FIG. 3, it can be seen that the ability of a portion including an end support stiffener 60, 62 (stiffened portion) to resist longitudinal tension forces in the standing cuffs 53, particularly along the edges 58, may be affected by one or more of planar and longitudinal stiffness of the stiffener. The pliability and relative comfort or discomfort for the wearer, associated with presence of a stiffened portion, may be affected by planar stiffness of the stiffener.

The stiffeners may also help the inserts 50 from bending inappropriately or undesirably after packing. In an embodiment, one or more stiffeners may be provided that help maintain or maintain the insert in an arcuate position longitudinally (much like when being positioned on a wearer) so that the insert can be easily inserted into a pant having a waist region with a continuous circumference.

One measure of stiffness relevant to the ability of a stiffened portion to resist longitudinal tension forces in standing cuffs is Edge Deflection Force, which is measured according to the Edge Deflection Force Measurement Method set forth below. In view of the potentially competing objectives of structural rigidity and comfort, it may be desired that a stiffened portion of an insert end, i.e., the portion of an end that includes an end support stiffener, have an average Edge Deflection Force (30) from at least about 0.2 N, alternatively at least about 0.5 N, or alternatively about 0.2 N to about 3.0 N, or about 0.4 N to about 2.0 N, or even about 0.50 N to about 1.70 N, as measured by the Edge Deflection Force Measurement Method set forth below. (Where the terms "Peak Edge Deflection Force (y)" or "Edge Deflection Force (y)" are used herein, "y" is the lateral dimension in millimeters of distance 1010 as described in the Edge Deflection Force Measurement Method and depicted in FIG. 19A herein.)

Other measures of stiffness relevant to the comfort of a stiffened portion are the Peak Bending Force and Bending Stiffness, which are measured according to the Bending Stiffness Measurement Method set forth below. In view of concerns for comfort, it may be desired that a stiffened portion of an insert end, i.e., the portion of an end that includes an end support stiffener, have an average Peak Bending Force of between about 0.1 N and 4.0 N, alternatively between about 0.1 N and 3.7 N, alternatively, between about 0.2 N and 3.0 N, or between about 0.5 N and 2.5 N. Additionally, or in the alternative, it may be desired that a stiffened portion of an insert end have an average Bending Stiffness of between about 100 N/m and 1,000 N/m, alternatively between about 100 N/m and 600 N/m, or alternatively between about 200 N/m and 500 N/m, or 300 N/m and 400 N/m.

An end support stiffener 60, 62 may be located adjacent or near one or both ends of the insert 50 and may extend laterally from the lateral center thereof to stiffen the insert 50 along a substantial portion of its width. Alternatively, a stiffener may be disposed such that its longitudinally outermost edge (relative the insert 50, i.e., the edge farthest from lateral axis 70) is disposed at least about 0.5, 1, or 2 cm from the associated end of the insert 50, and may be substantially laterally centered about the longitudinal center line of the insert 50. The one or more end support stiffeners 60, 62 may have a width of at least about 30%, alternatively about 40%, or alternatively about 50% to about 100% of the width $W_i$, or may extend beyond the longitudinal edges of the other materials forming the insert 50. An end support stiffener 60, 62 may have any longitudinal dimension, although a longitudinal dimension less than 25% of the insert length L may better assure comfort for the wearer, and therefore, may be desired. In some examples, the longitudinal dimension $L_{is}$ (see FIGS. 2W, 2X) of an end support stiffener 60 may range from about 5 mm to about 50 mm, measured from the longitudinally outermost edge of the stiffener, to the longitudinally innermost extent (i.e., nearest lateral axis 70) of the stiffener. A stiffener also may extend laterally beyond one or both of the longitudinal edges of other materials forming the insert 50, and may extend longitudinally beyond the lateral edge(s) of other materials forming the insert 50 at its end. One or both ends of the insert 50 may include an end support stiffener. A stiffener may include, be formed of, or be further stiffened by, a fastener component such as a strip or patch of hooks material. In examples where the insert 50 comprises an end support stiffener at both ends, the respective end support stiffeners may have differing shapes, dimensions, stiffness, thickness, color, structure, placement, material(s) or composition. An end support stiffener also may include, or be integral with, a grasp structure or fastener component as described above, and as suggested in FIG. 3 (end support stiffener 60 is depicted as integral with grasp structure 59).

In an embodiment, a stiffener of an insert 50 may be provided in an I-shaped or X-shaped configuration, for example, that may be continuous or discontinuous. The top of the I-shaped or X-shaped stiffener may extend laterally in the forward region 54, the central portion of the I-shaped or X-shaped stiffener may extend longitudinally at least between the forward region 54 and the rearward region 55, and the bottom portion of the I-shaped or X-shaped stiffener may extend laterally through the rearward region 55. In an embodiment, such an I-shaped or X-shaped stiffener may be provided for pants. Such an I-shaped or X-shaped stiffener may help to maintain curvature of the insert 50, if desired, during insertion and removal of the insert 50 from the outer cover 20 and at other times.

Fastening Component Arrangement and End Stiffness Characteristics

As discussed above, use of an effectively force-decoupled, singularized/localized fastening system at an end of an insert 50 may present both advantages and disadvantages. Some of the disadvantages may be mitigated by the inclusion of an end support stiffener, or alternatively, by use of a more force-coupled fastening system that provides support at the insert corners.

Similarly, use of a fastening system having two separated fastener components at an end of an insert 50, at or near the corners, may present both advantages and disadvantages, including added cost and complexity for the manufacturer. Some of the disadvantages may be mitigated by the inclusion of an end support stiffener, and/or by use of a relatively force-decoupled, singularized/localized fastening system.

Inclusion of an end support stiffener on an insert 50 may have beneficial effects; however, it also may create issues of comfort for the wearer, and added cost and complexity for the manufacturer.

In view of the respective advantages and disadvantages presented by these various types of insert-to-outer cover fastening and/or support systems, it may be desirable to utilize combinations of these systems that strive for a balance between user convenience, fit, structural support, integrity and containment function for the insert 50 and standing cuffs 53, wearer comfort, and minimized cost and complexity for the manufacturer.

In some circumstances, inclusion of attachment zone/fastener component pairs which effectively attach the end corners of the insert 50 to the outer cover may be undesirable for reasons of cost and/or complexity, or may sacrifice the advantages of having only one singularized/localized and laterally centered fastening location proximate each end of the insert 50, as described above. For example, in the rear region of the outer cover 20, a singularized and relatively localized fastening location providing a force-decoupled arrangement may be desirable, for the reasons described above. If an effect of this, however, is an undesirable loss of corner support and support for the standing cuffs 53, an end support stiffener may be desirable in conjunction with a singularized/localized fastening system.

It may be desired that the portions of the insert 50 including one or more end support stiffeners 60, 62 are sufficiently stiff to effectively resist the tension forces in the standing cuffs 53 and substantially maintain the standing cuffs 53 and the edges 58 thereof in their gasketing configurations while the insert 50 is in use, and substantially maintain the corners of the insert 50 in laterally extended positions, preventing, or at least inhibiting, buckling or bunching of the same. The amount of added stiffness desired may depend upon various factors including the inherent stiffness of the insert materials without a supplemental end support stiffener, and the amount and/or range of tension in the standing cuffs 53 when the absorbent article 10 is worn, and the distance between the laterally outermost outside edge of the laterally outermost fastener component and the nearest longitudinal edge of the insert 50. At the same time, for purposes of wearer comfort, it may be desirable that the portions of the insert 50 including the one or more end support stiffeners 60, 62 are pliable enough to flex comfortably with the wearer's body movements, and to yield or collapse before a substantial potential for contusion, abrasion, or irritation is presented. It also may be desirable that stiffened portions are elastic in nature, in that they will tend to return to a particular shape (e.g., substantially flat or planar) configuration after being bent, folded or twisted. Thus, an end support stiffener may be formed of an elastomeric polymer material, a laminate material, and/or a composite material.

FIGS. 2W and 2X schematically depict two possible variations for an end of an insert 50 having standing cuffs 53 with free edges 58. FIG. 2W depicts an end having a laterally centralized, singularized fastener component 56. FIG. 2X depicts an end having two fastener components 56, laterally separated and disposed near the corners of the insert. In these figures, $W_i$ is the greatest width across the insert 50 not including an end support stiffener; $W_f$ is the portion of the width $W_i$ between the laterally outermost extents of the fastenably effective portions of the fastener components; LUD (laterally-outboard unsecured dimension) is the portion of the width $W_i$ that lies laterally outside the laterally outermost extents of the fastenably effective portions of either fastener component; and CUD (central unsecured dimension) is the portion of the width $W_i$ that lies between the laterally innermost extents of fastenably effective portions of two laterally separated fastener components. (For purposes herein, "fastenably effective portion" means any portion of a fastener component that effectively force-couples a portion of the width of an insert 50 to an outer cover 20.) $L_{is}$ is the longitudinal dimension of an end support stiffener measured from the longitudinally outermost edge of the stiffener, to the longitudinally innermost extent (i.e., nearest lateral axis 70) of the stiffener.

Without intending to be bound by any particular theory, it is believed that the following combinations of dimensions $W_f$, LUD, CUD, and/or bending stiffness for an insert end may be effective to strike a satisfactory balance among attributes including user convenience, fit, structural support, integrity and containment function for the insert 50 and the standing cuffs 53, and wearer comfort. Where the terms "Peak Edge Deflection Force (y)" or "Edge Deflection Force (y)" are used below, "y" is the lateral dimension in millimeters of distance 1010 as described in the Edge Deflection Force Measurement Method and depicted in FIG. 19A herein.

Insert End Bending Stiffness Regardless of Fastener Component Configuration

The insert end has a Bending Stiffness of at least about 100 N/m, or more preferably, respectively, at least about 200, 300 or 400 N/m; or alternatively, a Bending Stiffness of between about 200 and about 500 N/m.

The insert end has an end support stiffener and has a Bending Stiffness of at least about 100 N/m, or more preferably, respectively, at least about 200, 300 or 400 N/m; or alternatively, a Bending Stiffness of between about 200 and about 500 N/m.

The insert end has an end support stiffener and the end support stiffener has a Bending Stiffness of at least about 50 N/m, or more preferably, respectively, at least about 100, 200, or 300 N/m; or alternatively, a Bending Stiffness of between about 100 and 500 N/m.

The insert end has an end support stiffener having an $L_{is}$ of no more than about 50 mm, and the insert end has a Bending Stiffness of at least about 100 N/m, or more preferably, respectively, at least about 200, 300 or 400 N/m; or alternatively, a Bending Stiffness of between about 200 and about 600 N/m.

The insert end has an end support stiffener having an $L_{is}$ of at least about 10 mm, and the insert end has a Bending Stiffness of no more than about 1,000 N/m and more preferably no more than about 500 N/m.

The insert end has an end support stiffener having an $L_{is}$ of no more than about 50 mm, and the stiffener has a Bending Stiffness of at least about 50 N/m, or more preferably, respectively, at least about 100, 200 or 300 N/m; or alternatively, a Bending Stiffness of between about 100 and about 500 N/m.

Insert End Bending Stiffness and Peak Edge Deflection with Non-Zero LUD

The insert end has an LUD which is greater than zero (0) and has a Peak Edge Deflection Force (30) of at least about 0.50 N, more preferably, respectively, at least about 0.60 N, about 0.70 N, about 0.80 N, about 0.90 N, or about 1.0 N, or alternatively, between about 0.50 N and about 1.0 N.

Neither LUD at an insert end exceeds about 40 mm, and the insert end has a Bending Stiffness of at least about 200 N/m, more preferably at least about 300 N/m.

The insert end has an LUD of at least about 40 mm and the insert end has a Bending Stiffness of at least about 300 N/m, more preferably at least about 400 N/m.

The insert end has an LUD of at least about 5 mm and a Bending Stiffness of at least about 200 N/m, more preferably 300 N/m, even more preferably 400 N/m.

The insert end has an end support stiffener, has an LUD of at least about 40 mm, and has a Bending Stiffness of at least about 300 N/m, and even more preferably 400 N/m The insert end has an end support stiffener, has an LUD of at least about 40 mm, and the end support stiffener has a Bending Stiffness of at least about 50 N/m, more preferably 100 N/m, more preferably 200 N/m, and even more preferably 300 N/m.

The insert end has an LUD of at least about 40 mm and has an end support stiffener located in at least a portion of the insert end region comprising the LUD, the end support stiffener having a Bending Stiffness of at least about 50 N/m, more preferably 100 N/m, more preferably 200 N/m, and even more preferably 300 N/m.

The insert end has an end support stiffener and has an LUD of at least about 5 mm, and the end support stiffener has a Peak Edge Deflection Force (30) of at least about 0.2 N, more preferably, respectively, at least about 0.3 N, about 0.5 N, 0.7 N, or about 1.0 N.

Insert End Bending Stiffness with Non-Zero CUD

The insert end has a CUD of no more than about 100 mm, more preferably no more than about 80 mm, more preferably no more than about 60 mm, or alternatively, a CUD of from about 30 mm to about 80 mm, and a Bending Stiffness of at least about 200 N/m, more preferably at least about 300 N/m.

The insert end has a CUD of at least about 5.0 mm, more preferably at least about 10 mm, 20 mm, even more preferably at least about 50 mm, and less than about 80 mm; and a Bending Stiffness of at least about 300 N/m, more preferably about at least about 400 N/m, and no more than about 500 N/m.

The insert end includes a stiffener and has a CUD of no more than about 100 mm, more preferably 80 mm, even more preferably 60 mm, or alternatively, a CUD of from about 30 mm to about 80 mm, and has a Bending Stiffness of at least about 50 N/m, more preferably 100 N/m, and even more preferably 200 N/m.

The insert end has a CUD of at least about 5.0 mm, more preferably at least about 20 mm, even more preferably at least about 50 mm, and has a Peak Edge Deflection Force (30) of at least about 0.2 N, more preferably 0.5 N, and even more preferably 0.7 N.

Targeting, Orientation and Alignment Indicia

As discussed above, an insert 50 may be imparted with features that make it asymmetric about its lateral axis. Despite such asymmetrical configuration, as suggested by FIG. 4, the insert 50 may have an overall profile that does not appear to be asymmetric about its lateral axis. For example, as depicted in FIG. 4, the insert 50 may have an overall profile, when opened and laid flat, that is substantially rectangular, and thus, appears to be symmetric about its lateral axis 70. Other insert profiles are possible as well, which have overall profiles which appear symmetric about a lateral axis. Additionally, even where an insert 50 has an overall profile that is asymmetric about its lateral axis, it may not be clear just from the profile which portion is the forward portion and which portion is the rearward portion. Thus, absent a sufficiently perceptible signal indicating which portion of the insert 50 is the forward portion and which is the rearward portion, a user may have difficulty determining the same, and as a result, may attempt to install an insert 50 into an outer cover 20 with incorrect relative front-rear orientation—in turn, potentially resulting in sub-optimal fit, appearance, exudate containment and/or comfort.

The insert 50 and/or the outer cover 20 may comprise one or more insert targeting indicia to indicate, facilitate and/or compel correct positioning and association of portions of the insert 50 within the outer cover 20. The insert targeting indicia may comprise verbal or non-verbal instructive indicia, visual targeting indicia, cooperating geometrical features, cooperating types of fastener components, or cooperating designs of fastener components sized and formed to indicate or compel the engagement of the insert 50 with the correct region of, and in correct orientation with, the outer cover 20 so as to enable the optimum performance of the wearable absorbent article 10. Other examples of possible targeting indicia components include one or more cooperating colors, shapes, patterns, lines, outlines, silhouettes, other geometrical features, protrusions or depressions, textures, patterns, targeting lines or crosshairs, bulls-eye representations, and the like, disposed on the outer cover 20 and/or the insert 50 to indicate correct positioning of the insert 50 within the outer cover 20. In one example, the inner surface 25 of the outer cover 20 may be imprinted with an outline of an insert 50, or a silhouette of an insert 50, or a portion thereof, as illustrated in FIG. 2M (corner outline images 80). In another example depicted in FIG. 2Y, one or more portions of an insert 50, such as a grasp tab 59, may have a targeting indicium in the form of hole or window 59a therethrough, and the inside of the outer cover 20 may have a corresponding targeting indicium thereon (such as a dot or other image) (not shown) which is visible through and/or aligns with the hole/window 59a when the insert 50 is properly positioned within the outer cover 20. Alternatively, one or both of the forward and rearward regions 54, 55 of the insert 50 may have disposed thereon a pictogram showing the outer cover shape, or a generalized version thereof, with the front and back of the outer cover 20 indicated via size, color, contrast, or some other indicator, showing the correct insert installation orientation. For example, an outer cover pictogram disposed in the rearward region 55 of the insert 50 may have the rear outer cover region, or portions thereof, indicated with a brighter color, an arrow, a circle, etc., while an outer cover pictogram disposed in the forward region 54 of the insert 50 may have the front outer cover region, or portions thereof, indicated similarly.

Targeting indicia also may comprise at least two cooperating components, one on the outer cover 20 and one on insert 50, such that when these two components are associated, the respective components of outer cover/insert system will be properly oriented with respect to one another and will perform most optimally. In one example, the inner surface 25 of the outer cover 20 may be imprinted with a first arrow pointing at an insert location, and the insert 50 may be imprinted with a second arrow pointing at the first arrow when the insert 50 and outer cover 20 are correctly relatively positioned.

Indicia may be cognitively correlating, or non-correlating, a correlation indicating a correct optimal placement, and a non-correlation indicating an incorrect sub-optimal placement. Respective cognitively correlating targeting indicia may include an indicium on the outer cover 20 that cognitively correlates with an indicium on the insert 50, indicating to the user the correct relative positioning and engagement of the insert 50 and the outer cover 20. For example, respective cognitively correlating indicia on the insert 50 and the outer cover 20 may have a common color, shape, or texture. (As used herein, "common color" includes any first color and recognizable shades or variants thereof, which in view of all features of the absorbent article is visibly and cognitively distinguishable from another color on the absorbent article.)

In an embodiment, the outer cover 20 may comprise one or more "windows," transparent portions, or openings defined therein. The insert 50 may comprise one or more wetness indicators, loading indicators, or any other suitable indicators known to those of skill in the art, on an outer surface thereof. The wetness indicator is configured to indicate to a user when the insert 50 needs to be replaced. The loading indicator is configured to indicate to a user the loading (e.g., wetness %) of the insert 50 to indicate how much longer the insert 50 can be worn without replacement. Multiple indicators may be provided on the insert 50 with multiple windows, transparent portions, or openings provided on the outer cover 20. The various indicators should be aligned with the windows, transparent portions, or openings defined in the outer cover 20 such that the caregiver can view the indicators. In addition, the user will be intuitively instructed to align the indicator with the window, transparent portion, or opening when attaching the insert 50 to the outer cover 20. In an embodiment, the indicators may be provided on the outer cover 20 instead of or in addition to the insert 50.

Referring to FIGS. 2B, 3 and 4, when an insert 50 is asymmetrical as described above, it may have only one optimal forward region 54 and only one optimal rearward region 55. Similarly, when an outer cover 20 is asymmetrical as described above, it may have only one optimal front region 27 and only one optimal rear region 28. Thus, in the event either or both of these asymmetries are substantial, installation of the insert 50 into the outer cover 20 with incorrect relative front-rear orientation may cause the wearable absorbent article 10 not to fit and/or function optimally. Accordingly, it may be desirable in some circumstances to incorporate one or more indicia into the outer cover 20 and/or the insert 50 that are adapted to inform the user as to the correct respective front-rear orientation of these components. Such indicia may provide such information to the user functionally, tactilely and/or visually.

Functional indicia may include fastener components that function properly, effectively and/or optimally with correct front-rear orientation, but do not function properly, effectively and/or optimally with incorrect front-rear orientation.

For example, referring to FIGS. 2B and 3, the front attachment zone 33 on the outer cover 20 may be cooperative to effect optimal/maximum fastening security only with the front fastener component 56 on the insert 50, but not with the rear fastener component 57 on the insert 50. Similarly, the rear attachment zone 32 on the outer cover 20 may be cooperative to effect optimal/maximum fastening security only with the rear fastener component 57 on the insert 50, but not with the front fastener component 56 on the insert 50.

In a more specific example conceptually appreciated from FIGS. 2K-2L, the front insert fastener component 33 on the outer cover 20 may include a patch of loops, while the front fastener component 56 on the insert 50 may include a mating patch of hooks (mating relationship indicated by hatching of attachment zone/fastener component 33, 56 in FIGS. 2K-2L). Correspondingly, the rear attachment zone 32 on the outer cover 20 may include a patch of hooks, while the rear fastener component 57 on the insert 50 may include a mating patch of loops (mating relationship indicated by absence of hatching of the attachment zone/fastener component 32, 57 in FIGS. 2K-2L). Thus, in this particular example, if a user mistakenly attempts to fasten the rear fastener component 57 on the insert 50 (loops) to the front attachment zone 33 on the outer cover 20 (loops), proper or optimal fastening will not be effected, which will communicate to the user that he/she must rotate the insert 50 by 180 degrees to install it with correct/optimal front-rear orientation on the outer cover 20.

In another specific example also conceptually appreciated from FIGS. 2K-2L, the front attachment zone 33 on the outer cover 20 may include a female snap fastener component, while front fastener component 56 on insert 50 may include a mating male snap fastener component (mating relationship indicated by hatching of attachment zone/fastener component 33, 56 in FIGS. 2K-2L). Correspondingly, the rear attachment zone 32 on the outer cover 20 may include a male snap fastener component, while the rear fastener component 57 on the insert 50 may include a mating female snap fastener component (mating relationship indicated by absence of hatching of attachment zone/fastener component 32, 57 in FIGS. 2K-2L). Thus, in this particular example, if a user mistakenly attempts to fasten the rear fastener component 57 on the insert 50 (female snap fastener component) to the front attachment zone 33 on the outer cover 20 (female snap fastener component), the components will not fit properly together and proper/optimal fastening will not be effected, which will communicate to the user that he/she must rotate insert 50 by 180 degrees to install it with correct/optimal front-rear orientation.

Thus, functional indicia may include any attachment zones/fastener components that will function properly and/or optimally to effect fastening and maximum fastening security between the insert 50 and the outer cover 20 when the two are properly oriented, but will not function properly or optimally otherwise. Any different types of attachment zones/fastener components or systems may be combined to differentiate the forward and rearward regions 54, 55 of the insert 50 and indicate correct orientation within the outer cover 20. Generally, with the use such functional indicia, the fastener components types in the forward region 54 of the insert 50 and the front waist region 27 of the outer cover 20 are respectively incompatible, or significantly less effective, with the respective fastener components types in the rearward region 55 of the insert 50 and rear waist region 28 of the outer cover 20. As another example of such functional indicia, the front insert attachment zone/fastener pair 33, 56 may be a hook and loop fastening system, while the rear insert attachment zone/fastener pair 32, 57 may be a snap fastening system. In another example, the front insert attachment zone/fastener component(s) may include a pocket or flap structure, while the rear attachment zone/fastener components embody a dissimilar fastening system. The front and rear attachment zone/fastening components may comprise any two different fastening systems as disclosed herein, or as otherwise available.

In another example, functional indicia may be embodied by attachment zone/fastener pairs 33, 56 and 32, 57 having mutually exclusive geometries of similar or compatible fastening system types. For example, as depicted in FIGS. 2E-2F and 2G-2H, the front attachment zone/fastener component pair 33, 56 may have a first placement and geometry, while the rear attachment zone/fastener component pair 32, 57 may have a second placement and geometry, such that if installation of the insert 50 within the outer cover 20 with incorrect front-rear orientation is attempted, the attachment zone/fastener component pairs will not align to provide visibly correct and functionally effective attachment, communicating to the user that that he/she must rotate the insert 50 by 180 degrees to install it with correct/optimal front-rear orientation. In another similar example (not depicted), the front insert fastening system may have an open circle, or doughnut-like, geometry, while the rear insert fastening system may have a geometry of a circle with a diameter less than that of the central opening in the open circle of the front insert fastening system. In yet another example (not depicted), the front and rear insert fastening systems may be located primarily on one side of the longitudinal axis of the absorbent article 10 (i.e., the longitudinal axes of both the insert 50 and the outer cover 20). In this example, if the insert 50 is applied to the outer cover 20 in the incorrect front-to-back orientation, the attachment zone/fastener components will not align correctly. In another example (not depicted), the front insert fastening system may comprise an interlocking fastener oriented along the direction of the longitudinal axis of the absorbent article 10, while the rear fastening system may comprise an interlocking fastener oriented along the direction of a waist edge or lateral axis of the absorbent article 10. In another example which may be conceptually appreciated from FIGS. 2E-2F, and 2G-2H the front fastening system may include one or more attachment zone/fastener components 33, 56 disposed along or near the longitudinal edges of the insert 50, while the rear fastening system may include a single attachment zone/fastener component pair 32, 57 having a width less than the insert width and disposed on the longitudinal axis of the absorbent article 10.

In an example of an adult incontinence pant product that uses an adhesive to bond the insert to the outer cover, the outer cover may have a lateral line indicating where the longitudinal midpoint of the insert should be positioned. Also, such an outer cover may have markings for aligning the corners or edges of the insert. The insert, in turn, may have a lateral line extending through its longitudinal midpoint. When the pant is pulled down near or past the knees, a wearer or caregiver can correctly align the lateral line on the insert to the lateral line on the outer cover and then attach the insert in the crotch region of the outer cover. The wearer or caregiver can then work his/her way towards the front and back ends of the insert, while ensuring that the corners or edges of the insert align with the corner or edge markings on the outer cover.

This is one possible execution for women's adult incontinence products, since many women apply menstrual pads or liners to their panties in this fashion. In order to improve the attachment of the insert to the outer cover, and give her a better "stay in place" experience, an additional layer of non-stretch nonwoven or film may be added to the outer cover in at least a portion of, or all of, the insert attachment area. This additional layer may make it easier to attach the insert to the outer cover.

In an embodiment, the outer cover may have corners or edges or other lines marked for two or more different sizes of inserts. It is possible that the caregiver or wearer may want to choose the appropriate insert for his/her desired need. For example, he/she may use a more absorbent insert, which may have larger dimensions and/or a greater absorbent capacity, if he/she is going to be out and away from a restroom for an extended period of time. For shorter usage periods, he/she may choose to use an insert having smaller dimensions and/or a smaller absorbent capacity, which will be more comfortable and also economical for him/her. Also, at night when there is a potential for leakage through the front and back ends of the insert, he/she may choose to use inserts that are larger and/or more absorbent.

Functional indicia need not necessarily be limited to attachment zones/fastener components. Functional indicia also may be embodied in other features of the outer cover 20 and the insert 50 that affect how the two fit or function together in correct, optimal front-rear orientation versus incorrect (reverse), sub-optimal front-rear orientation. Thus, functional indicia may additionally be associated with or combined with another functional element of the outer cover 20 or the insert 50. Indicia may be associated with elements of the outer cover 20 such as a waistband, side panel, stretch element, leg cuff, physical retention fastener component (e.g., a pocket or retaining strap), and the like. Indicia may be associated with elements of the insert 20, such as a waist cap, waist band, standing cuff, fecal management feature, insert positioning aid, insert stiffening aid, insert removal aid, or insert disposal aid.

From the foregoing it will be appreciated that other forms of functional orientation indicia are possible, within the principle of the foregoing description. Additionally, any of the differing types of indicia described may be included in a single absorbent article, in any combination.

In other possible examples, instead of respective functionally cooperative/uncooperative pairs of attachment zones/fastener components as described above, the insert 50 and the outer cover 20 may include respective non-functional indicia, such as tactile or other sensory indicia.

For example, the front insert and outer cover attachment zone/fastener components may be selected or formed so as to have a first tactile attribute, while the rear insert and outer cover attachment zone/fastener components may be selected or formed so as to have a second tactile attribute. In another example, features of the insert and outer cover may have features such as 3-dimensional shapes that are mating or geometrically cooperating with optimal front-rear orientation, but not mating or geometrically cooperating with reversed, suboptimal front-rear orientation.

In other possible examples, instead of or in addition to respective functionally cooperative/uncooperative pairs of attachment zones/fastener components or tactile indicia components as described above, the insert 50 and the outer cover 20 may include respective visual indicia. The outer cover 20 may include respective front and rear visual indicia 73, 74 disposed on the front waist region 27 and rear waist region 28, respectively. Respective visual indicia disposed on the insert 50 and the outer cover 20 may be adapted to provide a visual cue to the user of correct/optimal orientation and placement of the insert 50 within the outer cover 20.

For example, components of visual indicia and a visual cue may involve use of a common color or light and dark colors. In one particular example, front and/or rear visual indicia 73, 74 (see FIG. 2B) disposed on the outer cover 20 may comprise respective common colors visibly distinct from one another. (As used herein, "common color" includes any first color and recognizable shades or variants thereof, which in view of all features of the absorbent article is visibly and cognitively distinguishable from another color on the absorbent article.) The insert 50 may have respective cooperating indicia disposed or embodied thereon. Thus, for example, the forward and rearward user grasp structures 59, 61 on the insert 50 may bear or be colored with colors respectively common and corresponding with those comprised by the front and/or rear visual indicia 73, 74. More particularly, for example, the front visual indicium 73 and an insert feature such as the forward user grasp structure 59 may both bear or be colored a first common color, and the rear visual indicium 74 and a feature such as the rearward user grasp structure 61 may either or both be colored a second common color, visibly distinguishable from the first common color.

In another particular example which may be conceptually appreciated from FIGS. 2I-2J, 2M-2N, and 3, the front and rear visual indicia 73, 74 disposed on the outer cover 20 may embody, or bear images of, respective shapes or sizes to match, or cognitively correlate visually correlate with, corresponding shapes or sizes embodied, or pictured on, insert features such as the forward and rearward user grasp structures 59, 61 and/or the fastener components 56, 57. More particularly, for example, the front visual indicium 73 or the forward user grasp structure 59 may both embody or bear images of triangles, and the rear visual indicium 74 or the rearward user grasp structure 61 may both embody or bear images of circles. Other examples of cognitively correlating indicia respectively disposed on an insert and corresponding location on an outer cover include: a baseball and glove, soccer ball and goal, a tennis racket and a tennis ball, a golf club and a golf ball, bird and nest, and any other images of components of well-recognized pairings which would indicate to a user that two portions bearing or embodying such images are to be brought together during installation of the insert 50 within the outer cover 20.

In another particular example, the front and rear visual indicia 73, 74 disposed on the outer cover 20 may bear images of words or symbolic indications for "front" and "rear", to match corresponding words or symbolic indications on insert features such as the forward and rearward user grasp structures 59, 61. In a more particular example, the front visual indicium 73 and the forward user grasp structure 59 may both bear an image of the letter "F" (i.e., for "front"), and the rear visual indicium 74 and the rearward user grasp structure 61 may both bear an image of the letter "R" (i.e., for "rear").

In another particular example, the front and/or rear visual indicia 73, 74 disposed on the outer cover 20 may embody, or bear images of, respective portions of expectedly user-recognizable shapes, characters, objects, etc., to match corresponding portions of expectedly user-recognizable shapes, characters, objects, etc., embodied, or pictured on, insert features such as the forward and/or rearward user grasp structures 59, 61. In a more particular example, the front visual indicium 73 and the forward user grasp structure 59 may both embody or bear respective portions of a first image that, when brought together properly, form a cognitively complete image of an expectedly user-recognizable first shape, character, object, etc.; and/or the rear visual indicium 74 and the rearward user grasp structure 61 may both embody or bear respective portions of a second image that, when brought together properly, form a cognitively complete image of an expectedly user-recognizable second shape, character, object, etc., distinctive from the first. To illustrate an example, referring to FIG. 2Z, a visual indicium 73a disposed on one end of an insert 50 may be a first portion of an expectedly user-recognizable image (such as a heart shape) cut off along an edge 73c of insert 50, while a visual indicium 73b disposed on an outer cover 20 may be the second portion of the same image, such the expectedly user-recognizable image is completed upon proper orientation and positioning of the insert 50 within the outer cover 20 such that respective indicia 73a and 73b meet and match to complete the image. It will be understood that the heart shape image depicted is but one example among any number of expectedly user-recognizable images and respective portions thereof that may serve in such manner as targeting and/or alignment indicia. The image and portions thereof may also take the form of a trademark or particular distinctive or distinguishing artwork used by the manufacturer in connection with the product.

In yet another particular example, visual orientation indicia may be simplified into a single pair of visual indicia appearing, respectively, on the outer cover 20 and the insert 50. In one such example, an inner surface 25 of the outer cover 20 may bear an image of an arrow pointing longitudinally toward the front edge 21, and the insert 50 may bear an image of an arrow pointing longitudinally toward its forward end.

Examples of other suitable visual orientation indicia adapted to provide orientation information may include alphanumeric text including words, arrows, symbols, diagrams, pictographs, icons, cartoons, schematics, and any other visual indicia.

It may be desired that indicia associated with the front portions of the outer cover and insert will not cognitively correlate, or will cognitively not correlate, with indicia associated with rear portions of the outer cover and insert, and vice versa, when the user views both sets of indicia.

From the foregoing it will be appreciated that other forms of visual orientation indicia are possible, within the principle of the foregoing description.

In addition to providing indicia that indicate and/or compel the correct front-rear orientation of the insert 50 with respect to the outer cover 20, it also may be desirable to provide indicia that indicate and/or compel correct longitudinal and lateral alignment of the insert 50 within the outer cover 20, in order to provide for the designed optimal containment, fit, comfort and appearance of the absorbent article. In the examples shown in FIGS. 2E-2N, respective attachment zone/fastener component pairs 32, 57 and 33, 56 are configured and disposed to serve as alignment indicia. It can be appreciated from these examples that fastener components may be configured and disposed to not only indicate and/or compel correct front/rear orientation, but also indicate and/or compel correct longitudinal and lateral alignment of the insert 50 with respect to the outer cover 20, because co-location of one or both of these fastener component pairs to effect proper fastening will also effect proper longitudinal and lateral alignment. In other examples, separate visual indicia may be included for this purpose, such as, for example, longitudinal alignment indicia 79a, 79b and lateral alignment indicia 78a, 78b disposed respectively on the outer cover 20 and the insert 50 (FIGS. 2E-2F). Referring to FIGS. 2E-2F, it can be seen that the insert 50 may be longitudinally and laterally aligned within the outer cover 20 by ensuring that alignment indicia pairs 78a, 78b and 79a, 79b meet, or are closely proximate each other, when the insert 50 is installed into the outer cover 20. Visual alignment indicia may take other forms, including, but not limited to, matching line segments, shapes, insert end or corner outline images 80 disposed on the inner surfaces of the outer cover 20 (see, e.g., FIGS. 2M-2N), etc.

In an embodiment, the attachment zone/fastener component pairs 33, 56 and 32, 57 may be two shades of a particular color to indicate alignment. For example, the attachment zone 33 and the fastener component 56 may be dark blue, while the attachment zone 32 and the fastener component 56 may be light blue. Any other suitable colors or shades thereof may also be used. In an embodiment, the attachment zones/fasteners components 33, 56 and 33, 57 may glow in the dark to allow changing of a wearer under limited light conditions. Each pair of attachment zones/fastener components may glow a different color to indicate alignment. Alternatively, only one pair of attachment zones/fastener components may glow to again indicate alignment.

Article of Commerce

It is contemplated that an article of commerce including one or a plurality of outer covers and one or a plurality of inserts, as described herein, may be prepared and sold as such. For example, a package containing from one to 12, or more, outer covers, together with one or a plurality of associated inserts, may be assembled and sold together as packaged. The respective outer cover(s) and inserts in a package may have matching/complementary fastening systems, orientation indicia and/or alignment indicia as described herein.

For such an article of commerce it may be desirable to determine a ratio of inserts to outer covers suitable to constitute a set of convenient numbers of outer covers and inserts, respectively. For example, it may be deemed suitable to include approximately a half day or day's supply of inserts for each outer cover included in the set. Thus, for example, the article of commerce may include inserts and outer covers in a ratio of inserts to outer covers of 1:1, 2:1, 3:1, 4:1, 5:1 or even 6:1. Accordingly, for example, a package associating a set may include one outer cover and 1, 2, 3, 4, 5 or 6 inserts; two outer covers and 2, 4, 6, 8, 10 or 12 inserts; three outer covers and 3, 6, 9, 12, 15 or 18 inserts, and so on. For a "starter" set for certain consumers such as first-time purchasers, or in other circumstances, it may be desirable for a package to contain from 2 to 14 outer covers—which may correspond roughly to from one day's to one week's supply of clean outer covers available before laundering becomes necessary.

It may also be desirable to include, in a set including a plurality of inserts, inserts of differing designs, adapted for use under differing circumstances. In one example, one or more of the inserts in the plurality may be adapted for extended or nighttime use (sleep-use), and one or more for daytime use, with respect to features such as, e.g., location of absorbent material and absorbent capacity. Half of the number of inserts in the plurality, or fewer than half, may be adapted for sleep-use. In one example of this embodiment, the set also may include one or more outer covers decorated with nighttime/sleep themes, such as, for example, images of the moon, stars, nighttime sky colors and other nighttime scenes, images of sleeping animals, sleeping people, sleeping anthropomorphic characters, etc.; and one or more outer covers decorated with daytime/play themes, such as, for example, sun, birds, bright colors, daytime sky colors and other daytime scenes, images of awake/playing animals, people, anthropomorphic characters, etc.

In a further embodiment, a set in a package may be specially adapted for either boys or girls. For example, a package may include one or more outer covers having surface decoration and ornamentation associated with little girls, e.g., inclusion of pink, lavender and/or other soft pastel color schemes, images of flowers, butterflies, bunnies, kittens, little girls, princesses, feminine cartoon characters or feminine anthropomorphic characters, etc., or other decorative features generally associated with little girls. Conversely, a package may include one or more outer covers having decoration and ornamentation associated with little boys, e.g., inclusion of blue, black, dark or bold color schemes, images of cars, trains, planes, boats, rockets, spaceships, objects associated with sports, little boys, masculine cartoon characters or masculine anthropomorphic characters, etc., or other decorative features generally associated with little boys. A package designed for either boys or girls also may include associated corresponding inserts specially adapted for either boys or girls, whether by functional elements or by non-functional, ornamental/decorative elements. Alternatively, a package may contain one or more outer covers and inserts adapted for use with either boys or girls, having gender-neutral decoration/ornamentation and functional elements.

In a further embodiment, a set in a package may include several types of inserts, having functional designs that differ in other respects. For example, a package may include one or more inserts having one or more of a feces acceptance aperture in a topsheet, space beneath the topsheet for isolation of feces, and/or related features such as described in, for example, U.S. Pat. Nos. 8,016,803, 7,771,406 and 7,771,408.

In a further embodiment, a set in a package may be specially adapted for use in specific circumstances. For example, a set may include one or more outer covers and associated inserts adapted for wearing while swimming or public bathing. In this example, the outer cover(s) and inserts may be adapted for satisfactory use and to substantially retain structural integrity while soaked and/or immersed in water. For example, the included outer cover(s) may be constructed of materials which do not substantially lose tensile strength, stretch or sag when soaked. In this example, it may be desirable to form the outer cover(s) predominately of polymeric, hydrophobic materials and/or elasticized textile materials. Similarly, it may be desirable to form included inserts of materials that will withstand immersion and soaking without substantial loss of structural integrity during the period of intended use. It also may be desirable to form such inserts without inclusion of superabsorbent polymer or absorbent gelling material. While these absorbent materials are often included in the absorbent cores of regular diapers, they may be deemed unsuitable for use in articles to be worn while swimming or bathing, because such materials would quickly absorb water, and swell and bulge with the absorbed water, upon being immersed—giving up their absorptive capacity, adding bulk and weight, and retaining no benefit. Within the same set, however, one or more inserts may be included for non-swimming, non-bathing use, such that the same outer cover(s) may be used for swimming/bathing and non-swimming, non-bathing activities. The one or more inserts for non-swimming, non-bathing use may have absorbent cores including superabsorbent polymer or absorbent gelling material.

In a further embodiment, a set in a package may contain a plurality of durable outer covers 20, having leg openings defined by leg opening edges 23 that differ in dimension from one durable outer cover to another durable outer cover. Sequential use of such durable outer covers may be useful to effect a change in the location(s) at which leg band portions 36 and leg opening edges 23 encircle and contact the wearer's skin, each time a durable outer cover in the plurality is replaced by another durable outer cover in the plurality having such differing dimensions. This may provide the advantage of reducing the likelihood or severity of chafing of the wearer's skin in the location(s) of such contact that may result from the wearer's movements. Such chafing may otherwise be caused or exacerbated by repeated use of successive durable outer covers having leg openings of substantially unchanging dimensions, which may result in repeated encircling contact with the skin in a more concentrated or localized fashion. Thus, for example, a user may apply a first durable outer cover in the plurality and the wearer may wear it for a first period of time (such as a day), and the user may apply a second durable outer cover in the plurality and the wearer may wear it for a second period of time (such as the ensuing night or following day), and so on—effectively varying the location(s) on the wearer's skin at which leg opening edges and leg bands encircle and contact it—and reducing the likelihood or severity of chafing. Referring to FIG. 2C, it will be appreciated that varying any of, or any combination of, outer cover crotch width $WC_c$, outer cover front width $WC_f$, outer cover rear width $WC_r$, outer cover length LC and leg band length LLB, can have the effect of varying the size of the leg openings of a durable outer cover 20 when applied to the same wearer. Accordingly, a set of at least first and second outer cover in a package may have a difference between them in any of outer cover crotch width $WC_c$, outer cover front width $WC_f$, outer cover rear width $WC_r$, outer cover length LC or leg band length LLB, as measured with each outer cover laid out horizontally on a flat surface, extended to its fullest unstretched (relaxed) dimensions. Any of dimensions $WC_c$, $WC_f$, $WC_r$, LC or LLB may differ between the first and second durable outer covers by at least about 10%, 15%, 20% or more. In another example, however, the tension forces in leg bands 36 may be varied from one durable outer cover to the next, by use of, for example, differing types of elastic strands or strips, or differing sizes of elastic strands or strips, or differing numbers of elastic strands or strips, respectively included by leg band portions 36, or even differing constructions of leg band portions 36—any of which may effect differences in dimensions of leg opening edges 23 from one durable outer cover to another durable outer cover within the package.

In a further embodiment, a variety of packages containing a variety of types of sets may be presented as a variety of articles of commerce. In one example, one or more outer covers forming part of a set in a package may be seasonal in nature, either by reasons of function or decorative/ornamental elements or both. Distinctive sets of outer covers may differ from set to set in attributes such as material basis weight, insulation properties, breathability, etc. For example, a "winter" or "cold weather" outer cover may be formed of materials individually or in combination having a relatively higher basis weight, while a "summer" or "warm weather" outer cover may be formed of relatively lighter materials and/or materials having greater breathability (as may be characterized and compared by WVTR).

In another example, one or more outer covers forming part of a set in a first package may all have decorative/ornamental elements designed by a first designer and/or be labeled or branded with the first designer's name or brand, while one or more outer covers forming part of a set in a second package may all have decorative/ornamental elements designed by a second designer and/or be labeled or branded with the second designer's name or brand. In another example, one or more outer covers forming part of a set in a first package may all have decorative/ornamental elements and/or a label and/or a brand associated with a first particular "collection" or design theme of a designer, while one or more outer covers forming part of a set in a second package may all have decorative/ ornamental elements and/or a label and/or a brand associated with a second particular "collection" or design theme of the designer.

In any of the above examples, the outer cover(s) and associated insert(s) in each individual article of commerce will be sized to fit optimally with each other. Thus, in a further example, respective packages may be prepared and presented with sets of outer cover(s) and associated insert(s) distinguished by size. For example, a first package may contain outer cover(s) and associated insert(s) adapted for "size 1" children; a second package may contain outer cover(s) and associated insert(s) adapted for "size 2" children; and so on.

In an embodiment, one or more outer covers of the present disclosure may be sold and used without an insert in toilet-training circumstances or other circumstances. This may make the outer cover a suitable training tool when a child is transitioning from diapers to underwear. In an example, the outer cover may be used without an insert during the day, or a portion thereof, and used with an insert at night. In an embodiment, an insert may be provided that does not include an absorbent core, again for toilet-training purposes. In still another embodiment, an insert may be provided that does include an absorbent core, but the absorbent core may have no or a very small amount of AGM or superabsorbent polymers (e.g., less than 10% by weight). This may increase the wetness sensation felt by a wearer for toilet training purposes. Such an insert may also be useful in a swimming diaper context as well since excessive swelling will not likely occur without the presence of the superabsorbent polymers.

In another embodiment, one or more outer covers may be sold together with sensitive skin inserts or the sensitive skin inserts may be sold separately. The inserts may have lotion or other additives thereon. In such an embodiment, the outer covers may also be configured for use with wearers having sensitive skin.

A package of inserts may be configured for use in a daycare setting where the wearer is usually changed every few hours. In such an embodiment, the inserts may not have any superabsorbent polymers in a core thereof, or have reduced material in the core since the inserts will only be used for a few hours and then discarded. Packages of inserts may include daycare inserts, normal use inserts, and nighttime use inserts.

In an embodiment, the inserts may be made of washable or recyclable materials. In other embodiments, the inserts may be made of flushable materials to enable flushing of the inserts after use.

In an embodiment for adult incontinence products, one or more outer covers with inserts attached may be sold in a package. Additional inserts and/or outer covers may be purchased separately. This gives a wearer or a caregiver a range of choices from using the fully assembled product one time and then disposing of it to having the choice of tailoring his/her absorbency needs with a specific outer cover/insert combination. Lower outer cover disposal translates into one or more of the following benefits to the wearer or caregiver: lower cost, superior outer cover and/or insert performance, and sustainability.

Lateral Length of Stretchable Regions

Figure 9:
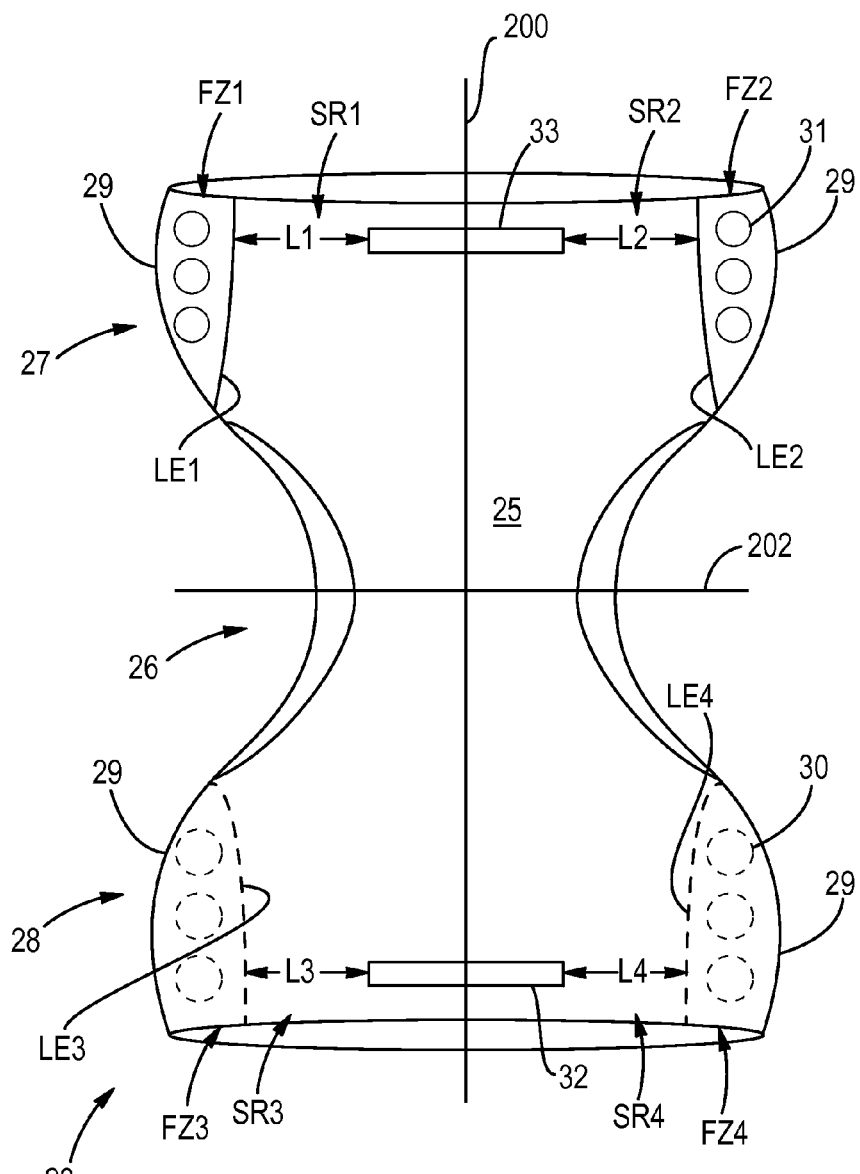
FIG. 9 is a plan view of an outer cover opened and laid flat, inner surface facing the viewer in accordance with a non-limiting embodiment of the present disclosure.

At least some of the pants of the present disclosure have outer covers comprising various stretchable regions having lateral lengths. Referring to FIG. 9, individual stretchable regions "SR" may be located between the attachment zones (e.g., 33 and 32) and the fastening zones "FZ" comprising fastening components 30 or receiving fastening components 31. The stretchable regions may also extend in other regions of the pants, such as areas more proximal to the lateral axis then the attachment zones, but that span the same lateral length as the attachment zones. These additional stretchable regions will be discussed below and will be referred to as auxiliary stretchable regions.

In FIG. 9, the fastening components 30 and the receiving fastening components 31 together form snaps or magnets, although any other suitable fastening components 30/fastening receiving components 31 may be used. In one embodiment, only one fastening component 30 in each fastening zone may be provided, while multiple receiving fastening components 31 may be provided in the fastening zone. In such an embodiment, the single fastening component 30 may be engaged with any of the multiple receiving fastening components 31 to allow for adjustability (lateral or longitudinal) of the pant on a wearer. Other suitable fastening components include hook and loop fasteners, adhesives, cohesive, buttons, and/or any other suitable fasteners known to those of skill in the art. The fastening components 30 and the fastening receiving components 31 may extend in a longitudinal direction, or substantially in a longitudinal direction, within the fastening zones, FZ. Also, the fastening zones may extend longitudinally (i.e., parallel to, or substantially parallel to, the longitudinal axis 200) and in a direction generally perpendicular or transverse to the lateral axis 202. The most laterally inboard edges of the fastening zones, FZ, are indicated in FIG. 9 as "LE".

Referring again to FIG. 9, a reusable outer cover 20 is configured to be formed into a portion of a pant and is configured to form a pant when an insert (e.g., FIG. 3) is attached thereto. The reusable outer cover 20 comprises a front waist region 27 positioned on a first side of the lateral axis 202, a rear waist region 28 positioned on a second side of the lateral axis 202, and a crotch region 26 spanning the lateral axis 202 and positioned intermediate the front waist region 27 and the rear waist region 28. The outer cover 20 may also comprise a first fastening zone positioned on a first side (e.g., right side) of the longitudinal axis 200. The first fastening zone may comprise a first portion (e.g., ear panel 29) positioned on the first side of the lateral axis 202 (in the front waist region 27) and a second portion (e.g., ear panel 29) positioned on the second side of the lateral axis 202 (in the rear waist region 28) when the outer cover 20 is opened and laid flat. The outer cover 20 may also comprise a second fastening zone positioned on a second side (e.g., left side) of the longitudinal axis 200. The second fastening zone may comprise a first portion (e.g., ear panel 29) positioned on the first side of the lateral axis 202 (in the front waist region 27) and a second portion (e.g., ear panel 29) positioned on the second side of the lateral axis 202 (in the rear waist region 28) when the outer cover 20 is laid flat. The outer cover 20 may comprise a front stretchable region formed in the front waist region 27 and having a first lateral length (L1+L2) and a rear stretchable region formed in the rear waist region 28 and having a second lateral length (L3+L4). The lateral lengths of the front and rear stretchable regions are measured as described below in the Lateral Length of the Front and Rear Stretchable Regions test. The lateral length of the front stretchable region may be equal to, less than, or greater than the lateral length of the rear stretchable region.

In an embodiment, referring again to FIG. 9, the front stretchable region (L1+L2) may comprise a first portion (L1) extending laterally between the laterally inboard edge, LE1, of the first fastening zone, FZ1, and a first end portion (most proximate to LE1) of the front attachment zone 33. The front stretchable region (L1+L2) may also comprise a second portion (L2) extending laterally between the laterally inboard edge, LE2, of the second fastening zone, FZ2, and a second end portion (most proximate to LE2) of the front attachment zone 33. The rear stretchable region (L3+L4) may comprise a first portion (L3) extending laterally between the laterally inboard edge, LE3, of the third fastening zone, FZ3, and a first end portion (most proximate to LE3) of the rear attachment zone 32. The rear stretchable region (L3+L4) may also comprise a second portion (L4) extending laterally between the laterally inboard edge, LE4, of the fourth fastening zone, FZ4, and a second end portion (most proximate to LE4) of the rear attachment zone 32.

Referring again to FIG. 9, in the front stretchable region, the lateral length of L1 may be equal to, different than, greater than, or less than the lateral length of L2, likewise, in the rear stretchable region, the lateral length of L3 may be equal to, different than, greater than, or less than the lateral length of L4. In an embodiment, the lateral length of L1 may be equal to, different than, greater than, or less than the lateral length of L3 or L4 and the lateral length of L2 may be equal to, different than, greater than, or less than the lateral length of L3 or L4. In various embodiments, the lateral lengths of L1, L2, L3, and/or L4 may be in the range of about 30 mm to about 40 mm, about 35 mm, 35 mm, or in the range of about 20 mm to about 70 mm, specifically reciting all 0.5 mm increments within the above-specified ranges and all ranges formed therein or thereby. Again in various embodiments, the lateral inboard edges LE1, LE2, LE3, and/or LE4 may have a length in the range about 80 mm to about 110 mm, about 95 mm, 95 mm, or in the range of about 30 mm to about 150 mm, specifically reciting all 0.5 mm increments within the above-specified ranges and all ranges formed therein or thereby. The front attachment zone 33 and/or the rear attachment zone 32 may have a length in the range of about 60 mm to about 90 mm, about 75 mm, 75 mm, or in the range of about 10 mm to about 120 mm, specifically reciting all 0.5 mm increments within the above-specified ranges and all ranges formed therein or thereby. In an adult incontinence context, the insert may be primarily located in the crotch region of the outer cover.

Figure 10:
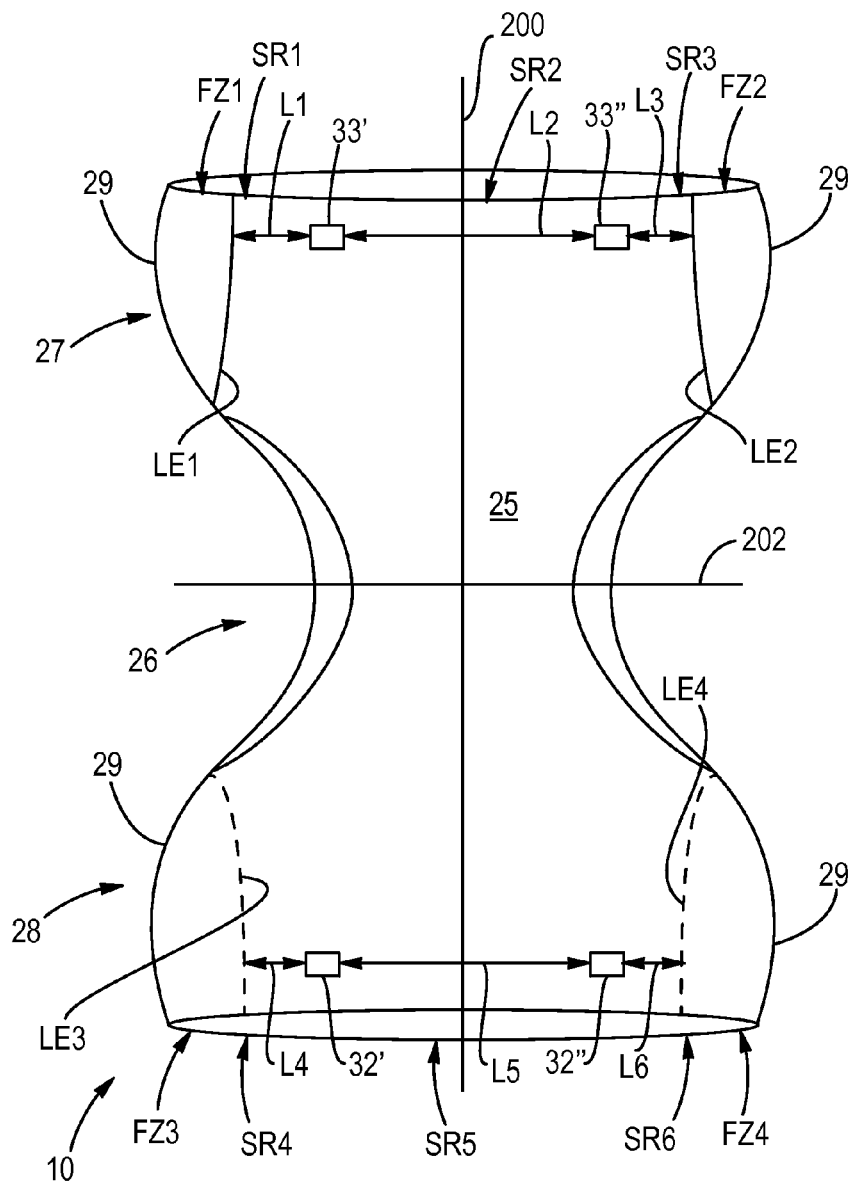
FIG. 10 is a plan view of an outer cover opened and laid flat, inner surface facing the viewer in according with a non-limiting embodiment of the present disclosure.

Referring to FIG. 10, the outer cover 20 may comprise a front attachment zone comprising a first fastening element 33' and a second fastening element 33" in the front waist region 27 and a rear attachment zone comprising a first fastening element 32' and a second fastening element 32" in the rear waist region 28. Other features of the outer cover 20 may be the same as or different than that described with respect to FIG. 9. For example, the fastening zones in FIG. 10 may comprise hook components and mating loop components instead of snaps. The hook components and mating loop components may still extend in the longitudinal direction or in substantially the longitudinal direction. The outer cover 20 may comprise a front stretchable region formed in the front waist region 27 and having a first lateral length (L1+L2+L3) and a rear stretchable region formed in the rear waist region 28 and having a second lateral length (L4+L5+L6). The lateral lengths of the front and rear stretchable regions are measured as described below in the Lateral Length of the Front and Rear Stretchable Regions test. The lateral length of the front stretchable region may be equal to, less than, or greater than the lateral length of the rear stretchable region. FIGS. 9 and 10 merely illustrate two examples of front and rear stretchable regions having lateral lengths. Any other suitable configuration of attachment zones would also provide lateral lengths for the front and rear stretchable regions. In an embodiment, more than 3 stretchable regions may be provided in a front waist region and/or a rear waist region, for example.

In an embodiment, referring again to FIG. 10, the front stretchable region (L1+L2+L3) may comprise a first portion (L1) extending laterally between the laterally inboard edge, LE1, of the first fastening zone, FZ1, and a first end portion (most proximate to LE1) of the first fastening element 33'. The front stretchable region (L1+L2+L3) may also comprise a second portion (L2) extending laterally between a second end portion (most distal to LE1) of the first fastening element 33' and the first end portion (most proximate to LE1) of the second fastening element 33". The front stretchable region (L1+L2+L3) may also comprise a third portion (L3) extending laterally between a second end portion (most distal to LE1) of the second fastening element 33" and the laterally inboard edge, LE2, of the second fastening zone, FZ2. The rear stretchable region (L4+L5+L6) may comprise a first portion (L4) extending laterally between the laterally inboard edge, LE3, of the third fastening zone, FZ3, and a first end portion (most proximate to LE3) of the first fastening element 32'. The rear stretchable region (L4+L5+L6) may also comprise a second portion (L5) extending laterally between a second end portion (most distal to LE3) of the first fastening element 32' and the first end portion (most proximate to LE3) of the second fastening element 32". The rear stretchable region (L4+L5+L6) may also comprise a third portion (L6) extending laterally between a second end portion (most distal to LE3) of the second fastening element 32" and the laterally inboard edge, LE4, of the fourth fastening zone, FZ4. The lateral length of the front stretchable region (L1+L2+L3) may be the same as, different than, greater than, or less than the lateral length of the rear stretchable region (L4+L5+L6).

Referring to FIG. 10, in the front stretchable region, the lateral length of L1 may be equal to, different than, greater than, or less than the lateral length of L2 or L3, likewise, in the rear stretchable region, the lateral length of L4 may be equal to, different than, greater than, or less than the lateral length of L5 or L6. In an embodiment, the lateral length of L1 may be equal to, different than, greater than, or less than the lateral length of L4, L5, or L6 and the lateral length of L4 may be equal to, different than, greater than, or less than the lateral length of L1, L2, or L3. In various embodiments, the lateral lengths of L1, L3, L4, and/or L6 may be in the range of about 10 mm to about 30 mm, about 20 mm, 20 mm, or in the range of about 10 mm to about 70 mm, specifically reciting all 0.5 mm increments within the above-specified ranges and all ranges formed therein or thereby. The lateral lengths L2 and/or L5 may have lengths in the range of about 70 mm to about 100 mm, about 85 mm, 85 mm, or in the range of about 10 mm to about 120 mm, specifically reciting all 0.5 mm increments within the above-specified ranges and all ranges formed therein or thereby. Again in various embodiments, the lateral inboard edges LE1, LE2, LE3, and/or LE4 may have a length in the range about 80 mm to about 110 mm, about 95 mm, 95 mm, or in the range of about 30 mm to about 150 mm, specifically reciting all 0.5 mm increments within the above-specified ranges and all ranges formed therein or thereby. The lateral inboard edges LE1, LE2, LE3, and/or LE4 may represent the longitudinal length of the fastening zones. The first fastening element 33' and/or the second fastening element 33" of the front attachment zone may have a length in the range of about 5 mm to about 75 mm, in the range of about 10 mm to about 60 mm, or in the range of about 15 mm to about 30 mm, specifically reciting all 0.5 mm increments within the above-specified ranges and all ranges formed therein or thereby. The first fastening element 32' and/or the second fastening element 32" of the rear attachment zone may have a length in the range of about 5 mm to about 75 mm, in the range of about 10 mm to about 60 mm, in the range of about 15 mm to about 30 mm, specifically reciting all 0.5 mm increments within the above-specified ranges and all ranges formed therein or thereby.

In an embodiment, although not illustrated, a plurality of generally laterally extending fastening elements may be provided in the front waist region 27. At least some of the fastening elements may be continuous or discontinuous. In such an embodiment, the total lateral length of the front stretchable regions will be the lateral length between LE1 and LE2 minus the total lateral length of all of the fastening elements. The rear waist region 28 may have the same or similar features.

Figures 11, 12, 13:
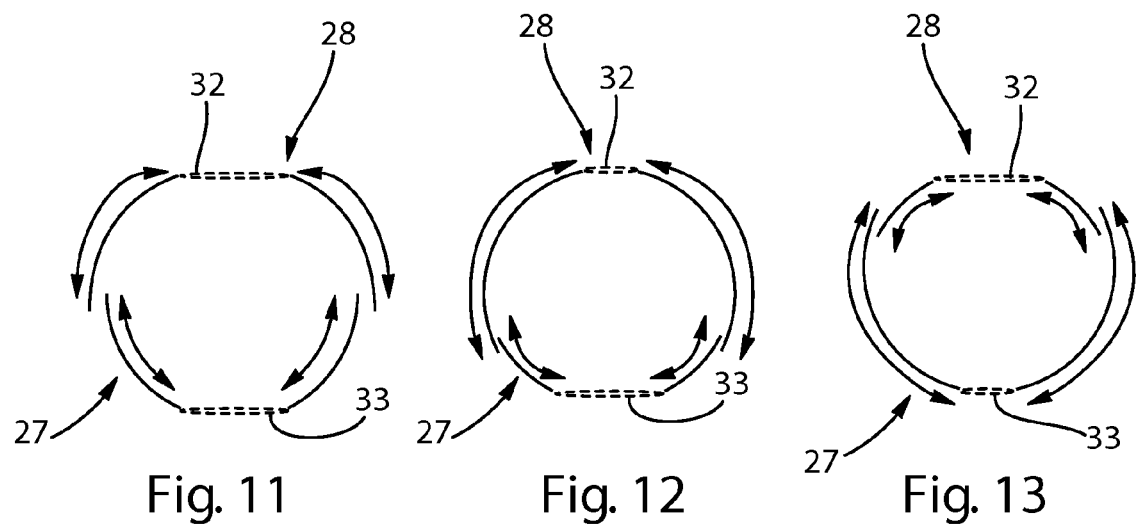
FIG. 11 is top view of an outer cover configured to receive an insert and having front and rear stretchable regions, wherein the lateral length of front stretchable region is equal to, or substantially equal to, the lateral length of the rear stretchable region, in according with a non-limiting embodiment of the present disclosure.
FIG. 12 is top view of an outer cover configured to receive an insert and having front and rear stretchable regions, wherein the lateral length of the front stretchable region is less than the lateral length of the rear stretchable region, in according with a non-limiting embodiment of the present disclosure.
FIG. 13 is top view of an outer cover configured to receive an insert and having front and rear stretchable regions, wherein the lateral length of the front stretchable region is greater than the lateral length of the rear stretchable region, in according with a non-limiting embodiment of the present disclosure.

Referring to FIGS. 11-13, top view schematic representations of pants are illustrated. Each pant has a front attachment zone 33 in a front waist region 27 and a rear attachment zone 32 in a rear waist region 28. FIG. 11 illustrates fastening zones on the side portion of the pant, FIG. 12 illustrates fastening zones on the front portion of the pant, and FIG. 13 illustrates fastening zones on the rear portion of the pant. In FIG. 11, the lateral length of the front stretchable region is the same as, or substantially the same as (e.g. +/–1 cm), the lateral length of the rear stretchable region. In FIG. 12, the lateral length of the front stretchable region is less than the lateral length of the rear stretchable region. In FIG. 13, the lateral length of the front stretchable region is greater than the lateral length of the rear stretchable region.

In an embodiment, the outer cover may comprise elastic strands as the stretch mechanism in the entire waist region or waist circumference. The elastic strands may be prestretched and laminated between two nonwovens to deliver stretch. The amount of prestretch in the elastic strands may vary between about 50% and about 250% or between about 100% and about 150%, specifically reciting all 1% increments within the specified ranges and all ranges formed therein or thereby. These elastic strands may be positioned in the lateral direction, substantially in the lateral direction, or other direction, of the outer cover. In some instances, these elastic strands may be positioned in the front and rear waist regions, but not in the crotch region of the outer cover. Spacing between the strands may be the same or different, and these strands may have different deniers, so as to be able to control the forces in different regions of the outer cover. Straight or curved elastics, in the form of strands, for example, may also be used in the leg opening regions of the outer covers.

In another embodiment, the outer cover may comprise an elastomeric film, for example an elastomeric polypropylene film, such as Vistamaxx film, that either runs the full length and width of the product, or is in the front and rear waist regions of the product. A laminate of this film with two nonwovens may be made stretchable either by incremental stretching either in the lateral or in the longitudinal direction of the outer cover, or by "live stretch," which is stretching the film and then laminating it to a couple of layers of nonwovens, or both. This elastomeric film may be apertured for breathability and skin health. Typical stretch in the outer cover may range from about 50% to about 200% or from about 80% to about 150%, specifically reciting all 1% increments within the specified ranges and all ranges formed therein or thereby.

In yet another embodiment, the outer cover may comprise an elastomeric nonwoven, comprising elastomeric fibers, such as polyurethane and elastomeric polypropylene, in addition to standard polypropylene fibers. This elastic nonwoven may be incrementally stretched or may be bonded to one or more nonelastomeric nonwovens by live stretch. Typically, this elastic nonwoven has about 50% to about 150% stretch or from about 60% to about 120% stretch, specifically reciting all 1% increments within the specified ranges and all ranges formed therein or thereby.

The insert may extend the full length and/or width of the outer cover or less than the full length or width of the outer cover. The insert may be mainly positioned in the crotch region with only portions of the insert extending into the front and rear waist regions. This at least inhibits the outer cover's stretch being somewhat limited by the insert in the front and rear waist regions. The length and width of the insert may vary from about 25% of the longitudinal length of the outer cover to about 100% of the longitudinal length of the outer cover or from about 50% to about 80% of the longitudinal length of the outer cover, specifically reciting all 1% increments within the specified ranges and all ranges formed therein or thereby.

In various embodiments, an adult incontinence product may have an outer cover having a longitudinal length in the range of about 650 mm to about 870 mm, specifically reciting all 1 mm increments within the specified ranges and all ranges formed therein or thereby. An insert may have a longitudinal length of about 460 mm to about 480 mm, or about 471 mm, for a moderately absorbent insert and a longitudinal length of about 535 mm to about 565 mm, or about 548 mm for a maximum absorbent insert. The percentage of insert longitudinal length to outer cover longitudinal length may be in the range of about 55% to about 95%, about 60% to about 85%, about 55%, about 62%, about 65%, about 69%, about 72%, or about 81%, specifically reciting all 1% increments within the specified ranges and all ranges formed therein or thereby.

The features discussed below provide an outer cover for use as a pant that is easy to pull up over the thighs and buttocks and that remains in place when fully pulled up.

Average Modulus of a Closed Waist Outer Cover

The average modulus of a closed waist outer cover without an insert positioned therein is measured using the Whole Outer Cover Waist Opening Circumference Extension Force Test set forth below to first determine the force in Newtons (N) at 110 mm extension and at 170 mm extension. The force at 110 mm in Newtons (N) is then subtracted from the force at 170 mm in Newtons (N). The resulting force in Newtons is then divided by the strain or the distance of extension, 60 mm (i e, 170 mm-110 mm), which converted to meters, is 0.06 m. As such, the average modulus has units of Newtons/meter. Example average moduli for the outer covers of the present disclosure without an insert positioned therein may be in the range of about 40 N/m to about 200 N/m, about 60 N/m to about 170 N/m, or less than about 250 N/m, but greater than about 30 N/m, specifically reciting all 1.0 (N/m) increments within the above-specified ranges and all ranges formed therein or thereby. Example closed outer cover forces at 110 mm extension may be in the range of about 2 N to about 12 N, about 4 N to about 10 N, or about 5 N to about 9 N, specifically reciting all 0.1 N increments within the above-specified ranges and all ranges formed therein or thereby. Example closed outer cover forces at 170 mm extension may be in the range of about 5 N to about 20 N, about 9 N to about 17 N, or about 10 N to about 15.5 N, specifically reciting all 0.1 N increments within the above-specified ranges and all ranges formed therein or thereby. The ratio of the extension force at 110 mm to the extension force at 170 mm for a closed waist outer cover may be between about 0.3 and 0.8, specifically reciting all 0.05 increments within the specified range and all ranges formed therein.

Recovery Force at 110 mm

The recovery force at 110 mm of a closed waist reusable outer cover is measured using the Whole Outer Cover Waist Opening Circumference Extension Force Test set forth below.

The recovery force of the closed waist reusable outer cover at 110 mm extension may be in the range of about 1 N to about 8 N, about 1.5 N to about 6 N, about 2 N to about 4 N, about 2 N to about 3 N, or about 2.5 N, specifically reciting all 0.1 N increments within the above-specified ranges and all ranges formed therein or thereby.

Average Modulus of Front/Rear Waist Regions of the Outer Cover

The average modulus of the front/rear waist regions of the outer cover without an insert positioned therein is measured using the Whole Outer Cover Waist Opening Circumference Extension Force Test set forth below. The average modulus of the front/rear waist regions of the outer cover is calculated by subtracting the force (N) applied by the front or rear waist region at 55 mm extension from the force applied by the front or rear waist region, respectively, at 85 mm extension and then dividing the result by 0.03 meters (30 mm or 85 mm minus 55 mm). In some examples, the average modulus of the front or rear waist regions of the outer covers of the present disclosure may be in the range of about 15 N/m to about 100 N/m, about 20 N/m to about 90 N/m, or less than about 100 N/m, but greater than about 10 N/m, specifically reciting all 1.0 increments (N/m) within the above-specified ranges and all ranges formed therein or thereby. The average modulus of a front waist region of a reusable outer cover may be the same as, similar to, or different than the average modulus of a rear waist region of the same reusable outer cover.

Extension at 20 N of a Closed Waist Outer Cover

The extension at 20 N force of a closed waist outer cover is determined using the using the Whole Outer Cover Waist Opening Circumference Extension Force Test set forth below. The distance of extension may be in the range of about 150 mm to about 450 mm, about 160 mm to about 350 mm, or about 150 mm to about 600 mm, specifically reciting all 1.0 mm increments within the above-specified ranges and all ranges formed therein or thereby. Other extension distances are also within the scope of the present disclosure.

Waist Width of Closed Waist Outer Cover

The waist widths (relaxed and extended to a 20 N force) of a closed waist outer cover are measured as described in the Whole Outer Cover Waist Opening Circumference Extension Force Test as set forth herein. The waist width is the relaxed waist opening circumference, reported to the nearest 1 mm, and divided by 2 (see FIG. 26 and related description below). To measure the waist width of an outer cover with a 20 N extension applied thereto, the hooks 512 are moved away from each other until a 20 N+/−0.1 N force is read. The waist width is the waist opening circumference at 20 N of force, measured as in FIG. 26, reported to the nearest 1 mm, and divided by 2.

The waist width of a relaxed closed waist outer cover for a wearer in the 8-15 kg range may be in the range of about 90 mm to about 250 mm, about 110 mm to about 200 mm, or of about 110 mm to about 190 mm, specifically reciting all 1.0 mm increments within the above-specified ranges and all ranges formed therein or thereby. The waist width of a closed waist outer cover for a wearer in the 8-15 kg range with an extension force of 20 N applied to it may be in the range of about 270 mm to about 450 mm or of about 290 mm to about 450 mm, specifically reciting all 1.0 mm increments within the above-specified ranges and all ranges formed therein or thereby. The waist width of a relaxed closed waist outer cover for any wearer (not necessarily in the 8-15 kg range) may be in the range of about 90 mm to about 300 mm, of about 150 mm to about 275 mm, or of about 200 mm to about 275 mm, specifically reciting all 1.0 mm increments within the above-specified ranges and all ranges formed therein or thereby. The waist width of a closed waist outer cover for any wearer with an extension force of 20 N applied to it may be in the range of about 270 mm to about 1000 mm, of about 270 mm to about 800 mm, or of about 270 mm to about 775 mm, specifically reciting all 1.0 mm increments within the above-specified ranges and all ranges formed therein or thereby.

Waist Circumference of a Closed Waist Outer Cover

The circumference (relaxed and extended to a 20 N force) of the waist opening of a closed waist outer cover may be measured as described below within the Whole Outer Cover Waist Opening Circumference Extension Force Test. The circumference of the waist opening is the relaxed waist opening circumference (see e.g., FIG. 26 and related description below). To measure the circumference of the waist opening of an outer cover with a 20 N extension applied thereto, the hooks 512 are moved away from each other until a 20 N+/−0.1 N force is read. The circumference of the waist opening at 20 N extension is measured as in FIG. 26 and reported to the nearest 1 mm.

The circumference of a relaxed closed waist outer cover for a wearer in the 8-15 kg range may be in the range of about 200 mm to about 450 mm, of about 220 mm to about 400 mm, or of about 220 mm to about 380 mm, specifically reciting all 1.0 mm increments within the above-specified ranges and all ranges formed therein or thereby. The circumference of a closed waist outer cover for a wearer in the 8-15 kg range with an extension force of 20 N applied to it may be in the range of about 580 mm to about 850 mm or of about 600 mm to about 950 mm, specifically reciting all 1.0 mm increments within the above-specified ranges and all ranges formed therein or thereby. The circumference of a relaxed closed waist outer cover for any wearer (not necessarily within the 8-15 kg range) may be in the range of about 200 mm to about 600 mm, of about 200 mm to about 550 mm, or of about 220 mm to about 525 mm, specifically reciting all 1.0 mm increments within the above-specified ranges and all ranges formed therein or thereby. The circumference of a closed waist outer cover for any wearer with an extension force of 20 N applied to it may be in the range of about 550 mm to about 2000 mm, of about 600 mm to about 1700 mm, or of about 600 mm to about 1550 mm, specifically reciting all 1.0 mm increments within the above-specified ranges and all ranges formed therein or thereby. It is important to note that the outer covers and inserts of the present disclosure may be used with adult incontinence products as well for users of any size.

Area of Stretchable Regions

Figure 14A:
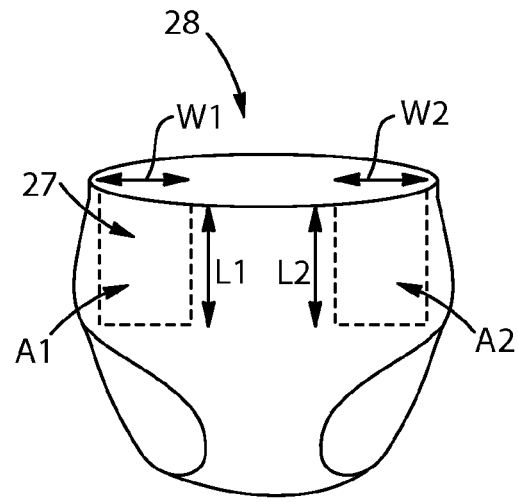
FIG. 14A is a front view of an outer cover configured to receive an insert and having a front stretchable area in accordance with a non-limiting embodiment of the present disclosure.
Figure 14B:
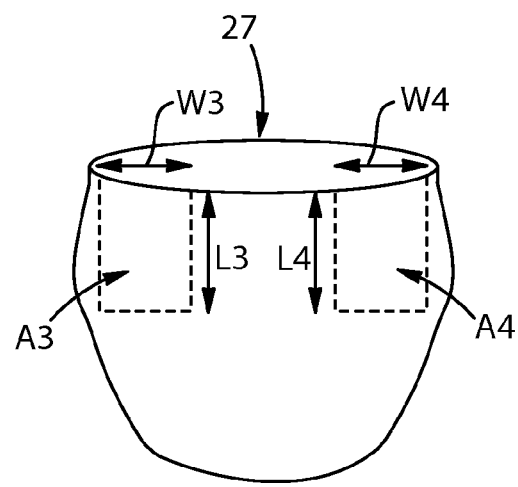
FIG. 14B is a rear view of an outer cover configured to receive an insert and having a rear stretchable area in accordance with a non-limiting embodiment of the present disclosure.
Figure 15:
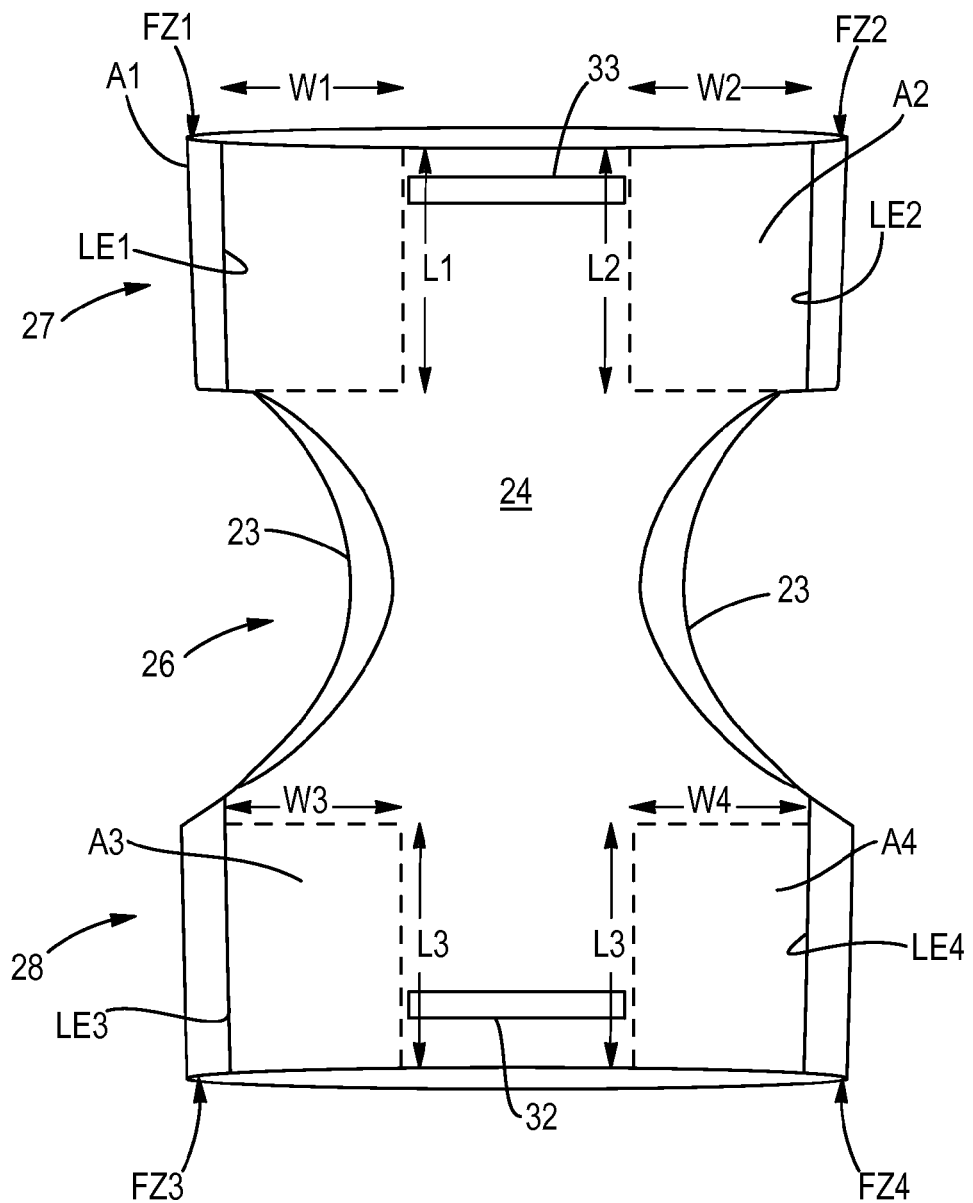
FIG. 15 is a plan view of an outer cover opened and laid flat with stretchable areas, inner surface facing the viewer in accordance with a non-limiting embodiment of the present disclosure.

In an embodiment, referring to FIGS. 14A, 14B, and 15, the front stretchable region may have a first area (A1+A2) and the rear stretchable region may have a second area (A3+A4). The first area may be equal to, different than, less than, or greater than the second area. Area A1 may be equal to or different than area A2 in the front stretchable region likewise, area A3 may be equal to or different than area A4 in the rear stretchable region. In other embodiments, all of the areas may be the same or different. The areas that make up each stretchable region are illustrated in FIGS. 14A, 14B, and 15. As can be seen, areas A1 and A2 together make up the area of the front stretchable region and areas A3 and A4 together make up the area of the rear stretchable region. Each area (e.g., area A1) has a length and a width. To determine the area of the front stretchable region, one would add areas A1 and A2 together and, likewise, to determine the area of the rear stretchable region, one would add areas A3 and A4 together. Areas of the stretchable regions are measured according to the Area of the Stretchable Regions test set forth below.

In various embodiments, referring to FIGS. 14A-15, the widths W1, W2, W3, and/or W4 may have dimensions in the range of about 30 mm to about 40 mm, about 35 mm, 35 mm, or in the range of about 20 mm to about 70 mm, specifically reciting all 1.0 mm increments within the above-specified ranges and all ranges formed therein or thereby. The lengths L1, L2, L3, and/or L4 may have dimensions in the range of about 80 mm to about 110 mm, about 95 mm, 95 mm, or in the range of about 30 mm to about 150 mm, specifically reciting all 1.0 mm increments within the above-specified ranges and all ranges formed therein or thereby. The lateral inboard lengths LE1, LE2, L3, and/or LE4 in FIG. 15 may be the same as the lateral inboard lengths LE1, LE2, LE3, and/or LE4 specified in relation to FIGS. 9 and 10. The areas, A1, A2, A3, and/or A4 may be in the range of about 25 $cm^2$ to about 40 $cm^2$, about 33.5 $cm^2$, 33.25 $cm^2$, or in the range of about 6 $cm^2$ to about 105 $cm^2$, specifically reciting all 0.5 $cm^2$ increments within the above-specified ranges and all ranges formed therein or thereby.

In an embodiment, referring to FIG. 15 as an example, a size 4 reusable outer cover configured to receive an insert may have the following values. Values L1-L4 may be about 90 mm, value W1 may be about 60 mm, value W2 may be about 60 mm, value W3 may be about 70 mm, and value W4 may be about 70 mm. As such, in this example, area A1 is about 54 $cm^2$, area A2 is about 54 $cm^2$, area A3 is about 63 $cm^2$, and area A4 is about 63 $cm^2$. Therefore, the area of the front stretchable region is A1+A2 or 108 $cm^2$ and the area of the rear stretchable region is A3+A4 or 126 $cm^2$. Those of skill in the art will understand that many other areas will apply to the reusable outer covers of the present disclosure.

Auxiliary Stretchable Regions

Figure 16:
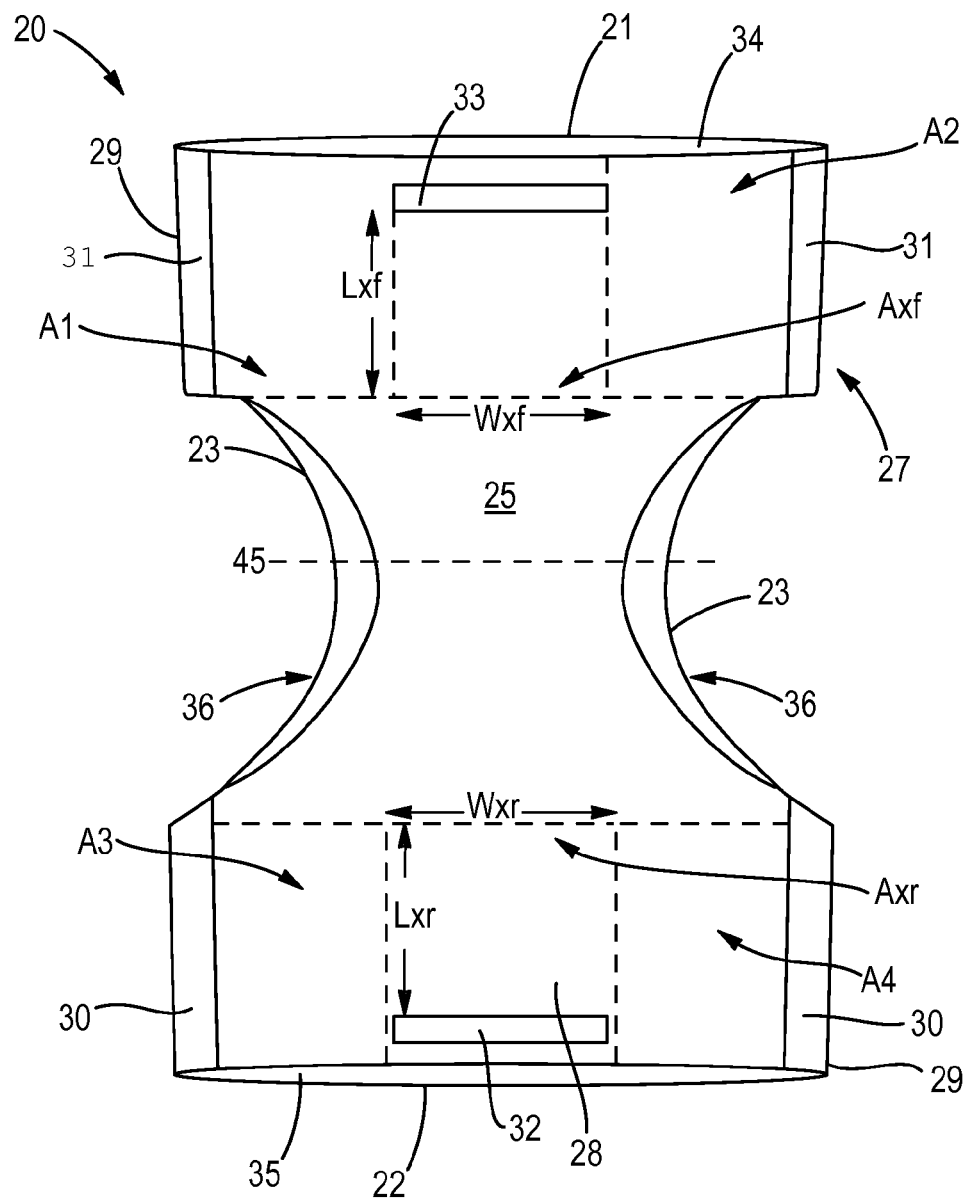
FIG. 16 is a plan view of an outer cover opened and laid flat with stretchable areas and auxiliary stretchable areas, inner surface facing the viewer in accordance with a non-limiting embodiment of the present disclosure.

In an embodiment, referring to FIG. 16, a reusable outer cover 20 may have one or more auxiliary stretchable regions in the front or rear waist regions 27 and 28. There may be one auxiliary stretchable region, Axf, in the front waist region 27 and another auxiliary stretchable region, Axr, in the rear waist region 28. The auxiliary stretchable regions, Axf and Axr, may extend longitudinally between the most longitudinally inboard edge of the attachment zones 33 and 32, respectively, and a line (in each waist region) extending laterally across the outer cover 20 and connecting the beginnings of the leg openings 23. The auxiliary stretchable regions, Axf and Axr, may also extend laterally between the areas A1 and A2 and A3 and A4, respectively. In some embodiments, the fasteners of the attachment zones 33 and 32 may be stretchable or may not be stretchable. The widths, Wxf and Wxr, of the auxiliary stretchable regions, Axf and Axr, may be measured by measuring the length of the attachment zones 33 and 32. The lengths, Lxf and Lxr, of the auxiliary stretchable regions, Axf and Axr, may be measured from a lateral line connecting the beginning of the leg openings 23 to the longitudinally inboard edge of each attachment zone 33, 32. For instance, the width of the auxiliary stretchable region, Axf, may be determined by measuring the lateral width of the attachment zone 33 and the length may be determined by measuring the longitudinal length between the longitudinally inboard edge of the attachment zone 33 to a lateral line connecting the beginning of the leg opening 23. Any areas of insert attachment to the outer cover within the Axf or Axr (e.g., additional attachment zones within the Axf or Axr) may be subtracted from the measured width or length as suitable. The area of the front auxiliary stretchable region, Axf, may be different than, larger than, smaller than, or equal to the area of the rear auxiliary stretchable region, Axr. The length and width of the front auxiliary stretchable region, Axf, may be different than, the same as, greater than, or less than, the length and the width of the rear auxiliary stretchable region, Axr. In an embodiment, the length of the front auxiliary stretchable region, Axf, may be different than or the same as the length of the auxiliary stretchable region Axr, while the widths of each of the regions may be the same or different or vice versa. Other auxiliary stretchable regions may be provided depending, at least in part, on the configuration of the attachment zones for the insert. In certain embodiments, a plurality of auxiliary stretchable regions may be provided in each of the front and rear waist regions 27 and 28.

In various embodiments, referring again to FIG. 16, dimensions Lxf and Lxr may be in the range of about 60 mm to about 90 mm, about 70 mm, 70 mm, or in the range of about 20 mm to about 120 mm, specifically reciting all 0.5 increments within the above-specified ranges and all ranges formed therein or thereby. Dimensions Wxf and Wxr may be in the range of about 60 mm to about 90 mm, about 75 mm, 75 mm or in the range of about 10 mm to about 120 mm, specifically reciting all 0.5 increments within the above-specified ranges and all ranges formed therein or thereby. The areas Axf and Axr may be in the range of about 40 $cm^2$ to about 60 $cm^2$, about 52.5 $cm^2$, 52.5 $cm^2$, or in the range of about 5 $cm^2$ to about 144 $cm^2$, specifically reciting all 0.5 $cm^2$ increments within the above-specified ranges and all ranges formed therein or thereby.

In an embodiment, the ratio of the width of the front waist region (measured at the waist edge) to the width of the rear waist region (measured at the waist edge) is about 1 to 1, about 1 to 1.5, about 1 to 2, about 1 to 2.5, about 1 to 3, about 1 to 3.5, or about 1 to 4, specifically reciting all ratios within the above-specified ranges and all ranges formed therein or thereby.

Extension of Front/Rear Waist Regions of the Outer Cover

The outer cover front waist region extension force at 85 mm extension may be between about 1 N and about 10 N or about 1 N and about 2 N, specifically reciting all 0.1 N increments within the specified ranges and any ranges formed therein or thereby, as measured according to the Outer Cover Front or Rear Waist Region Extension Force Test described below. The outer cover rear waist region extension force at 85 mm extension may be the same as the front waist region or different than the front waist region. The outer cover front waist region extension force at 55 mm extension may be between about 0.4 N and about 5 N or about 0.5 N and about 2 N, specifically reciting all 0.1 N increments within the specified ranges and any ranged formed therein or thereby, as measured by the Outer Cover Front or Rear Waist Region Extension Force Test described below. The outer cover rear waist region extension force at 55 mm extension may be the same as the front waist region or different than the front waist region at 55 mm extension.

Extension at 10 N Force

The extension at 10 N force of the front waist region or the rear waist region of an outer cover is measured using the Outer Cover Front or Rear Waist Region Extension Force Test described below. The extension at the 10 N force may be in the range of about 150 mm to about 300 mm, of about 175 mm to about 275 mm, of about 180 mm to about 250 mm, specifically reciting all 1.0 mm increments within the specified ranges and all ranges formed therein or thereby.

Fastening Component/Receiving Fastening Component Configurations

Figure 17:
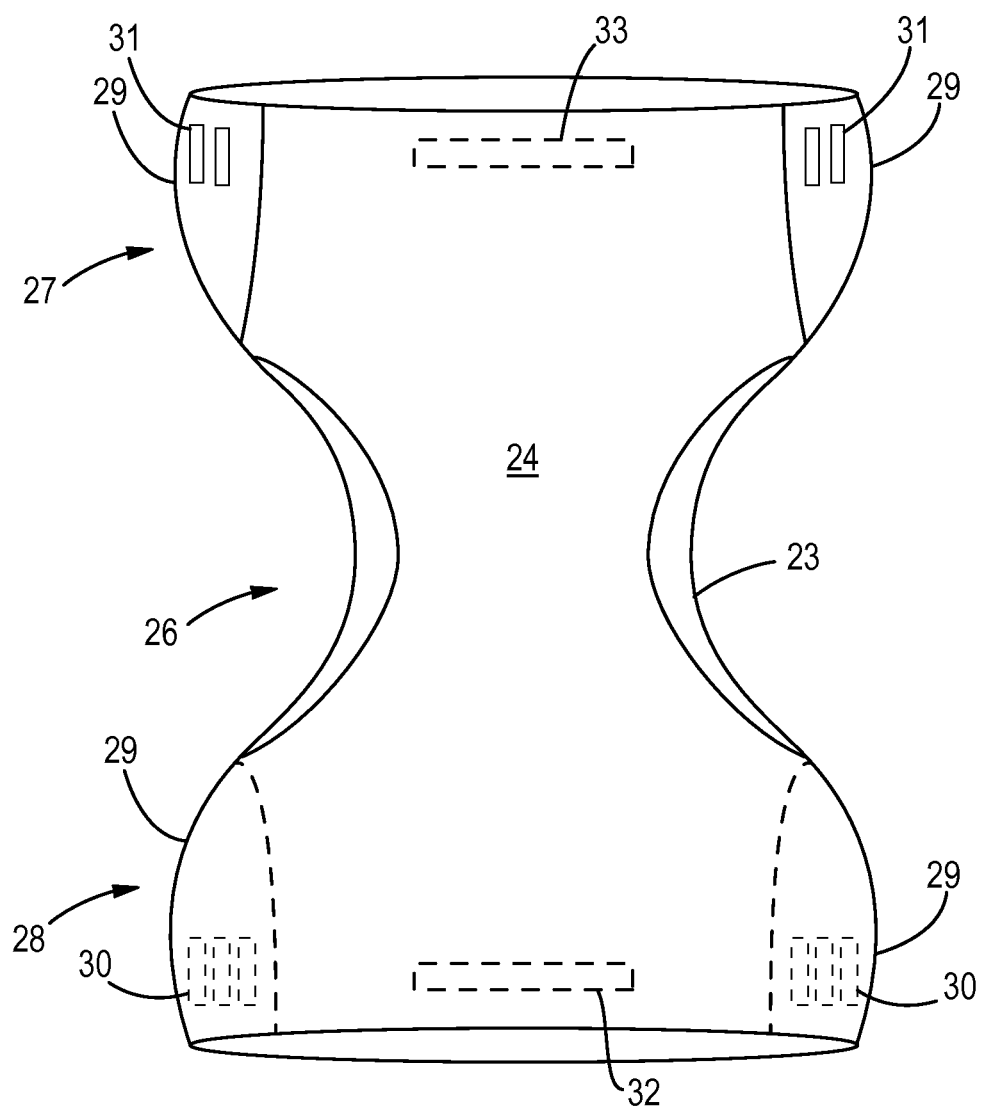
FIGS. 17 and 18 are plan views of outer covers open and laid flat with adjustable fastening components and receiving fastening components, inner surface facing the viewer in accordance with a non-limiting embodiment of the present disclosure.
Figure 18:
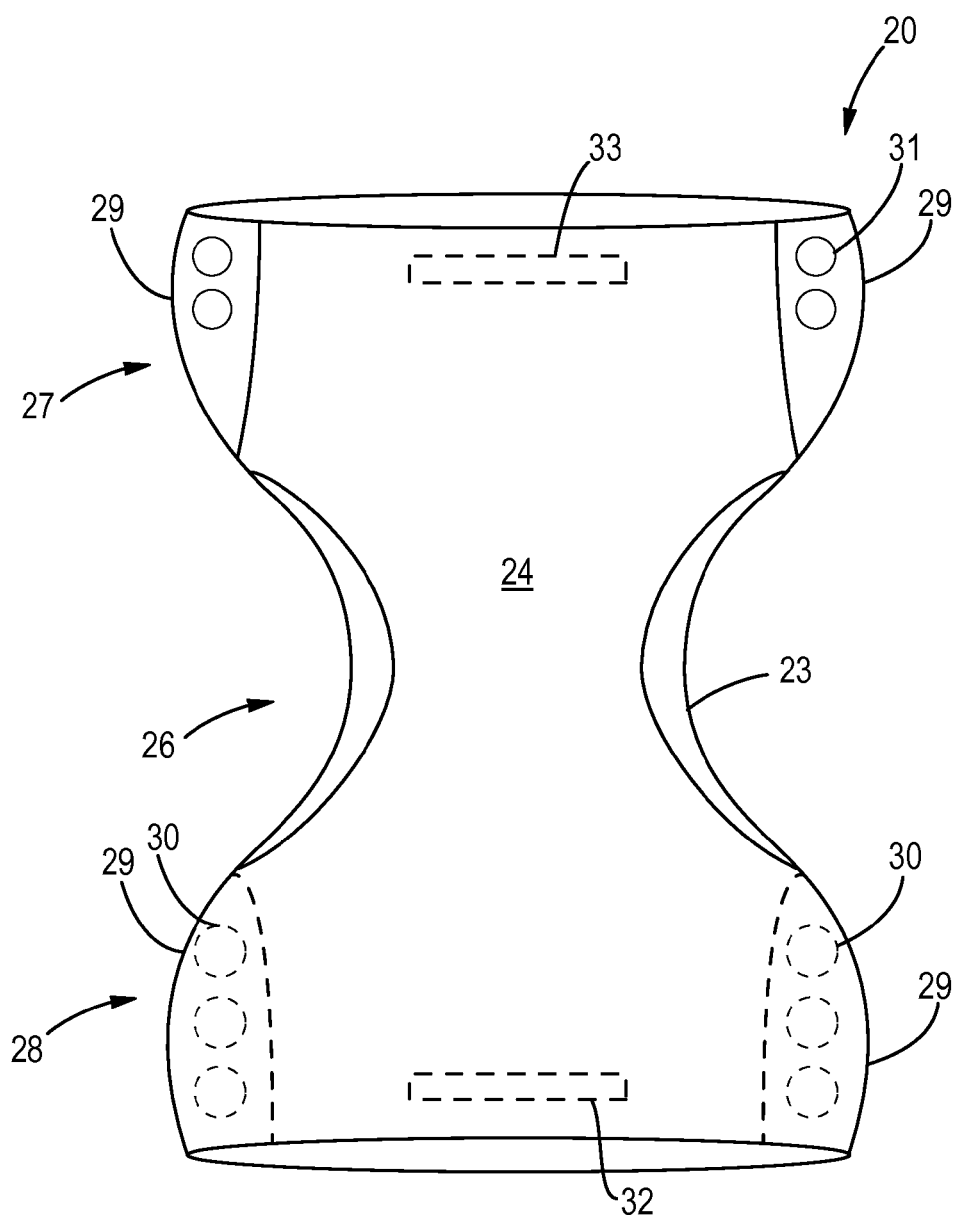

FIGS. 17 and 18 illustrate various example configurations of fastening components 30 and receiving fastening components 31 positioned on the fastening ears 29. Referring to FIG. 17, the fastening components 30 may be strips of hooks, while the receiving fastening components 31 may be strips of loops configured to be engaged by the hooks. In other embodiments, the fastening components 30 and the receiving fastening components 31 may be magnets or any other suitable fastener pairs known to those of skill in the art. One or more fastening components 30 and one or more receiving fastener components 31 may be provided on each fastening ear 29. By providing more than one fastening component 30 and/or more than one fastening component 31 on one or more ears 29, the closed waist circumference of the outer cover 20 may be adjusted to fit a particular wearer. The adjustment may allow variance in the closed waist circumference of up to two inches, for example. Either separate from or in addition to the features described with respect to FIG. 17, longitudinal adjustment may also be accomplished. Referring to FIG. 18, the fastening components 30 may be female portions of snaps and the receiving fastening components 31 may be male portions of snaps. Alternatively, the fastening components 30 and the receiving fastening components may be magnets. One or more of the fastening components 30 and one or more of the receiving fastening components 31 may be provided on each ear panel 29. The fastening components 30 and the receiving fastening components 31 of FIG. 18 may allow for longitudinal adjustment of the outer cover 20 to properly fit a particular wearer. Those of skill in the art will recognize that other longitudinal and lateral adjustment features may also be incorporated into the outer cover.

In an embodiment, the outer covers of the present disclosure may have ratio of closed waist circumference (measured at the waist edges) to total stretchable area of the front stretchable region area and the rear stretchable region area of about 1 to about 10 to about 1 to about 50. The outer covers may also have a ratio of closed waist circumference to a longitudinal length of a fastening zone (measured from the waist edge to the beginning of the leg opening) of about 10 to about 1 to about 2 to about 1. In various embodiments, the outer covers may have a ratio of a closed waist circumference to the lateral width of a fastening zone or lateral distance between two fastener elements in a fastening zone of about 20 to about 1 to about 2 to about 1. The outer cover may have a ratio of a longitudinal length (measured about the longitudinal axis from waist edge to waist edge) of the outer cover to the longitudinal length of a fastening zone of about 10 to about 1 to about 2 to about 1. The outer cover may have a ratio of a longitudinal length of the outer cover to the difference between the minimum and the maximum close waist circumference of about 10 to about 1 to about 2 to about 1. All ratios within the above-referenced ranges are specifically recited herein, but are not listed in detail for brevity.

A two-piece wearable absorbent article having some or all of the features described herein may provide advantages over both conventional wholly reusable cloth diapers and conventional wholly disposable diapers. The potential for use of semi-durable materials, and more so durable materials, to form an outer cover, provides for an outer cover that may be used more than once, and, depending upon the materials selected, used and laundered many times. An outer cover having some or all of the features described herein may eliminate the necessity for a disposable outer cover structure, thereby reducing the volume of soiled waste the user must dispose of, as compared with typical disposable diapers. Additionally, because the possibility of a reusable outer cover that bears most of the structural loading generally imposed upon a disposable diaper is presented, disposable absorbent portions may have more simplified designs, reducing manufacturing and material costs as compared with those of disposable diapers. The possibility for making a disposable absorbent insert of non-traditional renewable materials (such as paper) is presented. At the same time, a disposable absorbent insert and outer cover having some or all of the features described herein may in many circumstances prevent, or at least inhibit, most or all soiling of the outer cover by the wearer's exudates, thereby mitigating sanitation and odor problems associated with handling and storage, reducing the frequency of laundering necessary, and reducing the need for laundering resources, efforts and/or expenses, associated with conventional cloth diapers. A disposable absorbent insert having some or all of the features described herein also may provide better absorbency and better isolation of exudates from both the wearer's skin, and the wearer's clothing and environment, than conventional cloth diapers.

Use of durable materials for an outer cover also may provide other incidental benefits, in creating choices in use of materials for improved and/or more appealing comfort, fit, designs, colors, patterns, etc. as compared with disposable diapers. An outer cover having features described herein provides a wide variety of choices for making a wearable absorbent article look more attractive and/or more like an article of clothing, outerwear, or underwear. In addition to the foregoing advantages, the use of an insert having an asymmetric structure together with orientation indicia allows for the design of an insert tailored to wearer anatomy and bodily functions as they differ front-to-rear, better performance, and increased economy in design, construction and use of materials, while enabling the user to ensure correct front-rear orientation of the insert within the outer cover. Other advantages are apparent from the description above.

Test Methods

All testing is performed at 23°±2° C. and 50±2% relative humidity, unless otherwise specified. All samples are equilibrated at that environment for at least 2 hours before testing.

Edge Deflection Force Measurement Method

Figures 19A, 19B:
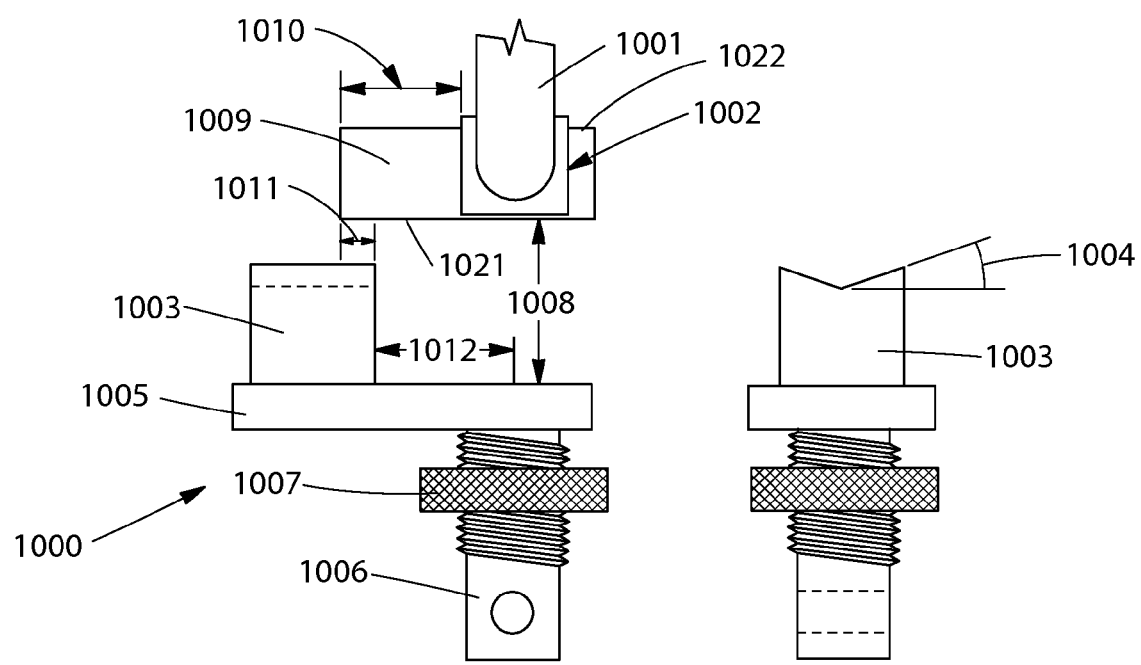
FIG. 19A is a front view of fixtures used on a constant rate of extension tensile tester for use in the Edge Deflection Force Measurement Method herein, with an included test sample.
FIG. 19B is a side view of a lower fixture used on a constant rate of extension tensile tester for use in the Edge Deflection Force Measurement Method herein.

Edge Deflection Force is measured on a constant rate of extension tensile tester with a computer interface (a suitable instrument is the MTS QTest/1L using Testworks 4.0 software, as available from MTS Systems Corp., Eden Prairie, Minn.) using a load cell for which the forces measured are within 10% to 90% of the limit of the cell. Referring to FIG. 19A, the movable (upper) pneumatic jaws 1001 are fitted with 1 inch×1 inch diamond-faced grips 1002.

The tensile tester is configured for a compression test. Program the tensile tester to lower the crosshead at a rate of 5.0 mm/min until a force of 0.01 N is detected. Zero the time and extension channels and begin data collection at an acquisition rate of 100 Hz. Lower the crosshead at a rate of 50 mm/min for 10 mm and then return the crosshead to its original gauge length. From the force versus extension curve, program the software to report the peak force (N).

Referring to FIGS. 19A and 19b, the lower fixture 1000 consists of a base 1005 90 mm wide by 40 mm deep by 6 mm thick. The base 1005 is affixed to a suitable mounting device that includes lower mounting shaft 1006, adapted to connect to the stationary mount of the tester. Lower mounting shaft 1006 is threaded as shown and has a locking collar 1007. When the lower mounting shaft 1006 is connected to the stationary mount of the tester, the locking collar 1007 is turned against the stationary mount to immobilize the base 1005 relative the stationary mount of the tester, such that it will remain stationary with the stationary mount, without any interplay therebetween, during testing. Mounted on the base 1005 is a V notched block 1003 that is 30 mm wide by 30 mm deep by 30 mm in height which is made of a low friction material such as Teflon. Referring to the perspective FIG.

19B, the block 1003 is notched from side to center with a "V" at an angle 1004 of 10 degrees. As mounted on the base 1005, the block is centered front to back and offset a distance 1012 of 32.7 mm from the center axis of the mounting shaft 1006, with the line defined by the vertex of the "V" notch intersecting the center axis of the mounting shaft 1006.

Obtain 10 samples from 10 inserts for testing as follows: Determine which of front or rear portions of the inserts are to be tested, and take all 10 samples from such portions accordingly. Lay the insert on a horizontal surface, outer/garment-facing surface up.

(a) Samples of Insert End (Including all Layers and Components)

Figure 20:
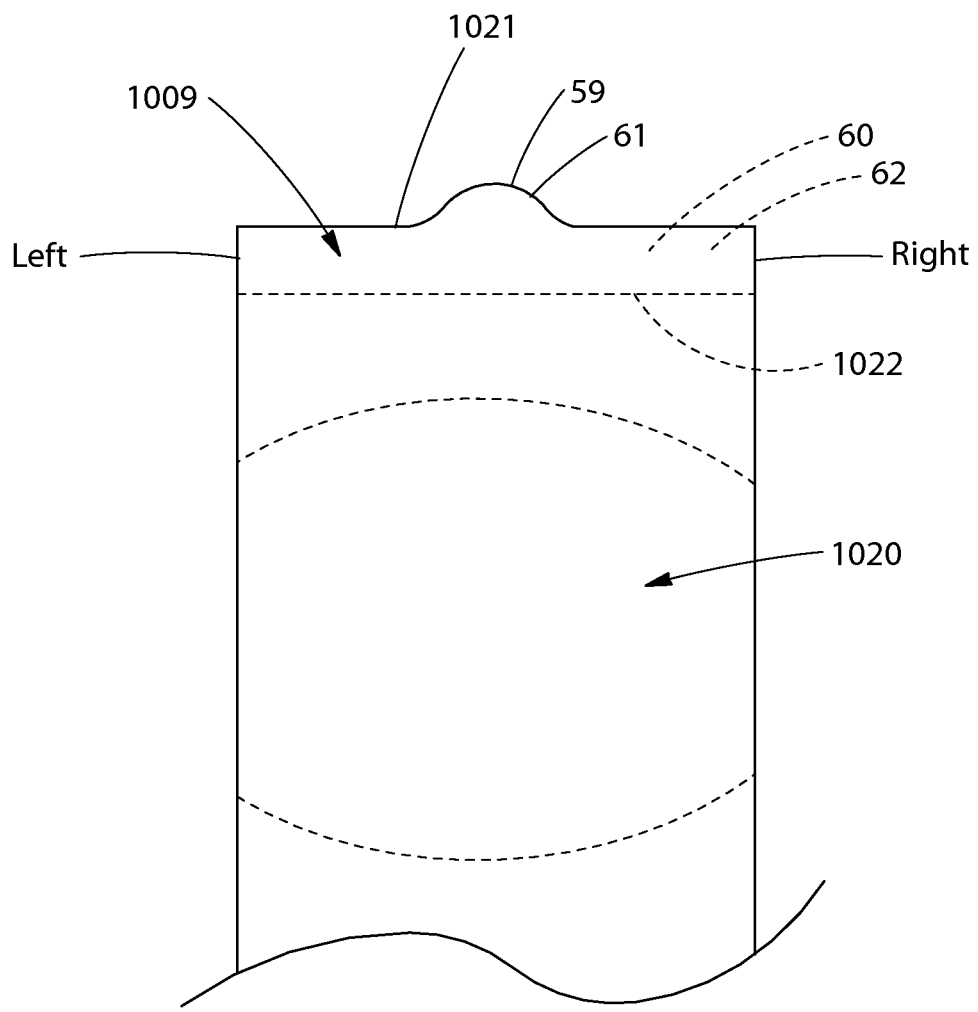
FIG. 20 illustrates preparation of a test sample of an insert including an end support stiffener, for testing in the Edge Deflection Force Measurement Method herein.

If measuring values for the insert end including all layers and components thereof, obtain samples as follows: Referring to FIG. 20, visually identify the inside edge 1022 of the stiffened portion 1009 of the end (i.e., the portion having end support stiffener 60 or 62). If visually identifying inside edge 1022 is difficult due to the particular construction of the insert, inside edge 1022 may be identified by flattening the insert along the region including the subject end, to its full longitudinal extent (stretching it out against any contraction caused by cuff elastics), laying one hand over the insert near the end to hold the insert in the stretched/flattened position, generally in the location indicated as 1020, and using the other hand to lift outer end edge 1021 vertically. The insert will tend to fold first along inside edge 1022, since a natural "hinge" location will exist at the juncture between the stiffened portion and the adjacent unstiffened portion. Cut the stiffened portion 1009 away from the insert, along edge 1022. Stiffened portion 1009 will now be the sample to be tested. (If the end portion has no stiffened portion clearly discernible by the method described above: Lay the insert on a horizontal surface, wearer-facing surface up. Considering FIG. 2W for reference, measure inward on the insert from the longitudinally end-most extent 101 of the material forming either edge 58 of cuff 53, a distance of 30 mm. Sever the end portion of the insert along a line 1023 located at such distance and parallel to the insert lateral axis. The severed portion will be the sample.) Do not remove any components such as fastener components, grasp structures, etc. If outer edge 1021 is not inherently readily distinguishable from the cut edge by a distinctive feature such as a grasp structure 59, 61, mark outer end edge 1021 for later identification.

(b) Samples of Insert End Stiffener (Removed from Insert)

If measuring values of an added insert end support stiffener by itself, obtain samples of insert ends according to the previous section (a). Apply a freeze spray as necessary to reduce the tenacity of any adhesives, and gently peel away all other components or layers of the end samples from the end support stiffener portion, taking care to avoid damaging the stiffener portion.

Referring to FIG. 19A for directional and positional orientation, locate a sample 1009 in the grips 1002 with inside edge 1022 horizontal and oriented upward, and outer end edge 1021 oriented downward, and in line with the bottom edges of the grips 1002. Additionally, locate sample 1009 in the grips 1002 such that distance 1010 is as designated for the Peak Edge Deflection Force (y) or Edge Deflection Force (y) value to be determined, and distance 1011 is 10 mm. Close the grips 1002 so that sample 1009 is gripped securely enough so as not to allow it to slip or rotate during testing, but not so tightly as to cause tearing of the sample at the grips during testing.

Zero the load cell and the crosshead position. Start the tensile tester's program, and record the data. Report the peak force (Edge Deflection Force) (in N) to ±0.001 N. For each sample, perform the test on both the left and right sides (see FIG. 7), and record the Edge Deflection Force for both sides. Test 10 samples. Calculate the average Edge Deflection Force found of the 10 samples, both sides.

Bending Stiffness Measurement Method

Figure 21:
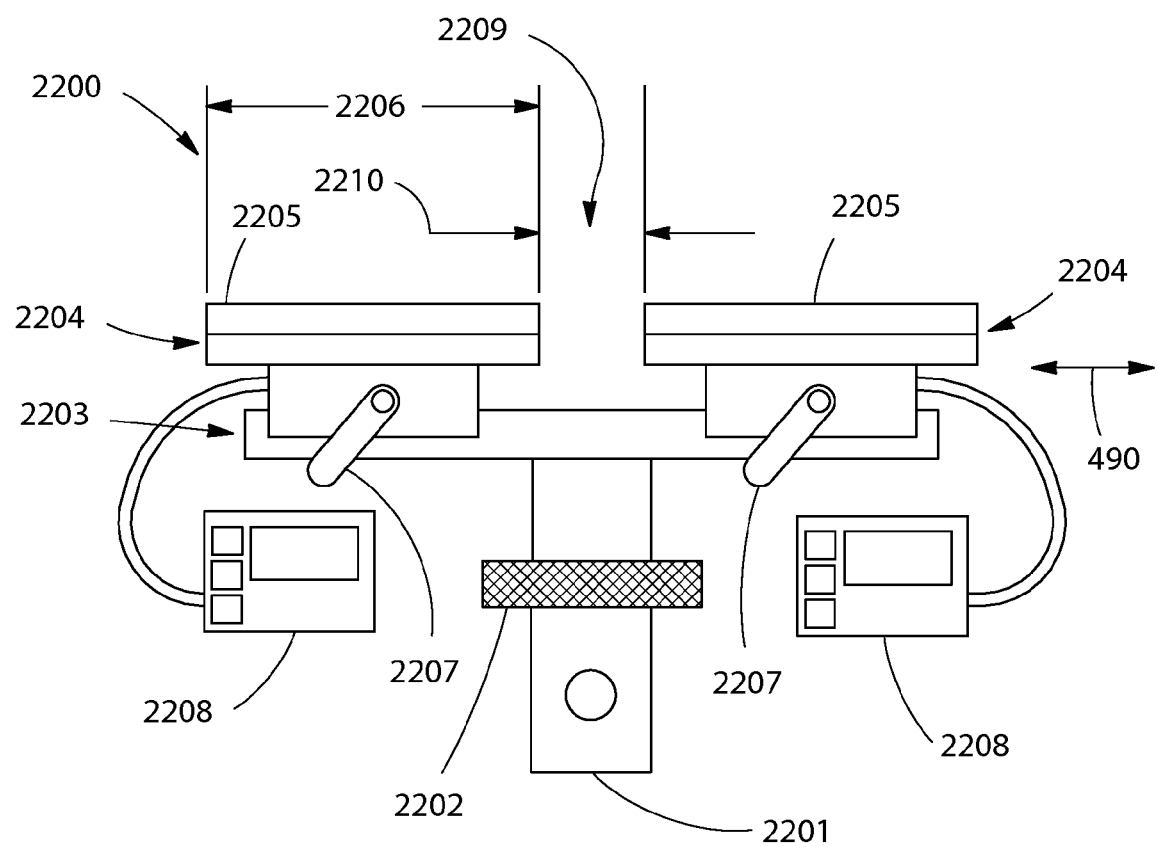
FIG. 21 is a front view of a lower fixture used on a constant rate of extension tensile tester for use in the Bending Stiffness Measurement Method herein.
Figure 22:
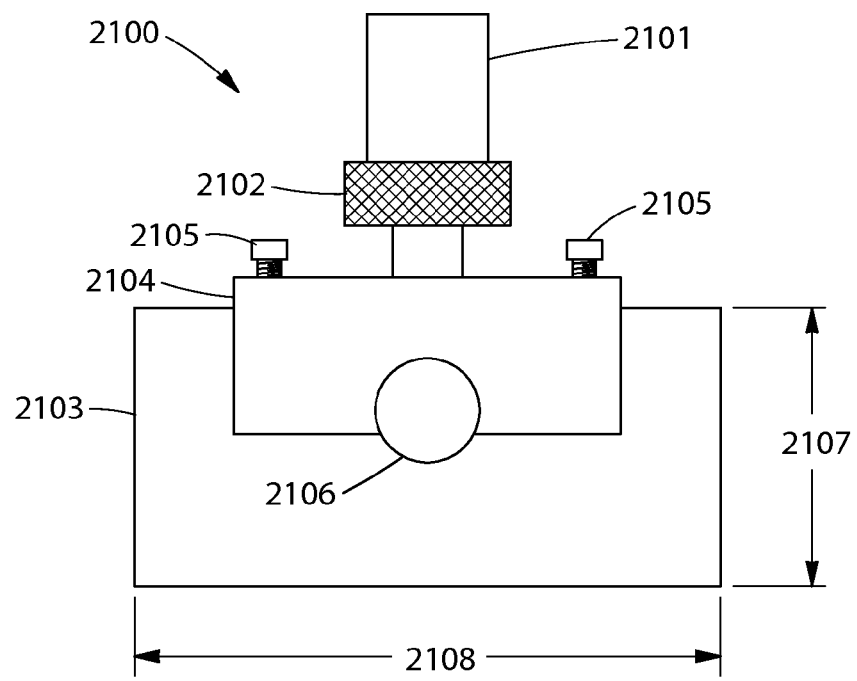
FIG. 22 is a side view of an upper fixture used on a constant rate of extension tensile tester for use in the Bending Stiffness Measurement Method herein.
Figure 23:
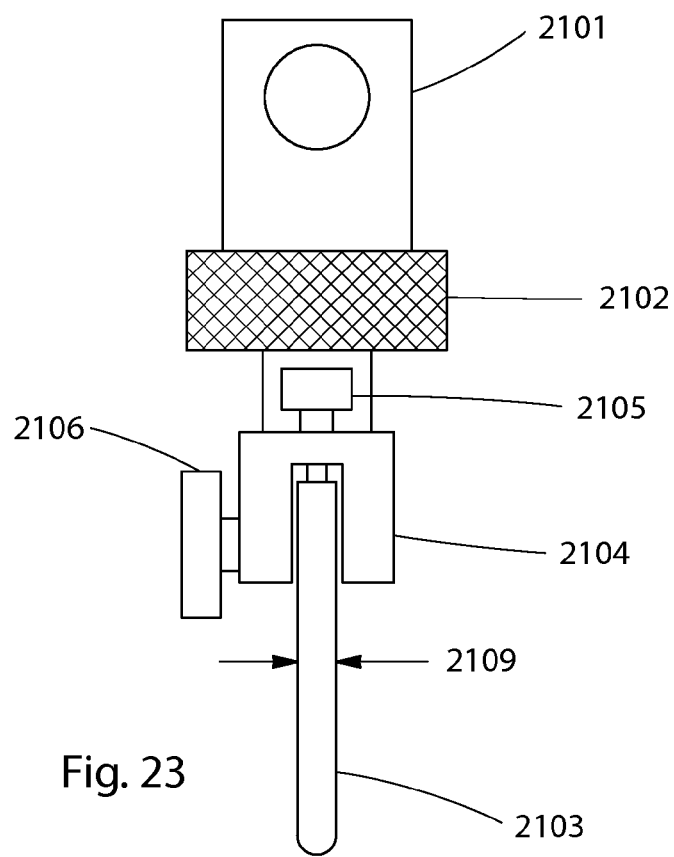
FIG. 23 is a front view of an upper fixture used on a constant rate of extension tensile tester for use in the Bending Stiffness Measurement Method herein.

Peak Bending Force and Bending Stiffness are measured using a constant rate of extension tensile tester with computer interface (a suitable instrument is an MTS Alliance under TestWorks 4 software, as available from MTS Systems Corp., Eden Prairie, Minn.) fitted with a 10 N load cell. A plunger blade 2100, shown in FIG. 22 (front view) and FIG. 23 (side view), is used for the upper movable test fixture. Base support platforms 2200, shown in FIG. 21, are used as the lower stationary test fixture.

Components of the plunger 2100 are made of a light weight material such as aluminum to maximize the available load cell capacity. The shaft 2101 is machined to fit the tensile tester and has a locking collar 2102 to stabilize the plunger and maintain alignment orthogonal to base support platforms 2204. The blade 2103, is 115 mm long 2108 by 65 mm high 2107 by 3.25 mm wide 2109, and has a material contact edge with a continuous radius of 1.625 mm. The bracket 2104 is fitted with set screws 2105 that are used to level the blade and a main set screw 2106 to firmly hold it in place after adjustment.

The bottom fixture 2200 is attached to the tensile tester with the shaft 2201 and locking collar 2202. Two movable support platforms 2204 are mounted on a rail 2203. Each test surface 2205 is 85 mm wide 2206 by 115 mm long (into plane of drawing) and made of polished stainless steel so as to have a minimal coefficient of friction. Each platform has a digital position monitor 2208 which reads the individual platform positions, and set screws 2207 to lock their position after adjustment. The two platforms 2204 are square at the gap edge and the plate edges should be parallel front to back. The two platforms form a gap 2209 with an adjustable gap width 2210.

Accurately (±0.02 mm) align the plunger blade 2103 so that it is orthogonal to the top surface of the support platforms 2204 and exhibits no skew relative to their gap edges. Using the position monitors 2208, accurately set the gap 2210 to 25.00±0.02 mm between the two gap edges of the support platforms 2204, with the plunger blade 2103 accurately (±0.02 mm) centered in the gap. Program the tensile tester for a compression test. Set the gauge length from the bottom of the plunger blade 2103 to the top surface of the support platform 2204 to 15 mm.

Set the crosshead to lower at 500 mm/min for a distance of 25 mm. Set the data acquisition rate to 200 Hz.

Obtain 10 test samples 1009 as described in the description of the Edge Deflection Force Measurement Method, above. (Do not remove any components such as attachment zones/fastener components, grasp structures, etc., except that if any release paper is present on any adhesive fastener component, remove the release paper.) Precondition samples at about 23 C±2 C and about 50%±2% relative humidity for 2 hours prior to testing.

Examine the sample 1009 to be tested for any exposed adhesive and deactivate any exposed adhesive by applying baby powder to it as necessary. Place the sample flat onto the surface of the support platform 2204 over the gap 2209 with the wearer-facing surface facing upward. Center the sample 1009 across the gap, with edge 1022 perpendicular to the gap. Zero the load cell; start the tensile tester and the data acquisition.

Figure 24:
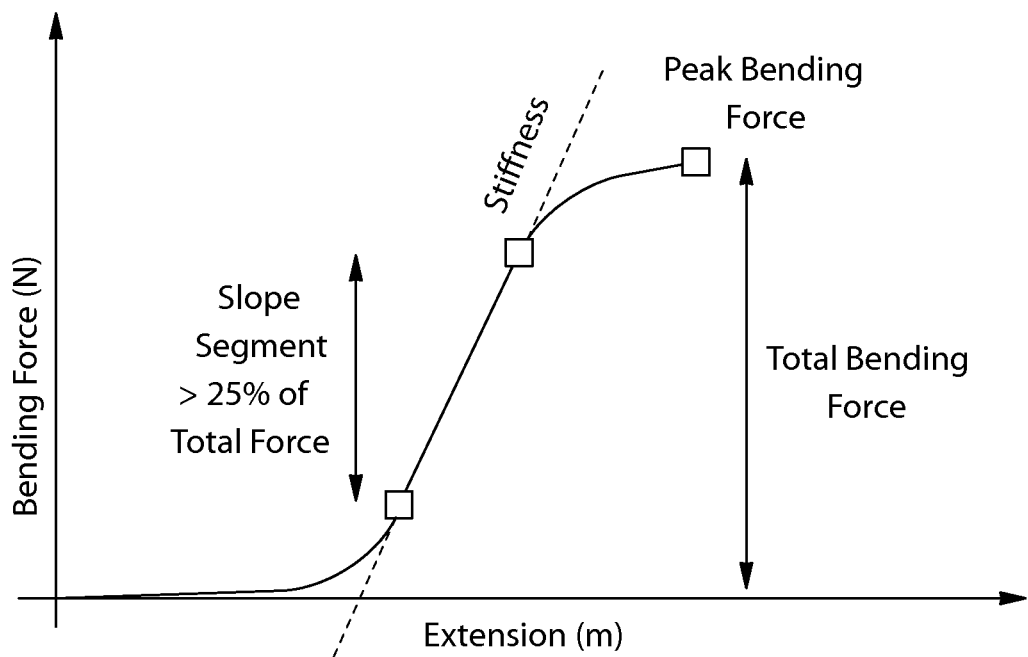
FIG. 24 is a graph showing Peak Bending Force and slope calculation areas on a bending curve.

Program the software to calculate the maximum peak bending force (N) and Stiffness (N/m) from the constructed force (N) verses extension (m) curve. Stiffness is measured as the maximum slope of the bending/extension curve as calculated from a fitted line segment which has a length of at least 25% of the total peak bending force (see FIG. 24).

Report Peak Bending Force to the nearest 0.1 N and the Bending Stiffness to the Nearest 0.1 N/m, and record the results. Repeat the test and record the results for all 10 samples. Calculate the average Peak Bending Force and average Bending Stiffness.

Whole Outer Cover Waist Opening Circumference Extension Force Test

This method is used for measuring the extensibility of a continuous waist opening circumference of a reusable outer cover of a pant. The pant is formed of the reusable outer cover and a disposable absorbent insert attachable to the reusable outer cover and positionable at least partially therein. The insert is removed from the outer cover before performing this method, so that only the outer cover is tested. If applicable, the one or more refastenable side seams (i.e., fastening zones) of the outer cover will be in a closed configuration for this method (i.e., formed such that the outer cover has a continuous waist opening circumference). When closing the refastenable side seams, the fasteners are aligned if they are the same size, shape, and position on each side of the side seams. For fasteners that are not the same size and shape, but do have the same or substantially similar positions on each side of the side seams, their midpoints should be aligned.

Whole outer cover waist opening circumference extension forces are measured on a constant rate of extension tensile tester with a computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. The initial relaxed waist opening circumference is measured using a flexible tape measure. The accuracy of the flexible tape measure is either traceable to NIST or other standards organization, or verified for accuracy against a traceable ruler. Five substantially similar reusable outer covers are analyzed and the results are averaged.

Figure 25:
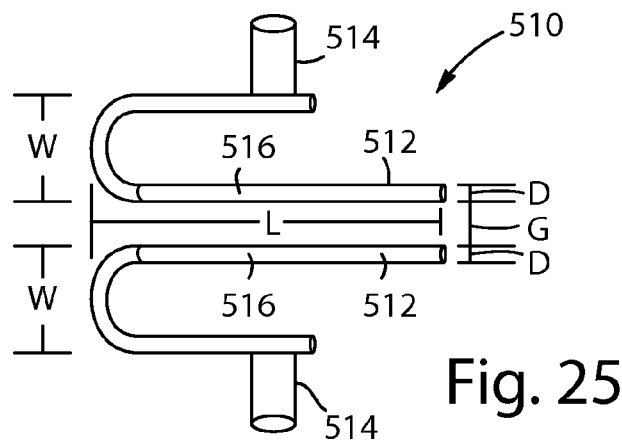
FIG. 25 illustrates a set of custom hooked used for the Whole Outer Cover Waist Opening Circumference Force Test.

For this test, referring to FIG. 25, a custom hook fixture 510 is used. The hook fixture 510 comprises a pair of J-shaped hooks 512, each with an attachment member 514 designed to mount to the tester's stationary base and upper movable crosshead (via the load cell). Each J-shaped hook 512 has a substantially circular cross-sectional shape with a diameter, D, of 1 cm. The hooks 512 exhibit a smooth curvature to form the two engaging arms 516 that are positioned perpendicular to the longitudinal axes of the attachment members 514. Each attachment member is fitted with a locking collar 513 which fixes the engagement arms 516 of the hooks 512 parallel to one another and perpendicular to the pull axis of the tensile tester. The engaging arms 516 have a width, W, of 13 cm, as indicated in FIG. 25.

As used herein, 100% strain means that the sample's circumference has been elongated by 100% of its original length, measured under no applied load. For example, a sample with an original circumference of 100 mm will have a 100% strain when elongated to a circumference of 200 mm. As used herein, "extension" means the distance the two hooks 512 are moved apart.

Program the tensile tester to move the crosshead up at a rate of 254 mm/min to 100% strain, hold at 100% strain for 30 seconds, and then return the crosshead to its starting position at a rate of 254 mm/min. Set the data acquisition rate at 100 Hz.

Figure 26:
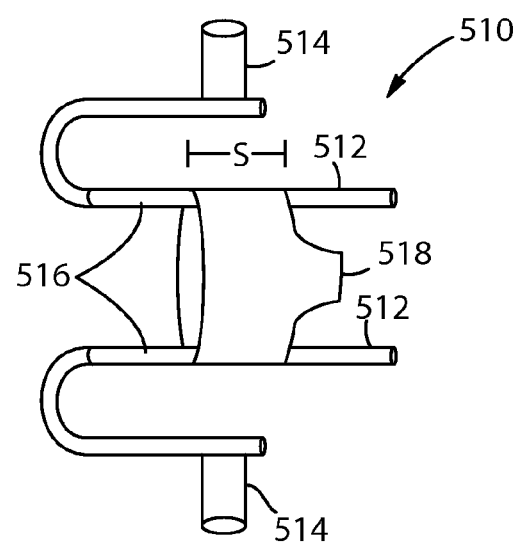
FIG. 26 illustrates the set of custom hooks of FIG. 25 with a reusable outer cover engaged thereon.

Manually move the crosshead up. Hang the reusable outer cover from the top engaging arm 516 such that the reusable outer cover is solely supported from the top arm, and zero the load cell. Lower the top engaging arm 516 so that the reusable outer cover 519 can be slid onto the engaging arms 516, as illustrated in FIG. 26. Adjust the engaging arms 516 to remove any slack from the reusable outer cover 519, but ensure that no more than 5 grams of force is measured on the load cell. Zero the crosshead. With the flexible measuring tape 517 (described above), graduated in mm, measure the relaxed waist opening circumference of the reusable outer cover by wrapping the tape around the engaging arms 516 proximate to the waist opening of the reusable outer cover as illustrated in FIG. 26. Record the relaxed waist opening circumference to the nearest 1 mm and input the relaxed waist opening circumference divided by 2 into the software as the gauge length. Start the tensile tester's program, and record force and extension data. Program the software to calculate the following from the constructed force (N) verses extension (mm) curve:
 a) Waist Opening Circumference at 20 N=Relaxed Waist Opening Circumference+(2× extension at 20 N). Report to the nearest 1.0 mm.
 b) Force at 110 mm extension. Report to the nearest 0.1 N.
 c) Force at 170 mm extension. Report to the nearest 0.1 N.
 d) Recovery force at 110 mm extension, from the return cycle. Report to the nearest 0.1 N.
 e) Average Modulus ((result of step c(N)−result of step b(N))/0.06 m) N/m. Report to the nearest 1 N/m.
 f) Extension at 20 N force. Report to the nearest 1 mm.

Repeat the test for remaining samples. Calculate and report the average of the above reportables.

Outer Cover Front or Rear Waist Region Extension Force Test

The pant to be tested includes a reusable outer cover and a disposable absorbent insert. Prior to testing, the disposable absorbent insert is removed from the reusable outer cover, so that only the outer cover is tested. The outer cover can have permanent side seams or refastenable side seams (e.g., fastening zones), such that it forms a portion of the pant with a continuous waist opening circumference. If the outer cover has any refastenable side seams, these refastenable side seams should be separated prior to testing. If the outer cover has one or two permanent side seams, these permanent side seams should be cut longitudinally along the seam's central axis prior to testing.

Outer cover waist region extension forces are measured on a constant rate of extension tensile tester with a computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. The tester should have an upper movable pneumatic jaw and a lower stationary pneumatic jaw. Both the movable (upper) and stationary (lower) pneumatic jaws are fitted with 1 inch×1 inch diamond faced grips. Air pressure supplied to the jaws should be sufficient to prevent sample slippage. Linear measurements are performed with a calibrated ruler graduated to the nearest mm traceable to NIST or other standards organization. Five substantially similar reusable outer covers are analyzed and the results are averaged.

As used herein, 100% strain means that the sample has been elongated by 100% of its original length, measured under no applied load. For example, a sample with an original length of 100 mm will have a 100% strain when elongated to a length of 200 mm.

Program the tensile tester to move the crosshead up at a rate of 254 mm/min to 100% strain, hold at 100% strain for 30 seconds, and then return the crosshead to its starting position at a rate of 254 mm/min. Set the data acquisition rate at 100 Hz.

Lay the opened reusable outer cover flat on a flat lab bench. With the calibrated ruler, measure the length along the rear waist region of the reusable outer cover from distal edge of the separated side panel to the distal edge of the opposite separated side panel and record to the length to the nearest 1 mm. Set the gauge length of the tensile tester (bottom edge of the upper grip faces to the top edge of the lower grip faces) to the measured rear waist region length minus 2 inches. Zero the crosshead position and enter the gauge length into the software. Grasp the reusable outer cover such that the interior of the reusable outer cover is facing the operator, with the rear right side panel directed upward and the rear left side panel directed downward. Insert the rear waist region of the right side panel (distal of the longitudinal center line of the product) between the upper grip faces, aligning the seam edge of the reusable outer cover with the upper edges of the grip faces and the waist edge of the reusable outer cover with the left edges of the grip faces. Close the upper jaw. Manually raise the crosshead of the tensile tester such that the reusable outer cover is completely suspended from the upper grip of the tester. Zero the load cell. Lower the crosshead to the original gauge length. Insert the rear waist region of the left side panel (distal of the longitudinal center line of the product) between the lower grip faces, aligning the seam edge with the bottom edges of the grip faces and the waist edge with left edges of the grip faces. Close the lower jaw. Allow the front waist region and the crotch region of the reusable outer cover to hang downward.

Start the tensile tester's program, and record force and extension data for the test. Program the software to calculate the following from the constructed force (N) verses extension (mm) curve:
  a) Force at 55 mm extension. Report to the nearest 0.1 N.
  b) Force at 85 mm extension. Report to the nearest 0.1 N
  c) Extension at 10 N force. Report to the nearest 1 mm.
  d) Force at 55 mm extension on the return cycle. Report to the nearest 0.1 N.
  e) Average Modulus ((result of step b(N)–result of step a(N))/0.03 m) N/m. Report to the nearest 1 N/m.
Repeat the test for remaining samples. Calculate and report the average of the above rear waist region reportables.

Like testing is also performed on the front waist regions of the reusable outer covers.

Lay the opened reusable outer cover flat on a flat lab bench. With the calibrated ruler, measure the length along the front waist region of the reusable outer cover from distal edge of the separated side panel to the distal edge of the opposite separated side panel and record to the nearest 1 mm. Set the gauge length of the tensile tester (bottom edge of the upper grip faces to the top edge of the lower grip faces) to the measured front waist region length minus 2 inches. Zero the crosshead position and enter the gauge length into the software. Grasp the reusable outer cover such that the interior of the reusable outer cover is facing the operator, with the front right side panel directed upward and the front left side panel directed downward. Insert the front waist region of the right side panel (distal of the longitudinal center line of the product) between the upper grip faces, aligning the seam edge of the reusable outer cover with the upper edges of the grip faces and the waist edge of the reusable outer cover with the left edges of the grip faces. Close the upper jaw. Manually raise the crosshead of the tensile tester such that the reusable outer cover is completely suspended from the upper grip of the tester. Zero the load cell. Lower the crosshead to the original gauge length. Insert the front waist region of the left side panel (distal of the longitudinal center line of the product) between the lower grip faces, aligning the seam edge with the bottom edges of the grip faces and the waist edge with left edges of the grip faces. Close the lower jaw. Allow the rear waist region and the crotch region of the reusable outer cover to hang downward.

Start the tensile tester's program, and record force and extension data for the test. Program the software to calculate the following from the constructed force (N) verses extension (mm) curve:
  a) Force at 55 mm extension. Report to the nearest 0.1 N.
  b) Force at 85 mm extension. Report to the nearest 0.1 N
  c) Extension at 10 N force. Report to the nearest 1 mm.
  d) Force at 55 mm extension on the return cycle. Report to the nearest 0.1 N.
  e) Average Modulus ((result of step b(N)–result of step a(N))/0.03 m) N/m. Report to the nearest 1 N/m.
Repeat the test for remaining samples. Calculate and report the average of the above front waist region reportables.

Lateral Length of the Front and Rear Stretchable Regions

Remove the insert from the outer cover of the pant, if attached.

The outer cover can have permanent side seams or refastenable side seams (e.g., fastening zones) such that it forms a portion of the pant with a continuous waist opening circumference. If the outer cover has any refastenable side seams, the refastenable side seams should be separated prior to measurement. If the outer cover has any permanent side seams, the permanent side seams should be cut longitudinally about their central axis prior to testing. The outer cover should then be placed on a flat surface and flattened for measurement.

Lateral Length of Front Stretchable Region: To determine the lateral length of the front stretchable region follow the following steps:

If only one attachment zone is present in the front waist region:
  a) Situate the outer cover in a flat, laid out condition (i.e., elastic induced contraction pulled out) on a flat surface with the wearer-facing surface 25 facing away from the flat surface;
  b) determine the lateral mid-point of the front and back waist edges and draw a line connecting them to indicate the longitudinal axis of the outer cover;
  c) determine the mid-point of the longitudinal axis (e.g., length of the longitudinal axis/2) and draw a line perpendicular to the longitudinal axis and crossing the longitudinal axis at the midpoint to indicate the lateral axis;
  d) find the most laterally inboard portion of the laterally inboard edge of the first fastening zone in the front waist region and draw a line parallel to the longitudinal axis which extends to the lateral axis;
  e) find the most laterally outboard portion of the laterally outboard edge (edge most proximal to the line drawn in step d of the insert attachment zone) and draw a line parallel to the longitudinal axis which extends to the lateral axis;

f) measure the lateral distance between the two longitudinally oriented lines in steps d and e to determine the lateral length of one portion of the front stretchable region;
g) find the most laterally inboard portion of the laterally inboard edge of the second fastening zone in the front waist region and draw a line parallel to the longitudinal axis which extends to the lateral axis;
h) find the most laterally outboard portion of the laterally outboard edge (edge most proximal to the line drawn in step g of the insert attachment zone) and draw a line parallel to the longitudinal axis which extends to the lateral axis;
i) measure the lateral distance between the two longitudinally oriented lines in steps g and h to determine the lateral length of another portion of the front stretchable region; and
j) add the measurement from steps f and i to determine the total lateral length of the front stretchable region;

If more than one attachment zone is present in the front waist region:
a) Follow steps a-c above;
b) find the most laterally inboard portion of the laterally inboard edge of the first fastening zone in the front waist region and draw a line parallel to the longitudinal axis which extends to the lateral axis;
c) find the most laterally outboard portion of the laterally outboard edge (edge most proximal to the line drawn in step b) of the attachment zone most proximal to the line drawn in step b and draw a line parallel to the longitudinal axis which extends to the lateral axis;
d) measure the lateral distance between the two longitudinally oriented lines in steps b and c to determine the lateral length of one portion of the front stretchable region, and record the length to within +/−1 mm;
e) find the other end of the attachment zone discussed in step c and draw a line parallel to the longitudinal axis which extends to the lateral axis;
f) find an end of the most proximal attachment zone to the attachment zone discussed in step e and draw a line parallel to the longitudinal axis which extends to the lateral axis;
g) measure the lateral distance between the two longitudinally oriented lines in steps e and f, and record the length to within +/−1 mm;
h) perform steps e-g to measure the lateral distance between additional attachment zones;
i) find the most laterally inboard portion of the laterally inboard edge of the second fastening zone in the front waist region and draw a line parallel to the longitudinal axis which extends to the lateral axis;
j) find the most laterally outboard portion of the laterally outboard edge (edge most proximal to the line drawn in step i) of the most proximal insert attachment zone and draw a line parallel to the longitudinal axis which extends to the lateral axis;
k) measure the lateral distance between the two longitudinally oriented lines in steps i and j to determine the lateral length of another portion of the front stretchable region; and
l) add all of the measurements from steps d, g, h, and k together to determine the total lateral length of the front stretchable region.

Lateral Length of Rear Stretchable Region: To determine the lateral length of the rear stretchable region follow the following steps:

If only one attachment zone is present in the rear waist region:
a) Situate the outer cover in a flat, laid out condition (i.e., elastic induced contraction pulled out) on a flat surface with the wearer-facing surface 25 facing away from the flat surface;
b) determine the lateral mid-point of the front and back waist edges and draw a line connecting them to indicate the longitudinal axis of the outer cover;
c) determine the mid-point of the longitudinal axis (e.g., length of the longitudinal axis/2) and draw a line perpendicular to the longitudinal axis and crossing the longitudinal axis at the midpoint to indicate the lateral axis;
d) find the most laterally inboard portion of the laterally inboard edge of the first fastening zone in the rear waist region and draw a line parallel to the longitudinal axis which extends to the lateral axis;
e) find the most laterally outboard portion of the laterally outboard edge (edge most proximal to the line drawn in step d of the insert attachment zone) and draw a line parallel to the longitudinal axis which extends to the lateral axis;
f) measure the lateral distance between the two longitudinally oriented lines in steps d and e to determine the lateral length of one portion of the rear stretchable region;
g) find the most laterally inboard portion of the laterally inboard edge of the second fastening zone in the rear waist region and draw a line parallel to the longitudinal axis which extends to the lateral axis;
h) find the most laterally outboard portion of the laterally outboard edge (edge most proximal to the line drawn in step g of the insert attachment zone) and draw a line parallel to the longitudinal axis which extends to the lateral axis;
i) measure the lateral distance between the two longitudinally oriented lines in steps g and h to determine the lateral length of another portion of the rear stretchable region; and
j) add the measurement from steps f and i to determine the total lateral length of the rear stretchable region;

If more than one attachment zone is present in the rear waist region:
a) Follow steps a-c of the "If only one attachment zone is present in the rear waist region" method above;
b) find the most laterally inboard portion of the laterally inboard edge of the first fastening zone in the rear waist region and draw a line parallel to the longitudinal axis which extends to the lateral axis;
c) find the most laterally outboard portion of the laterally outboard edge (edge most proximal to the line drawn in step b) of the attachment zone most proximal to the line drawn in step b and draw a line parallel to the longitudinal axis which extends to the lateral axis;
d) measure the lateral distance between the two longitudinally oriented lines in steps b and c to determine the lateral length of one portion of the rear stretchable region, and record the length to within +/−1 mm;
e) find the other end of the attachment zone discussed in step c and draw a line parallel to the longitudinal axis which extends to the lateral axis;
f) find an end of the most proximal attachment zone to the attachment zone discussed in step e and draw a line parallel to the longitudinal axis which extends to the lateral axis;

g) measure the lateral distance between the two longitudinally oriented lines in steps e and f, and record the length to within +/−1 mm;
h) perform steps e-g to measure the lateral distance between additional attachment zones;
i) find the most laterally inboard portion of the laterally inboard edge of the second fastening zone in the rear waist region and draw a line parallel to the longitudinal axis which extends to the lateral axis;
j) find the most laterally outboard portion of the laterally outboard edge (edge most proximal to the line drawn in step i) of the most proximal insert attachment zone and draw a line parallel to the longitudinal axis which extends to the lateral axis;
k) measure the lateral distance between the two longitudinally oriented lines in steps i and j to determine the lateral length of another portion of the rear stretchable region; and
l) add all of the measurements from steps d, g, h, and k together to determine the total lateral length of the rear stretchable region.

In essence, the lateral length of the front stretchable region is the lateral distance between the most laterally inboard edge of the first fastening zone to the most laterally inboard edge of the second fastening zone minus the total lateral length of the attachment zones in the front stretchable region. The same logic applies to the lateral length of the rear stretchable region.

Area of the Stretchable Regions

To find the area of the front and rear stretchable regions, one must first measure the lateral length of each portion of the front and rear stretchable regions as described above. In the front waist region, locate the two most longitudinally outboard extents of each leg opening 23 and draw a line parallel to the lateral axis between these two points. Perform the same step in the rear waist region. In each portion of the front stretchable region measure the longitudinal length between the line drawn parallel to the lateral axis in the front waist region and the front waist edge, and record the length to within +/−1 mm. In each portion of the rear stretchable region measure the longitudinal length between the line drawn parallel to the lateral axis in the rear waist region and the rear waist edge, and record the length to within +/−1 mm. For each portion of the front stretchable region, multiply the measured longitudinal length by the measured lateral length of the same portion to determine the area of each portion. Once all of the areas of the portions of the front stretchable region have been determined, take the sum of those areas to determine the total area of the front stretchable region. For each portion of the rear stretchable region, multiply the measured longitudinal length by the measured lateral length of the same portion to determine the area of each portion. Once all of the areas of the portions of the rear stretchable region have been determined, take the sum of those areas to determine the total area of the rear stretchable region. Areas should be determined to within ±0.5 cm$^2$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended that the appended claims cover all such changes and modifications, and that nothing in the foregoing description or the figures, but rather, only the appended claims, limit the scope of the invention.

What is claimed is:

1. An outer cover forming a portion of a pant and having a longitudinal axis and a lateral axis, the outer cover comprising:
    a front waist region positioned on a first side of the lateral axis;
    a rear waist region positioned on a second side of the lateral axis;
    a crotch region positioned intermediate the front waist region and the rear waist region;
    a fastening zone positioned on a side of the longitudinal axis, wherein the fastening zone comprises a first portion in the front waist region and a second portion in the rear waist region;
    wherein the outer cover is configured to at least partially receive a disposable absorbent insert to form the pant; and
    wherein the outer cover has an average modulus between 170 mm extension and 110 mm extension in the range of 20 N/m to 250 N/m measured according to the Whole Outer Cover Waist Opening Circumference Extension Force Test;
    a front stretchable region formed in the front waist region and comprising a front stretchable zone, wherein the front stretchable zone has a first longitudinal length extending in a direction parallel to the longitudinal axis and a first lateral length extending in a direction parallel to the lateral axis, and wherein the first longitudinal length is greater than the first lateral length; and
    a rear stretchable region formed in the rear waist region and comprising a rear stretchable zone, wherein the rear stretchable zone has a second longitudinal length extending in the direction parallel to the longitudinal axis and a second lateral length extending in the direction parallel to the lateral axis, and wherein the second longitudinal length is greater than the second lateral length.

2. The outer cover of claim 1, wherein the average modulus of the outer cover between the 170 mm extension and the 110 mm extension is in the range of 40 N/m to 200 N/m.

3. The outer cover of claim 1, wherein the average modulus of the outer cover between the 170 mm extension and the 110 mm extension is in the range of 60 N/m to 170 N/m.

4. The outer cover of claim 1, wherein a force applied by the outer cover at the 170 mm extension is in the range of 5 N to 20 N.

5. A pant comprising:
the reusable outer cover of claim 1; and
a disposable absorbent insert comprising:
   a topsheet;
   a backsheet; and
   an absorbent core disposed at least partially intermediate the topsheet and the backsheet, wherein the disposable absorbent insert is configured to be attached to a first attachment zone and to at least a second attachment zone of the reusable outer cover to releasably join the disposable absorbent insert to the reusable outer cover.

6. An outer cover forming a portion of a pant and having a longitudinal axis and a lateral axis, the outer cover comprising:
   a front waist region positioned on a first side of the lateral axis;
   a rear waist region positioned on a second side of the lateral axis;
   a crotch region positioned intermediate the front waist region and the rear waist region;
   a fastening zone positioned on a side of the longitudinal axis, wherein the fastening zone comprises a first portion in the front waist region and a second portion in the rear waist region;
   wherein the outer cover is configured to at least partially receive a disposable absorbent insert to form the pant; and
   wherein the outer cover has a recovery force at 110 mm extension in the range of 1 N to 8 N measured according to the Whole Outer Cover Waist Opening Circumference Extension Force Test;
   a front stretchable region formed in the front waist region and comprising a front stretchable zone, wherein the front stretchable zone has a first longitudinal length extending in a direction parallel to the longitudinal axis and a first lateral length extending in a direction parallel to the lateral axis, and wherein the first longitudinal length is greater than the first lateral length; and
   a rear stretchable region formed in the rear waist region and comprising a rear stretchable zone, wherein the rear stretchable zone has a second longitudinal length extending in the direction parallel to the longitudinal axis and a second lateral length extending in the direction parallel to the lateral axis, and wherein the second longitudinal length is greater than the second lateral length.

7. The outer cover of claim 6, wherein the outer cover has a recovery force at 110 mm extension in the range of 1.5 N to 6 N.

8. The outer cover of claim 6, wherein the outer cover has a recovery force at 110 mm extension in the range of 2 N to 4 N.

9. The outer cover of claim 6, wherein the outer cover has a recovery force at 110 mm extension in the range of 2 N to 3 N.

10. The outer cover of claim 6, wherein the outer cover has a recovery force at 110 mm extension of about 2.5 N.

11. A pant comprising:
the reusable outer cover of claim 6; and
a disposable absorbent insert comprising:
   a topsheet;
   a backsheet; and
   an absorbent core disposed at least partially intermediate the topsheet and the backsheet, wherein the disposable absorbent insert is configured to be attached to a first attachment zone and to at least a second attachment zone of the reusable outer cover to releasably join the disposable absorbent insert to the reusable outer cover.

12. A reusable outer cover forming or configured to be formed into a portion of a pant and having a longitudinal axis and a lateral axis, the reusable outer cover comprising:
   a front waist region positioned on a first side of the lateral axis;
   a rear waist region positioned on a second side of the lateral axis;
   a first fastening zone positioned on a first side of the longitudinal axis, wherein the first fastening zone comprises a first portion in the front waist region and a second portion in the rear waist region;
   a second fastening zone positioned on a second side of the longitudinal axis, wherein the second fastening zone comprises a first portion in the front waist region and a second portion in the rear waist region;
   wherein the reusable outer cover is configured to at least partially receive a disposable absorbent insert to form the pant;
   a front stretchable region formed in the front waist region and comprising a front stretchable zone having a first area, wherein the front stretchable zone has a first longitudinal length extending in a direction parallel to the longitudinal axis and a first lateral length extending in a direction parallel to the lateral axis, and wherein the first longitudinal length is greater than the first lateral length; and
   a rear stretchable region formed in the rear waist region and comprising a rear stretchable zone having a second, different area, wherein the rear stretchable zone has a second longitudinal length extending in the direction parallel to the longitudinal axis and a second lateral length extending in the direction parallel to the lateral axis, and wherein the second longitudinal length is greater than the second lateral length.

13. The reusable outer cover of claim 12, wherein the first area is greater than the second area, and wherein the first area is in the range of about 50 cm$^2$ to about 150 cm$^2$.

14. The reusable outer cover of claim 12, wherein the first area is less than the second area.

15. The reusable outer cover of claim 12, wherein the first lateral length is in the range of 50 mm to 120 mm.

16. The reusable outer cover of claim 12, wherein the second lateral length is in the range of 50 mm to 120 mm.

17. The reusable outer cover of claim 12, wherein the front stretchable region has a first average modulus between 170mm and 110mm extension, and wherein the second stretchable region has a second average modulus between 170 mm and 110 mm extension.

18. The reusable outer cover of claim 17, wherein the first average modulus is different than the second average modulus.

19. The reusable outer cover of claim 12, wherein the first fastening zone has a longitudinal component that extends at least 50 mm in a direction generally parallel to the longitudinal axis.

20. The reusable outer cover of claim 12, wherein the second fastening zone has a longitudinal component that extends at least 50 mm in a direction generally parallel to the longitudinal axis.

* * * * *